US008491913B2

(12) United States Patent
Offner et al.

(10) Patent No.: US 8,491,913 B2
(45) Date of Patent: Jul. 23, 2013

(54) COMPOSITIONS AND METHODS USING RECOMBINANT MHC MOLECULES FOR THE TREATMENT OF STROKE

(75) Inventors: Halina Offner, Portland, OR (US); Arthur A. Vandenbark, Portland, OR (US); Gregory G. Burrows, Portland, OR (US); Patricia D. Hurn, Portland, OR (US)

(73) Assignees: Oregon Health & Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 204 days.

(21) Appl. No.: 12/661,038

(22) Filed: Mar. 8, 2010

(65) Prior Publication Data

US 2011/0217308 A1    Sep. 8, 2011

Related U.S. Application Data

(60) Provisional application No. 61/209,428, filed on Mar. 7, 2009.

(51) Int. Cl.
*A61K 39/00*   (2006.01)
*C07K 14/00*   (2006.01)

(52) U.S. Cl.
USPC ..................................................... 424/192.1

(58) Field of Classification Search
None
See application file for complete search history.

(56) References Cited

U.S. PATENT DOCUMENTS

| 6,270,772 | B1 | 8/2001 | Burrows et al. |
| 2003/0007978 | A1 | 1/2003 | Burrows et al. |
| 2005/0142142 | A1 | 6/2005 | Burrows et al. |
| 2009/0280135 | A1 | 11/2009 | Offner et al. |
| 2011/0008382 | A1 | 1/2011 | Burrows et al. |

FOREIGN PATENT DOCUMENTS

WO    WO 96/40944    12/1996

OTHER PUBLICATIONS mayoclinic.com/health/stroke/ds00150/dsection=causes, Jun. 1, 2012, pp. 1-3.*
Akiyoshi et al., "Recombinant T cell receptor ligands improve outcome after experimental cerebral ischemia," *Transl. Stroke Res.* vol. 2, pp. 404-410, 2011 (NIH Public Access Author Manuscript, 12 pages).
Chang et al. "Design, Engineering, and Production of Human recombinant T Cell Receptor Ligands Derived from Human Leukocyte Antigen DR2," *J. Biol. Chem.*, vol. 276, pp. 24170-24176, 2001.
Dziennis et al., "Therapy with recombinant T-cell receptor ligand reduces infarct size and infiltrating inflammatory cells in brain after middle cerebral artery occlusion in mice," *Metab. Brain Dis.* vol. 26, pp. 123-133, 2011.
Fissolo et al., "Naturally Presented Peptides on Major Histocompatibility Complex I and II Molecules Eluted from Central Nervous System of Multiple Sclerosis Patients," *Mol. Cell. Proteomics*, vol. 8, pp. 2090-2101, 2009.
Huan et al. "Rationally designed mutations convert complexes of human recombinant T cell receptor ligands into monomers that retain biological activity," *J. Chem. Technol. Biotechnol.*, vol. 80, pp. 2-12, 2005.
Hurn et al. "T- and B-cell deficient mice with experimental stroke have reduced lesion size and inflammation," *J. Cereb. Blood Flow Metab.* vol. 27, pp. 1798-1805, 2007.
Offner et al. "Experimental stroke induces massive, rapid activation of the peripheral immune system," *J. Cereb. Blood Flow Metab.* vol. 26, pp. 654-665, 2006.
Offner et al. "Splenic atrophy in experimental stroke is accompanied by increased regulatory T cells and circulating macrophages," *J. Immunol.* vol. 176, pp. 6523-6531, 2006.
Ren et al. "CD4+FoxP3+ regulatory T-cells in cerebral ischemic stroke," *Metab. Brain Dis.* vol. 26, pp. 87-90, 2011 (NIH Public Access Author Manuscript, 6 pages).
Sinha et al. "A Promising Therapeutic Approach for Multiple Sclerosis: Recombinant T-Cell Receptor Ligands Modulate Experimental Autoimmune Encephalomyelitis by Reducing Interleukin-17 Production and Inhibiting Migration of Encephalitogenic Cells into the CNS," *J. Neurosci.*, vol. 27, pp. 12531-12539, 2007.
Sinha et al. "RTL551 Treatment of EAE Reduces CD226 and T-bet+ CD4 T Cells in Periphery and Prevents Infiltration of T-bet+ IL-17, IFN-γ Producing T Cells into CNS," *PLoS ONE*, vol. 6, e21868, 2011 (12 pages).
Subramanian et al. "Recombinant T Cell Receptor Ligand Treats Experimental Stroke," *Stroke*, vol. 40, pp. 2539-2545, 2009.
Vandenbark et al. "Recombinant TCR ligand induces tolerance to myelin oligodendrocyte glycoprotein 35-55 peptide and reverses clinical and histological signs of chronic experimental autoimmune encephalomyelitis in HLA-DR2 transgenic mice," *J. Immunol.* 171:127-133, 2003.

* cited by examiner

*Primary Examiner* — Gerald R Ewoldt
*Assistant Examiner* — Marianne Dibrino
(74) *Attorney, Agent, or Firm* — Klarquist Sparkman, LLP

(57) ABSTRACT

Two-domain MHC polypeptides are useful for modulating activities of antigen-specific T-cells, including for modulating pathogenic potential and effects of antigen-specific T-cells. Exemplary MHC class II-based recombinant T-cell ligands (RTLs) of the invention include covalently linked β1 and α1 domains, and MHC class I-based molecules that comprise covalently linked α1 and α2 domains. These polypeptides may also include covalently linked antigenic determinants, toxic moieties, and/or detectable labels. The disclosed polypeptides can be used to target antigen-specific T-cells, and are useful, among other things, to detect and purify antigen-specific T-cells, to induce or activate T-cells, to modulate T-cell activity, including by regulatory switching of T-cell cytokine and adhesion molecule expression, to treat conditions mediated by antigen-specific T-cells, including treatment and/or prevention of central nervous system damage relating to stroke.

5 Claims, 31 Drawing Sheets

FIG. 1A

```
     β1α1
     NcoI                    ▼
  -2 CCATGGGCAGAGACTCCCCAAGGGATTTCGTGTACCAGTTCAAGGGCCTGTGCTACTACACC 60
     M  G  R  D  S  P  R  D  F  V  Y  Q  F  K  G  L  C  Y  Y  T

61 AACGGGACGCAGCGCATACGGGATGTGATCAGATACATCTACAACCAGGAGGAGTACCTG  120
     N  G  T  Q  R  I  R  D  V  I  R  Y  I  Y  N  Q  E  E  Y  L

121 CGCTACGACAGCGACGTGGGCGAGTACCGCGCGCTGACCGAGCTGGGGCGGCCCTCAGCC  180
     R  Y  D  S  D  V  G  E  Y  R  A  L  T  E  L  G  R  P  S  A
                                                         Pst I
 181 GAGTACTTTAACAAGCAGTACCTGGAGCAGACGCGGGCCGAGCTGGACACGGTCTGCAGA  240
     E  Y  F  N  K  Q  Y  L  E  Q  T  R  A  E  L  D  T  V  C  R
                                          end of β1  ▼ start of α1
 241 CACAACTACGAGGGGTCGGAGGTCCGCACCTCCCTGCGGCGGCTTGGAGGTCAAGACGAC  300
     H  N  Y  E  G  S  E  V  R  T  S  L  R  R  L  G  G  Q  D  D 301 ATTGAGGCCGACCACGTAGCCGCCTATGGTATAAATATGTATCAGTATTATGAATCCAGA  360
     I  E  A  D  H  V  A  A  Y  G  I  N  M  Y  Q  Y  Y  E  S  R 361 GGCCAGTTCACACATGAATTTGATGGTGACGAGGAATTCTATGTGGACTTGGATAAGAAG  420
     G  Q  F  T  H  E  F  D  G  D  E  E  F  Y  V  D  L  D  K  K 421 GAGACCATCTGGAGGATCCCCGAGTTTGGACAGCTGACAAGCTTTGACCCCCAAGGTGGA  480
     E  T  I  W  R  I  P  E  F  G  Q  L  T  S  F  D  P  Q  G  G 481 CTTCAAAATATAGCTATAATAAAACACAATTTGGAAATCTTGATGAAGAGGTCAAATTCA  540
     L  Q  N  I  A  I  I  K  H  N  L  E  I  L  M  K  R  S  N  S
                                    Xho I
 541 ACCCAAGCTGTCAACTAACTCGAG
     T  Q  A  V  N  end
```

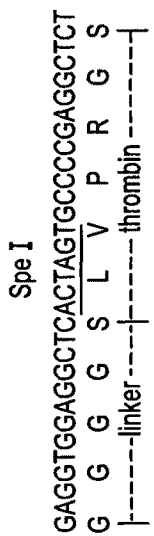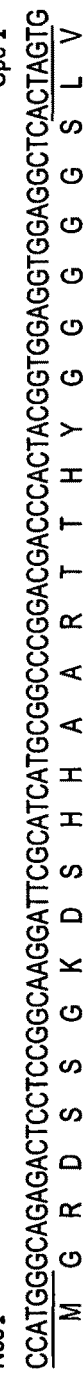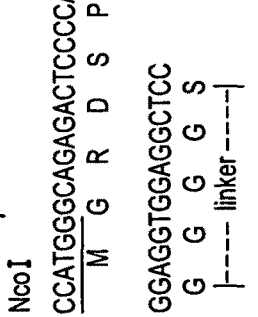

FIG. 6A

β1 domain:
ARG4 -PRO5-ARG6-PHE7-LEU8-TRP9-GLN10-LEU11-LYS12-PHE13-GLU14-CYS15-
HIS16-PHE17-PHE18-ASN19-GLY20-THR21-GLU22-ARG23-VAL24-ARG25-LEU26-
LEU27-GLU26-ARG29-CYS30-ILE31-TYR32-ASN33-GLN34-GLU35-GLU36-SER37-
VAL38-ARG39-PHE40-ASP41-SER42-ASP43-VAL44-GLY45-GLU46-TYR47-ARG48-
ALA49-VAL50-THR51-GLU52-LEU53-GLY54-ARG55-PRO56-ASP57-ALA58-GLU59-
TYR60-TRP61-ASN62-SER63-GLN64-LYS65-ASP66-LEU67-LEU68-GLU69-GLN70-
ARG71-ARG72-ALA73-ALA74-VAL75-ASP76-THR77-TYR78-CYS79-ARG80-HIS81-
ASN82-TYR83-GLY84-VAL85-GLY86-GLU87-SER88-PHE89-THR90-VAL91-GLN92-
ARG93-ARG94-VAL95

α1 domain:
GLU3-GLU4-HIS5-VAL6-ILE7-ILE8-GLN9-ALA10-GLU11-PHE12-TYR13-LEU14-
ASN15-PRO16-ASP17-GLN18-SER19-GLY20-GLU21-PHE22-MET23-PHE24-ASP25-
PHE26-ASP27-GLY28-ASP29-GLU30-ILE31-PHE32-HIS33-VAL34-ASP35-MET36-
ALA37-LYS38-LYS39-GLU40-THR41-VAL42-TRP43-ARG44-LEU45-GLU46-GLU47-
PHE48-GLY49-ARG50-PHE51-ALA52-SER53-PHE54-GLU55-ALA56-GLN57-GLY58-
ALA59-LEU60-ALA61-ASN62-ILE63-ALA64-VAL65-ASP66-LYS67-ALA68-ASN69-
LEU70-GLU71-ILE72-MET73-THR74-LYS75-ARG76-SER77-ASN78-TYR79-THR80-
PRO81-ILE82-THR83 ASN84

FIG. 6B

β1 domain:
ARG4 - PRO5- TRP6- PHE7- LEU8- GLU9- TYR10- CYS11- LYS12- SER13- GLU14- CYS15- HIS16- PHE17- TYR18- ASN19- GLY20- THR21- GLN22- ARG23- VAL24- ARG25- LEU26- LEU27- VAL28- ARG29- TYR30- PHE31- TYR32- ASN33- LEU34- GLU35- GLU36- ASN37- LEU38- ARG39- PHE40- ASP41- SER42- ASP43- VAL44- GLY45- GLU46- PHE47- ARG48- ALA49- VAL50- THR51- GLU52- LEU53- GLY54- ARG55- PRO56- ASP57- ALA58- GLU59- ASN60- TRP61- ASN62- SER63- GLN64- PRO65- GLU66- PHE67- LEU68- GLU69- GLN70- LYS71- ARG72- ALA73- GLU74- VAL75- ASP76- THR77- VAL78- CYS79- ARG80- HIS81- ASN82- TYR83- GLU84- ILE85- PHE86- ASP87- ASN88- PHE89- LEU90- VAL91- PRO92- ARG93- ARG94- VAL95

α1 domain:
GLU3- GLU4- HIS5- THR6- ILE7- ILE8- GLN9- ALA10- GLU11- PHE12- TYR13- LEU14- LEU15- PRO16- ASP17- LYS18- ARG19- GLY20- GLU21- PHE22- MET23- PHE24- ASP25- PHE26- ASP27- GLY28- ASP29- GLU30- ILE31- PHE32- HIS33- VAL34- ASP35- ILE36- GLU37- LYS38- SER39- GLU40- THR41- ILE42- TRP43- ARG44- LEU45- GLU46- GLU47- PHE48- ALA49- LYS50- PHE51- ALA52- SER53- PHE54- GLU55- ALA56- GLN57- GLY58- ALA59- LEU60- ALA61- ASN62- ILE63- ALA64- VAL65- ASP66- LYS67- ALA68- ASN69- LEU70- ASP71- VAL72- MET73- LYS74- GLU75- ARG76- SER77- ASN78- ASN79- THR80- PRO81- ASP82- ALA83- ASN84

FIG. 6C

β1 domain:
MET(-2)-GLY(-1)-ARG1-ASP2-SER3-PRO4-ARG5-ASP6-PHE7-VAL8-TYR9- GLN10- PHE11- LYS12- GLY13- LEU14- CYS15- TYR16- TYR17- THR18- ASN19- GLY20- THR21- GLN22- ARG23- ILE24- ARG25- ASP26- VAL27- ILE28- ARG29- TYR30- ILE31- TYR32- ASN33- GLN34- GLU35- GLU36- TYR37- LEU38- ARG39- TYR40- ASP41- SER42- ASP43- VAL44- GLY45- GLU46- TYR47- ARG48- ALA49- LEU50- THR51- GLU52- LEU53- GLY54- ARG55- PRO56- SER57- ALA58- GLU59- TYR60- TRP61- ASN62- SER63- GLN64- LYS65- GLN66- TYR67- LEU68- GLU69- GLN70- THR71- ARG72- ALA73- GLU74- LEU75- ASP76- THR77- VAL78- CYS79- ARG80- HIS81- ASN82- TYR83- GLU84- GLY85- SER86- GLU87- VAL88- ARG89- THR90- SER91- LEU92- ARG93- ARG94- LEU95

α1 domain:
ALA2-ASP3-HIS4-VAL5-ALA6-ALA7-TYR8-GLY9-ILE10-ASN11-MET12-TYR13- GLN14- TYR15- TYR16- GLU17- SER18- ARG19- GLY20- GLN21- PHE22- THR23- HIS24- GLU25- PHE26- ASP27- GLY28- ASP29- GLU30- GLU31- PHE32- TYR33- VAL34- ASP35- LEU36- ASP37- LYS38- LYS39- GLU40- THR41- ILE42- TRP43- ARG44- ILE45- PRO46- GLU47- PHE48- GLY49- GLN50- LEU51- THR52- SER53- PHE54- ASP55- PRO56- GLN57- GLY58- GLY59- LEU60- GLN61- ASN62- ILE63- ALA64- ILE65- ILE66- LYS67- HIS68- ASN69- LEU70- GLU71- ILE72- LEU73- MET74- LYS75- ARG76- SER77- ASN78- SER79- THR80- GLN81- ALA82- VAL83- ASN84

FIG. 7

α1 domain:
GLY1-SER2-HIS3-SER4-MET5-ARG6-TYR7-PHE8-TYR9-THR10-ALA11-MET12-
SER13-ARG14-PRO15-GLY16-ARG17-GLY18-GLU19-PRO20-ARG21-PHE22-ILE23-
ALA24-VAL25-GLY26-TYR27-VAL28-ASP29-ASP30-THR31-GLN32-PHE33-VAL34-
ARG35-PHE36-ASP37-SER38-ASP39-ALA40-ALA41-SER42-PRO43-ARG44-THR45-
GLU46-PRO47-ARG48-PRO49-PRO50-TRP51-ILE52-GLU53-GLN54-GLU55-GLY56-
PRO57-GLU58-TYR59-TRP60-ASP61-ARG62-ASN63-THR64-GLN65-ILE66-PHE67-
LYS68-THR69-ASN70-THR71-GLN72-THR73-TYR74-ARG75-GLU76-ASN77-LEU78-
ARG79-ILE80-ALA81-LEU82-ARG83-TYR84-

α2 domain:
TYR85-ASN86-GLN87-SER88-GLU89-ALA90-GLY91-SER92-HIS93-ILE94-ILE95-
GLN96-ARG97-MET98-TYR99-GLY100-CYS101-ASP102-LEU103-GLY104-PRO105-
ASP106-GLY107-ARG108-LEU109-LEU110-ARG111-GLY112-HIS113-ASP114-
GLN115-SER116-ALA117-TYR118-ASP119-GLY120-LYS121-ASP122-TYR123-
ILE124-ALA125-LEU126-ASN127-GLU128-ASP129-LEU130-SER131-SER132-
TRP133-THR134-ALA135-ALA136-ASP137-THR138-ALA139-ALA140-GLN141-
ILE142-THR143-GLN144-ARG145-LYS146-TRP147-GLU148-ALA149-ALA150-
ARG151-VAL152-ALA153-GLU154-GLN155-LEU156-ARG157-ALA158-TYR159-
LEU160-GLU161-GLY162-LEU163-CYS164-VAL165-GLU166-TRP157-LEU168-
ARG169-ARG170-TYR171-LEU172-GLU173-ASN174-GLY175-LYS176-GLU177-
THR178-LEU179-GLN180-ARG181-ALA182-ASP183-PRO184

FIG. 19A
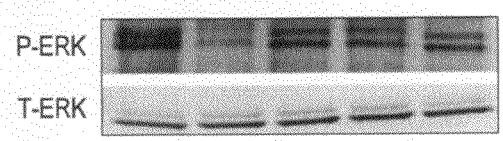
FIG. 19B
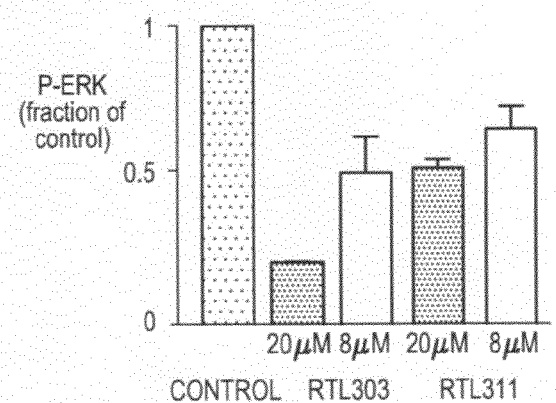
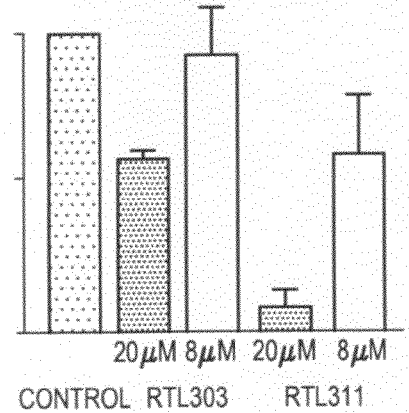

FIG. 29

A. CONTROL
LUMBAR
EAE 3.5

B. RTL TREATED
LUMBAR
1d; EAE 1.5

C. CONTROL
LOWER THORACIC
EAE 3.5

D. RTL TREATED
LOWER THORACIC
1d; EAE 1.5

FIG. 30
A. CONTROL
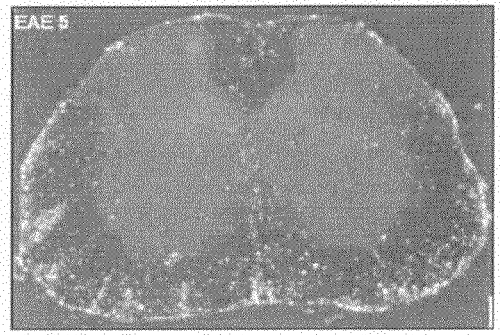
LUMBAR
B. RTL TREATED
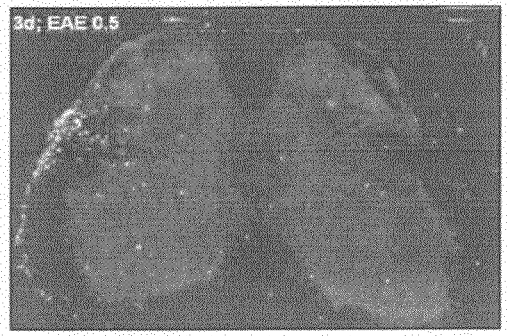
LUMBAR
C. CONTROL
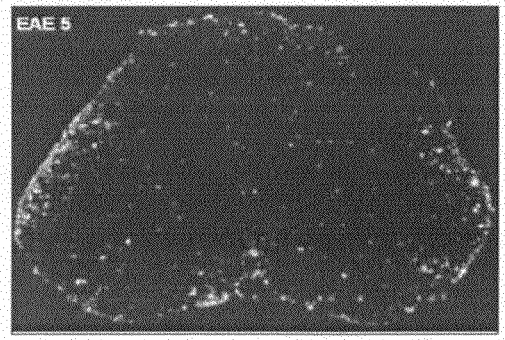
LOWER THORACIC
D. RTL TREATED
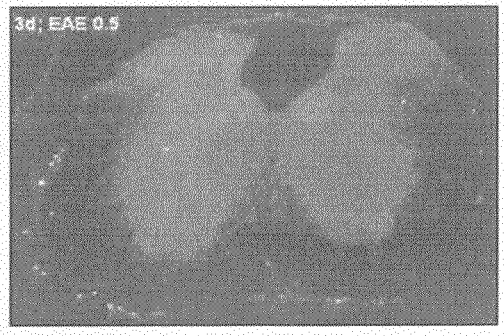
LOWER THORACIC

FIG. 31

A. CONTROL
LUMBAR

B. RTL TREATED
LUMBAR

C. CONTROL
LOWER THORACIC

D. RTL TREATED
LOWER THORACIC

Infarction size after 60 min MCAO and 96h reperfusion

|  | CTX | STR | Total |
|---|---|---|---|
| Vehicle (n=9) | 49.1 | 89.2 | 39.7 |
| RTL (n=7) | 25.6 | 79.8 | 26.5 |
| Ttest | 0.009 | 0.169 | 0.041 |

Cell counts from spleen and thymus after MCAO

|  | Spleen count | Thymus count |
|---|---|---|
| Vehicle (n=9) | 5.9 | 1.5 |
| RTL (n=7) | 22.9 | 3.3 |
| Ttest | 0.031 | 0.187 |

SEQUENCE LISTING

```
<160> NUMBER OF SEQ ID NOS: 95

<210> SEQ ID NO 1
<211> LENGTH: 566
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3)..(557)

<400> SEQUENCE: 1 cc atg ggc aga gac tcc cca agg gat ttc gtg tac cag ttc aag ggc         47
   Met Gly Arg Asp Ser Pro Arg Asp Phe Val Tyr Gln Phe Lys Gly
   1               5                   10                  15 ctg tgc tac tac acc aac ggg acg cag cgc ata cgg gat gtg atc aga        95
Leu Cys Tyr Tyr Thr Asn Gly Thr Gln Arg Ile Arg Asp Val Ile Arg
                20                  25                  30 tac atc tac aac cag gag gag tac ctg cgc tac gac agc gac gtg ggc       143
Tyr Ile Tyr Asn Gln Glu Glu Tyr Leu Arg Tyr Asp Ser Asp Val Gly
            35                  40                  45 gag tac cgc gcg ctg acc gag ctg ggg cgg ccc tca gcc gag tac ttt       191
Glu Tyr Arg Ala Leu Thr Glu Leu Gly Arg Pro Ser Ala Glu Tyr Phe
        50                  55                  60 aac aag cag tac ctg gag cag acg cgg gcc gag ctg gac acg gtc tgc       239
Asn Lys Gln Tyr Leu Glu Gln Thr Arg Ala Glu Leu Asp Thr Val Cys
    65                  70                  75
```

```
aga cac aac tac gag ggg tcg gag gtc cgc acc tcc ctg cgg cgg ctt    287
Arg His Asn Tyr Glu Gly Ser Glu Val Arg Thr Ser Leu Arg Arg Leu
 80              85                  90                  95 gga ggt caa gac gac att gag gcc gac cac gta gcc gcc tat ggt ata    335
Gly Gly Gln Asp Asp Ile Glu Ala Asp His Val Ala Ala Tyr Gly Ile
            100                 105                 110 aat atg tat cag tat tat gaa tcc aga ggc cag ttc aca cat gaa ttt    383
Asn Met Tyr Gln Tyr Tyr Glu Ser Arg Gly Gln Phe Thr His Glu Phe
        115                 120                 125 gat ggt gac gag gaa ttc tat gtg gac ttg gat aag aag gag acc atc    431
Asp Gly Asp Glu Glu Phe Tyr Val Asp Leu Asp Lys Lys Glu Thr Ile
130                 135                 140 tgg agg atc ccc gag ttt gga cag ctg aca agc ttt gac ccc caa ggt    479
Trp Arg Ile Pro Glu Phe Gly Gln Leu Thr Ser Phe Asp Pro Gln Gly
    145                 150                 155 gga ctt caa aat ata gct ata ata aaa cac aat ttg gaa atc ttg atg    527
Gly Leu Gln Asn Ile Ala Ile Ile Lys His Asn Leu Glu Ile Leu Met
160                 165                 170                 175 aag agg tca aat tca acc caa gct gtc aac taactcgag                  566
Lys Arg Ser Asn Ser Thr Gln Ala Val Asn
                180                 185

<210> SEQ ID NO 2
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gly Arg Asp Ser Pro Arg Asp Phe Val Tyr Gln Phe Lys Gly Leu
1               5                   10                  15

Cys Tyr Tyr Thr Asn Gly Thr Gln Arg Ile Arg Asp Val Ile Arg Tyr
            20                  25                  30

Ile Tyr Asn Gln Glu Glu Tyr Leu Arg Tyr Asp Ser Asp Val Gly Glu
        35                  40                  45

Tyr Arg Ala Leu Thr Glu Leu Gly Arg Pro Ser Ala Glu Tyr Phe Asn
    50                  55                  60

Lys Gln Tyr Leu Glu Gln Thr Arg Ala Glu Leu Asp Thr Val Cys Arg
65                  70                  75                  80

His Asn Tyr Glu Gly Ser Glu Val Arg Thr Ser Leu Arg Arg Leu Gly
                85                  90                  95

Gly Gln Asp Asp Ile Glu Ala Asp His Val Ala Ala Tyr Gly Ile Asn
            100                 105                 110

Met Tyr Gln Tyr Tyr Glu Ser Arg Gly Gln Phe Thr His Glu Phe Asp
        115                 120                 125

Gly Asp Glu Glu Phe Tyr Val Asp Leu Asp Lys Lys Glu Thr Ile Trp
    130                 135                 140

Arg Ile Pro Glu Phe Gly Gln Leu Thr Ser Phe Asp Pro Gln Gly Gly
145                 150                 155                 160

Leu Gln Asn Ile Ala Ile Ile Lys His Asn Leu Glu Ile Leu Met Lys
                165                 170                 175

Arg Ser Asn Ser Thr Gln Ala Val Asn
            180                 185

<210> SEQ ID NO 3
<211> LENGTH: 113
<212> TYPE: DNA
```

<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3)..(113)

<400> SEQUENCE: 3

```
cc atg ggc aga gac tcc cca cag aag agc cag agg act cag gat gag      47
   Met Gly Arg Asp Ser Pro Gln Lys Ser Gln Arg Thr Gln Asp Glu
   1               5                  10                  15 aac cca gtg gtg cac ttc gga ggt gga ggc tca cta gtg ccc cga ggc      95
Asn Pro Val Val His Phe Gly Gly Gly Gly Ser Leu Val Pro Arg Gly
                20                  25                  30 tct gga ggt gga ggc tcc                                             113
Ser Gly Gly Gly Gly Ser
        35
```

<210> SEQ ID NO 4
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Gly Arg Asp Ser Pro Gln Lys Ser Gln Arg Thr Gln Asp Glu Asn
1               5                  10                  15

Pro Val Val His Phe Gly Gly Gly Gly Ser Leu Val Pro Arg Gly Ser
            20                  25                  30

Gly Gly Gly Gly Ser
        35
```

<210> SEQ ID NO 5
<211> LENGTH: 83
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (3)..(83)

<400> SEQUENCE: 5

```
cc atg ggc aga gac tcc tcc ggc aag gat tcg cat cat gcg gcg cgg      47
   Met Gly Arg Asp Ser Ser Gly Lys Asp Ser His His Ala Ala Arg
   1               5                  10                  15 acg acc cac tac ggt gga ggt gga ggc tca cta gtg                     83
Thr Thr His Tyr Gly Gly Gly Gly Gly Ser Leu Val
                20                  25
```

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Met Gly Arg Asp Ser Ser Gly Lys Asp Ser His His Ala Ala Arg Thr
1               5                  10                  15

Thr His Tyr Gly Gly Gly Gly Gly Ser Leu Val
            20                  25
```

<210> SEQ ID NO 7
<211> LENGTH: 89
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: CDS
<222> LOCATION: (3)..(89)

<400> SEQUENCE: 7

```
cc atg ggc aga gac tcc aaa ctg gaa ctg cag tcc gct ctg gaa gaa      47
   Met Gly Arg Asp Ser Lys Leu Glu Leu Gln Ser Ala Leu Glu Glu
     1               5                  10                  15 gct gaa gct tcc ctg gaa cac gga ggt gga ggc tca cta gtg            89
Ala Glu Ala Ser Leu Glu His Gly Gly Gly Gly Ser Leu Val
                20                  25
```

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

```
Met Gly Arg Asp Ser Lys Leu Glu Leu Gln Ser Ala Leu Glu Glu Ala
 1               5                  10                  15

Glu Ala Ser Leu Glu His Gly Gly Gly Gly Ser Leu Val
            20                  25
```

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
aattcctcga gatggctctg cagacccc                    28

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tcttgacctc aagccgccg cagggaggtg                    30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
cggcggcttg gaggtcaaga cgacattgag g                 31

```
<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcctcggtac cttagttgac agcttgggtt gaatttg                              37

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagggaccat gggcagagac tcccca                                         26

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcctcctcga gttagttgac agcttgggtt                                     30

<210> SEQ ID NO 15
<211> LENGTH: 128
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaaatcccgc ggggagcctc cacctccaga gcctcggggc actagtgagc ctccacctcc    60
gaagtgcacc actgggttct catcctgagt cctctggctc ttctgtgggg agtctctgcc   120
ctcagtcc                                                            128

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gctccccgcg ggatttcgtg taccagttca a                                   31

<210> SEQ ID NO 17
<211> LENGTH: 92
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tattaccatg gcagagact cctccggcaa ggattcgcat catgcggcgc ggacgaccca     60
```
ctacggtgga ggtggaggct cactagtgcc cc                                    92

<210> SEQ ID NO 18
<211> LENGTH: 92
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggggcactag tgagcctcca cctccaccgt agtgggtcgt ccgcgccgca tgatgcgaat       60
ccttgccgga ggagtctctg cccatggtaa ta                                    92

<210> SEQ ID NO 19
<211> LENGTH: 98
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tattaccatg ggcagagact ccaaactgga actgcagtcc gctctggaag aagctgaagc       60
ttccctggaa cacggaggtg gaggctcact agtgcccc                              98

<210> SEQ ID NO 20
<211> LENGTH: 98
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggggcactag tgagcctcca cctccgtgtt ccagggaagc ttcagcttct tccagagcgg       60
actgcagttc cagtttggag tctctgccca tggtaata                              98

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
attaccatgg gggacacccg accacgttt                                        29

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggatgatcac atgttcttct ttgatgactc gccgctgcac tgtga                      45

<210> SEQ ID NO 23
<211> LENGTH: 45
<212> TYPE: DNA
<213> ORGANISM: Artificial Sequence
<220> FEATURE:

-continued

<223> OTHER INFORMATION: Description of Artificial Sequence: Synthetic
     primer

<400> SEQUENCE: 23
tcacagtgca gcggcgagtc atcaaagaag aacatgtgat catcc                45

<210> SEQ ID NO 24
<211> LENGTH: 92
<212> TYPE: PRT
<213> ORGANISM: Homo sapiens

<400> SEQUENCE: 24

Arg Pro Arg Phe Leu Trp Gln Leu Lys Phe Glu Cys His Phe Phe Asn
1               5                   10                  15

Gly Thr Glu Arg Val Arg Leu Leu Glu Arg Cys Ile Tyr Asn Gln Glu
            20                  25                  30

Glu Ser Val Arg Phe Asp Ser Asp Val Gly Glu Tyr Arg Ala Val Thr
        35                  40                  45

Glu Leu Gly Arg Pro Asp Ala Glu Tyr Trp Asn Ser Gln Lys Asp Leu
    50                  55                  60

Leu Glu Gln Arg Arg Ala Ala Val Asp Thr Tyr Cys Arg His Asn Tyr
65                  70                  75                  80

Gly Val Gly Glu Ser Phe Thr Val Gln Arg Arg Val
                85                  90

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 25

Gly Ser Leu Pro Gln Lys Ser Gln Arg Ser Gln Asp Glu Asn Pro Val
1               5                   10                  15

Val His Phe

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 26

Ser Gly Lys Asp Ser His His Ala Ala Arg Thr Thr His Tyr Gly
1               5                   10                  15

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 27

Lys Leu Glu Leu Gln Ser Ala Leu Glu Glu Ala Glu Ala Ser Leu Glu
1               5                   10                  15

His

```
<210> SEQ ID NO 28
<211> LENGTH: 95
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tattaccatg ggcagagact ccccacagaa gagccagagg tctcaggatg agaacccagt     60
ggtgcacttc ggaggtggag gctcactagt gcccc                               95

<210> SEQ ID NO 29
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggggcactag tgagcctcca cctccgaagt gcaccactgg gttctcatcc tgagacctct     60
ggctcttctg tggggagtct ctgcccatgg taat                                94

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ser Leu Pro Gln Lys Ser Gln Arg Thr Gln Asp Glu Asn Pro Val
1               5                   10                  15

Val His Phe

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tggtgctcga gttaattggt gatcggagta tagttgg                             37

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
taatacgact cactataggg                                                20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 33
gctagttatt gctcagcgg                                            19

<210> SEQ ID NO 34
<211> LENGTH: 132
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aggctgccac aggaaacgtg ggcctccacc tccagagcct cggggcacta gtgagcctcc    60
acctccacgc ggggtaacga tgtttttgaa gaagtgaaca accgggtttt ctcgggtgtc   120
ccccatggta at                                                      132

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccacgtttcc tgtggcagcc                                           20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tcaaagtcaa acataaactc gc                                        22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcgagtttat gtttgacttt ga                                        22

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Asn Pro Val Val His Phe Phe Lys Asn Ile Val Thr Pro Arg
1               5                   10                  15

<210> SEQ ID NO 39
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 39

Ala Thr Gly Phe Lys Gln Ser Ser Lys Ala Leu Gln Arg Pro Val Ala
1               5                   10                  15

Ser

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Ser Leu Gly Lys Trp Leu Gly His Pro Asp Lys Phe
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asn Thr Trp Thr Thr Cys Gln Ser Ile Ala Phe Pro Ser Lys
1               5                   10

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Met Glu Val Gly Trp Tyr Arg Ser Pro Phe Ser Arg Val Val His Leu
1               5                   10                  15

Tyr Arg Asn Gly Lys
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val His Phe Phe Lys Asn Ile Val Thr Pro Arg Thr Pro Pro Pro Ser
1               5                   10                  15

Gln Gly Lys Gly Arg
            20

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 44

Gly Gly Gln Asp Asp
1               5

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Gly Ser Leu Val Pro Arg Gly Ser Gly Gly Gly Gly
1               5                   10                  15

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggaaacccag aggcattgac                                           20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tcaggatctg gcccttgaac                                           20

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgctgatggg aggagatgtc t                                         21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgctgtctgg cctgctgtta                                           20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 50
cagccgatgg gttgtacctt                                              20

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggcagccttg tcccttga                                                18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gatgccccag gcagagaa                                                18

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cacccaggga attcaaatgc                                              20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccacggcctt ccctacttc                                               19

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tgggagtggt atcctctgtg aa                                           22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
```

```
gggacagatc ttgagcaagc                                              20
```

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
tgcagccttc ctccctctc                                               19
```

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
cctcaccatc atcctcactg ca                                           22
```

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

```
tcttctctgg gttggcacac ac                                           22
```

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

```
tgggctgctg tccctcaa                                                18
```

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

```
cccgggtgct gtttgtttt                                               19
```

<210> SEQ ID NO 62
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

```
cgatgacggg ccagtga                                                 17
```

-continued

```
<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63 cgcaggatg atttcaagct                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gggccctagc catcttagct                                                   20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tcccactggg ccttaaaaaa                                                   20

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtgtacatag caacaagcct caaag                                             25

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cccccacata gggatcatga                                                   20

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gggcaccacc ctgtgaaa                                                     18
```

```
<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tggaggcagg agccatga                                                     18

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
caattttcca gcaagacaat cct                                               23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tctcctgtgg atcgggtata gac                                               23

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aagatgcctg gcttcctctg t                                                 21

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggtctgcctg gagatgtagc tt                                                22

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccaggcacgc aactttgag                                                    19

<210> SEQ ID NO 75
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
actaccacca cggcaatgat c                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccagcgatct tcccattctt c                                              21

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gccctgcaca ctcccctta                                                 19

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ccgcttctgc tcccactc                                                  18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggtacctccc cctggctt                                                  18

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
actgctcagc tacacaaagc aact                                           24

<210> SEQ ID NO 81
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 81
tgagatgccc agggatggt                                                    19

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggagatggat gtgccaaacg                                                   20

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cgagctcact ctctgtggtg tt                                                22

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggcccttctc caggacaga                                                    19

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gctgatcatg gctgggttgt                                                   20

<210> SEQ ID NO 86
<211> LENGTH: 82
<212> TYPE: PRT
<213> ORGANISM: Homo sapiens

<400> SEQUENCE: 86

Glu Glu His Val Ile Ile Gln Ala Glu Phe Tyr Leu Asn Pro Asp Gln
1               5                   10                  15

Ser Gly Glu Phe Met Phe Asp Phe Asp Gly Asp Glu Ile Phe His Val
            20                  25                  30

Asp Met Ala Lys Lys Glu Thr Val Trp Arg Leu Glu Glu Phe Gly Arg
        35                  40                  45

Phe Ala Ser Phe Glu Ala Gln Gly Ala Leu Ala Asn Ile Ala Val Asp
    50                  55                  60
```

-continued

Lys Ala Asn Leu Glu Ile Met Thr Lys Arg Ser Asn Tyr Thr Pro Ile
65                  70                  75                  80

Thr Asn

<210> SEQ ID NO 87
<211> LENGTH: 92
<212> TYPE: PRT
<213> ORGANISM: Mus musculus

<400> SEQUENCE: 87

Arg Pro Trp Phe Leu Glu Tyr Cys Lys Ser Glu Cys His Phe Tyr Asn
1               5                   10                  15

Gly Thr Gln Arg Val Arg Leu Leu Val Arg Tyr Phe Tyr Asn Leu Glu
            20                  25                  30

Glu Asn Leu Arg Phe Asp Ser Asp Val Gly Phe Arg Ala Val Thr
        35                  40                  45

Glu Leu Gly Arg Pro Asp Ala Glu Asn Trp Asn Ser Gln Pro Glu Phe
    50                  55                  60

Leu Glu Gln Lys Arg Ala Glu Val Asp Thr Val Cys Arg His Asn Tyr
65                  70                  75                  80

Glu Ile Phe Asp Asn Phe Leu Val Pro Arg Arg Val
                85                  90

<210> SEQ ID NO 88
<211> LENGTH: 82
<212> TYPE: PRT
<213> ORGANISM: Mus musculus

<400> SEQUENCE: 88

Glu Glu His Thr Ile Ile Gln Ala Glu Phe Tyr Leu Leu Pro Asp Lys
1               5                   10                  15

Arg Gly Glu Phe Met Phe Asp Phe Asp Gly Asp Glu Ile Phe His Val
            20                  25                  30

Asp Ile Glu Lys Ser Glu Thr Ile Trp Arg Leu Glu Glu Phe Ala Lys
        35                  40                  45

Phe Ala Ser Phe Glu Ala Gln Gly Ala Leu Ala Asn Ile Ala Val Asp
    50                  55                  60

Lys Ala Asn Leu Asp Val Met Lys Glu Arg Ser Asn Asn Thr Pro Asp
65                  70                  75                  80

Ala Asn

<210> SEQ ID NO 89
<211> LENGTH: 97
<212> TYPE: PRT
<213> ORGANISM: Rattus rattus

<400> SEQUENCE: 89

Met Gly Arg Asp Ser Pro Arg Asp Phe Val Tyr Gln Phe Lys Gly Leu
1               5                   10                  15

Cys Tyr Tyr Thr Asn Gly Thr Gln Arg Ile Arg Asp Val Ile Arg Tyr
            20                  25                  30

Ile Tyr Asn Gln Glu Glu Tyr Leu Arg Tyr Asp Ser Asp Val Gly Glu
        35                  40                  45

Tyr Arg Ala Leu Thr Glu Leu Gly Arg Pro Ser Ala Glu Tyr Trp Asn
    50                  55                  60

Ser Gln Lys Gln Tyr Leu Glu Gln Thr Arg Ala Glu Leu Asp Thr Val
65                  70                  75                  80

Cys Arg His Asn Tyr Glu Gly Ser Glu Val Arg Thr Ser Leu Arg Arg 85                  90                  95
Leu

<210> SEQ ID NO 90
<211> LENGTH: 83
<212> TYPE: PRT
<213> ORGANISM: Rattus rattus

<400> SEQUENCE: 90

Ala Asp His Val Ala Ala Tyr Gly Ile Asn Met Tyr Gln Tyr Tyr Glu
1               5                   10                  15

Ser Arg Gly Gln Phe Thr His Glu Phe Asp Gly Asp Glu Glu Phe Tyr
            20                  25                  30

Val Asp Leu Asp Lys Lys Glu Thr Ile Trp Arg Ile Pro Glu Phe Gly
        35                  40                  45

Gln Leu Thr Ser Phe Asp Pro Gln Gly Gly Leu Gln Asn Ile Ala Ile
    50                  55                  60

Ile Lys His Asn Leu Glu Ile Leu Met Lys Arg Ser Asn Ser Thr Gln
65                  70                  75                  80

Ala Val Asn

<210> SEQ ID NO 91
<211> LENGTH: 84
<212> TYPE: PRT
<213> ORGANISM: Homo sapiens

<400> SEQUENCE: 91

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Thr Glu Pro Arg
        35                  40                  45

Pro Pro Trp Ile Glu Gln Glu Gly Pro Glu Tyr Trp Asp Arg Asn Thr
    50                  55                  60

Gln Ile Phe Lys Thr Asn Thr Gln Thr Tyr Arg Glu Asn Leu Arg Ile
65                  70                  75                  80

Ala Leu Arg Tyr

<210> SEQ ID NO 92
<211> LENGTH: 100
<212> TYPE: PRT
<213> ORGANISM: Homo sapiens

<400> SEQUENCE: 92

Tyr Asn Gln Ser Glu Ala Gly Ser His Ile Ile Gln Arg Met Tyr Gly
1               5                   10                  15

Cys Asp Leu Gly Pro Asp Gly Arg Leu Leu Arg Gly His Asp Gln Ser
            20                  25                  30

Ala Tyr Asp Gly Lys Asp Tyr Ile Ala Leu Asn Glu Asp Leu Ser Ser
        35                  40                  45

Trp Thr Ala Ala Asp Thr Ala Ala Gln Ile Thr Gln Arg Lys Trp Glu
    50                  55                  60

Ala Ala Arg Val Ala Glu Gln Leu Arg Ala Tyr Leu Glu Gly Leu Cys
65                  70                  75                  80

Val Glu Trp Leu Arg Arg Tyr Leu Glu Asn Gly Lys Glu Thr Leu Gln
                85                  90                  95

```
Arg Ala Asp Pro
        100

<210> SEQ ID NO 93
<211> LENGTH: 641
<212> TYPE: DNA
<213> ORGANISM: Homo sapiens
<220> FEATURE:
<221> NAME/KEY: CDS
<222> LOCATION: (3)..(632)

<400> SEQUENCE: 93 cc atg ggg gac acc cga gaa aac ccg gtt gtt cac ttc ttc aaa aac         47
   Met Gly Asp Thr Arg Glu Asn Pro Val Val His Phe Phe Lys Asn
   1               5                   10                  15 atc gtt acc ccg cgt gga ggt gga ggc tca cta gtg ccc cga ggc tct        95
Ile Val Thr Pro Arg Gly Gly Gly Gly Ser Leu Val Pro Arg Gly Ser
                20                  25                  30 gga ggt gga ggc cca cgt ttc ctg tgg cag cct aag agg gag tgt cat       143
Gly Gly Gly Gly Pro Arg Phe Leu Trp Gln Pro Lys Arg Glu Cys His
        35                  40                  45 ttc ttc aat ggg acg gag cgg gtg cgg ttc ctg gac aga tac ttc tat       191
Phe Phe Asn Gly Thr Glu Arg Val Arg Phe Leu Asp Arg Tyr Phe Tyr
    50                  55                  60 aac cag gag gag tcc gtg cgc ttc gac agc gac gtg ggg gag ttc cgg       239
Asn Gln Glu Glu Ser Val Arg Phe Asp Ser Asp Val Gly Glu Phe Arg
65                  70                  75                  80 gcg gtg acg gag ctg ggg cgg cct gac gct gag tac tgg aac agc cag       287
Ala Val Thr Glu Leu Gly Arg Pro Asp Ala Glu Tyr Trp Asn Ser Gln
                85                  90                  95 aag gac atc ctg gag cag gcg cgg gcc gcg gtg gac acc tac tgc aga       335
Lys Asp Ile Leu Glu Gln Ala Arg Ala Ala Val Asp Thr Tyr Cys Arg
            100                 105                 110 cac aac tac ggg gtt gtg gag agc ttc aca gtg cag cgg cga gtc atc       383
His Asn Tyr Gly Val Val Glu Ser Phe Thr Val Gln Arg Arg Val Ile
        115                 120                 125 aaa gaa gaa cat gtg atc atc cag gcc gag ttc tat ctg aat cct gac       431
Lys Glu Glu His Val Ile Ile Gln Ala Glu Phe Tyr Leu Asn Pro Asp
    130                 135                 140 caa tca ggc gag ttt atg ttt gac ttt gat ggt gat gag att ttc cat       479
Gln Ser Gly Glu Phe Met Phe Asp Phe Asp Gly Asp Glu Ile Phe His
145                 150                 155 gtg gat atg gca aag aag gag acg gtc tgg cgg ctt gaa gaa ttt gga       527
Val Asp Met Ala Lys Lys Glu Thr Val Trp Arg Leu Glu Glu Phe Gly
160                 165                 170                 175 cga ttt gcc agc ttt gag gct caa ggt gca ttg gcc aac ata gct gtg       575
Arg Phe Ala Ser Phe Glu Ala Gln Gly Ala Leu Ala Asn Ile Ala Val
                180                 185                 190 gac aaa gcc aac ttg gaa atc atg aca aag cgc tcc aac tat act ccg       623
Asp Lys Ala Asn Leu Glu Ile Met Thr Lys Arg Ser Asn Tyr Thr Pro
            195                 200                 205 atc acc aat taactcgag                                                  641
Ile Thr Asn
        210

<210> SEQ ID NO 94
<211> LENGTH: 210
<212> TYPE: PRT
<213> ORGANISM: Homo sapiens

<400> SEQUENCE: 94

Met Gly Asp Thr Arg Glu Asn Pro Val Val His Phe Phe Lys Asn Ile
1               5                   10                  15
```

```
Val Thr Pro Arg Gly Gly Gly Ser Leu Val Pro Arg Gly Ser Gly
        20              25              30

Gly Gly Gly Pro Arg Phe Leu Trp Gln Pro Lys Arg Glu Cys His Phe
            35              40              45

Phe Asn Gly Thr Glu Arg Val Arg Phe Leu Asp Arg Tyr Phe Tyr Asn
    50              55                  60

Gln Glu Glu Ser Val Arg Phe Asp Ser Asp Val Gly Glu Phe Arg Ala
65              70              75              80

Val Thr Glu Leu Gly Arg Pro Asp Ala Glu Tyr Trp Asn Ser Gln Lys
            85              90              95

Asp Ile Leu Glu Gln Ala Arg Ala Ala Val Asp Thr Tyr Cys Arg His
            100             105             110

Asn Tyr Gly Val Val Glu Ser Phe Thr Val Gln Arg Arg Val Ile Lys
            115             120             125

Glu Glu His Val Ile Ile Gln Ala Glu Phe Tyr Leu Asn Pro Asp Gln
        130             135             140

Ser Gly Glu Phe Met Phe Asp Phe Asp Gly Asp Glu Ile Phe His Val
145             150             155             160

Asp Met Ala Lys Lys Glu Thr Val Trp Arg Leu Glu Glu Phe Gly Arg
            165             170             175

Phe Ala Ser Phe Glu Ala Gln Gly Ala Leu Ala Asn Ile Ala Val Asp
            180             185             190

Lys Ala Asn Leu Glu Ile Met Thr Lys Arg Ser Asn Tyr Thr Pro Ile
        195             200             205

Thr Asn
    210

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Gly Gly Ser
1               5
```

COMPOSITIONS AND METHODS USING RECOMBINANT MHC MOLECULES FOR THE TREATMENT OF STROKE

CROSS REFERENCES TO RELATED APPLICATIONS

This application is entitled to priority benefit of U.S. Provisional patent application 61/209,428, filed Mar. 7, 2009 which is incorporated herein in its entirety by reference.

STATEMENT REGARDING GOVERNMENT SPONSORED RESEARCH

Aspects of this work were supported by grants from the National Institutes of Health (A143960, ESI0554, NS41965, 5R42NS046877, 1R01NS047661, NS49210, NS 47661, and AI043960), the National Multiple Sclerosis Society (RG3012A and RG3468), and the Department of Veterans Affairs. The United States government has certain rights in the subject matter.

SEQUENCE LISTING

The instant application contains a Sequence Listing which has been submitted in ASCII format via EFS-Web and is hereby incorporated by reference in its entirety. Said ASCII copy, created on Aug. 20, 2010, is named OHS602US.txt and is 39,154 bytes in size.

TECHNICAL FIELD

The present invention relates to the use of recombinant polypeptides comprising major histocompatibility complex (MHC) molecular domains that mediate antigen binding and T-cell receptor (TCR) recognition in the prevention and treatment of brain damage caused by stroke.

BACKGROUND OF THE INVENTION

Stroke is a cerebrovascular event which occurs when the normal blood flow to the brain is disrupted, and the brain receives too little blood. Approximately 15 million people worldwide suffer a stroke each year.

There are two forms of stroke: ischemic stoke, caused by a blood clot that blocks or prevents the flow of blood, and hemorrhagic stroke, caused by bleeding into the brain. Ischemic stroke is responsible for about one third of all deaths in industrialized countries and is the major cause of serious, long-term disability in adults over the age of 45.

Ischemic stroke results from insufficient cerebral circulation of blood caused by obstruction of the inflow of blood. The most common cause is narrowing of the arteries in the neck or head such as through atherosclerosis. Blood clots may form that can block the artery where they are formed (thrombosis), or can dislodge and become trapped in arteries closer to the brain (embolism). Another cause of stroke is blood clots dislodged from the heart. Blood clots can occur as a result of irregular heartbeat (for example, atrial fibrillation), heart attack, or abnormalities of the heart valves. Additional causes of ischemic stroke include the use of street drugs, traumatic injury to the blood vessels of the neck, or disorders of blood clotting During acute ischemic stroke, the arterial occlusion results in an infarcted core of brain tissue, where cerebral blood flow is reduced to below 10% to 25%. The infarcted core suffers irreversible damage due to significant cell death. The ischemic penumbra, ischemic but still viable tissue, suffers a delayed and less severe infarct.

Administration of thrombolytic agents, such as tissue plasminogen activator (tPA), which dissolve blood clots and thus restore blood flow to affected regions, have limited applicability. In particular, administration of tPA is only effective if given within three hours from the time of stroke onset. There is therefore an unmet need for other methods for the prevention and treatment of brain damage due to stroke.

SUMMARY OF EXEMPLARY EMBODIMENTS

Innate and adaptive immunity play an important role for the outcome after focal cerebral ischemia (stroke). After stroke, leukocytes home toward the lesion, and brain parenchymal cells (microglia, astrocytes, endothelia, even neurons) transform to an inflammatory phenotype. Macrophages and microglia produce a host of trophic cytokines when activated, and macrophages or T-cells exposed to certain central nervous system (CNS)-specific antigens ex vivo partake in tissue repair and recovery after nerve transsection and spinal cord injury. However, these benefits may be at least partially offset not only by bystander toxicity of inflammation but also by scar formation, which in peripheral tissues is key to wound closure, but in the brain is a major impediment of regeneration and plasticity. (Dirnagl, Ulrich MD; Klehmet, Juliane MD; Braun, Johann S. MD; Harms, Hendrik MD; Meisel, Christian MD; Ziemssen, Tjalf MD; Prass, Konstantin MD; Meisel, Andreas MD Stroke. 38 (2, Part 2) Supplement 1:770-773, February 2007)

The initiation of an immune response against a specific antigen in mammals is brought about by the presentation of that antigen to T-cells by a major histocompatibility (MHC) complex. MHC complexes are located on the surface of antigen presenting cells (APCs); the 3-dimensional structure of MHCs includes a groove or cleft into which the presented antigen fits. When an appropriate receptor on a T-cell interacts with the MHC/antigen complex on an APC in the presence of necessary co-stimulatory signals, the T-cell is stimulated, triggering various aspects of the well characterized cascade of immune system activation events, including induction of cytotoxic T-cell function, induction of B-cell function and stimulation of cytokine production This invention is founded on the discovery that mammalian MHC function, including but not limited to, human MHC function, can be mimicked through the use of recombinant polypeptides that include only those domains of MHC molecules that define the antigen binding cleft. The molecules provided herein may be used in clinical and laboratory applications to detect, quantify and purify antigen-specific T-cells, induce anergy in T-cells, or to induce T suppressor cells, as well as to stimulate T-cells, and to treat conditions mediated by antigen-specific T-cells, including, but not limited to, inflammation, autoimmune and neurodegenerative diseases.

It is shown herein that antigen-specific T-cell binding can be accomplished with a monomeric molecule comprising, in the case of human class II MHC molecules, only the α1 and β1 domains in covalent linkage (and in some examples in association with an antigenic determinant). For convenience, such MHC class II polypeptides are hereinafter referred to as "β1α1". Equivalent molecules derived from human MHC class I molecules are also provided herein. Such molecules comprise the α1 and α2 domains of class I molecules in covalent linkage and in association with an antigenic determinant. Such MHC class I polypeptides are referred to as "α1α2". These two domain molecules may be readily produced by recombinant expression in prokaryotic or eukaryotic cells, and readily purified in large quantities. Moreover, these molecules may easily be loaded with any desired peptide antigen, making production of a repertoire of MHC molecules with different T-cell specificities a simple task.

It is shown that despite lacking the Ig fold domains and transmembrane portions that are part of intact MHC molecules, these two domain MHC molecules refold in a manner that is structurally analogous to "whole" MHC molecules, and bind peptide antigens to form stable MHC/antigen complexes. Moreover, these two domain MHC/epitope complexes bind T-cells in an epitope-specific manner, and inhibit epitope-specific T-cell proliferation in vitro. In addition, administration of human β1α1 molecules loaded with an antigenic epitope, including, but not limited to, for example an epitope of myelin basic protein (MBP) or myelin oligodendracyte glucoprotein (MOG), induces a variety of T-cell transduction processes and modulates effector functions, including the cytokine and proliferation response. Thus, the two domain MHC molecules display powerful and epitope-specific effects on T-cell activation resulting in secretion of anti-inflammatory cytokines. As a result, the disclosed MHC molecules are useful in a wide range of both in vivo and in vitro applications. These MHC molecules are described in further detail in prior U.S. patent application Ser. No. 11/800,011, U.S. patent application Ser. No. 11/601,877, filed Nov. 10, 2006, and U.S. patent application Ser. No. 11/373,047, filed Mar. 10, 2006, which is entitled to priority benefit of U.S. Provisional patent application 60/663,048, filed Mar. 18, 2005, and U.S. Provisional patent application 60/713,230, filed Aug. 31, 2005 each of which are incorporated herein by reference in their entirety for all intents and purposes.

Various formulations of human two domain molecules are provided by the invention. In their most basic form, human two domain MHC class II molecules comprise β1 and α1 domains of a mammalian MHC class II molecule wherein the amino terminus of the α1 domain is covalently linked to the carboxy terminus of the β1 domain and wherein the polypeptide does not include the α2 or β2 domains. The human two domain MHC class I molecules comprise α1 and α2 domains of a mammalian class I molecule, wherein the amino terminus of the α2 domain is covalently linked to the carboxy terminus of the α1 domain, and wherein the polypeptide does not include an MHC class I α3 domain. For most applications, these molecules are associated, by covalent or non-covalent interaction, with an antigenic determinant, such as a peptide antigen. In certain embodiments, the peptide antigen is covalently linked to the amino terminus of the β1 domain of the class II molecules, or the α1 domain of the class I molecules. The two domain molecules may also comprise a detectable marker, such as a fluorescent label or a toxic moiety, such as ricin A, or an antigen, such as myelin basic protein (MBP), proteolipid protein (PLP), and myelin oligodedrocyte glycoprotein (MOG). In this instance, administering molecules loaded with the MOG 33-35 peptide (such molecules are named RTL 551) protects the cortex from damage after stroke. Moreover, treatment with RTL 551 prevents the characteristic reduction in the size and cellularity of the spleen in animals in which middle cerebral artery occlusion has been induced compared to control animals.

Also provided are nucleic acid molecules that encode the human two domain MHC molecules, as well as expression vectors that may be conveniently used to express these molecules. In particular embodiments, the nucleic acid molecules include sequences that encode the antigenic peptide as well as the human two domain MHC molecule. For example, one such nucleic acid molecule may be represented by the formula Pr-P-B-A, wherein Pr is a promoter sequence operably linked to P (a sequence encoding the peptide antigen), B is the class I α1 or the class II β1 domain, and A is the class I α2 domain or the class II α1 domain. In these nucleic acid molecules, P, B and A comprise a single open reading frame, such that the peptide and the two human MHC domains are expressed as a single polypeptide chain. In one embodiment, B and A are connected by a linker.

The two domain molecules may also be used in vivo to target specified antigen-specific T-cells. By way of example, a β1α1 molecule loaded with a portion of myelin basic protein (MBP) and administered to patients suffering from multiple sclerosis may be used to induce anergy in MBP-specific T-cells, or to induce suppressor T-cells, thus alleviating the disease symptoms. Alternatively, such molecules may be conjugated with a toxic moiety to more directly kill the disease-causing T-cells.

In vitro, the human two domain MHC molecules may be used to detect and quantify T-cells, and regulate T-cell function. When conjugated with a toxic moiety, the two domain molecules may be used to kill T-cells having a particular antigen specificity. Alternatively, the molecules may also be used to induce anergy in such T-cells, or to induce suppressor T-cells. In further embodiments, compositions and methods of the present invention may be used to kill T-cells having multiple antigen specificities.

The methods and compositions of the present invention may additionally be used in the treatment of mammalian subjects who have suffered a stroke as well as in the prevention of strokes or damage due to a stroke. These and other subjects are effectively treated by administering to the subject an effective amount of the human two domain molecules effective to treat, ameliorate, prevent or arrest the progression of the T-cell mediated reaction prior to or following a stroke.

The compositions and methods of the present invention may further be used to prevent or decrease infiltration of activated inflammatory cells into the central nervous system of mammalian subjects, including humans.

The various formulations and compositions of the present invention may be administered with one or more additional active agents, that are combinatory formulated or coordinately administered with the purified MHC polypeptides for the treatment of T-cell mediated diseases. Such additional therapeutic agents include, but are not limited to, immunoglobulins (e.g., a CTLA4Ig, such as BMS-188667; see, e.g., Srinivas et al., *J. Pharm. Sci.* 85 (1):1-4, (1996), incorporated herein by reference); copolymer 1, copolymer 1-related peptides, and T-cells treated with copolymer 1 or copolymer 1-related peptides (see, e.g., U.S. Pat. No. 6,844,314, incorporated herein by reference); blocking monoclonal antibodies; transforming growth factor-β; anti-TNF α antibodies; glatiramer acetate; recombinant β interferons; anti-coagulants including but not limited to, warfarin, heprin; anti-platelet medications including but not limited to aspirin, clopidogrel or aggrenox; clot dissolving medications including, but not limited to tissue plasminogen activating factor (tPA); angiotensin-converting enzyme (ACE) inhibitors, including but not limited to benazepril, captopril, enalapril, fosinopril, lisinopril, perindopril, quinapril, ramipril, and trandolapril; angiotensin II receptor blockers (ARBs) including but not limited to candesartan cilexetil, eprosartan mesylate, irbesartan, losartan, olmesartan, telmisartan, or valsartan; beta-blockers including but not limited to acebutolol, atenolol, betaxolol, carvedilol, labetalol, metoprolol, nadolol, penbutolol, pindolol, propranolol, timolol; diuretics including but not limited to chlorthalidone and chlorthalidone combinations, chlorothiazide, hydrochlorothiazide and hydrochlorothiazide combinations, indapamide, bumetanide, furosemide, torsemide, amiloride, spironolactone and spironolactone combinations, triamterene and triamterene combinations, metolazone; and calcium channel blockers including but not limited to amlodipine, amlodipine and atorvastatin, amlodipine and benazepril hydrochloride, diltiazem, enalapril maleate-felodipine ER, felodipine, isradipine, nicardipine, nifedipine, nisoldipine, verapamil; neuroprotectants; statins; anti-inflammatory agents; immunosuppresive agents; alkylating agents; anti-metabolites; antibiotics; corticosteroids; proteosome inhibitors; diketopiperazines; and steroidal agents including but not limited to estrogens, progesterones, testosterones, corticosteroids and anabolic steroids.

A distinguishing aspect of all such coordinate treatment methods is that the purified MHC polypeptide composition may elicit a favorable clinical response, which may or may not be in conjunction with a secondary clinical response provided by the secondary therapeutic agent. Often, the coordinate administration of a purified MHC polypeptide with a secondary therapeutic agent as contemplated herein will yield an enhanced therapeutic response beyond the therapeutic response elicited by either or both the purified MHC polypeptide and/or secondary therapeutic agent alone. In some embodiments, the enhanced therapeutic response may allow for lower doses or suboptimal doses of the purified MHC polypeptide and/or the secondary therapeutic agent to be used to yield the desired therapeutic response beyond the therapeutic response expected to be elicited by either or both the purified MHC polypeptide and/or secondary therapeutic agent alone.

The foregoing and other objects, features, aspects and advantages of the present invention will become more apparent from the following sections.

BRIEF DESCRIPTION OF THE DRAWINGS

FIG. 1A shows the sequences (SEQ ID NOS 1 and 2, respectively, in order of appearance) of the prototypical $\beta 1 \propto 1$ cassette without an antigen coding region. Unique NcoI, PstI, and XhoI restriction sites are in bold. The end of the $\beta 1$ domain and start of the $\alpha 1$ domain are indicated. FIG. 1B shows the sequence (SEQ ID NOS 3 and 4, respectively, in order of appearance) of an in-frame antigenic peptide/linker insertion sequence that can be incorporated into the expression cassette at the insertion site shown in FIG. 1A. This sequence includes the rat MBP-72-89 antigen, a flexible linker with an embedded thrombin cleavage site, and a unique SpeI restriction site that can be used for facile exchange of the antigen coding region. Example 2 below discusses the use of the equivalent peptide from Guinea pig, which has a serine in place of the threonine residue in the MBP-72-89 sequence. FIGS. 1C and 1D show exemplary Nco1/SpeI fragments that can be inserted into the expression cassette in place of the MBP-72-89 antigen coding region. FIG. 1C includes the MBP-55-69 antigen (SEQ ID NOS 5 and 6, respectively, in order of appearance), FIG. 1D includes the CM-2 antigen (SEQ ID NOS 7 and 8, respectively, in order of appearance).

FIG. 2A shows the rat class II RT1.B loaded with the encephalitogenic MBP-69-89 peptide (non-covalent association).

FIG. 3A is a histogram showing staining of the A1 hybridoma. FIG. 3B is a histogram showing staining of the CM-2 cell line.

FIGS. 6A, 6B, and 6C show the amino acid sequences of exemplary human (DRA and DRB1 0101) (SEQ ID NOS 24 and 86, respectively, in order of appearance) (6A), mouse (I-E$^K$) (SEQ ID NOS 87 and 88, respectively, in order of appearance) (6B) and rat (RT1.B) (SEQ ID NOS 89 and 90, respectively, in order of appearance) (6C) $\beta 1$ and $\alpha 1$ domains (the initiating methione and glycine sequences in the rat sequence were included in a construct for translation initiation reasons).

FIG. 7 shows the amino acid sequences (SEQ ID NOS 91 and 92, respectively, in order of appearance) of exemplary $\alpha 1$ and $\alpha 2$ domains derived from human MHC class I B*5301.

FIG. 8(A) is a schematic scale model of an MHC class II molecule on the surface of an APC. The polypeptide backbone extracellular domain is based on the known crystallographic coordinates of HLA-DR2 (PDB accession code 1BX2). The transmembrane domains are shown schematically as 0.5 nm cylinders, roughly the diameter of a poly-glycine alpha-helix. The $\alpha 1$, $\alpha 2$, □1 and □2 domains are labeled, as well as the carboxyl termini of the MHC class II heterodimers. FIG. 8(B) is a schematic of the RTL303 molecule containing covalently linked □1 and $\alpha 1$ domains from HLA-DR2 and covalently coupled MBP85-99 peptide. The view of the RTLs is symmetry-related to the MHC class II molecule in panel (a) by rotation around the long-axis of bound peptide by ~45□□ (y-axis) and ~45□□ (Z-axis). Top, the same shading scheme as in panel (a), with primary T-cell receptor (TCR) contact residues H11, F12, K14 and N15 labeled. Middle, shaded according to electrostatic potential (EP). The shading ramp for EP ranges from dark (most positive) to light (most negative). Bottom, shaded according to lipophilic potential (LP). The shading ramp for LP ranges from dark (most lipophilic area of the molecule) to light (most hydrophilic area).

FIG. 10 shows the purification of human HLA-DR2-derived RTL303.

FIG. 19 is a set of bar graphs demonstrating that ERK activity is decreased in RTL treated T-cells. DR2 restricted T-cell clone MR#3-1 specific for the MBP-85-99 peptide or MR#2-87 specific for CABL b3a2 peptide were incubated for 15 min. at 37 □C with no addition (control), and with 20 or 8 μM RTL303 or RTL311. At the end of the 15-min. incubation period, cells were assayed for activated, phosphorylated ERK (P-ERK) and total ERK (T-ERK). Quantification of activated P-ERK is presented as the fraction of the total in control (untreated) cells. Each experiment shown is representative of at least three independent experiments. Bars represent mean ☐☐SEM.

FIG. 29 is a series of photographs showing the infiltration of GFP+ cells in the lumbar region (A and B) and thoracic region (C and D) of the spinal cord from two mice immunized with MOG-35-55 peptide in CFA one day after the initiation of treatment with RTL551 (B and D) or vehicle (A and C).

FIG. 30 is a series of photographs showing the infiltration of GFP+ cells in the lumbar region (A and B) and thoracic region (C and D) of the spinal cord from two mice immunized with MOG-35-55 peptide in CFA three days after the initiation of treatment with RTL551 (B and D) or vehicle (A and C).

FIG. 31 is a series of photographs showing the infiltration of GFP+ cells in the lumbar region (A and B) and thoracic region (C and D) of the spinal cord from two mice immunized with MOG-35-55 peptide in CFA on day 8 of treatment with RTL551 (B and D) or vehicle (A and C).

DETAILED DESCRIPTION OF EXEMPLARY EMBODIMENTS

Figure 2:
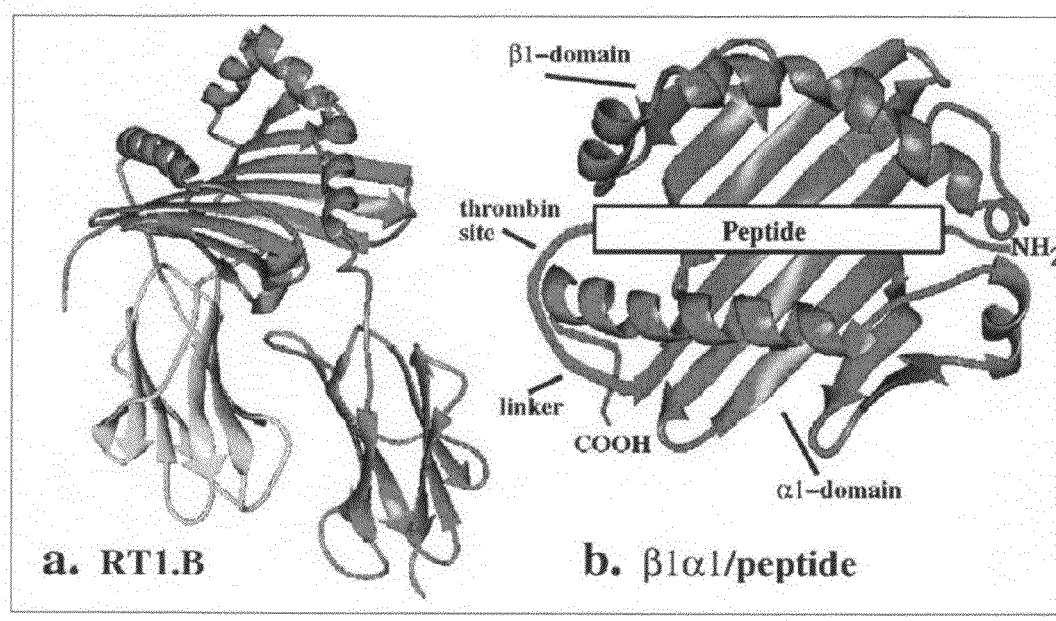
FIGS. 2A and B illustrate the structure-based design of the $\beta 1\alpha 1$ molecule.
FIG. 2B shows the single-chain $\beta 1\alpha 1$ molecule loaded with MBP-69-89.

In order to facilitate review of the various embodiments of the invention, the following definitions of terms and explanations of abbreviations are provided:

β1α1 Polypeptide: A recombinant polypeptide comprising the α1 and β1 domains of a MHC class II molecule in covalent linkage. To ensure appropriate conformation, the orientation of the polypeptide is such that the carboxy terminus of the β1 domain is covalently linked to the amino terminus of the α1 domain. In one embodiment, the polypeptide is a human β1α1 polypeptide, and includes the α1 and β1 domains for a human MHC class II molecule. One specific, non-limiting example of a human β1α1 polypeptide is a molecule wherein the carboxy terminus of the β1 domain is covalently linked to the amino terminus of the α1 domain of an HLA-DR molecule. An additional, specific non-limiting example of a human β1α1 polypeptide is a molecule wherein the carboxy terminus of the β1 domain is covalently linked to the amino terminus of the α1 domain of an a HLA-DR (either A or B), a HLA-DP (A and B), or a HLA-DQ (A and B) molecule. In one embodiment, the β1α1 polypeptide does not include a β2 domain. In another embodiment, the β1α1 polypeptide does not include an α2. In yet another embodiment, the β1α1 polypeptide does not include either an α2 or a β2 domain.

β1α1 Gene: A recombinant nucleic acid sequence including a promoter region operably linked to a nucleic acid sequence encoding a β1α1 polypeptide. In one embodiment the β1α1 polypeptide is a human β1α1 polypeptide.

α1α2 Polypeptide: A polypeptide comprising the α1 and α2 domains of a MHC class I molecule in covalent linkage. The orientation of the polypeptide is such that the carboxy terminus of the α1 domain is covalently linked to the amino terminus of the α2 domain. An α1α2 polypeptide comprises less than the whole class I α chain, and usually omits most or all of the α3 domain of the α chain. Specific non-limiting examples of an α1α2 polypeptide are polypeptides wherein the carboxy terminus of the α1 domain is covalently linked to the amino terminus of the α2 domain of an HLA-A, -B or -C molecule. In one embodiment, the α3 domain is omitted from an α1α2 polypeptide, thus the α1α2 polypeptide does not include an α3 domain.

α1α2 Gene: A recombinant nucleic acid sequence including a promoter region operably linked to a nucleic acid sequence encoding an α1α2 polypeptide.

Antigen (Ag): A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes and antigenic determinants.

Antigen Presenting Cell: Any cell that can process and present antigenic peptides in association with class II MHC molecules and deliver a co-stimulatory signal necessary for T-cell activation. Typical antigen presenting cells include macrophages, dendritic cells, B cells, thymic epithelial cells and vascular endothelial cells.

CD8+ T-cell mediated immunity: An immune response implemented by presentation of antigens to CD8+ T-cells.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Cytokine: Proteins made by cells that affect the behavior of other cells, such as lymphocytes. In one embodiment, a cytokine is a chemokine, a molecule that affects cellular trafficking.

Domain: A domain of a polypeptide or protein is a discrete part of an amino acid sequence that can be equated with a particular function. For example, the α and β polypeptides that constitute a MHC class II molecule are each recognized as having two domains, α1, α2 and β1, β2, respectively. Similarly, the α chain of MHC class I molecules is recognized as having three domains, α1, α2 and α3. The various domains in each of these molecules are typically joined by linking amino acid sequences. In one embodiment of the present invention, the entire domain sequence is included in a recombinant molecule by extending the sequence to include all or part of the linker or the adjacent domain. For example, when selecting the α1 domain of HLA-DRA, the selected sequence will generally extend from amino acid residue number 1 of the α chain, through the entire α1 domain and will include all or part of the linker sequence located at about amino acid residues 76-90 (at the carboxy terminus of the α1 domain, between the α1 and α2 domains). The precise number of amino acids in the various MHC molecule domains varies depending on the species of mammal, as well as between classes of genes within a species. The critical aspect for selection of a sequence for use in a recombinant molecule is the maintenance of the domain function rather than a precise structural definition based on the number of amino acids. One of skill in the art will appreciate that domain function may be maintained even if somewhat less than the entire amino acid sequence of the selected domain is utilized. For example, a number of amino acids at either the amino or carboxy termini of the α1 domain may be omitted without affecting domain function. Typically however, the number of amino acids omitted from either terminus of the domain sequence will be no greater than 10, and more typically no greater than 5 amino acids. The functional activity of a particular selected domain may be assessed in the context of the two-domain MHC polypeptides provided by this invention (i.e., the class II β1α1 or class I α1α2 polypeptides) using the antigen-specific T-cell proliferation assay as described in detail below. For example, to test a particular β1 domain, the domain will be linked to a functional α1 domain so as to produce a β1α1 molecule and then tested in the described assay. A biologically active β1α1 or α1α2 polypeptide will inhibit antigen-specific T-cell proliferation by at least about 50%, thus indicating that the component domains are functional. Typically, such polypeptides will inhibit T-cell proliferation in this assay system by at least 75% and sometimes by greater than about 90%.

Demyelination: Loss of myelin, a substance in the white matter that insulates nerve endings. Myelin helps the nerves receive and interpret messages from the brain at maximum speed. When nerve endings lose this substance they can not function properly, leading to patches of scarring or sclerosis.

Epitope: An antigenic determinant. These are particular chemical groups or peptide sequences on a molecule that are antigenic, i.e. that elicit a specific immune response. An antibody binds a particular antigenic epitope.

Functionally Equivalent: Sequence alterations, in either an antigen epitope or a β1α1, or an α1α2 peptide, that yield the same results as described herein. Such sequence alterations can include, but are not limited to, conservative substitutions, deletions, mutations, frame shifts, and insertions.

IL-10: A cytokine that is a homodimeric protein with subunits having a length of 160 amino acids. Human IL-10 has a 73 percent amino acid homology with murine IL-10. The human IL-10 gene contains four exons and maps to chromosome 1 (for review see de Waal-Malefyt R et al., *Curr. Opin. Immunology* 4: 314-20, 1992; Howard and O'Garra, *Immunology Today* 13: 198-200, 1992; Howard et al., *J. Clin. Immunol.* 12: 239-47, 1992).

IL-10 is produced by murine T-cells (Th2 cells but not Th1 cells) following their stimulation by lectins. In humans, IL-10 is produced by activated CD 8+ peripheral blood T-cells, by Th0, Th1-, and Th2-like CD4+ T-cell clones after both antigen-specific and polyclonal activation, by B-cell lymphomas, and by LPS-activated monocytes and mast cells. B-cell lines derived from patients with acquired immunodeficiency syndrome and Burkitt's lymphoma constitutively secrete large quantities of IL10.

IL-10 has a variety of biological functions. For example, IL-10 inhibits the synthesis of a number of cytokines such as IFN-γ, IL-2 and TNF-α in Th1 subpopulations of T-cells but not of Th2 cells. This activity is antagonized by IL-4. The inhibitory effect on IFN-γ production is indirect and appears to be the result of a suppression of IL-12 synthesis by accessory cells. In the human system, IL-10 is produced by, and down-regulates the function of, Th1 and Th2 cells. IL-10 is also known to inhibit the synthesis of IL-1, IL-6, and TNF-α by promoting, among other things, the degradation of cytokine mRNA. Expression of IL-10 can also lead to an inhibition of antigen presentation. In human monocytes, IFN-γ and IL-10 antagonize each other's production and function. In addition, IL-10 has been shown also to be a physiologic antagonist of IL-12. IL-10 also inhibits mitogen- or anti-CD3-induced proliferation of T-cells in the presence of accessory cells and reduces the production of IFN-γ and IL-2. IL-10 appears to be responsible for most or all of the ability of Th2 supernatants to inhibit cytokine synthesis by Th1 cells.

IL-10 can be detected with a sensitive ELISA assay. In addition, the murine mast cell line D36 can be used to bioassay human IL-10. Flow cytometry methods have also been used to detect IL-10 (See Abrams et al. *Immunol. Reviews* 127: 5-24, 1992; Fiorentino et al., *J. Immunol.* 147: 3815-22, 1991; Kreft et al, *J. Immunol. Methods* 156: 125-8, 1992; Mosmann et al., *J. Immunol.* 145: 2938-45, 1990), see also the Examples section below.

Immune response: A response of a cell of the immune system, such as a B cell, or a T-cell, to a stimulus. In one embodiment, the response is specific for a particular antigen (an "antigen-specific response"). In another embodiment, an immune response is a T-cell response, such as a Th1, Th2, or Th3 response. In yet another embodiment, an immune response is a response of a suppressor T-cell. In an additional embodiment, an immune response is a response of a dendritic cell.

Isolated: An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Linker sequence: A linker sequence is an amino acid sequence that covalently links two polypeptide domains. Linker sequences may be included in the recombinant MHC polypeptides of the present invention to provide rotational freedom to the linked polypeptide domains and thereby to promote proper domain folding and inter- and intra-domain bonding. By way of example, in a recombinant polypeptide comprising Ag-β1-α1 (where Ag=antigen) linker sequences may be provided between both the Ag and β1 domains and between β1 and α1 domains. Linker sequences, which are generally between 2 and 25 amino acids in length, are well known in the art and include, but are not limited to, the glycine(4)-serine spacer described by Chaudhary et al. (1989). Other linker sequences are described in the Examples section below.

Recombinant MHC class I α1α2 polypeptides according to the present invention include a covalent linkage joining the carboxy terminus of the α1 domain to the amino terminus of the α2 domain. The α1 and α2 domains of native MHC class I α chains are typically covalently linked in this orientation by an amino acid linker sequence. This native linker sequence may be maintained in the recombinant constructs; alternatively, a recombinant linker sequence may be introduced between the α1 and α2 domains (either in place of or in addition to the native linker sequence).

Mammal: This term includes both human and non-human mammals. Similarly, the term "patient" or "subject" includes both human and veterinary subjects.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. Generally, operably linked DNA sequences are contiguous and, where necessary to join two protein coding regions, the open reading frames are aligned.

ORF (open reading frame): A series of nucleotide triplets (codons) coding for amino acids without any termination codons. These sequences are usually translatable into a polypeptide.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful with the polypeptides and nucleic acids described herein are conventional. *Remington's Pharmaceutical Sciences*, by E. W. Martin, Mack Publishing Co., Easton, Pa., 15$^{th}$ Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to an ischemic event such as a stroke. An example of a person with a known predisposition is someone with a history of stoke in the family, has had a previous stroke, has risk factors for a stroke, or someone who has a genetic marker for a disease, or someone who has been exposed to factors that predispose the subject to a condition. "Preventing" a disease may also halt progression of the disease or stop relapses of a disease in someone who is exhibiting symptoms or who is currently in remission, with or without a known predisposition. "Treatment" refers to a therapeutic intervention that ameliorates a sign or symptom of a disease or pathological condition after it has begun to develop. Effectiveness of the treatment can be evaluated through a decrease in signs or symptoms of the disease or arresting or reversal of the progression of the disease, prevention of the recurrence of symptoms or prolonged periods of remission.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5,© 1991, Whitehead Institute for Biomedical Research, Cambridge, Mass.).

Purified: The term purified does not require absolute purity; rather, it is intended as a relative term. Thus, for example, a purified recombinant MHC protein preparation is one in which the recombinant MHC protein is more pure than the protein in its originating environment within a cell. A preparation of a recombinant MHC protein is typically purified such that the recombinant MHC protein represents at least 50% of the total protein content of the preparation. However, more highly purified preparations may be required for certain applications. For example, for such applications, preparations in which the MHC protein comprises at least 75% or at least 90% of the total protein content may be employed.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Variants of MHC domain polypeptides will possess a relatively high degree of sequence identity when aligned using standard methods. (An "MHC domain polypeptide" refers to a $\beta1$ or an $\alpha1$ domain of an MHC class II polypeptide or an $\alpha1$ or an $\alpha2$ domain of an MHC class I polypeptide).

Methods of alignment of sequences for comparison are well known in the art. Altschul et al. (1994) presents a detailed consideration of sequence alignment methods and homology calculations. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is available at the NCBI website, as are the default parameters.

Variants of MHC domain polypeptides are typically characterized by possession of at least 50% sequence identity counted over the full length alignment with the amino acid sequence of a native MHC domain polypeptide using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% amino acid sequence identity. When less than the entire sequence is being compared for sequence identity, variants will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website. Variants of MHC domain polypeptides also retain the biological activity of the native polypeptide. For the purposes of this invention, that activity is conveniently assessed by incorporating the variant domain in the appropriate $\beta1\alpha1$ or $\alpha1\alpha2$ polypeptide and determining the ability of the resulting polypeptide to inhibit antigen specific T-cell proliferation in vitro, or to induce T suppressor cells or the expression of IL-10 as described in detail below.

Therapeutically effective dose: A dose sufficient to prevent advancement, or to cause regression of the disease, or which is capable of relieving symptoms caused by the disease, including, but not limited to, pain, swelling, numbness, spasticity, vertigo, dizziness, vision problems, motor control problems, balance or coordination problems, bowl dysfunction, and incontinence.

Tolerance: Diminished or absent capacity to make a specific immune response to an antigen. Tolerance is often produced as a result of contact with an antigen in the presence of a two domain MHC molecule, as described herein. In one embodiment, a B cell response is reduced or does not occur. In another embodiment, a T-cell response is reduced or does not occur. Alternatively, both a T-cell and a B cell response can be reduced or not occur.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art. The term "vector" includes viral vectors, such as adenoviruses, adeno-associated viruses, vaccinia, and retroviruses vectors.

Additional definitions of terms commonly used in molecular genetics can be found in Benjamin. Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The following sections provide detailed guidance on the design, expression and uses of the recombinant MHC molecules of the invention. Unless otherwise stated, standard molecular biology, biochemistry and immunology methods are used in the present invention unless otherwise described. Such standard methods are described in Sambrook et al. (1989), Ausubel et al. (1987), Innis et al. (1990) and Harlow and Lane (1988). The following U.S. patents which relate to conventional formulations of MHC molecules and their uses are incorporated herein by reference to provide additional background and technical information relevant to the present invention: U.S. Pat. Nos. 5,130,297; 5,194,425; 5,260,422; 5,284,935; 5,468,481; 5,595,881; 5,635,363; 5,734,023.

Innate and adaptive immunity play an important role for the outcome after focal cerebral ischemia (stroke). Focal cerebral ischemia elicits a strong inflammatory response involving early recruitment of granulocytes and delayed infiltration of ischemic areas and the boundary zones by T cells and macrophages. (Guido Stoll, Sebastian Jander and Michael Schroeter. Inflammation and glial responses in ischemic brain lesions Progress in Neurobiology Volume 56, Issue 2, October 1998, Pages 149-171)

Within hours of a stoke, transcription factors such as nuclear factor KB are activated locally in the brain tissue. These transcription factors upregulate proinflammatory genes including TNFα, interleukin 1β, interleukin 6, and IL-1 receptor agonist and chemokines such as IL-8, interferon inducible protein-10 and monocyte chemoattactant protein-1 (O'Neill L A, et al., *Trends Neurosci* 20:252-8 (1997), Liu et al. *Stroke* 25:1481-8 (1994), Wang et al., *Mol. Chem Neuropathol* 23:103-14 (2004), Liu et al. *Stroke* 25:1481-8 (1993), Wang et al., *Stroke* 26:661-6 (1995), Wang et al., *J Cereb Blood Flow Metab* 15:166-71 (1995), Wang et al., *Stroke* 28:155-62 (1997), Kim et al., *Neuroimmunol* 56:127-34 (1995), Wang et al., *Jneurochem* 71:1194-204 (1998)). These factors promote expression of adhesion molecules by vascular endothelial cells that allow infiltration into the brain of blood neutrophils, monocytes, macrophages and T cells that promote further brain injury. (Barone, F C et al., *Cerebral Blood Flow Metab* 19:819-34). Additionally, inflammatory and antigenic products derived from the brain such as myelin basic protein may leak across a damaged blood brain barrier and produce reciprocal system activation (Offner, Halina et al., *J of Cerebral Blood Flow & Metabolism* 26, 654-655 (2006).

The initiation of an immune response against a specific antigen in mammals is brought about by the presentation of that antigen to T-cells by a major histocompatibility (MHC) complex. MHC complexes are located on the surface of antigen presenting cells (APCs); the 3-dimensional structure of MHCs includes a groove or cleft into which the presented antigen fits. When an appropriate receptor on a T-cell interacts with the MHC/antigen complex on an APC in the presence of necessary co-stimulatory signals, the T-cell is stimulated, triggering various aspects of the well characterized cascade of immune system activation events, including induction of cytotoxic T-cell function, induction of B-cell function and stimulation of cytokine production.

There are two basic classes of MHC molecules in mammals, MHC class I and MHC class II. Both classes are large protein complexes formed by association of two separate proteins. Each class includes transmembrane domains that anchor the complex into the cell membrane. MHC class I molecules are formed from two non-covalently associated proteins, the α chain and β2-microglobulin. The α chain comprises three distinct domains, α1, α2 and α3. The three-dimensional structure of the α1 and α2 domains forms the groove into which antigen fit for presentation to T-cells. The α3 domain is an Ig-fold like domain that contains a transmembrane sequence that anchors the α chain into the cell membrane of the APC. MHC class I complexes, when associated with antigen (and in the presence of appropriate co-stimulatory signals) stimulate CD8 cytotoxic T-cells, which function to kill any cell which they specifically recognize.

The two proteins which associate non-covalently to form MHC class II molecules are termed the α and β chains. The α chain comprises α1 and α2 domains, and the β chain comprises β1 and β2 domains. The cleft into which the antigen fits is formed by the interaction of the α1 and β1 domains. The α2 and β2 domains are transmembrane Ig-fold like domains that anchor the α and β chains into the cell membrane of the APC. MHC class II complexes, when associated with antigen (and in the presence of appropriate co-stimulatory signals) stimulate CD4 T-cells. The primary functions of CD4 T-cells are to initiate the inflammatory response, to regulate other cells in the immune system, and to provide help to B cells for antibody synthesis.

The genes encoding the various proteins that constitute the MHC complexes have been extensively studied in humans and other mammals. In humans, MHC molecules (with the exception of class I β2-microglobulin) are encoded by the HLA region, which is located on chromosome 6 and constitutes over 100 genes. There are 3 class I MHC α chain protein loci, termed HLA-A, -B and -C. There are also 3 pairs of class II MHC α and β chain loci, termed HLA-DR (A and B), HLA-DP (A and B), and HLA-DQ (A and B). In rats, the class I α gene is termed RT1.A, while the class II genes are termed RT1.B α and RT1.B β. More detailed background information on the structure, function and genetics of MHC complexes can be found in *Immunobiology: The Immune System in Health and Disease* by Janeway and Travers, Current Biology Ltd./Garland Publishing, Inc. (1997) (ISBN 0-8153-2818-4), and in Bodmer et al. (1994) "Nomenclature for factors of the HLA system" *Tissue Antigens* vol. 44, pages 1-18.

The key role that MHC complexes play in triggering immune recognition has led to the development of methods by which these complexes are used to modulate the immune response. Building on the observation that isolated MHC class II molecules (loaded with the appropriate antigen) can substitute for APCs carrying the MHC class II complex and can bind to antigen-specific T-cells, a number of researchers have proposed that isolated MHC/antigen complexes may be used to treat autoimmune disorders. Thus U.S. Pat. Nos. 5,194,425 (Sharma et al.), and 5,284,935 (Clark et al.), disclose the use of isolated MHC class II complexes loaded with a specified autoantigen and conjugated to a toxin to eliminate T-cells that are specifically immunoreactive with autoantigens. In another context, it has been shown that the interaction of isolated MHC II/antigen complexes with T-cells, in the absence of co-stimulatory factors, induces a state of non-responsiveness known as anergy. (Quill et al., *J. Immunol.*, 138:3704-3712 (1987)). Following this observation, Sharma et al. (U.S. Pat. Nos. 5,468,481 and 5,130,297) and Clark et al. (U.S. Pat. No. 5,260,422) have suggested that such isolated MHC II/antigen complexes may be administered therapeutically to anergize T-cell lines which specifically respond to particular autoantigenic peptides.

Design of Recombinant MHC Class II β1α1 Molecules

The amino acid sequences of mammalian MHC class II α and β chain proteins, as well as nucleic acids encoding these proteins, are well known in the art and available from numerous sources including GenBank. Exemplary sequences are provided in Auffray et al. (1984) (human HLA DQ α); Larhammar et al. (1983) (human HLA DQ β); Das et al. (1983) (human HLA DR α); Tonnelle et al. (1985) (human HLA DR β); Lawrance et al. (1985) (human HLA DP α); Kelly et al. (1985) (human HLA DP β); Syha et al. (1989) (rat RT1.B α); Syha-Jedelhauser et al. (1991) (rat RT1.B β); Benoist et al. (1983) (mouse I-A α); Estess et al. (1986) (mouse I-A β), all of which are incorporated by reference herein in their entirety. In one embodiment of the present invention, the MHC class II protein is a human MHC class II protein.

The recombinant MHC class II molecules of the present invention comprise the β1 domain of the MHC class II β chain covalently linked to the α1 domain of the MHC class II α chain. The α1 and β1 domains are well defined in mammalian MHC class II proteins. Typically, the α1 domain is regarded as comprising about residues 1-90 of the mature chain. The native peptide linker region between the α1 and α2 domains of the MHC class II protein spans from about amino acid 76 to about amino acid 93 of the α chain, depending on the particular α chain under consideration. Thus, an α1 domain may include about amino acid residues 1-90 of the α chain, but one of skill in the art will recognize that the C-terminal cut-off of this domain is not necessarily precisely defined, and, for example, might occur at any point between amino acid residues 70-100 of the α chain. The composition of the α1 domain may also vary outside of these parameters depending on the mammalian species and the particular α chain in question. One of skill in the art will appreciate that the precise numerical parameters of the amino acid sequence are much less important than the maintenance of domain function.

Similarly, the β1 domain is typically regarded as comprising about residues 1-90 of the mature β chain. The linker region between the β1 and the β2 domains of the MHC class II protein spans from about amino acid 85 to about amino acid 100 of the β chain, depending on the particular α chain under consideration. Thus, the β1 protein may include about amino acid residues 1-100, but one of skill in the art will again recognize that the C-terminal cut-off of this domain is not necessarily precisely defined, and, for example, might occur at any point between amino acid residues 75-105 of the β chain. The composition of the β1 domain may also vary outside of these parameters depending on the mammalian species and the particular the β chain in question. Again, one of skill in the art will appreciate that the precise numerical parameters of the amino acid sequence are much less important than the maintenance of domain function.

Exemplary β1α1 molecules from human, rat and mouse are depicted in FIG. 1. In one embodiment, the β1α1 molecules do not include a β2 domain. In another embodiment, the β1α1 molecules do not include an α2 domain. In yet a further embodiment, the β1α1 molecules do not include either an α2 or a β2 domain.

Nucleic acid molecules encoding these domains may be produced by standard means, such as amplification by polymerase chain reaction (PCR). Standard approaches for designing primers for amplifying open reading frames encoding these domains may be employed. Libraries suitable for the amplification of these domains include, for example, cDNA libraries prepared from the mammalian species in question. Such libraries are available commercially, or may be prepared by standard methods. Thus, for example, constructs encoding the β1 and α1 polypeptides may be produced by PCR using four primers: primers B1 and B2 corresponding to the 5' and 3' ends of the β1 coding region, and primers A1 and A2 corresponding to the 5' and 3' ends of the α1 coding region. Following PCR amplification of the β1 and α1 domain coding regions, these amplified nucleic acid molecules may each be cloned into standard cloning vectors, or the molecules may be ligated together and then cloned into a suitable vector. To facilitate convenient cloning of the two coding regions, restriction endonuclease recognition sites may be designed into the PCR primers. For example, primers B2 and A1 may each include a suitable site such that the amplified fragments may be readily ligated together following amplification and digestion with the selected restriction enzyme. In addition, primers B1 and A2 may each include restriction sites to facilitate cloning into the polylinker site of the selected vector. Ligation of the two domain coding regions is performed such that the coding regions are operably linked, i.e., to maintain the open reading frame. Where the amplified coding regions are separately cloned, the fragments may be subsequently released from the cloning vector and gel purified, preparatory to ligation.

In certain embodiments, a peptide linker is provided between the β1 and α1 domains. Typically, this linker is between 2 and 25 amino acids in length, and serves to provide flexibility between the domains such that each domain is free to fold into its native conformation. The linker sequence may conveniently be provided by designing the PCR primers to encode the linker sequence. Thus, in the example described above, the linker sequence may be encoded by one of the B2 or A1 primers, or a combination of each of these primers.

Design of Recombinant MHC Class I α α1α2 Molecules

The amino acid sequences of mammalian MHC class I α chain proteins, as well as nucleic acids encoding these proteins, are well known in the art and available from numerous sources including GenBank. Exemplary sequences are provided in Browning et al. (1995) (human HLA-A); Kato et al. (1993) (human HLA-B); Steinle et al. (1992) (human HLA-C); Walter et al. (1995) (rat Ia); Walter et al. (1994) (rat Ib); Kress et al. (1983) (mouse H-2-K); Schepart et al. (1986) (mouse H-2-D); and Moore et al. (1982) (mouse H-2-l), which are incorporated by reference herein. In one embodiment, the MHC class I protein is a human MHC class I protein.

The recombinant MHC class I molecules of the present invention comprise the α1 domain of the MHC class I α chain covalently linked to the α2 domain of the MHC class I chain. These two domains are well defined in mammalian MHC class I proteins. Typically, the α1 domain is regarded as comprising about residues 1-90 of the mature chain and the α2 chain as comprising about amino acid residues 90-180, although again, the beginning and ending points are not precisely defined and will vary between different MHC class I molecules. The boundary between the α2 and α3 domains of the MHC class I α protein typically occurs in the region of amino acids 179-183 of the mature chain. The composition of the α1 and α2 domains may also vary outside of these parameters depending on the mammalian species and the particular α chain in question. One of skill in the art will appreciate that the precise numerical parameters of the amino acid sequence are much less important than the maintenance of domain function. An exemplary α1α2 molecule is shown in FIG. 2. In one embodiment, the α1α2 molecule does not include an α3 domain.

The α1α2 construct may be most conveniently constructed by amplifying the reading frame encoding the dual-domain (α1 and α2) region between amino acid number 1 and amino acids 179-183, although one of skill in the art will appreciate that some variation in these end-points is possible. Such a molecule includes the native linker region between the α1 and α2 domains, but if desired that linker region may be removed and replaced with a synthetic linker peptide. The general considerations for amplifying and cloning the MHC class I α1 and α2 domains apply as discussed above in the context of the class II β1 and α1 domains.

Genetic Linkage of Antigenic Polypeptide to β1α1 and α1α2 Molecules

The class II β1α1 and class I α1α2 polypeptides of the invention are generally used in conjunction with an antigenic peptide. Any antigenic peptide that is conventionally associated with class I or class II MHC molecules and recognized by a T-cell can be used for this purpose. Antigenic peptides from a number of sources have been characterized in detail, including antigenic peptides from honey bee venom allergens, dust mite allergens, toxins produced by bacteria (such as tetanus toxin) and human tissue antigens involved in autoimmune diseases. Detailed discussions of such peptides are presented in U.S. Pat. Nos. 5,595,881, 5,468,481 and 5,284,935 to Kendrich et al., Sharma et al., and Clark et al., respectively, each of which is incorporated herein by reference. Exemplary peptides include, but are not limited to, MOG 35-55 peptide.

As is well known in the art (see for example U.S. Pat. No. 5,468,481 to Sharma et al.) the presentation of antigen in MHC complexes on the surface of APCs generally does not involve a whole antigenic peptide. Rather, a peptide located in the groove between the β1 and α1 domains (in the case of MHC II) or the α1 and α2 domains (in the case of MHC I) is typically a small fragment of the whole antigenic peptide. As discussed in Janeway & Travers (1997), peptides located in the peptide groove of MHC class I molecules are constrained by the size of the binding pocket and are typically 8-15 amino acids long, more typically 8-10 amino acids in length (but see Collins et al., 1994 for possible exceptions). In contrast, peptides located in the peptide groove of MHC class II molecules are not constrained in this way and are often much larger, typically at least 13 amino acids in length. Peptide fragments for loading into MHC molecules can be prepared by standard means, such as use of synthetic peptide synthesis machines.

The β1α1 and α1α2 molecules of the present invention may be "loaded" with peptide antigen in a number of ways, including by covalent attachment of the peptide to the MHC molecule. This may be conveniently achieved by operably linking a nucleic acid sequence encoding the selected peptide to the 5' end of the construct encoding the MHC protein such that, in the expressed peptide, the antigenic peptide domain is linked to the N-terminus of β1 in the case of β1α1 molecules and α1 in the case of α1α2 molecules. One way of obtaining this result is to incorporate a sequence encoding the antigen into the PCR primers used to amplify the MHC coding regions. Typically, a sequence encoding a linker peptide sequence will be included between the molecules encoding the antigenic peptide and the MHC polypeptide. As discussed above, the purpose of such linker peptides is to provide flexibility and permit proper conformational folding of the peptides. For linking antigens to the MHC polypeptide, the linker should be sufficiently long to permit the antigen to fit into the peptide groove of the MHC polypeptide. Again, this linker may be conveniently incorporated into the PCR primers. However, as discussed in Example 1 below, it is not necessary that the antigenic peptide be ligated exactly at the 5' end of the MHC coding region. For example, the antigenic coding region may be inserted within the first few (typically within the first 10) codons of the 5' end of the MHC coding sequence.

This genetic system for linkage of the antigenic peptide to the MHC molecule is particularly useful where a number of MHC molecules with differing antigenic peptides are to be produced. The described system permits the construction of an expression vector in which a unique restriction site is included at the 5' end of the MHC coding region (i.e., at the 5' end of β1 in the case of β1α1-encoding constructs and at the 5' end of α1 in the case of α1α2-encoding constructs). In conjunction with such a construct, a library of antigenic peptide-encoding sequences is made, with each antigen-coding region flanked by sites for the selected restriction enzyme. The inclusion of a particular antigen into the MHC molecule is then performed simply by (a) releasing the antigen-coding region with the selected restriction enzyme, (b) cleaving the MHC construct with the same restriction enzyme, and (c) ligating the antigen coding region into the MHC construct. In this manner, a large number of MHC-polypeptide constructs can be made and expressed in a short period of time.

An exemplary design of an expression cassette allowing simple exchange of antigenic peptides in the context of a β1α1 molecule is shown in FIG. 1. FIG. 1A shows the nucleic acid sequence encoding a prototype β1α1 molecule derived from rat MHC class II RT1.B, without the presence of the antigenic peptide. The position of the insertion site for the peptide and linker between the $5^{th}$ and $6^{th}$ (serine and proline) residues of the β1 domain is indicated by a τ symbol. In order to integrate the antigen coding region, a PCR primer comprising the sequence shown in FIG. 1B joined with additional bases from the FIG. 1A construct 3' of the insertion site is employed in conjunction with a PCR primer reading from the 3' end of the construct shown in FIG. 1A.) Amplification yields a product that includes the sequence shown in FIG. 1B integrated into the β1α1 construct (i.e., with the antigenic peptide and linker sequences positioned between the codons encoding the $5^{th}$ and $6^{th}$ amino acid residues of the β1α1 sequence). In the case illustrated, the antigenic peptide is the Myelin Basic Protein (MBP)-72-89 antigen.

Notably, the MBP-72-89 coding sequence is flanked by unique Nco I and Spe I restriction enzyme sites. These enzymes can be used to release the MBP-72-89 coding region and replace it with coding regions for other antigens, for example those illustrated in FIGS. 1C and 1D.

The structure of the expressed β1α1 polypeptide with covalently attached antigen is illustrated in FIG. 2B; FIG. 2A shows the secondary structure of the complete RT1B molecule (including β1, β2, α1 and α2 domains).

Nucleic acid expression vectors including expression cassettes designed as explained above will be particularly useful for research purposes. Such vectors will typically include sequences encoding the dual domain MHC polypeptide (β1α1 or α1α2) with a unique restriction site provided towards the 5' terminus of the MHC coding region, such that a sequence encoding an antigenic polypeptide may be conveniently attached. Such vectors will also typically include a promoter operably linked to the 5' terminus of the MHC coding region to provide for high level expression of the sequences.

β1α1 and α1α2 molecules may also be expressed and purified without an attached peptide (as described below), in which case they may be referred to as "empty". The empty MHC molecules may then be loaded with the selected peptide as described below in "Antigen Loading of Empty β1α1 and α1α2 Molecules".

Expression and Purification of Recombinant β1α1 and α1α2 Molecules

In their most basic form, nucleic acids encoding the MHC polypeptides of the invention comprise first and second regions, having a structure A-B wherein, for class I molecules, region A encodes the class I α1 domain and region B encodes the class I α2 domain. For class II molecules, A encodes the class II α1 domain and B encodes the class II β1 domain. Where a linker sequence is included, the nucleic acid may be represented as B-L2-A, wherein L2 is a nucleic acid sequence encoding the linker peptide. Where an antigenic peptide is covalently linked to the MHC polypeptide, the nucleic acid molecule encoding this complex may be represented as P-B-A. A second linker sequence may be provided between the antigenic protein and the region B polypeptide, such that the coding sequence is represented as P-L2-B-L1-A. In all instances, the various nucleic acid sequences that comprise the MHC polypeptide (i.e., L1, L2, B, A and P) are operably linked such that the elements are situated in a single reading frame.

Nucleic acid constructs expressing these MHC polypeptides may also include regulatory elements such as promoters (Pr), enhancers and 3' regulatory regions, the selection of which will be determined based upon the type of cell in which the protein is to be expressed. When a promoter sequence is operably linked to the open reading frame, the sequence may be represented as Pr-B-A, or (if an antigen-coding region is included) Pr-P-B-A, wherein Pr represents the promoter sequence. The promoter sequence is operably linked to the P or B components of these sequences, and the B-A or P-B-A sequences comprise a single open reading frame. The constructs are introduced into a vector suitable for expressing the MHC polypeptide in the selected cell type.

Numerous prokaryotic and eukaryotic systems are known for the expression and purification of polypeptides. For example, heterologous polypeptides can be produced in prokaryotic cells by placing a strong, regulated promoter and an efficient ribosome binding site upstream of the polypeptide-encoding construct. Suitable promoter sequences include the β-lactamase, tryptophan (trp), 'phage T7 and lambda $P_L$ promoters. Methods and plasmid vectors for producing heterologous proteins in bacteria are described in Sambrook et al. (1989). Suitable prokaryotic cells for expression of large amounts of $_2$m fusion proteins include *Escherichia coli* and *Bacillus subtilis*. Often, proteins expressed at high levels are found in insoluble inclusion bodies; methods for extracting proteins from these aggregates are described by Sambrook et al. (1989, see ch. 17). Recombinant expression of MHC polypeptides in prokaryotic cells may alternatively be conveniently obtained using commercial systems designed for optimal expression and purification of fusion proteins. Such fusion proteins typically include a protein tag that facilitates purification. Examples of such systems include, but are not limited to: the pMAL protein fusion and purification system (New England Biolabs, Inc., Beverly, Mass.); the GST gene fusion system (Amersham Pharmacia Biotech, Inc., Piscataway, N.J.); and the pTrcHis expression vector system (Invitrogen, Carlsbad, Calif.). For example, the pMAL expression system utilizes a vector that adds a maltose binding protein to the expressed protein. The fusion protein is expressed in *E. coli* and the fusion protein is purified from a crude cell extract using an amylose column. If necessary, the maltose binding protein domain can be cleaved from the fusion protein by treatment with a suitable protease, such as Factor Xa. The maltose binding fragment can then be removed from the preparation by passage over a second amylose column.

The MHC polypeptides can also be expressed in eukaryotic expression systems, including *Pichia pastoris, Drosophila*, Baculovirus and Sindbis expression systems produced by Invitrogen (Carlsbad, Calif.). Eukaryotic cells such as Chinese Hamster ovary (CHO), monkey kidney (COS), HeLa, *Spodoptera frugiperda*, and *Saccharomyces cerevisiae* may also be used to express the MHC polypeptides. Regulatory regions suitable for use in these cells include, for mammalian cells, viral promoters such as those from CMV, adenovirus and SV40, and for yeast cells, the promoter for 3-phosphoglycerate kinase and alcohol dehydrogenase.

The transfer of DNA into eukaryotic, in particular human or other mammalian cells is now a conventional technique. The vectors are introduced into the recipient cells as pure DNA (transfection) by, for example, precipitation with calcium phosphate or strontium phosphate, electroporation, lipofection, DEAE dextran, microinjection, protoplast fusion, or microprojectile guns. Alternatively, the nucleic acid molecules can be introduced by infection with virus vectors. Systems are developed that use, for example, retroviruses, adenoviruses, or Herpes virus.

An MHC polypeptide produced in mammalian cells may be extracted following release of the protein into the supernatant and may be purified using an immunoaffinity column prepared using anti-MHC antibodies. Alternatively, the MHC polypeptide may be expressed as a chimeric protein with, for example, b-globin. Antibody to b-globin is thereafter used to purify the chimeric protein. Corresponding protease cleavage sites engineered between the b-globin gene and the nucleic acid sequence encoding the MHC polypeptide are then used to separate the two polypeptide fragments from one another after translation. One useful expression vector for generating b-globin chimeric proteins is pSG5 (Stratagene, La Jolla, Calif.).

Expression of the MHC polypeptides in prokaryotic cells will result in polypeptides that are not glycosylated. Glycosylation of the polypeptides at naturally occurring glycosylation target sites may be achieved by expression of the polypeptides in suitable eukaryotic expression systems, such as mammalian cells.

Purification of the expressed protein is generally performed in a basic solution (typically around pH 10) containing 6M urea. Folding of the purified protein is then achieved by dialysis against a buffered solution at neutral pH (typically phosphate buffered saline (PBS) at around pH 7.4).

Antigen Loading of Empty β1α1 and α1α2 Molecules

Where the β1α1 and α1α2 molecules are expressed and purified in an empty form (i.e., without attached antigenic peptide), the antigenic peptide may be loaded into the molecules using standard methods. Methods for loading antigenic peptides into WIC molecules are described in, for example, U.S. Pat. No. 5,468,481 to Sharma et al. herein incorporated by reference in its entirety. Such methods include simple co-incubation of the purified MHC molecule with a purified preparation of the antigen.

By way of example, empty β1α1 molecules (1 mg/ml; 40 uM) may be loaded by incubation with a 10-fold molar excess of peptide (1 mg/ml; 400 uM) at room temperature, for 24 hours. Thereafter, excess unbound peptide may be removed by dialysis against PBS at 4° C. for 24 hours. As is known in the art, peptide binding to β1α1 can be quantified by silica gel thin layer chromatography (TLC) using radiolabeled peptide. Based on such quantification, the loading may be altered (e.g., by changing the molar excess of peptide or the time of incubation) to obtain the desired result.

Additional description relating to various aspects and embodiments of the invention are provided in related patent applications, including U.S. Ser. No. 11/811,011, filed Jun. 6, 2007; U.S. Ser. No. 12/510,223, filed Jul. 27, 2009; U.S. Provisional Application No. 61/435,518, filed Sep. 25, 2009; and U.S. Ser. No. 11/726,709, filed Mar. 21, 2007, each incorporated herein by reference in its entirety for all purposes. These related disclosures detail additional subject matter regarding construction and use of RTLs within the present invention, and for purposes of economy and ease of description the supplemental descriptions provided in these disclosures are incorporated by reference.

Other Considerations (a) Sequence Variants

While the foregoing discussion uses naturally occurring MHC class I and class II molecules and the various domains of these molecules as examples; one of skill in the art will appreciate that variants of these molecules and domains may be made and utilized in the same manner as described. Thus, reference herein to a domain of an MHC polypeptide or molecule (e.g., an MHC class II β1 domain) includes both naturally occurring forms of the referenced molecule, as well as molecules that are based on the amino acid sequence of the naturally occurring form, but which include one or more amino acid sequence variations. Such variant polypeptides may also be defined in the degree of amino acid sequence identity that they share with the naturally occurring molecule. Typically, MHC domain variants will share at least 80% sequence identity with the sequence of the naturally occurring MHC domain. More highly conserved variants will share at least 90% or at least 95% sequence identity with the naturally occurring sequence. Variants of MHC domain polypeptides also retain the biological activity of the naturally occurring polypeptide. For the purposes of this invention, that activity is conveniently assessed by incorporating the variant domain in the appropriate β1α1 or α1α2 polypeptide and determining the ability of the resulting polypeptide to inhibit antigen specific T-cell proliferation in vitro, as described in detail below.

Variant MHC domain polypeptides include proteins that differ in amino acid sequence from the naturally occurring MHC polypeptide sequence but which retain the specified biological activity. Such proteins may be produced by manipulating the nucleotide sequence of the molecule encoding the domain, for example by site-directed mutagenesis or the polymerase chain reaction. The simplest modifications involve the substitution of one or more amino acids for amino acids having similar biochemical properties, i.e. a "conservative substitution." Conservative substitution tables providing functionally similar amino acids are well known in the art. The following six groups each contain amino acids that are conservative substitutions for one another and are likely to have minimal impact on the activity of the resultant protein.
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (W. H. Freeman & Co., New York, N.Y. 1984)).

More substantial changes in biological function or other features may be obtained by selecting substitutions that are less conservative than those shown above, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cystyl or prolyl is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanyl, is substituted for (or by) one not having a side chain, e.g., glycyl. The effects of these amino acid substitutions or deletions or additions may be assessed through the use of the described T-cell proliferation assay.

At the nucleic acid level, one of skill in the art will appreciate that the naturally occurring nucleic acid sequences that encode class I and II MHC domains may be employed in the expression vectors, but that the invention is not limited to such sequences. Any sequence that encodes a functional MHC domain may be employed, and the nucleic acid sequence may be adapted to conform with the codon usage bias of the organism in which the sequence is to be expressed.

(b) Incorporation of Detectable Markers

For certain in vivo and in vitro applications, the MHC molecules of the present invention may be conjugated with a detectable label. A wide range of detectable labels are known, including radionuclides (e.g., gamma-emitting sources such as indium-111), paramagnetic isotopes, fluorescent markers (e.g., fluorescein), enzymes (such as alkaline phosphatase), cofactors, chemiluminescent compounds and bioluminescent compounds such as green fluorescent protein (GFP). The binding of such labels to the MHC polypeptides may be achieved using standard methods. U.S. Pat. No. 5,734,023 (incorporated herein by reference) contains an extensive discussion of the labeling of MHC polypeptide derivatives using such labels. Where the detectable marker is to be covalently linked to the MHC molecule in a directed manner (i.e., rather than being randomly attached) it will generally be linked to the C terminus of the molecule so as to minimize interference with a peptide antigen linked at the N terminus.

(c) Conjugation of Toxic Moieties

For certain uses of the disclosed MHC polypeptides, particularly in vivo therapeutic applications aimed at depleting certain T-cell populations, the polypeptides may be conjugated with a toxic moiety. Numerous toxic moieties suitable for disrupting T-cell function are known, including, but not limited to, protein toxins, chemotherapeutic agents, antibodies to a cytotoxic T-cell surface molecule, lipases, and radioisotopes emitting "hard" e.g., beta radiation. Examples of such toxins and methods of conjugating toxins to MHC molecules are described in U.S. Pat. No. 5,284,935 (incorporated herein by reference). Protein toxins include ricin, diphtheria and, *Pseudomonas* toxin. Chemotherapeutic agents include doxorubicin, daunorubicin, methotrexate, cytotoxin, and antisense RNA. Radioisotopes such as yttrium-90, phosphorus-32, lead-212, iodine-131, or palladium-109 may also be used. Where the toxic moiety is to be covalently linked to the MHC molecule in a directed manner (i.e., rather than being randomly attached) it will generally be linked to the C terminus of the molecule so as to minimize interference with a peptide antigen linked at the N terminus.

In other aspects of the invention, modified recombinant T-cell receptor ligands (RTL) are designed and constructed which comprise a major histocompatibility complex (MHC) component that incorporates one or more redesigned surface structural features which have been recombinantly introduced into an otherwise native MHC polypeptide sequence. Typically, modified RTLs of the invention are rationally designed and constructed to introduce one or more amino acid changes at a solvent-exposed target site located within, or defining, a self-binding interface found in the native MHC polypeptide.

The self-binding interface that is altered in the modified RTL typically comprises one or more amino acid residue(s) that mediate(s) self-aggregation of a native MHC polypeptide, or of an "unmodified" RTL incorporating the native MHC polypeptide. Although the self-binding interface is correlated with the primary structure of the native MHC polypeptide, this interface may only appear as an aggregation-promoting surface feature when the native polypeptide is isolated from the intact MHC complex and incorporated in the context of an "unmodified" RTL.

Thus, in certain embodiments, the self-binding interface may only function as a solvent-exposed residue or motif of an unmodified RTL after the native polypeptide is isolated from one or more structural element(s) found in an intact MHC protein. In the case of exemplary MHC class II RTLs described herein (e.g., comprising linked β1 and α1 domains), the native β1α1 structure only exhibits certain solvent-exposed, self-binding residues or motifs after removal of Ig-fold like, β2 and α2 domains found in the intact MHC II complex. These same residues or motifs that mediate aggregation of unmodified β1α1 RTLs, are presumptively "buried" in a solvent-inaccessible conformation or otherwise "masked" (i.e., prevented from mediating self-association) in the native or progenitor MHC II complex (likely through association with the Ig-fold like, β2 and α2 domains).

Certain modified RTLs of the invention include a multi-domain structure comprising selected MHC class I or MHC class II domains, or portions of multiple MHC domains that are necessary to form a minimal Ag recognition/T-cell receptor (TCR) interface (i.e., which is capable of mediating Ag binding and TCR recognition). In certain embodiments, the modified RTL comprises a "minimal TCR interface", meaning a minimal subset of MHC class I or MHC class II domain residues necessary and sufficient to mediate functional peptide binding and TCR-recognition. TCR recognition requires that the modified RTL be capable of interacting with the TCR in an Ag-specific manner to elicit one or more TCR-mediated T-cell responses, as described herein.

In the case of modified RTLs derived from human class II MHC molecules, the RTLs will most often comprise α1 and β1 MHC polypeptide domains of an MHC class II protein, or portions thereof sufficient to provide a minimal TCR interface. These domains or subportions thereof may be covalently linked to form a single chain (sc) MHC class II polypeptide. Such RTL polypeptides are hereinafter referred to as "α1β1" sc MHC class II polypeptides. Equivalent sc MHC constructs can be modeled from human MHC class I proteins, for example to form RTLs comprising α1 and α2 domains (or portions thereof sufficient to provide a minimal TCR interface) of a class I MHC protein, wherein the RTL is optionally "empty" or associated with an Ag comprising a CD8+ T-cell epitope.

RTL constructs comprising sc MHC components have been shown to be widely useful for such applications as preventing and treating Ag-induced autoimmune disease responses in mammalian model subjects predictive of autoimmune disease therapeutic activity in humans (Burrows et al., *J. Immunol.* 161:5987, 1998; Burrows et al., *J. Immunol.* 164:6366, 2000). In other aspects, these types of RTLs have been demonstrated to inhibit T-cell activation and induce anti-inflammatory cytokine (e.g., IL-10) secretion in human DR2-restricted T-cell clones specific for MBP-85-95 or BCR-ABL b3a2 peptide (CABL) (Burrows et al., *J. Immunol.* 167:4386, 2001; Chang et al., *J. Biol. Chem.* 276:24170, 2001).

Additional RTL constructs have been designed and tested by inventors in the instant application, which include a myelin oligodendrocyte glycoprotein (MOG)-35-55/DR2 construct (VG312) shown to potently inhibit autoimmune responses and lead to immunological tolerance to the encephalitogenic MOG-35-55 peptide and reverse clinical and histological signs of experimental autoimmune encephalomyelitis (EAE) (Vandenbark et al., *J. Immunol.* 171:127-33, 2003) as well as protect from damage due to stroke. Numerous additional RTL constructs that are useful for modulating T-cell immune responses and can be employed within the invention are available for use within the methods and compositions of the invention (see, e.g., U.S. Pat. No. 5,270,772, issued Aug. 7, 2001; U.S. Provisional Patent Application No. 60/200,942, filed May 1, 2000; U.S. patent application Ser. No. 10/936,467, filed by Burrows et al. on Sep. 7, 2004; U.S. Pat. No. 6,270,772, issued Aug. 7, 2001; U.S. patent application Ser. No. 09/847,172, filed May 1, 2001; and U.S. Pat. No. 6,815,171, issued Nov. 9, 2004, each incorporated herein by reference).

To evaluate the biological function and mechanisms of action of modified RTLs of the invention, antigen-specific T-cells bearing cognate TCRs have been used as target T-cells for various assays (see, e.g., Burrows et al., *J. Immunol.* 167:4386, 2001). More recently, inventors in the current application have provided novel T-cell hybridomas that are uniquely adapted for use in screens and assays to identify and characterize RTL structure and function (see, e.g., U.S. Provisional Patent Application No. 60/586,433, filed Jul. 7, 2004; and Chou et al., *J. Neurosci. Res.* 77: 670-680, 2004). To practice these aspects of the invention, T-cell hybrids are constructed and selected that display an Ag-specific, TCR-mediated proliferative response following contact of the hybrid with a cognate Ag and APCs. This proliferative response of T hybrids can in turn be detectably inhibited or stimulated by contacting the T-cell hybrid with a modified RTL of interest, which yields a modified, Ag-specific, TCR-mediated proliferation response of the hybrid. The modified proliferation response of the hybrid cell accurately and reproducibly indicates a presence, quantity, and/or activity level of the modified RTL in contact with the T-cell hybrid.

Within certain embodiments of the invention, an isolated, modified recombinant RTL which has a reduced potential for aggregation in solution comprises an "MHC component" in the form of a single chain (sc) polypeptide that includes multiple, covalently-linked MHC domain elements. These domain elements are typically selected from a) α1 and β1 domains of an MHC class II polypeptide, or portions thereof comprising an Ag-binding pocket/T-cell receptor (TCR) interface; or b) α1 and α2 domains of an MHC class I polypeptide, or portions thereof comprising an Ag-binding pocket/TCR interface. The MHC component of the RTL is modified by one or more amino acid substitution(s), addition(s), deletion(s), or rearrangement(s) at a target site corresponding to a "self-binding interface" identified in a native MHC polypeptide component of an unmodified RTL. The modified RTL exhibits a markedly reduced propensity for aggregation in solution compared to aggregation exhibited by an unmodified, control RTL having the same fundamental MHC component structure, but incorporating the native MHC polypeptide defining the self-binding interface.

As used herein, "native MHC polypeptide" refers to intact, naturally-occurring MHC polypeptides, as well as to engineered or synthetic fragments, domains, conjugates, or other derivatives of MHC polypeptides that have an identical or highly conserved amino acid sequence compared to an aligned sequence in the naturally-occurring MHC polypeptide (e.g., marked by 85%, 90%, 95% or greater amino acid identity over an aligned stretch of corresponding residues. The "native MHC polypeptide" having the self-associating interface will often be an MHC polypeptide domain incorporated within an unmodified RTL, and the self-associating interface may only be present in such a context, as opposed to when the native MHC polypeptide is present in a fully intact, native MHC protein (e.g., in a heterodimeric MHC class II protein complex).

Thus, in the case of MHC class II RTLs, removal of the β2 and α2 domains to create a smaller, more useful (e.g., β1α1) domain structure for the RTL (comprising a minimal TCR interface) results in "unmasking" (i.e., rendering solvent-exposed) certain self-binding residues or motifs that comprise target sites for RTL modification according to the invention. These unmasked residues or motifs can be readily altered, for example by site-directed mutagenesis, to reduce or eliminate aggregation and render the RTL as a more highly monodisperse reagent in aqueous solution.

To evaluate the extent of monodispersal of these modified RTLs, an unmodified or "control" RTL may be employed which has the same basic polypeptide construction as the modified RTL, but features the native MHC polypeptide sequence (having one or more amino acid residues or motifs comprising the self-binding interface and defining a solvent-exposed target site for the modification when the native polypeptide is incorporated in the RTL).

The modified RTLs of the invention yield an increased percentage of monodisperse molecules in solution compared to a corresponding, unmodified RTL (i.e., comprising the native MHC polypeptide and bearing the unmodified, self-binding interface). In certain embodiments, the percentage of unmodified RTL present as a monodisperse species in aqueous solution may be as low as 1%, more typically 5-10% or less of total RTL protein, with the balance of the unmodified RTL being found in the form of higher-order aggregates. In contrast, modified RTLs of the present invention will yield at least 10%-20% monodisperse species in solution. In other embodiments, the percentage of monomeric species in solution will range from 25%-40%, often 50%-75%, up to 85%, 90%, 95% or greater of the total RTL present, with a commensurate reduction in the percentage of aggregate RTL species compared to quantities observed for the corresponding, unmodified RTLs under comparable conditions.

The self-binding interface that is altered in the MHC polypeptide to form the modified RTL may comprise single or multiple amino acid residues, or a defined region, domain, or motif of the MHC polypeptide, which is characterized by an ability to mediate self-binding or self-association of the MHC polypeptide and/or RTL. As used herein, "self-binding" and "self-association" refers to any intermolecular binding or association that promotes aggregation of the MHC polypeptide or RTL in a physiologically-compatible solution, such as water, saline, or serum.

As noted above, MHC class II molecules comprise non-covalently associated, α- and β-polypeptide chains. The α-chain comprises two distinct domains termed α1 and α2. The β-chain also comprises two domains, β1 and β2. The peptide binding pocket of MHC class II molecules is formed by interaction of the α1 and β1 domains. Peptides from processed antigen bind to MHC molecules in the membrane distal pocket formed by the β1 and α1 domains (Brown et al., 1993; Stern et al., 1994). Structural analysis of human MHC class II/peptide complexes (Brown et al., *Nature* 364:33-39, 1993; Stern et al., *Nature* 368:215, 1994) demonstrate that side chains of bound peptide interact with "pockets" comprised of polymorphic residues within the class II binding groove. The bound peptides have class II allele-specific motifs, characterized by strong preferences for specific amino acids at positions that anchor the peptide to the binding pocket and a wide tolerance for a variety of different amino acids at other positions (Stern et al., *Nature* 368:215, 1994; Rammensee et al., *Immunogenetics* 41: 178, 1995). Based on these properties, natural populations of MHC class II molecules are highly heterogeneous. A given allele of class II molecules on the surface of a cell has the ability to bind and present over 2000 different peptides. In addition, bound peptides dissociate from class II molecules with very slow rate constants. Thus, it has been difficult to generate or obtain homogeneous populations of class II molecules bound to specific antigenic peptides.

The α2 and β2 domains of HHC class II molecules comprise distinct, transmembrane Ig-fold like domains that anchor the α- and β-chains into the membrane of the APC. In addition, the α2 domain is reported to contribute to ordered oligomerization during T-cell activation (König et al., *J. Exp. Med.* 182:778-787, 1995), while the β2 domain is reported to contain a CD4 binding site that co-ligates CD4 when the MHC-antigen complex interacts with the TCR αβ heterodimer (Fleury et al., *Cell* 66:1037-1049, 1991; Cammarota et al., *Nature* 356:799-801, 1992; König et al., *Nature* 356:796-798, 1992; Huang et al., *J. Immunol.* 158:216-225, 1997).

RTLs modeled after MHC class II molecules for use within the invention typically comprise small (e.g., approximately 200 amino acid residues) molecules comprising all or portions of the α1 and β1 domains of human and non-human MHC class II molecules, which are typically genetically linked into a single polypeptide chain (with and without covalently coupled antigenic peptide). Exemplary MHC class II-derived "β1α1" molecules retain the biochemical properties required for peptide binding and TCR engagement (including TCR binding and/or partial or complete TCR activation). This provides for ready production of large amounts of the engineered RTL for structural characterization and immunotherapeutic applications. The MHC component of MHC class II RTLs comprise a minimal, Ag-binding/T-cell recognition interface, which may comprise all or portions of the MHC class II α1 and β1 domains of a selected MHC class II molecule. These RTLs are designed using the structural backbone of MHC class II molecules as a template. Structural characterization of RTLs using circular dichroism indicates that these molecules retain an antiparallel β-sheet platform and antiparallel α-helices observed in the corresponding, native (i.e., wild-type sequence) MHC class II heterodimer. These RTLs also exhibit a cooperative two-state thermal folding-unfolding transition. When the RTL is covalently linked with Ag peptide they often show increased stability to thermal unfolding relative to empty RTL molecules.

In exemplary embodiments of the invention, RTL design is rationally based on crystallographic coordinates of human HLA-DR, HLA-DQ, and/or HLA-DP proteins, or of a non-human (e.g., murine or rat) MHC class II protein. In this context, exemplary RTLs have been designed based on crystallographic data for HLA DR1 (PDB accession code 1AQD), which design parameters have been further clarified, for example, by sequence alignment with other MHC class II molecules from rat, human and mouse species. The program Sybyl (Tripos Associates, St Louis, Mo.) is an exemplary design tool that can be used to generate graphic images using, for example, an O2 workstation (Silicon Graphics, Mountain View, Calif.) and coordinates obtained for HLA-DR, HLA-DQ, and/or HLA-DP molecules. Extensive crystallographic characterizations are provided for these and other MHC class II proteins deposited in the Brookhaven Protein Data Bank (Brookhaven National Laboratories, Upton, N.Y.).

Detailed description of HLA-DR crystal structures for use in designing and constructing modified RTLs of the invention is provided, for example, in Ghosh et al., *Nature* 378:457, 1995; Stern et al., *Nature* 368:215, 1994; Murthy et al., *Structure* 5:1385, 1997; Bolin et al., *J. Med. Chem.* 43:2135, 2000; Li et al., *J. Mol. Biol.* 304:177, 2000; Hennecke et al., *Embo J.* 19:5611, 2000; Li et al., *Immunity* 14:93, 2001; Lang et al., *Nat. Immunol.* 3:940, 2002; Sundberg et al., *J. Mol. Biol.* 319:449, 2002; Zavala-Ruiz et al., *J. Biol. Chem.* 278:44904, 2003; Sundberg et al., *Structure* 11:1151, 2003. Detailed description of HLA-DQ crystal structures is provided, for example, in Sundberg et al., *Nat. Struct. Biol.* 6:123, 1999; Li et al., *Nat. Immunol.* 2:501, 2001; and Siebold et al., *Proc. Nat. Acad. Sci. USA* 101:1999, 2004. Detailed description of a murine MHC I-A$^U$ molecule is provided, for example, in He et al., *Immunity* 17:83, 2002. Detailed description of a murine MHC class II I-Ad molecule is provided, for example, in Scott et al., *Immunity* 8:319, 1998. Detailed description of a murine MHC class II I-Ak molecule is provided, for example, in Reinherz et al., *Science* 286:1913, 1999, and Miley et al., *J. Immunol.* 166:3345, 2001. Detailed description of a murine MHC allele I-A(G7) is provided, for example, in Corper et al., *Science* 288:501, 2000. Detailed description of a murine MHC class II H2-M molecule is provided, for example, in Fremont et al., *Immunity* 9:385, 1998. Detailed description of a murine MHC class II H2-Ieβ molecule is provided, for example, in Krosgaard et al., *Mol. Cell* 12:1367, 2003; Detailed description of a murine class II Mhc I-Ab molecule is provided, for example, in Zhu et al., *J. Mol. Biol.* 326:1157, 2003. HLA-DP Lawrance et al., Nucleic Acids Res. 1985 Oct. 25; 13 (20): 7515-7528

Structure-based homology modeling is based on refined crystallographic coordinates of one or more MHC class I or class II molecule(s), for example, a human DR molecule and a murine I-E$^k$ molecule. In one exemplary study by Burrows and colleagues (*Protein Engineering* 12:771-778, 1999), the primary sequences of rat, human and mouse MHC class II were aligned, from which it was determined that 76 of 256α-chain amino acids were identical (30%), and 93 of the 265 β-chain amino acids were identical (35%). Of particular interest, the primary sequence location of disulfide-bonding cysteines was conserved in all three species, and the backbone traces of the solved structures showed strong homology when superimposed, implying an evolutionarily conserved structural motif, with side-chain substitutions designed to allow differential antigenic-peptide binding in the peptide-binding groove.

Further analysis of MHC class I and class II molecules for constructing modified RTLs of the invention focuses on the "exposed" (i.e., solvent accessible) surface of the β-sheet platform/anti-parallel α-helix that comprise the domain(s) involved in peptide binding and T-cell recognition. In the case of MHC class II molecules, the α1 and β1 domains exhibit an extensive hydrogen-bonding network and a tightly packed and "buried" (i.e., solvent inaccessible) hydrophobic core. This tertiary structure is similar to molecular features that confer structural integrity and thermodynamic stability to the α-helix/β-sheet scaffold characteristic of scorpion toxins, which therefore present yet additional structural indicia for guiding rational design of modified RTLs herein (see, e.g., Zhao et al., *J. Mol. Biol.* 227:239, 1992; Housset, *J. Mol. Biol.* 238:88-91, 1994; Zinn-Justin et al., Biochemistry 35:8535-8543, 1996).

From these and other comparative data sources, crystals of native MHC class II molecules have been found to contain a number of water molecules between a membrane proximal surface of the β-sheet platform and a membrane distal surfaces of the α2 and β2 Ig-fold domains. Calculations regarding the surface area of interaction between domains can be quantified by creating a molecular surface, for example for the β1α1 and α2β2 Ig-fold domains of an MHC II molecule, using an algorithm such as that described by Connolly (*Biopolymers* 25:1229-1247, 1986) and using crystallographic coordinates (e.g., as provided for various MHC class II molecules in the Brookhaven Protein Data Base.)

For an exemplary, human DR1 MHC class II molecule (PDB accession numbers 1SEB, 1AQD), surface areas of the β1α1 and α2β2-Ig-fold domains were calculated independently, defined by accessibility to a probe of radius 0.14 nm, about the size of a water molecule (Burrows et al., *Protein Engineering* 12:771-778, 1999). The surface area of the MHC class II αβ-heterodimer was 156 $nm^2$, while that of the β1α1 construct was 81 $nm^2$ and the α2β2-Ig-fold domains was 90 $nm^2$. Approximately 15 $nm^2$ (18.5%) of the β1α1 surface was found to be buried by the interface with the Ig-fold domains in the MHC class II αβ-heterodimer. Side-chain interactions between the β1α1-peptide binding and Ig-fold domains (α2 and β2) were analyzed and shown to be dominated by polar interactions with hydrophobic interactions potentially serving as a "lubricant" in a highly flexible "ball and socket" type inter face.

These and related modeling studies suggest that the antigen binding domain of MHC class II molecules remain stable in the absence of the α2 and β2 Ig-fold domains, and this production has been born out for production of numerous, exemplary RTLs comprising an MHC class II "α1β1" architecture. Related findings were described by Burrows et al. (*J. Immunol.* 161:5987-5996, 1998) for an "empty" β1α1 RTL, and four α1β1 RTL constructs with covalently coupled rat and guinea pig antigenic peptides: β1 1-Rt-MBP-72-89, β1 1-Gp-MBP-72-89, β1 1-Gp-MBP-55-69 and β1 1-Rt-CM-2. For each of these constructs, the presence of native disulfide bonds between cysteines (β15 and β79) was demonstrated by gel shift assay with or without the reducing agent β-mercaptoethanol (β-ME). In the absence of β-ME, disulfide bonds are retained and the RTL proteins typically move through acrylamide gels faster due to their more compact structure. These data, along with immunological findings using MHC class II-specific monoclonal antibodies to label conserved epitopes on the RTLs generally affirm the conformational integrity of RTL molecules compared to their native MHC II counterparts (Burrows et al., 1998, supra; Chang et al., *J. Biol. Chem.* 276:24170-14176, 2001; Vandenbark et al., *J. Immunol.* 171:127-133, 2003). Similarly, circular dichroism (CD)

studies of MHC class II-derived RTLs reveal that β1α1 molecules have highly ordered secondary structures. Typically, RTLs of this general construction shared the β-sheet platform/anti-parallel α-helix secondary structure common to all class II antigen binding domains. In this context, β1α1 molecules have been found to contain, for example, approximately 30% α-helix, 15% β-strand, 26% β-turn and 29% random coil structures. RTLs covalently bound to Ag peptide (e.g., MBP-72-89, and CM-2) show similar, although not identical, secondary structural features. Thermal denaturation studies reveal a high degree of cooperativity and stability of RTL molecules, and the biological integrity of these molecules has been demonstrated in numerous contexts, including by the ability of selected RTLs to detect and inhibit rat encephalitogenic T-cells and treat experimental autoimmune encephalomyelitis.

According to these and related findings provided herein (or described in the cited references which are collectively incorporated herein for all disclosure purposes), RTL constructs of the invention, with or without an associated antigenic peptide, retain structural and conformational integrity consistent with that of refolded native MHC molecules. This general finding is exemplified by results for soluble single-chain RTL molecules derived from the antigen-binding/TCR interface comprised of all or portions of the MHC class II β1 and α1 domains. In more detailed embodiments, these exemplary MHC class II RTLs lack the α2 domain and β2 domain of the corresponding, native MHC class II protein, and also typically exclude the transmembrane and intra-cytoplasmic sequences found in the native MHC II protein. The reduced size and complexity of these RTL constructs, exemplified by the "β1α1" MHC II RTL constructs, provide for ready and predictable expression and purification of the RTL molecules from bacterial inclusion bodies in high yield (e.g., up to 15-30 mg/l cell culture or greater yield).

In native MHC class II molecules, the Ag peptide binding/T-cell recognition domain is formed by well-defined portions of the α1 and β1 domains of the α and β polypeptides which fold together to form a tertiary structure, most simply described as β-sheet platform upon which two anti-parallel helical segments interact to form an antigen-binding groove. A similar structure is formed by a single exon encoding the α1 and α2 domains of MHC class I molecules, with the exception that the peptide-binding groove of MHC class II is open-ended, allowing the engineering of single-exon constructs that encode the peptide binding/T-cell recognition domain and an antigenic peptide ligand.

As exemplified herein for MHC class II proteins, modeling studies highlighted important features regarding the interface between the β1α1 and α2β2-Ig-fold domains that have proven critical for designing modified, monodisperse RTLs of the invention. The α1 and β1 domains show an extensive hydrogen-bonding network and a tightly packed and "buried" (i.e., solvent inaccessible) hydrophobic core. The β1α1 portion of MHC class II proteins may have the ability to move as a single entity independent from the α2β2-Ig-fold 'platform'. Besides evidence of a high degree of mobility in the side-chains that make up the linker regions between these two domains, crystals of MHC class II I-Ek contained a number of water molecules within this interface (Jardetzky et al., Nature 368: 711-715, 1994; Fremont et al., Science 272:1001-1004, 1996; Murthy et al., Structure 5:1385, 1997). The interface between the β1α1 and α2β2-Ig-fold domains appears to be dominated by polar interactions, with hydrophobic residues likely serving as a 'lubricant' in a highly flexible 'ball and socket' type interface. Flexibility at this interface may be required for freedom of movement within the α1 and β1 domains for binding/exchange of peptide antigen. Alternatively or in combination, this interaction surface may play a role in communicating information about the MHC class II-peptide molecular interaction with TCRs back to the APC.

Following these rational design guidelines and parameters, the instant inventors have successfully engineered modified, monodisperse derivatives of single-chain human RTLs comprising peptide binding/TCR recognition portions of human MHC class II molecules (e.g., as exemplified by a HLA-DR2b (DRA*0101/DRB1*1501). Unmodified RTLs constructed from the α1 and β1 domains of this exemplary MHC class II molecule retained biological activity, but formed undesired, higher order aggregates in solution.

To resolve the problem of aggregation in this exemplary, unmodified RTL, site-directed mutagenesis was directed towards replacement of hydrophobic residues with polar (e.g., serine) or charged (e.g., aspartic acid) residues to modify the β-sheet platform of the DR2-derived RTLs. According to this rational design procedure, novel RTL variants were obtained that were determined to be predominantly monomeric in solution. Size exclusion chromatography and dynamic light scattering demonstrated that the novel modified RTLs were monomeric in solution, and structural characterization using circular dichroism demonstrated a highly ordered secondary structure of the RTLs.

According to the present invention, desired surface modification of an RTL comprising an MHC class II component to yield much less aggregation prone form can be achieved, for example, by replacement of one or more hydrophobic residues identified in the β-sheet platform of the MHC component with non-hydrophobic residues, for example polar or charged residues. Modified RTL constructs exemplifying this aspect of the invention were constructed by replacing one or more target, hydrophobic residues identified in the β-sheet platform of an HLA-DR2 component of RTL 302 with one or more exemplary polar (e.g., serine) residue(s) and, alternatively exemplary charged (e.g., aspartate) residue(s). Initially, a central core portion of the β-sheet platform was targeted for modification, comprising V102, I104, A106, F108, and L110. These residues were changed by site-directed mutagenesis, individually, or in various multiple-residue combinations to either a serine, or aspartate residue(s).

We grouped these residues, based on their location within the beta-sheet platform and on their relative level of interaction with residues from the α2 and β2 Ig-fold domains, and constructed a series of site-directed mutants, replacing single and then multiple residues with either serine or aspartic acid residues. The study developed in two stages, with the first stage focused on obtaining soluble proteins that were monodisperse, and the second focused on biophysical and biochemical characterization of the modified molecules. Reiterative site-directed mutagenesis allowed us to generate two modified RTLs that were suitable for further biological characterization (TABLE I).

TABLE I

Molecules used in this study

| Molecule | Description |
|---|---|
| RTL302 | Human HLA DR2 (DRB1 * 150101/DRA * 0101) β1α1 domains |
| RTL302 (5S) | RTL302 (V102S, I104S, A106S, F108S, L110S)[a] |
| RTL302 (5D) | RTL302 (V102D, I104D, A106D, F108D, L110D) |
| RTL303 | RTL302/MBP-85-99[b] |
| RTL312 | RTL302/MOG-35-55[c] |
| RTL320 | RTL303 (5S) |

TABLE I-continued

Molecules used in this study

| Molecule | Description |
|---|---|
| RTL340 | RTL303 (5D) |
| RTL342 | RTL312 (5D) |

[a] RTL302 numbering. These residues correspond to HLA-DR2 alpha-chain residues V6, I8, A10, F12, and L14. Residue numbering is increased in the Ag-tethered molecules to account for the Ag-peptide (variable length) plus linker (15 residues).
[b] MBP-85-99, ENPVVHFFKNIVTPR
[c] MOG-35-55, MEVGWYRSPFSRVVHLYRNGK RTL302 could be converted to a monomer with either five serine (5S) or five aspartate (5D) substitutions, RTL302(5S) and RTL302(5D), respectively, within a group of residues along the external face of the first strand of anti-parallel α-sheet derived from the alpha chain of the HLA-DR2 progenitor molecule. Comparison of the 5S or 5D modified molecules with RTL302 by size exclusion chromatography (SEC) demonstrated that both RTL302(5S) and RTL302(5D) behaved as approximately 25 kD monomers.

Peptide binding to these "empty," modified RTLs was quantified using biotinylated peptides, and functional studies showed that the modified RTLs containing covalently tethered peptides were able to inhibit antigen-specific T-cell proliferation in vitro. These studies demonstrated that RTLs encoding the Ag-binding/TCR recognition domain of MHC class II molecules are innately very robust structures. Despite modification of the RTLs as described herein, comprising site-directed mutations that modified the β-sheet platform of the RTL, these molecules retained potent biological activity separate from the Ig-fold domains of the progenitor class II structure, and exhibited a novel and surprising reduction in aggregation in aqueous solutions. Modified RTLs having these and other redesigned surface features and monodisperal characteristics retained the ability to bind Ag-peptides inhibit T-cell proliferation in an Ag-specific manner, and treat or prevent, inter alia, damage due to an ischemic event such as a stroke in vivo.

Additional modifications apart from the foregoing surface feature modifications can be introduced into modified RTLs of the invention, including particularly minor modifications in amino acid sequence(s) of the MHC component of the RTL that are likely to yield little or no change in activity of the derivative or "variant" RTL molecule. Preferred variants of non-aggregating MHC domain polypeptides comprising a modified RTLs are typically characterized by possession of at least 50% sequence identity counted over the full length alignment with the amino acid sequence of a particular non-aggregating MHC domain polypeptide using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, variants will typically possess at least 75% sequence identity over short windows of 10-20 amino acids, and may possess sequence identities of at least 85% or at least 90% or 95% depending on their similarity to the reference sequence. Methods for determining sequence identity over such short windows are known in the art as described above. Variants of modified RTLs comprising non-aggregating MHC domain polypeptides also retain the biological activity of the non-variant, modified RTL. For the purposes of this invention, that activity may be conveniently assessed by incorporating the variation in the appropriate MHC component of a modified RTL (e.g., a β1α1 MHC component) and determining the ability of the resulting RTL/Ag complex to inhibit Ag-specific T-cell proliferation in vitro, as described herein.

(d) Pharmaceutical Formulations

Suitable routes of administration of purified MHC polypeptides of the present invention include, but are not limited to, oral, buccal, nasal, aerosol, topical, transdermal, mucosal, injectable, slow release, controlled release, iontophoresis, sonophoresis, and other conventional delivery routes, devices and methods. Injectable delivery methods include, but are not limited to, intravenous, intramuscular, intraperitoneal, intraspinal, intrathecal, intracerebroventricular, intraarterial, and subcutaneous injection.

Amounts and regimens for the administration of the selected MHC polypeptides will be determined by the attending clinician. Effective doses for therapeutic application will vary depending on the nature and severity of the condition to be treated, the particular MHC polypeptide selected, the age and condition of the patient and other clinical factors. Typically, the dose range will be from about 0.1 μg/kg body weight to about 100 mg/kg body weight. Other suitable ranges include doses of from about 100 μg/kg to 1 mg/kg body weight. In certain embodiments, the effective dosage will be selected within narrower ranges of, for example, 1-75 μg/kg, 10-50 μg/kg, 15-30 μg/kg, or 20-30 μg/kg. These and other effective unit dosage amounts may be administered in a single dose, or in the form of multiple daily, weekly or monthly doses, for example in a dosing regimen comprising from 1 to 5, or 2-3, doses administered per day, per week, or per month. The dosing schedule may vary depending on a number of clinical factors, such as the subject's sensitivity to the protein. Examples of dosing schedules are 3 μg/kg administered twice a week, three times a week or daily; a dose of 7 μg/kg twice a week, three times a week or daily; a dose of 10 μg/kg twice a week, three times a week or daily; or a dose of 30 μg/kg twice a week, three times a week or daily.

The amount, timing and mode of delivery of compositions of the invention comprising an effective amount of purified MHC polypeptides will be routinely adjusted on an individual basis, depending on such factors as weight, age, gender, and condition of the individual, the severity of the T-cell mediated disease, whether the administration is prophylactic or therapeutic, and on the basis of other factors known to effect drug delivery, absorption, pharmacokinetics, including half-life, and efficacy. Thus, following administration of the purified MHC polypeptides composition according to the formulations and methods of the invention, test subjects will exhibit a 10%, 20%, 30%, 50% or greater reduction, up to a 75-90%, or 95% or greater, reduction, in one or more symptoms associated with a targeted T-cell mediated disease, as compared to placebo-treated or other suitable control subjects Within additional aspects of the invention, combinatorial formulations and coordinate administration methods are provided which employ an effective amount of purified MHC polypeptide, and one or more additional active agent(s) that is/are combinatorially formulated or coordinately administered with the purified MHC polypeptide—yielding an effective formulation or method to modulate, alleviate, treat or prevent a T-cell mediated disease in a mammalian subject. Exemplary combinatorial formulations and coordinate treatment methods in this context employ a purified MHC polypeptide in combination with one or more additional or adjunctive therapeutic agents. The secondary or adjunctive methods and compositions useful in the treatment of T-cell mediated diseases include, but are not limited to, combinatorial administration with immunoglobulins (e.g., a CTLA4Ig, such as BMS-188667; see, e.g., Srinivas et al., *J. Pharm. Sci.* 85 (1):1-4, (1996), incorporated herein by reference); copolymer 1, copolymer 1-related peptides, and T-cells treated with copolymer 1 or copolymer 1-related peptides (see, e.g., U.S. Pat. No. 6,844,314, incorporated herein by reference); blocking monoclonal antibodies, transforming growth factor-β, anti-TNF α antibodies; anti-coagulants including but not limited to, warfarin, heprin; anti-platelet medications including but not limited to aspirin, clopidogrel or aggrenox; clot dissolving medications including, but not limited to tissue plasminogen activating factor (tPA); angiotensin-converting enzyme (ACE) inhibitors, including but not limited to benazepril, captopril, enalapril, fosinopril, lisinopril, perindopril, quinapril, ramipril, and trandolapril; angiotensin II receptor blockers (ARBs) including but not limited to candesartan cilexetil, eprosartan mesylate, irbesartan, losartan, olmesartan, telmisartan, or valsartan; beta-blockers including but not limited to acebutolol, atenolol, betaxolol, carvedilol, labetalol, metoprolol, nadolol, penbutolol, pindolol, propranolol, timolol; diuretics including but not limited to chlorthalidone and chlorthalidone combinations, chlorothiazide, hydrochlorothiazide and hydrochlorothiazide combinations, indapamide, bumetanide, furosemide, torsemide, amiloride, spironolactone and spironolactone combinations, triamterene and triamterene combinations, metolazone; and calcium channel blockers including but not limited to amlodipine, amlodipine and atorvastatin, amlodipine and benazepril hydrochloride, diltiazem, enalapril maleate-felodipine ER, felodipine, isradipine, nicardipine, nifedipine, nisoldipine, verapamil; neuroprotectants; statins; anti-inflammatory agents; immunosuppressive agents; alkylating agents; anti-metabolites; antibiotics; corticosteroids; proteosome inhibitors; diketopiperazines; and steroidal agents including but not limited to estrogens, progesterones, testosterones, corticosteroids, and anabolic steroids. To practice the coordinate administration methods of the invention, a MHC polypeptide is administered, simultaneously or sequentially, in a coordinate treatment protocol with one or more of the secondary or adjunctive therapeutic agents contemplated herein, for example a secondary immune modulatory agent. The coordinate administration may be done in either order, and there may be a time period while only one or both (or all) active therapeutic agents, individually and/or collectively, exert their biological activities. A distinguishing aspect of all such coordinate treatment methods is that the purified MHC polypeptide composition may elicit a favorable clinical response, which may or may not be in conjunction with a secondary clinical response provided by the secondary therapeutic agent. Often, the coordinate administration of a purified MHC polypeptide with a secondary therapeutic agent as contemplated herein will yield an enhanced therapeutic response beyond the therapeutic response elicited by either or both the purified MHC polypeptide and/or secondary therapeutic agent alone. In some embodiments, the enhanced therapeutic response may allow for lower doses or suboptimal doses of the purified MHC polypeptide and/or the secondary therapeutic agent to be used to yield the desired therapeutic response beyond the therapeutic response expected to be elicited by either or both the purified MHC polypeptide and/or secondary therapeutic agent alone. Such lower, sub-therapeutic, or sub-optimal doses may be any dose lower than the dosage generally used to elicit a therapeutic effective response. In some embodiments, the use of therapeutic agents may be accompanied by physical intervention such as, for example, angioplasty, stents, carotid endarterectomy, revascularization and endovascular surgery.

The pharmaceutical compositions of the present invention may be administered by any means that achieve their intended purpose. The purified MHC polypeptides of the present invention are generally combined with a pharmaceutically acceptable carrier appropriate for the particular mode of administration being employed. Dosage forms of the purified MHC polypeptide of the present invention include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, effervescent agents and other conventional excipients and additives.

The compositions of the invention for treating T-cell mediated diseases and associated conditions and complications can thus include any one or combination of the following: a pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to patients without causing deleterious side effects or interactions with the active agent.

If desired, the purified MHC polypeptide of the invention can be administered in a controlled release form by use of a slow release carrier, such as a hydrophilic, slow release polymer. Exemplary controlled release agents in this context include, but are not limited to, hydroxypropyl methyl cellulose, having a viscosity in the range of about 100 cps to about 100,000 cps or other biocompatible matrices such as cholesterol.

Purified MHC polypeptides of the invention will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose, dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this invention include tablets, which may be prepared by any conventional method of preparing pharmaceutical oral unit dosage forms can be utilized in preparing oral unit dosage forms. Oral unit dosage forms, such as tablets, may contain one or more conventional additional formulation ingredients, including, but not limited to, release modifying agents, glidants, compression aides, disintegrants, lubricants, binders, flavors, flavor enhancers, sweeteners and/or preservatives. Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants.

Additional purified MHC polypeptides of the invention can be prepared and administered in any of a variety of inhalation or nasal delivery forms known in the art. Devices capable of depositing aerosolized purified MHC formulations in the sinus cavity or pulmonary alveoli of a patient include metered dose inhalers, nebulizers, dry powder generators, sprayers, and the like. Methods and compositions suitable for pulmonary delivery of drugs for systemic effect are well known in the art. Additional possible methods of delivery include deep lung delivery by inhalation (Edwards et al., 1997; Service, 1997). Suitable formulations, wherein the carrier is a liquid, for administration, as for example, a nasal spray or as nasal drops, may include aqueous or oily solutions of purified MHC polypeptides and any additional active or inactive ingredient(s).

Further compositions and methods of the invention are provided for topical administration of purified MHC polypeptides for the treatment of T-cell mediated diseases. Topical compositions may comprise purified MHC polypeptides and any other active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise purified MHC polypeptides dissolved or dispersed in a portion of water or other solvent or liquid to be incorporated in the topical composition or delivery device. It can be readily appreciated that the transdermal route of administration may be enhanced by the use of a dermal penetration enhancer known to those skilled in the art. Formulations suitable for such dosage forms incorporate excipients commonly utilized therein, particularly means, e.g. structure or matrix, for sustaining the absorption of the drug over an extended period of time, for example, 24 hours. Transdermal delivery may also be enhanced through techniques such as sonophoresis (Mitragotri et al., 1996).

Yet additional purified MHC polypeptide formulations are provided for parenteral administration, e.g. intravenously, intramuscularly, subcutaneously or intraperitoneally, including aqueous and non-aqueous sterile injection solutions which may optionally contain anti-oxidants, buffers, bacteriostats and/or solutes which render the formulation isotonic with the blood of the mammalian subject; and aqueous and non-aqueous sterile suspensions which may include suspending agents and/or thickening agents. The formulations may be presented in unit-dose or multi-dose containers. Purified MHC polypeptide formulations may also include polymers for extended release following parenteral administration. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such polymeric materials are well known to those of ordinary skill in the pharmaceutical compounding arts. Parenteral preparations typically contain buffering agents and preservatives, and injectable fluids that are pharmaceutically and physiologically acceptable such as water, physiological saline, balanced salt solutions, aqueous dextrose, glycerol or the like Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

In more detailed embodiments, purified MHC polypeptides may be encapsulated for delivery in microcapsules, microparticles, or microspheres, prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles and nanocapsules), through the use of viral vectors or in macroemulsions. These methods could be used to deliver the purified MHC polypeptides to cells in the nucleic acid form for subsequent translation by the host cell.

Exemplary Applications of Recombinant $\beta1\alpha1$ and $\alpha1\alpha2$ Molecules The class II $\beta1\alpha1$ and class I $\alpha1\alpha2$ polypeptides of the present invention are useful for a wide range of in vitro and in vivo applications. Indeed, as a result of the biological activities of these polypeptides, they may be used in numerous applications in place of either intact purified MHC molecules, or antigen presenting cells that express MHC molecules.

In vitro applications of the disclosed polypeptides include the detection, quantification and purification of antigen-specific T-cells. Methods for using various forms of MHC-derived complexes for these purposes are well known and are described in, for example, U.S. Pat. Nos. 5,635,363 and 5,595,881, each of which is incorporated by reference herein in its entirety. For such applications, the disclosed polypeptides may be free in solution or may be attached to a solid support such as the surface of a plastic dish, a microtiter plate, a membrane, or beads. Typically, such surfaces are plastic, nylon or nitrocellulose. Polypeptides in free solution are useful for applications such as fluorescence activated cell sorting (FACS). For detection and quantification of antigen-specific T-cells, the polypeptides are preferably labeled with a detectable marker, such as a fluorescent marker.

The T-cells to be detected, quantified or otherwise manipulated are generally present in a biological sample removed from a patient. The biological sample is typically blood or lymph, but may also be tissue samples such as lymph nodes, tumors, joints etc. It will be appreciated that the precise details of the method used to manipulate the T-cells in the sample will depend on the type of manipulation to be performed and the physical form of both the biological sample and the MHC molecules. However, in general terms, the $\beta1\alpha1$/peptide complex or $\alpha1\alpha2$/peptide complex is added to the biological sample, and the mixture is incubated for sufficient time (e.g., from about 5 minutes up to several hours) to allow binding. Detection and quantification of T-cells bound to the MHC/peptide complex may be performed by a number of methods including, where the MHC/peptide includes a fluorescent label, fluorescence microscopy and FACS. Standard immunoassays such as ELISA and RIA may also be used to quantify T-cell—MHC/peptide complexes where the MHC/peptide complexes are bound to a solid support. Quantification of antigen-specific T-cell populations will be especially useful in monitoring the course of a disease. For example, in a multiple sclerosis patient, the efficacy of a therapy administered to reduce the number of MBP-reactive T-cells may be monitored using MHC/MBP antigen complexes to quantify the number of such T-cells present in the patient. Similarly, the number of anti-tumor T-cells in a cancer patient may be quantified and tracked over the course of a therapy using MHC/tumor antigen complexes.

FACS may also be used to separate T-cell—MHC/peptide complexes from the biological sample, which may be particularly useful where a specified population of antigen-specific T-cells is to be removed from the sample, such as for enrichment purposes. Where the MHC/peptide complex is bound to magnetic beads, the binding T-cell population may be purified as described by Miltenyi et al. (1990).

A specified antigen-specific T-cell population in the biological sample may be anergized by incubation of the sample with MHC/peptide complexes containing the peptide recognized by the targeted T-cells. Thus, when these complexes bind to the TCR in the absence of other co-stimulatory molecules, a state of anergy is induced in the T-cell. Such an approach is useful in situations where the targeted T-cell population recognizes a self-antigen, such as in various autoimmune diseases. Alternatively, the targeted T-cell population may be killed directly by incubation of the biological sample with an MHC/peptide complex conjugated with a toxic moiety.

T-cells may also be activated in an antigen-specific manner by the polypeptides of the invention. For example, the disclosed MHC polypeptides loaded with a specified antigen may be adhered at a high density to a solid surface, such as a plastic dish or a magnetic bead. Exposure of T-cells to the polypeptides on the solid surface can stimulate and activate T-cells in an antigen-specific manner, despite the absence of co-stimulatory molecules. This is likely attributable to sufficient numbers of TCRs on a T-cell binding to the MHC/peptide complexes that co-stimulation is unnecessary for activation.

In one embodiment, suppressor T-cells are induced. Thus, when the complexes bind to the TCR in the proper context, suppressor T-cells are induced in vitro. In one embodiment, effector functions are modified, and cytokine profiles are altered by incubation with a MHC/peptide complex.

In vivo applications of the disclosed polypeptide include the amelioaration of conditions mediated by antigen specific T cells. Such conditions include, but are not limited to, damage due to stroke.

Other researchers have described various forms of MHC polypeptides that are equally useful with the MHC polypeptides of the present invention. Exemplary methodologies are described in U.S. Pat. Nos. 5,130,297, 5,284,935, 5,468,481, 5,734,023 and 5,194,425 (herein incorporated by reference). By way of example, the MHC/peptide complexes may be administered to a subject in order to induce anergy in self-reactive T-cell populations, or these T-cell populations may be treated by administration of MHC/peptide complexes conjugated with a toxic moiety. Alternatively, the MHC/peptide complexes may be administered to a subject to induce T suppressor cells or to modify a cytokine expression profile. The disclosed molecules may also be used to boost immune response in certain conditions such as cancer and infectious diseases.

In vivo applications of the disclosed polypeptides also include the amelioration of demyelination or neuroaxonal injury or loss. The compositions and methods of the present invention may also be administered to treat inflammation in subjects in need of such treatment. Inflammation may be present in the central nervous system (CNS), spinal cord, spleen, or other bodily system. The compositions and methods of the present invention may be administered to prevent or decrease infiltration of inflammatory cells into the CNS, spinal cord, spleen, or other bodily system, to upregulate anti-inflammatory factors, or to down regulate or inhibit inflammatory factors such as, but not limited to, IL-17, TNFα, IL-2 and IL-6. Such inflammation may be from any cause, for example preceding or following a stroke.

Treatments with the compositions and methods of the present invention may be administered alone or in a combinatorial formulation or coordinately with other therapeutic agents, including, but not limited to, interferon beta-1a; interferon beta-1b; glatiramer acetate; mitoxantrone; corticosteroids; tissue plasminogen activator anti-inflamatory agents, immunosuppresive agents; alkylating agents; anti-metabolites; antibiotics; corticosteroids; proteosome inhibitors; diketopiperazines; and steroidal agents including but not limited to estrogens, progensterones, testosterones, corticosteroids and anabolic steroids; muscle relaxants including but not limited to baclofen, dantrolene, tizanidine, cyclobenzaprine, clonazepam, and diazepam; anticholinergics including but not limited to, propantheline, tolterodine, and dicyclomine; tricyclic antidepressants including but not limited to amitriptyline and imipramine; anticonvulsants, including but not limited to, carbamazepine, phenyloin, and acetazolamide; central nervous system stimulants including pemoline; selective serotonin reuptake inhibitors (SSRIs) including, but not limited to, citalopram, fluoxetine, paroxetine, and sertraline; non-steroidal anti-inflammatories; anti-coagulants including but not limited to, warfarin, heprin; anti-platelet medications including but not limited to aspirin, clopidogrel or aggrenox; clot dissolving medications including, but not limited to tissue plasminogen activating factor (tPA); angiotensin-converting enzyme (ACE) inhibitors, including but not limited to benazepril, captopril, enalapril, fosinopril, lisinopril, perindopril, quinapril, ramipril, and trandolapril; angiotensin II receptor blockers (ARBs) including but not limited to candesartan cilexetil, eprosartan mesylate, irbesartan, losartan, olmesartan, telmisartan, or valsartan; beta-blockers including but not limited to acebutolol, atenolol, betaxolol, carvedilol, labetalol, metoprolol, nadolol, penbutolol, pindolol, propranolol, timolol; diuretics including but not limited to chlorthalidone and chlorthalidone combinations, chlorothiazide, hydrochlorothiazide and hydrochlorothiazide combinations, indapamide, bumetanide, furosemide, torsemide, amiloride, spironolactone and spironolactone combinations, triamterene and triamterene combinations, metolazone; and calcium channel blockers including but not limited to amlodipine, amlodipine and atorvastatin, amlodipine and benazepril hydrochloride, diltiazem, enalapril maleate-felodipine ER, felodipine, isradipine, nicardipine, nifedipine, nisoldipine, verapamil; neuroprotectants; statins. Such combinatorial administration may be done simultaneously or sequentially in either order, and there may be a time period while only one or both (or all) active therapeutic agents individually and/or collectively exert their biological activities. In some embodiments, administration of combinatorial formulations may allow for the use of lower doses of the MHC polypeptide and or secondary therapeutic agents than are generally used to elicit a therapeutically effective response. In additional embodiments, the use of therapeutic agents may be accompanied by physical intervention such as, for example, angioplasty, stents, carotid endarterectomy, revascularization and endovascular surgery Various additional aspects of the invention are provided herein which employ features, methods or materials that are known in the art or which are disclosed in Applicants' prior patent applications, including but not limited to: U.S. patent application Ser. No. 09/847,172, filed May 1, 2001; U.S. Provisional Patent Application No. 60/200,942, filed May 1, 2000; International Publication No. WO 02/087613 A1, published Nov. 7, 2002; U.S. Pat. No. 6,270,772; U.S. Provisional Patent Application No. 60/064,552, filed Sep. 16, 1997; and U.S. Provisional Patent Application No. 60/064,555, filed Oct. 10, 1997; U.S. Provisional Patent Application No. 60/500,660, filed Sep. 5, 2003; U.S. patent application Ser. No. 10/936,467, filed Sep. 7, 2004; and U.S. Provisional Patent Application No. 60/586,433, filed Jul. 8, 2004, each of which is incorporated herein by reference in its entirety for all purposes.

The following examples illustrate certain aspects of the invention, but are not intended to limit in any manner the scope of the invention.

EXAMPLE 1

Cloning, Expression and In Vitro Folding of β1α1 Molecules

A prototypical nucleic acid construct was produced that encoded a single polypeptide chain with the amino terminus of the MHC class II α1 domain genetically linked to the carboxyl terminus of the MHC class II β1 domain. The sequence of this prototypical construct, made from the rat RT1B- and β-chain cDNAs is shown in FIG. 1A (SEQ ID NO:1).

RT1B α1- and β1-domain encoding cDNAs were prepared by PCR amplification of cloned RT1B α- and β-chain cDNA coding sequences (α6, β118, respectively) obtained from Dr. Konrad Reske, Mainz, FRG (Syha et al., 1989; Syha-Jedelhauser et al., 1991). The primers used to generate β1 were: 5'-AATTCCTCGAGATGGCTCTGCAGACCCC-3' (XhoI 5' primer) (SEQ ID NO:9); 5'-TCTTGACCTCCAAGCCGC-CGCAGGGAGGTG-3' (3' ligation primer) (SEQ ID NO:10). The primers used to generate α1 were: 5'-CGGCGGCTTG-GAGGTCAAGACGACATTGAGG-3' (5' ligation primer) (SEQ ID NO:11); 5'-GCCTCGGTACCTTAGTTGA-CAGCTTGGGTTGAATTTG-3' (KpnI 3' primer) (SEQ ID NO: 12). Additional primers used were: 5'-CAGGGAC-CATGGGCAGAGACTCCCCA-3' (NcoI 5' primer) (SEQ ID NO:13); and 5'-GCCTCCTCGAGTTAGTTGACAGCT-TGGGTT-3' (XhoI 3' primer) (SEQ ID NO:14). Step one involved production of cDNAs encoding the β1 and α1 domains. PCR was conducted with Taq polymerase (Promega, Madison, Wis.) through 28 cycles of denaturation at 94.5° C. for 20 seconds, annealing at 55° C. for 1.5 minutes and extension at 72° C. for 1.5 minutes, using β118 as template and the XhoI 5' primer and 3' ligation primer as primers and α6 cDNA as template and the 5' ligation primer and KpnI 3' primer. PCR products were isolated by agarose gel electrophoresis and purified using GENECLEAN purification kit (Bio 101, Inc., La Jolla, Calif.).

In step two, these products were mixed together without additional primers and heat denatured at 94.5° C. for 5 minutes followed by 2 cycles of denaturation at 94.5° C. for 1 minute, annealing at 60° C. for 2 minutes and extension at 72° C. for 5 minutes. In step three, the annealed, extended product was heat denatured at 94.5° C. for 5 minutes and subjected to 26 cycles of denaturation at 94.5° C. for 20 seconds, annealing at 60° C. for 1 minute and extension at 72° C. for 1 minute, in the presence of the XhoI 5' primer and KpnI 3' primer. The final PCR product was isolated by agarose gel electrophoresis and purified with GENECLEAN purification kit. This produced a 656 base pair cDNA encoding the β1 1 molecule. The cDNA encoding the β1α1 molecule was moved into cloning vector pCR2.1 (Invitrogen, Carlsbad, Calif.) using Invitrogen's TA Cloning® kit. The cDNA in pCR2.1 was used as template and PCR was conducted through 28 cycles of denaturation at 94.5° C. for 20 seconds, annealing at 55° C. for 1.5 minutes and extension at 72° C. for 1.5 minutes, using the NcoI 5' primer and XhoI 3' primer. The PCR products were cleaved with the relevant restriction enzymes and directionally cloned into pET21d+ (Novagen, Madison, Wis.; Studier et al., 1990). The constructs were confirmed by DNA sequencing. The β1α1 molecule used in these studies differs from wild-type in that it contains a β-1 domain Q12R amino acid substitution.

For insertion of the peptide/linker cartridge (shown in FIG. 1A), the following approach was used. For insertion of the peptide/linker cartridge (shown in FIG. 1A), the following approach was used. The 210 bp peptide/linker cartridge was amplified using the XhoI 5' primer and a primer of sequence: 5'-GAAATCCCGCGGGGAGCCTCCACCTCCA-GAGCCTCGGGGCACTAGTGAGCC TCCACCTC-CGAAGTGCACCACTGGGTTCTCATCCT-GAGTCCTCTGGCTCTTCTGT GGGGAGTCTCTGCCCTCAGTCC-3' (3'-MBP-72-89/linker ligation primer) (SEQ ID NO:15) and the original full-length β118 cDNA as a template. A 559 bp cDNA with a 5' overhang for annealing to the peptide/linker cartridge cDNA was generated using a primer: 5'-GCTCCCCGCGG-GATTTCGTGTACCAGTTCAA-3' (5' peptide/linker ligation primer) (SEQ ID NO:16); and the KpnI 3' primer and the 656 bp β1α1 cDNA as the amplification template. Annealing and extension of the two cDNAs resulted in the 750 bp full-length β1α1/MBP-72-89 construct. Modifications at the 5' and 3' ends of the β1α1 and β1α1/MBP-72-89 cDNAs were made for subcloning into pET21d+ (Novagen, Madison, Wis.; Studier et al., 1990) using the NcoI 5' primer and the XhoI 3' primer. The primers used to generate the MBP-55-69/linker cartridge were 5'-TATTACCATGGGCA-GAGACTCCTCCGGCAAGGATTCGCAT-CATGCGGCGCG GACGACCCACTACGGTGGAGGTGGAG-GCTCACTAGTGCCCC-3' (5' MBP-55-69 primer) (SEQ ID NO:17) and 5'-GGGGCACTAGTGAGCCTCCACCTC-CACCGTAGTGGGTCGTCCGCGCCGCATG ATGC-GAATCCTTGCCGGAGGAGTCTCTGC-CCATGGTAATA-3' (3' MBP-55-69 primer) (SEQ ID NO:18). These were gel purified, annealed and then cut with NcoI and XhoI for ligation into β1α1/MBP-72-89 digested with NcoI and XhoI, to produce a plasmid encoding the β1α1/MBP-55-69 covalent construct. The primers used to generate the Guinea pig MBP-72-89/linker cartridge were 5'-TATTACCATGGGCAGAGACTCCCCACA-GAAGAGCCAGAGGTCTCAGGATGA GAACCCAGTG-GTGCACTTCGGAGGTGGAGGCTCACTAGTGCCCC-3' (5' Gp-MBP-72-89 primer) (SEQ ID NO:28) and 5'GGGGCACTAGTGAGCCTCCACCTC-CGAAGTGCACCACTGGGTTCTCATCCTG AGAC-CTCTGGCTCTTCTGTGGGGAGTCTCTGC-CCATGGTAAT-3' (3' Gp-MBP-72-89 primer) (SEQ ID NO:29). These were gel purified, annealed and then cut with NcoI and XhoI for ligation into β1α1/MBP-72-89 digested with NcoI and XhoI, to produce a plasmid encoding the β1α1/Gp-MBP-72-89 covalent construct. The primers used to generate the CM-2/linker cartridge were 5'-TATTAC-CATGGGCAGAGACTCCAAACTGGAACTG-CAGTCCGCTCTGGAAGA AGCTGAAGCTTCCCTG-GAACACGGAGGTGGAGGCTCACTAGTGCCCC-3' (5' CM-2 primer) (SEQ ID NO:19) and 5'-GGGGCACTAGT-GAGCCTCCACCTCCGTGTTCCAGG-GAAGCTTCAGCTTCTTC CAGAGCGGACTGCAGTTC-CAGTTTGGAGTCTCTGCCCATGGTAATA-3' (3' CM-2 primer) (SEQ ID NO:20). These were gel purified, annealed and then cut with NcoI and XhoI for ligation into β1α1/MBP-72-89 digested with NcoI and XhoI, to produce a plasmid encoding the β1α1/CM-2 covalent construct.

Protein expression was tested in a number of different *E. coli* strains, including a thioredoxin reductase mutant which allows disulfide bond formation in the cytoplasm (Derman et al., 1993). With such a small molecule, it became apparent that the greatest yield of material could be readily obtained from inclusion bodies, refolding the protein after solubilization and purification in buffers containing 6M urea. Accordingly, E. coli strain BL21(DE3) cells were transformed with the pET21d+construct containing the β1α1-encoding sequence. Bacteria were grown in one liter cultures to mid-logarithmic phase ($OD_{600}$=0.6-0.8) in Luria-Bertani (LB) broth containing carbenicillin (50 μg/ml) at 37° C. Recombinant protein production was induced by addition of 0.5 mM isopropyl β-D-thiogalactoside (IPTG). After incubation for 3 hours, the cells were centrifuged and stored at −80° C. before processing. All subsequent manipulations of the cells were at 4° C. The cell pellets were resuspended in ice-cold PBS, pH 7.4, and sonicated for 4×20 seconds with the cell suspension cooled in a salt/ice/water bath. The cell suspension was then centrifuged, the supernatant fraction was poured off, and the cell pellet resuspended and washed three times in PBS and then resuspended in 20 mM ethanolamine/6 M urea, pH 10, for four hours. After centrifugation, the supernatant containing the solubilized recombinant protein of interest was collected and stored at 4° C. until purification. Recombinant β1α1 construct was purified and concentrated by FPLC ion-exchange chromatography using Source 30Q anion-exchange media (Pharmacia Biotech, Piscataway, N.J.) in an XK26/20 column (Pharmacia Biotech), using a step gradient with 20 mM ethanolamine/6M urea/1M NaCl, pH 10. The homogeneous peak of the appropriate size was collected, dialyzed extensively against PBS at 4° C., pH 7.4, and concentrated by centrifugal ultrafiltration with CENTRICON-10 membranes (Amicon, Beverly, Mass.). The dialysis step, which removed the urea from the protein preparation and reduced the final pH, resulted in spontaneous re-folding of the expressed protein. For purification to homogeneity, a finish step used size exclusion chromatography on SUPERDEX 75 media (Pharmacia Biotech) in an HR16/50 column (Pharmacia Biotech). The final yield of purified protein varied between 15 and 30 mg/L of bacterial culture.

Conformational integrity of the molecules was demonstrated by the presence of a disulfide bond between cysteines β15 and β79 as detected on gel shift assay, and the authenticity of the purified protein was verified using the OX-6 monoclonal antibody specific for RT1B by Western Blotting. Circular dichroism (CD) reveals that the β1α1 molecules have highly ordered secondary structures. The empty β1α1 molecule contains approximately 30% alpha-helix, 15% beta-strand, 26% beta-turn, and 29% random coil structures. Comparison with the secondary structures of class II molecules determined by x-ray crystallography provides strong evidence that the β1α1 molecules share the beta-sheet platform/anti-parallel alpha-helix secondary structure common to all class II antigen binding domains. Furthermore, thermal denaturation revealed a high degree of cooperativity and stability of the molecules.

EXAMPLE 2

β1α1 Molecules Bind T Lymphocytes in an Epitope-Specific Manner

The β1α1 molecule produced as described above was tested for efficacy (T-cell binding specificity) using the Experimental Autoimmune Encephalomyelitis (EAE) system. EAE is a paralytic, inflammatory, and sometimes demyelinating disease mediated by CD4+ T-cells specific for central nervous system myelin components including myelin basic protein (MBP). EAE shares similar immunological abnormalities with the human demyelinating disease MS (Paterson, 1981) and has been a useful model for testing preclinical therapies. (Weiner et al., 1993; Vandenbark et al., 1989; Howell et al., 1989; Oksenberg et al., 1993; Yednock et al., 1992; Jameson et al., 1994; Vandenbark et al., 1994). In Lewis rats, the dominant encephalitogenic MBP epitope resides in the 72-89 peptide (Bourdette et al., 1991). Onset of clinical signs of EAE occurs on day 10-11, and the disease lasts four to eight days with the majority of invading T lymphocytes localized in the CNS during this period.

Test and control peptides for loading into the purified β1α1 molecules were synthesized as follows: Gp-MBP-69-89 peptide (GSLPQKSQRSQDENPVVHF) (SEQ ID NO:25), rat-MBP-69-89 peptide (GSLPQKSQRTQDENPVVHF) (SEQ ID NO:30), Gp-MBP-55-69 peptide (SGKDSHHAARTTHYG) (SEQ ID NO:26), and cardiac myosin peptide CM-2 (KLELQSALEEAEASLEH) (SEQ ID NO:27) (Wegmann et al., 1994) were prepared by solid-phase techniques (Hashim et al., 1986). The Gp-MBP peptides are numbered according to the bovine MBP sequence (Vandenbark et al., 1994; Martenson, 1984). Peptides were loaded onto β1α1 at a 1:10 protein:peptide molar ratio, by mixing at room temperature for 24 hours, after which all subsequent manipulations were performed at 4° C. Free peptide was then removed by dialysis or centrifugal ultrafiltration with CENTRICON-10 membranes, serially diluting and concentrating the solution until free peptide concentration was less than 2 μM.

T-cell lines and the A1 hybridoma were prepared as follows: short-term T-lymphocyte lines were selected with MBP-69-89 peptide from lymph node cells of naive rats or from rats immunized 12 days earlier with Gp-MBP/CFA as described by Vandenbark et al., 1985. The rat Vβ8.2+ T-cell hybridoma C14/BW12-12A1 (A1) used in this study has been described previously (Burrows et al., 1996). Briefly, the A1 hybridoma was created by fusing an encephalitogenic LEW (RT1[1]) T-cell clone specific for Gp-BP-72-89 (White et al., 1989; Gold et al, 1991) with a TCR (α/β) negative thymoma, BW5147 (Golding et al., 1985). Wells positive for cell growth were tested for IL-2 production after stimulation with antigen in the presence of APCs (irradiated Lewis rat thymocytes) and then subcloned at limiting dilution. The A1 hybridoma secretes IL-2 when stimulated in the presence of APCs with whole Gp-BP or Gp-BP-69-89 peptide, which contains the minimum epitope, MBP-72-89.

Two-color immunofluorescent analysis was performed on a FACSCAN flow cytometer instrument (Becton Dickinson, Mountain View, Calif.) using CELLQUEST software. Quadrants were defined using non-relevant isotype matched control antibodies. β1α1 molecules with and without loaded peptide were incubated with the A1 hybridoma (10 μM β1α1/peptide) for 17 hours, 4° C., washed three times, stained with fluorochrome (FITC or PE) conjugated antibodies specific for rat class II (OX6-PE), and TCR Vβ8.2 (PharMingen, San Diego, Calif.) for 15 minutes at room temperature, and analyzed by flow cytometry. The CM-2 cell line was blocked for one hour with unconjugated OX6, washed and then treated as the A1 hybridoma. Staining media was PBS, 2% fetal bovine serum, 0.01% azide.

Figure 3A:
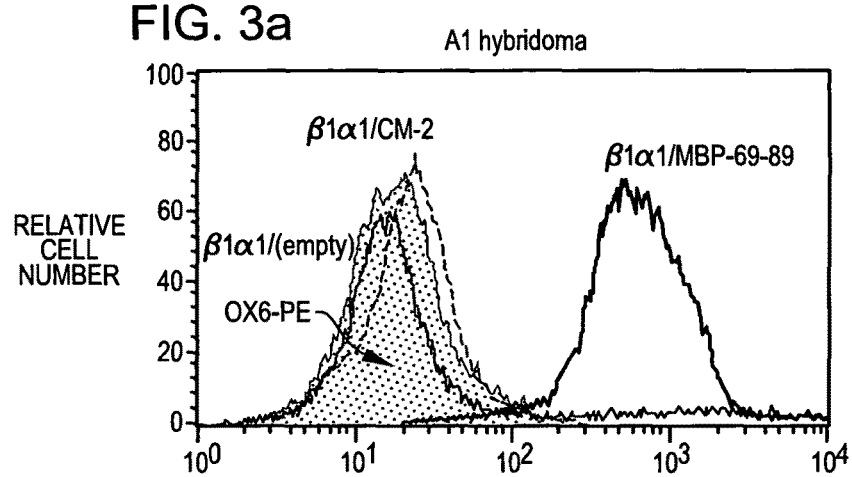
FIGS. 3A and 3B show direct detection of antigen-specific $\beta 1\alpha 1$/polypeptide molecules binding rat T-cells. The A1 T-cell hybridoma (BV8S2 TCR+) and the CM-2 cell line (BV8S2 TCR−) were incubated for 17 hours at 4 C with various $\beta 1\alpha 1$ constructs, washed, stained for 15 min. with OX6-PE ($\alpha$-RT1.B) or a PE-isotype control and then analyzed by FACS. Background expression of I-A on the CM-2 line was blocked with unlabeled OX-6.
Figure 3B:
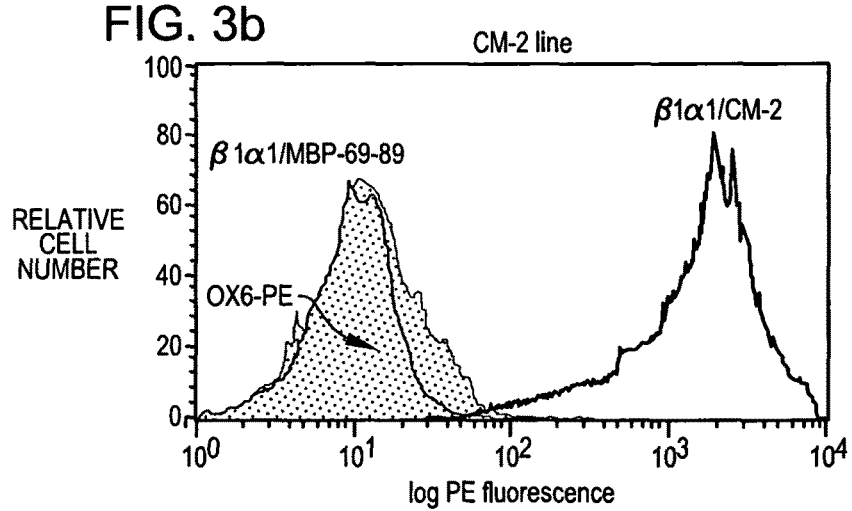

Epitope-specific binding was evaluated by loading the β1α1 molecule with various peptides and incubating β1α1/peptide complexes with the A1 hybridoma that recognizes the MBP-72-89 peptide (Burrows et al., 1997), or with a cardiac myosin CM-2-specific cell line. As is shown in FIG. 3A, the β1α1 construct loaded with MBP-69-89 peptide (β1α1/MBP-69-89) specifically bound to the A1 hybridoma, with a mean fluorescence intensity (MFI) of $0.8 \times 10^3$ Units, whereas the β1α1 construct loaded with CM-2 peptide (β1α1/CM-2) did not stain the hybridoma. Conversely, β1α1/CM-2 specifically bound to the CM-2 line, with a MFI of $1.8 \times 10^3$ Units, whereas the β1α1/MBP-69-89 complex did not stain the CM-2 line (FIG. 3B). The β1α1 construct without exogenously loaded peptide does not bind to either the A1 hybridoma (FIG. 3A) or the CM-2 line. Thus, bound epitope directed the specific binding of the β1α1/peptide complex.

EXAMPLE 3

β1α1 Molecules Conjugated with a Fluorescent Label

Figure 4:
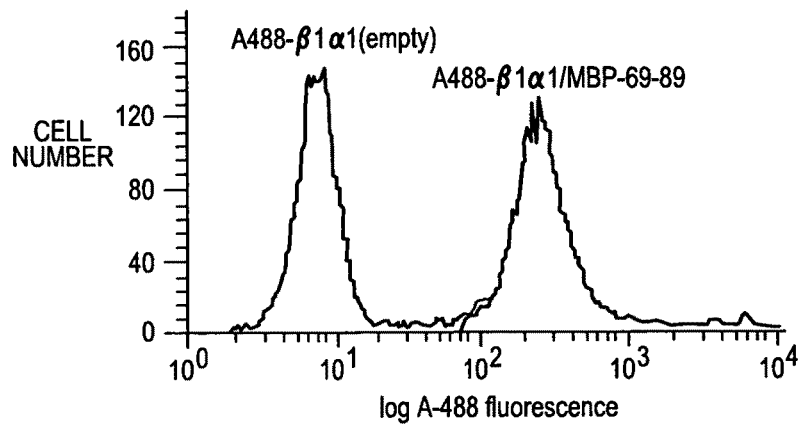
FIG. 4 is a graph illustrating binding of A488 conjugated $\beta 1\alpha 1$/polypeptide molecules to rat BV8S2 TCR. $\beta 1\alpha 1$ molecules were conjugated with Alexa-488 dye, loaded with MBP-69-89, incubated with the A1 T-cell hybridomas (BV8S2 TCR+) for 3 hours at 4° C. and then analyzed by FACS. A488-$\beta 1\alpha 1$(empty) and A488-$\beta 1\alpha 1$/MBP-69-89, as indicated.

To avoid using a secondary antibody for visualizing the interaction of β1α1/peptide molecules with TCR (such as OX-6, used above), a β1α1 molecule directly conjugated with a chromophore was produced. The Alexa-488™ dye (A488; Molecular Probes, Eugene, Oreg.) has a spectra similar to fluorescein, but produces protein conjugates that are brighter and more photo-stable than fluorescein conjugates. As is shown in FIG. 4, when loaded with MBP-69-89, A488-conjugated β1α1 (molar ratio dye/protein=1) bound to the A1 hybridomas (MCI=300 Units), whereas empty β1α1 did not.

EXAMPLE 4

β1α1 Molecules Inhibit Epitope-Specific T-Cell Proliferation In Vitro

T-cell proliferation assays were performed in 96-well plates as described previously (Vandenbark et al., 1985). Briefly, $4\times10^5$ cells in 200 µl/well (for organ stimulation assays) or $2\times10^4$ T-cells and $1\times10^6$ irradiated APCs (for short-term T-cell lines) were incubated in RPMI and 1% rat serum in triplicate wells with stimulation medium only, Con A, or antigen with or without supplemental IL-2 (20 Units/ml) at 37° C. in 7% $CO_2$. The cultures were incubated for three days, for the last 18 hr in the presence of [$^3$H]thymidine (0.5 µCi/10 µl/well). The cells were harvested onto glass fiber filters and [$^3$H]thymidine uptake was assessed by liquid scintillation. In some experiments, the T-cells were pretreated for 24 hours with β1α1 constructs (with and without loaded peptides), washed, and then used in proliferation assays with and without IL-2, as above. Mean counts per minute±SD were calculated from triplicate wells and differences between groups determined by Student's t-test.

Figure 5:
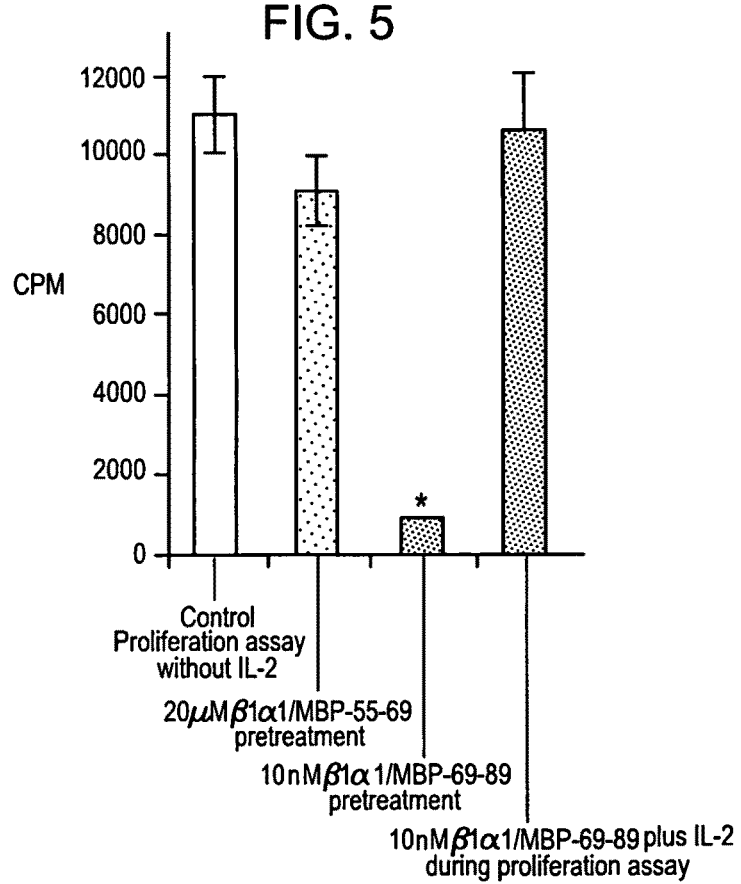
FIG. 5 is a bar graph illustrating that the $\beta 1\alpha 1$/MBP-69-89 complex blocks antigen specific proliferation in an IL-2 reversible manner. Short-term T-cell lines selected with MBP-69-89 peptide from lymph node cells from rats immunized 12 days earlier with Gp-MBP/CFA were pre-treated for 24 hours with $\beta 1\alpha 1$ constructs, washed, and then used in proliferation assays in which the cells were cultured with and without 20 Units/ml IL-2. Cells were incubated for three days, the last 18 hr in the presence of [$^3$H]thymidine (0.5 µCi/10 µl/well). Values indicated are the mean CPM±SEM. Background was 210 CPM. Column a. Control proliferation assay without IL-2. Column b. 20 µM $\beta 1\alpha 1$/MBP-55-69 pretreatment. Column c. 10 nM $\beta 1\alpha 1$/MBP-69-89 pretreatment. Column d. 10 nM $\beta 1\alpha 1$/MBP-69-89 plus IL-2 during the proliferation assay. A single representative experiment is shown; the experiment was done twice. *indicates significant ($p<0.001$) inhibition with $\beta 1\alpha 1$/MBP-69-89 versus control cultures.

A range of concentrations (10 nM to 20 µM) of peptide-loaded β1α1 complexes were pre-incubated with an MBP-69-89 specific T-cell line prior to stimulation with the MBP-69-89 peptide+APC (antigen-presenting cell). As is shown in FIG. 5, pre-treatment of MBP-69-89 specific T-cells with 10 nM β1α1/MBP-69-89 complex significantly inhibited proliferation (>90%), whereas pre-incubation with 20 µM β1α1/MBP-55-69 complex produced a nominal (27%) but insignificant inhibition. Of mechanistic importance, the response inhibited by the β1α1/MBP-69-89 complex could be fully restored by including 20 Units/ml of IL-2 during stimulation of the T-cell line (FIG. 5) suggesting that the T-cells had been rendered anergic by exposure to the β1α1/MBP-69-89 complex.

EXAMPLE 5

Design, Engineering and Production of Human Recombinant T-Cell Receptor Ligands Derived from HLA-DR2

Homology Modeling

Sequence alignment of MHC class II molecules from human, rat and mouse species provided a starting point for these studies (Burrows et al., 1999). Graphic images were generated with the program Sybyl (Tripos Associates, St. Louis, Mo.) and an O2 workstation (IRIX 6.5, Silicon Graphics, Mountain View, Calif.) using coordinates deposited in the Brookhaven Protein Data Bank (Brookhaven National Laboratories, Upton, N.Y.). Structure-based homology modeling was based on the refined crystallographic coordinates of human DR2 (Smith et al., 1998; Li et al., 2000) as well as DR1 (Brown et al., 1996; Murthy et al., 1997), murine I-$E_k$ molecules (Fremont et al., 1996), and scorpion toxins (Zhao et al., 1992; Housset et al., 1994; Zinn-Justin et al., 1996). Amino acid residues in human DR2 (PDB accession numbers 1BX2) were used. Because a number of residues were missing/not located in the crystallographic data (Smith et al., 1998), the correct side chains were inserted and the peptide backbone was modeled as a rigid body during structural refinement using local energy minimization.

Recombinant TCR Ligands (RTLs)

For production of the human RTLs, mRNA was isolated (OLIGOTEX Direct mRNA Mini Kit; Qiagen, Inc., Valencia, Calif.) from L466.1 cells grown in RPMI media. First strand cDNA synthesis was carried out using SUPERSCRIPT II Rnase H-reverse transcriptase (Gibco BRL, Grand Island, N.Y.).

Using the first strand reaction as template source, the desired regions of the DRB*1501 and DRA*0101 DNA sequences were amplified by PCR using Taq DNA polymerase (Gibco BRL, Grand Island, N.Y.), with an annealing temperature of 55° C. The primers used to generate β1 were 5'-ATTACCATGGGGGACACCCGACCACGTTT-3' (huNcoI→, SEQ ID NO: 21) and 5'-GGATGATCACATGTTCT-TCTTTGATGACTCGCCGCTGCACTGTGA-3' (hu β1α1 Lig←, SEQ ID NO: 22). The primers used to generate α1 were 5'-TCACAGTGCAGCGGCGAGTCATCAAA-GAAGAACATGTGATCATCC-3' (hu β1α1 Lig→, SEQ ID NO: 23) and 5'-TGGTGCTCGAGTTAATTGGTGATCG-GAGTATAGTTGG-3' (huXhoI←, SEQ ID NO:31).

The amplification reactions were gel purified, and the desired bands isolated (QIAQUICK Gel Extraction Kit; Qiagen, Inc., Valencia, Calif.). The overhanging tails at the 5'-end of each primer added overlapping segments and restriction sites (NcoI and XhoI) at the ends of each PCR amplification product. The two chains were linked in a two step PCR reaction. In the first step, 5 µl of each purified amplification product were added to a 50 µl primer free PCR reaction, and cycled five times at an annealing temperature of 55° C. A 50 µl reaction mix containing the huNcoI→and huXhoI←primers was then added directly to the initial reaction, and cycled 25 times at an annealing temperature of 50° C. Taq DNA Polymerase (Promega, Madison, Wis.) was used in each step. The final 100 µl reaction was gel purified, and the desired hu β1α1 amplification product isolated.

The hu β1α1 insert was ligated with the PCR 2.1 plasmid vector (TA Cloning kit, Invitrogen, Carlsbad, Calif.), and transformed into an INVa'F bacterial cloning host. PCR colony screening was used to select a single positive colony, from which plasmid DNA was isolated (QIAPREP Spin Mini Kit, Qiagen, Inc., Valencia Calif.). Plasmid was cut with NcoI and XhoI restriction enzymes (New England BioLabs Inc., Beverly, Mass.), gel purified, and the hu β1α1 DNA fragment isolated. The hu β1α1 DNA insert was ligated with NcoI/XhoI digested pET-21d(+) plasmid expression vector (Novagen, Inc., Madison, Wis.), and transformed into BL21 (DE3) expression host (Novagen, Inc., Madison, Wis.). Bacterial colonies were selected based on PCR colony and protein expression screening.

Plasmid DNA was isolated from positive colonies (QIAQUICK Gel Extraction Kit, Qiagen Inc., Valencia, Calif.) and sequenced with the T7 5'-TAATACGACTCAC-TATAGGG-3' (SEQ ID NO:32) and T7 terminator←5'-GCTAGTTATTGCTCAGCGG-3' (SEQ ID NO:33) primers. After sequence verification a single clone was selected for expression of the hu β1α1 peptide (RTL300).

A 30 amino acid huMBP-85-99/peptide linker cartridge was genetically inserted into the "empty" hu β1α1 (RTL300) coding sequence between Arg5 and Pro6. The 90 bp DNA sequence encoding peptide-Ag and linker was inserted at position 16 of the RTL300 DNA construct in a three step PCR reaction, using Taq DNA Polymerase (Promega, Madison, Wis.).

In the first step, pET-21d(+)/RTL300 plasmid was used as template in two separate PCR reactions. In the first reaction, the region from the start of the T7 priming site of the pET-21d(+) plasmid to the point of insertion within the hu β1α1 (RTL300) sequence was amplified with the following primers: 5'-GCTAGTTATTGCTCAGCGG-3'(T7→(SEQ ID NO:33), and 5'-AGGCTGCCACAGGAAACGTGGGC-CTCCACCTCCAGAGCCTCGGGGCACTAGT GAGC-CTCCACCTCCACGCGGGGTAACGAT-GTTTTTGAAGAAGTGAACAACCGGG TTTTCTCGGGTGTCCCCCATGGTAAT-3' (huMBP-85-99Lig←(SEQ ID NO:34).

In the second reaction, the region from the point of insertion within the hu β1α1 (RTL300) sequence to the end of the T7-terminator priming site was amplified with the following primers: 5'-CCACGTTTCCTGTGGCAGCC-3' (huMBP-85-99Lig→(SEQ ID NO:35), and 5'-GCTAGTTATTGCT-CAGCGG-3' (T7terminator←(SEQ ID NO:33). Each reaction was gel purified, and the desired bands isolated.

In the second step, 5 µl of each purified amplification product was added to a primer free 'anneal-extend' PCR reaction mix, and cycled for 5 times at an annealing temperature of 50° C. In the third step, a 50 µl PCR 'amplification mix' containing the 5'-TAATACGACTCACTATAGGG-3 (T7→(SEQ ID NO:32) and 5'-GCTAGTTATTGCT-CAGCGG-3' (T7terminator←(SEQ ID NO:33) primers was then added directly to the 'anneal-extend' reaction, and the entire volume cycled 25 times using a 55° C. annealing temperature. The non-complimentary 5' tail of the huMBP-85-99lig←primer included DNA encoding the entire peptide/linker cartridge, and the region down-stream from the point of insertion.

The resulting amplification product hybridized easily with the PCR product produced in the second reaction, via the complimentary 3' and 5' ends of each respectively. DNA polymerase then extended from the 3'-end of each primer, creating the full length hu β1α1/huMBP-85-99 (RTL301) construct, which acted as template in the 'amplification' step. The reaction was purified using agarose gel electrophoresis, and the desired hu β1α1/huMBP-85-99 (RTL301) band isolated. The PCR product was then cut with NcoI and XhoI restriction enzymes, gel purified, ligated with a similarly cut pET-21d(+) plasmid expression vector, and transformed into a BL21(DE3) E. coli expression host. Transformants were screened for protein expression and the presence of the desired insert with a PCR colony screen. Plasmid DNA was isolated from several positive clones and sequenced. A single positive clone was selected for expression of the hu β1α1/huMBP-85-99 peptide (RTL301).

Repeated sequence analysis of pET-21d(+)/RTL300 and pET-21d(+)/RTL301 plasmid DNA constructs revealed the same thymine to cytosine single base pair deviation at position 358 and position 458 (RTL300 and RTL301 numbering, respectively), than had been reported previously for HLA-DRA*0101 (Genebank accession #M60333), which resulted in an F150L mutation in the RTL300 and RTL301 molecules (RTL301 numbering).

Site directed mutagenesis was used to revert the sequence to the Genebank #M60333 sequence. Two PCR reactions were performed using the pET-21d(+)/RTL300 and pET-21d (+)/RTL301 plasmids as template. For RTL300 the primers: 5'-TAATACGACTCACTATAGGG-3' (T7→(SEQ ID NO:32), and 5'-TCAAAGTCAAACATAAACTCGC-3' (huBA-F150L←(SEQ ID NO:36) were used.

For RTL301 the primers: 5'-GCGAGTTTAT-GTTTGACTTTGA-3' (huBA-F150L→(SEQ ID NO:37), and 5'-GCTAGTTATTGCTCAGCGG-3' (T7terminator←(SEQ ID NO:33) were used.

The two resulting amplification products were gel purified and isolated (QIAQUICK gel extraction kit, Qiagen, Valencia, Calif.), annealed, and amplified as described earlier, based on the complimentary 3' and 5' ends of each of the PCR products. The final amplification reactions were gel purified, and the desired PCR products isolated. The NcoI and XhoI restriction sites flanking each were then used to subclone the RTL DNA constructs into fresh pET-21d(+) plasmid for transformation into BL21(DE3) competent cells and plasmid sequence verification. Positive clones were chosen for expression of the "empty" HLA-DR2 β1α1-derived RTL302 molecule and the MBP-85-99-peptide coupled RTL303 molecule (FIG. 2).

Expression and In Vitro Folding of the RTL Constructs

E. coli strain BL21(DE3) cells were transformed with the pET21d+/RTL vectors. Bacteria were grown in one liter cultures to mid-logarithmic phase ($OD_{600}$=0.6-0.8) in Luria-Bertani (LB) broth containing carbenicillin (50 µg/ml) at 37 ☐C. Recombinant protein production was induced by addition of 0.5 mM isopropyl B-D-thiogalactoside (IPTG). After incubation for 3 hours, the cells were collected by centrifugation and stored at −80° C. before processing. All subsequent manipulations of the cells were at 4° C. The cell pellets were resuspended in ice-cold PBS, pH 7.4, and sonicated for 4×20 seconds with the cell suspension cooled in a salt/ice/water bath. The cell suspension was then centrifuged, the supernatant fraction was poured off, the cell pellet resuspended and washed three times in PBS and then resuspended in 20 mM ethanolamine/6 M urea, pH 10, for four hours. After centrifugation, the supernatant containing the solubilized recombinant protein of interest was collected and stored at 4° C. until purification.

The recombinant proteins of interest were purified and concentrated by FPLC ion-exchange chromatography using Source 30Q anion-exchange media (Pharmacia Biotech, Piscataway, N.J.) in an XK26/20 column (Pharmacia Biotech), using a step gradient with 20 mM ethanolamine/6M urea/1M NaCl, pH 10. The proteins were dialyzed against 20 mM ethanolamine, pH 10.0, which removed the urea and allowed refolding of the recombinant protein. This step was critical. Basic buffers were required for all of the RTL molecular constructs to fold correctly, after which they could be dialyzed into PBS at 4° C. and concentrated by centrifugal ultrafiltration with CENTRICON-10 membranes (Amicon, Beverly, Mass.). For purification to homogeneity, a finish step was included using size exclusion chromatography on SUPERDEX 75 media (Pharmacia Biotech) in an HR16/50 column (Pharmacia Biotech). The final yield of purified protein varied between 15 and 30 mg/L of bacterial culture.

Circular Dichroism and Thermal Transition Measurements

CD spectra were recorded on a JASCO J-500A spectropolarimeter with an IF-500 digital interface and thermostatically controlled quartz cells (Hellma, Mulheim, Germany) of 2, 1, 0.5, 0.1 and 0.05 mm path length depending on peptide concentration. Data are presented as mean residue weight ellipticities. Calibration was regularly performed with (+)-10-camphorsulfonic acid (Sigma) to molar ellipticities of 7780 and −16,160 deg. cm$^2$/dmol at 290.5 and 192.5 nm, respectively (Chen et al., 1977). In general, spectra were the average of four to five scans from 260 to 180 nm recorded at a scanning rate of 5 nm/min. with a four second time constant. Data were collected at 0.1 nm intervals. Spectra were averaged and smoothed using the built-in algorithms of the Jasco program and buffer baselines were subtracted. Secondary structure was estimated with the program CONTIN (Provencher et al., 1981). Thermal transition curves were recorded at a fixed wavelength of 222 nm. Temperature gradients from 5 to 90 or 95° C. were generated with a programmer controlled circulating water bath (Lauda PM350 and RCS20D). Heating and cooling rates were between 12 and 18° C./h. Temperature was monitored in the cell with a thermistor and digital thermometer (Omega Engineering), recorded and digitized on an XY plotter (HP7090A, Hewlett Packard), and stored on disk. The transition curves were normalized to the fraction of the peptide folded (F) using the standard equation: $F=([U]-[U]u)/([U]n-[U]u)$, where $[U]n$ and $[U]u$ represent the ellipticity values for the fully folded and fully unfolded species, respectively, and $[U]$ is the observed ellipticity at 222 nm.

EXAMPLE 6

RTL Homology Modeling/Structure-Function Analysis

Previous protein engineering studies have described recombinant T-cell receptor ligands (RTLs) derived from the α-1 and α-1 domains of rat MHC class II RT1.B (Burrows et al., 1999). Homology modeling studies of the heterodimeric MHC class II protein HLA-DR2, and specifically, the α-1 and β-1 segments of the molecule that comprise the antigen binding domain, were conducted based on the crystal structures of human DR (Smith et al., 1998; Li et al., 2000; Brown et al., 1993; Murthy et al., 1997). In the modeling studies described herein, three facets of the source proteins organization and structure were focused on: (1) The interface between the membrane-proximal surface of the β-sheet platform and the membrane distal surfaces of the α-2 and β-2 Ig-fold domains, (2) the internal hydrogen bonding of the α-1 and β-1 domains that comprise the peptide binding/TCR recognition domain, and (3), the surface of the RTLs that was expected to interact with the TCR.

Side-chain densities for regions that correspond to primary sequence between the β-1 and β-2 domains of human DR and murine I-E$^K$ showed evidence of disorder in the crystal structures (Smith et al., 1998; Li et al., 2000; Brown et al., 1993; Murthy et al., 1997; Fremont et al., 1996), supporting the notion that these serve as linker regions between the two domains with residue side-chains having a high degree of freedom of movement in solution. High resolution crystals of MHC class II DR1 and DR2 (Smith et al., 1998; Li et al., 2000; Brown et al., 1993; Murthy et al., 1997) contained a large number of water molecules between the membrane proximal surface of the β-sheet platform and the membrane distal surfaces of the α2 and β21 g-fold domains. The surface area of interaction between domains was quantified by creating a molecular surface for the β1α1 and α2β2 Ig-fold domains with an algorithm developed by Michael Connolly (Connolly, 1986) using the crystallographic coordinates for human DR2 available from the Brookhaven Protein Data Base (1BX2). In this algorithm the molecular surfaces are represented by "critical points" describing holes and knobs. Holes (maxima of a shape function) are matched with knobs (minima). The surface areas of the α1β1 and α2β2-Ig-fold domains were calculated independently, defined by accessibility to a probe of radius 0.14 nm, about the size of a water molecule. The surface area of the MHC class II αβ-heterodimer was 160 nm$^2$, while that of the RTL construct was 80 nm 2 and the α2β2-Ig-fold domains was 90 nm$^2$. Approximately 15 nm$^2$ (19%) of the RTL surface was buried by the interface with the Ig-fold domains in the MHC class II αβ-heterodimer.

Human, rat and murine MHC class II alpha chains share 30% identity and the beta chains share 35% identity. The backbone traces of the structures solved using X-ray crystallography showed strong homology when superimposed, implying an evolutionarily conserved structural motif. The variability between the molecules is primarily within the residues that delineate the peptide-binding groove, with side-chain substitutions designed to allow differential antigenic-peptide binding. The α1 and β1 domains of HLA-DR showed an extensive hydrogen-bonding network and a tightly packed and buried hydrophobic core. This tertiary structure appears similar to the molecular interactions that provide structural integrity and thermodynamic stability to the alpha-helix/beta-sheet scaffold characteristic of scorpion toxins (Zhao et al., 1992; Housset et al., 1994; Zinn-Justin et al., 1996). The β1-domain of MHC class II molecules contains a disulfide bond that covalently couples the carboxyl-terminal end to the first strand of the anti-parallel β-sheet platform contributed by the β1-domain. This structure is conserved among MHC class II molecules from rat, human and mouse, and is conserved within the α2 domain of MHC class I. It appears to serve a critical function, acting as a "linchpin" that allows primary sequence diversity in the molecule while maintaining its tertiary structure. Additionally, a "network" of conserved aromatic side chains (Burrows, et al, 1999) appear to stabilize the RTLs. The studies described herein demonstrate that the antigen binding domain remains stable in the absence of the α2 and β2 Ig-fold domains.

EXAMPLE 7

Expression and Production of RTLs

Figure 9:
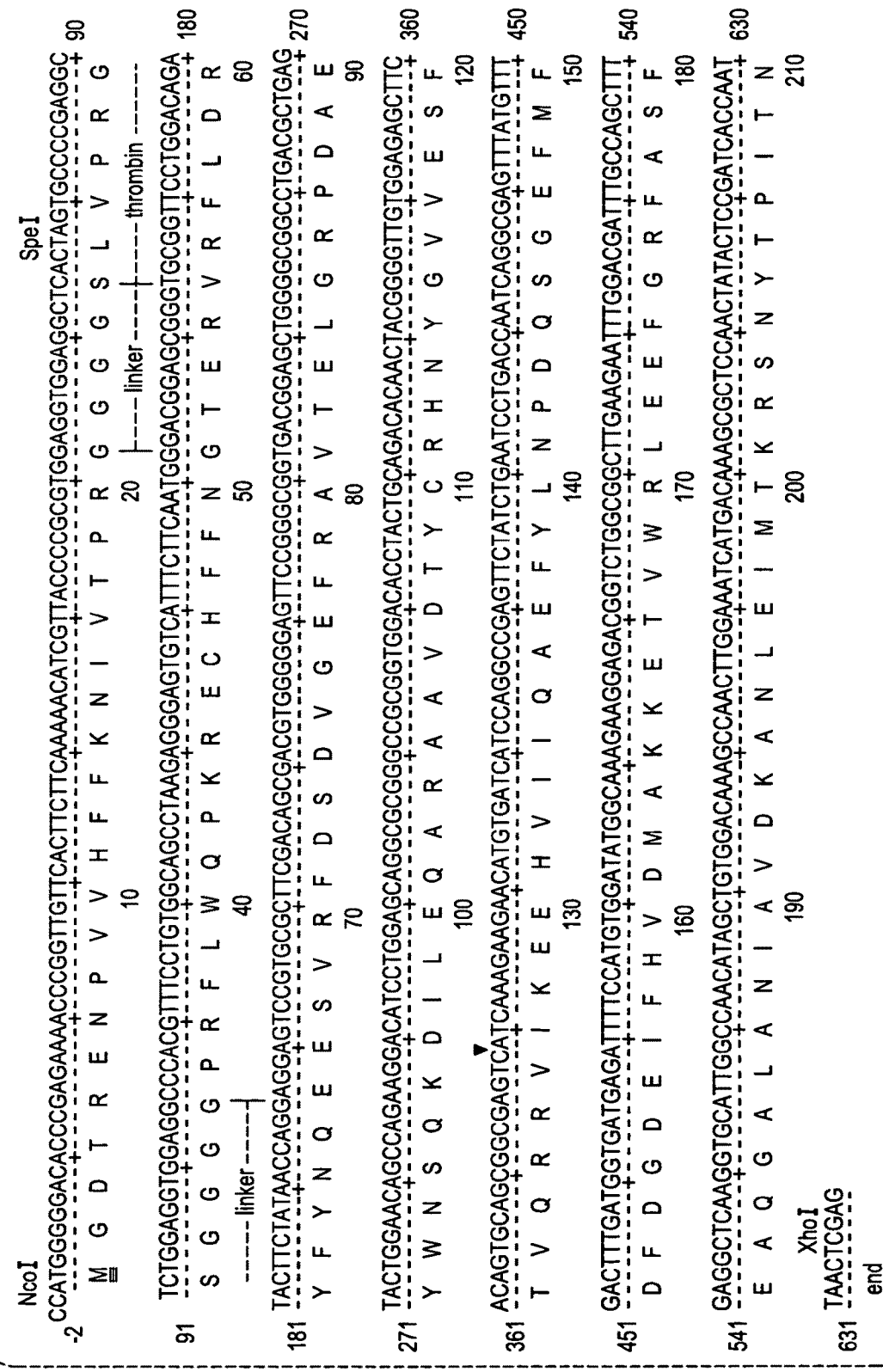
FIG. 9 is the nucleotide (SEQ ID NO: 93) and protein sequence (SEQ ID NO: 94) of human HLA-DR2-derived RTL303. RTL303 was derived from sequences encoding the β-1 and α-1 domains of HLA-DR2 (human DRB1*1501/DRA*0101) and sequence encoding the human MBP85-99 peptide. Unique NcoI, SpeI and XhoI restriction sites are in bold. The end of the β-1 domain and start of the α-1 domain are indicated by an arrow. RTL303 contains an in-frame peptide/linker insertion encoding the human MBP85-99 peptide (bold), a flexible linker with an embedded thrombin cleavage site, and a unique SpeI restriction site which can be used for rapidly exchanging the encoded amino-terminal peptide. RTL301 is identical to RTL303 except for a single point mutation resulting in an F150L substitution. Two additional proteins used in this study, RTL300 and RTL302, are "empty" versions of RTL301 and RTL303, respectively. These molecules lack the peptide/linker insertion (residues 16-115). Codon usage for glycines 32 and 51 have been changed from the native sequence for increased levels of protein expression in E. coli.
Figure 10A:
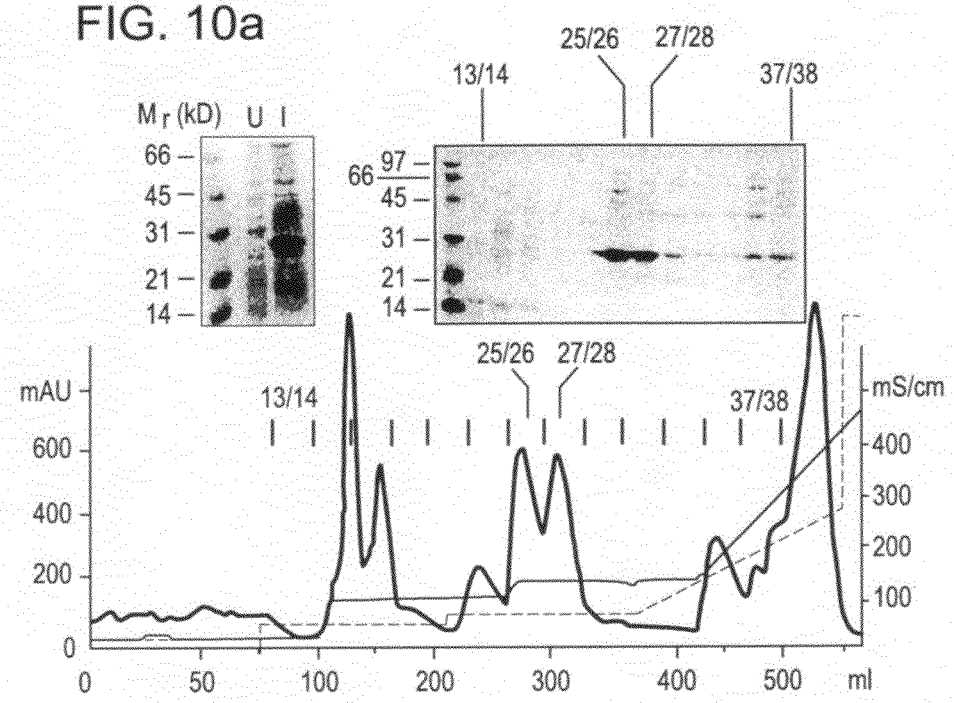
FIG. 10(A) is the ion exchange FPLC of RTL303. Insert left: Mr, molecular weight standards; U, uninduced cells; I, induced cells, showing high-level expression of RTL303. Insert Right: Fractions 25-28 contain partially purified RTL303.
Figure 10B:
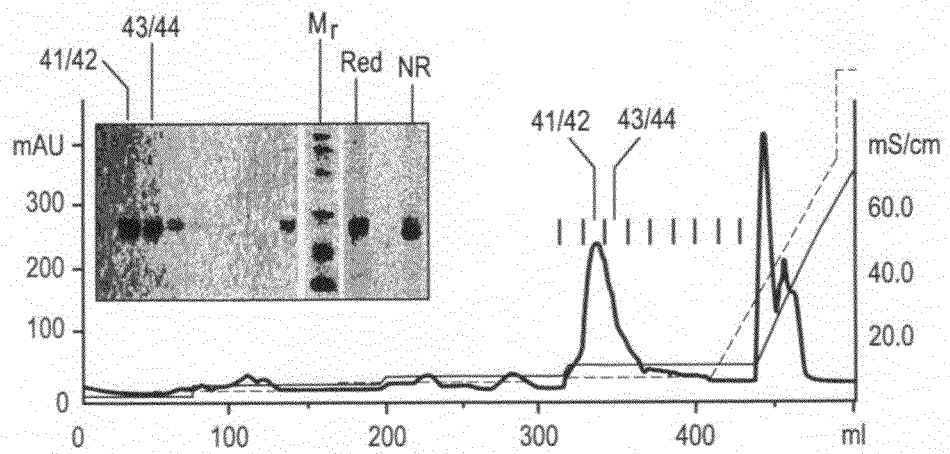
FIG. 10(B) is size-exclusion chromatography of RTL303. Insert: fractions 41-44, containing purified RTL303; Mr, molecular weight standards; Red, reduced RTL303; NR, non-reduced RTL303.

Novel genes were constructed by splicing sequence encoding the amino terminus of HLA-DR2α-1 domain to sequence encoding the carboxyl terminus of the □-1 domain. The nomenclature RTL ("recombinant TCR ligand") was used for proteins with this design (see U.S. Pat. No. 6,270,772). In the studies described herein, experiments are presented that used the "empty" RTL with the native sequence (RTL302), a covalent construct that contained the human MBP-85-99 antigenic peptide (RTL303), and versions of these molecules (RTL300, "empty"; RTL301, containing MBP-85-99) that had a single phenylalanine to leucine alteration (F150L, RTL303 numbering) that eliminated biological activity (See FIG. 9). Earlier work had demonstrated that the greatest yield of material could be readily obtained from bacterial inclusion bodies, refolding the protein after solubilization and purification in buffers containing 6M urea (Burrows et al., 1999). Purification of the RTLs was straightforward and included ion exchange chromatography followed by size exclusion chromatography (FIG. 10).

After purification, the protein was dialyzed against 20 mM ethanolamine, pH 10.0, which removed the urea and allowed refolding of the recombinant protein. This step was critical. Basic buffers were required for all of the RTL molecular constructs to fold correctly, after which they could be dialyzed into PBS at 4° C. for in vivo studies. The final yields of "empty" and antigenic peptide-coupled RTLs was approximately 15-30 mg/liter culture.

EXAMPLE 8

Biochemical Characterization and Structural Analysis of Human RTLs

Figure 11:
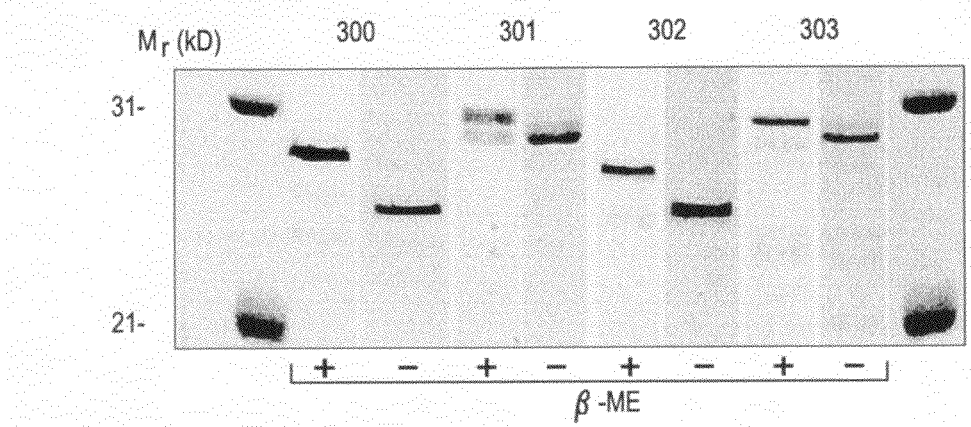
FIG. 11 is a digital image of a Western blot demonstrating purified and refolded DR2-derived RTLs have a native disulfide bond. Samples of RTLs were boiled for 5 minutes in Laemmli sample buffer with or without the reducing agent β-mercaptoethanol (β-ME), and then analyzed by SDS-PAGE (12%). Non-reduced RTLs (− lane) have a smaller apparent molecular weight than reduced RTLs (+ lane), indicating the presence of a disulfide bond. First and last lanes show the molecular weight standards carbonic anhydrase (31 kD) and soybean trypsin inhibitor (21.5 kD). RTLs (+/−β-ME), as indicated.

Oxidation of cysteines 46 and 110 (RTL303 amino acid numbering, corresponding to DR2 beta chain residues 15 and 79) to reconstitute the native disulfide bond was demonstrated by a gel shift assay (FIG. 11), in which identical samples with or without the reducing agent β-mercaptoeth-anol (β-ME) were boiled 5 minutes prior to SDS-PAGE. In the absence of β-ME disulfide bonds are retained and proteins typically demonstrate a higher mobility during electrophoresis through acrylamide gels due to their more compact structure. Representative examples of this analysis are shown for the "empty" RTL300 and RTL302, and the MBP-coupled RTL301 and RTL303 molecules (FIG. 11). All of the RTL molecules produced showed this pattern, indicating presence of the native conserved disulfide bond. These data represent a confirmation of the conformational integrity of the molecules.

Figure 12:
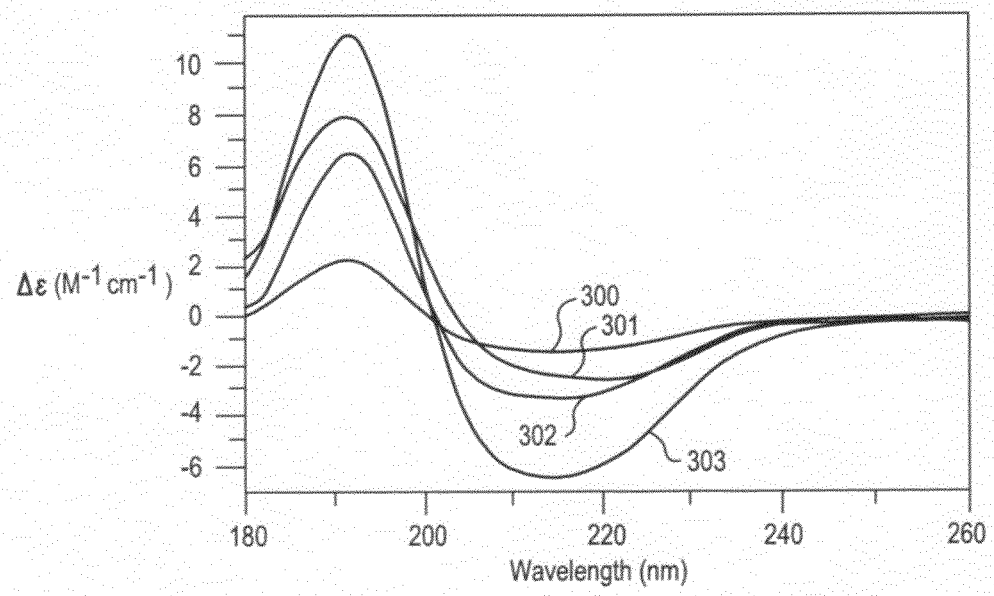
FIG. 12 is a digital image of circular dichroism showing that DR2-derived RTLs have highly ordered structures. CD measurements were performed at 20 □C on a Jasco J-500 instrument using 0.1 mm cells from 260 to 180 nm. Concentration values for each protein solution were determined by amino acid analysis. Buffer, 50 mM potassium phosphate, 50 mM sodium fluoride, pH 7.8. Analysis of the secondary structure was performed using the variable selection method.

Circular dichroism (CD) demonstrated the highly ordered secondary structures of RTL 302 and RTL303 (FIG. 12; Table 1). RTL303 contained approximately 38% alpha-helix, 33% beta-strand, and 29% random coil structures. Comparison with the secondary structures of class II molecules determined by x-ray crystallography (Smith et al., 1998; Li et al., 2000; Brown et al., 1993; Murthy et al., 1997; Fremont et al., 1996) provided strong evidence that RTL303 shared the beta-sheet platform/anti-parallel alpha-helix secondary structure common to all class II antigen binding domains (Table 1, FIG. 12).

Figure 13:
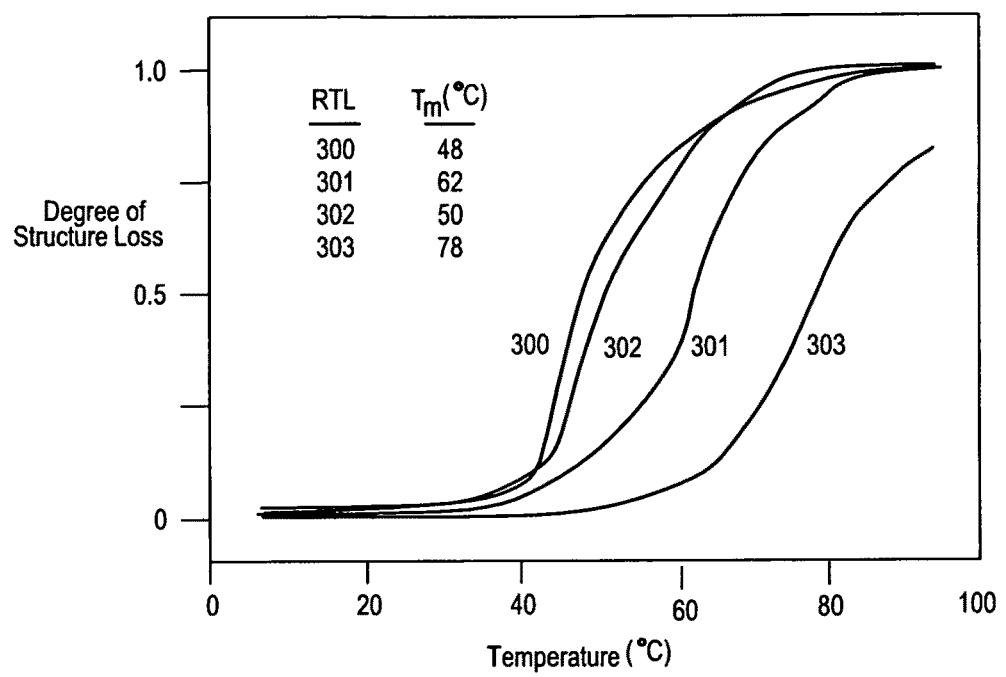
FIG. 13 is a graph of experiments that demonstrate the high degree of cooperativity and stability of DR2-derived RTLs subjected to thermal denaturation. CD spectra were monitored at 222 nm as a function of temperature. The heating rate was 10 □C/hr. The graph charts the percent of unfolding as a function of temperature. 1.0 corresponds to the completely unfolded structure.

Structure loss upon thermal denaturation indicated that the RTLs used in this study are cooperatively folded (FIG. 13). The temperature ($T_m$) at which half of the structure is lost for RTL303 is approximately 78° C., which is similar to that determined for the rat RT1.B MHC class II-derived RTL201 (Burrows et al., 1999). RTL302, which does not contain the covalently coupled Ag-peptide, showed a 32% decease in alpha-helical content compared to RTL303 (Table 1). This decrease in helix content was accompanied by a decrease in thermal stability of 36% (28° C.) compared to RTL303, demonstrating the stabilization of the RTL molecule, and by inference, the antigen-presentation platform of MHC class II molecules, that accompanies peptide binding. Again, this trend is similar to what has been observed using rat RTL molecules (Burrows et al., 1999), although the stabilization contributed by the covalently coupled peptide is approximately 3-fold greater for the human RTLs compared to rat RTLs.

Figure 14:
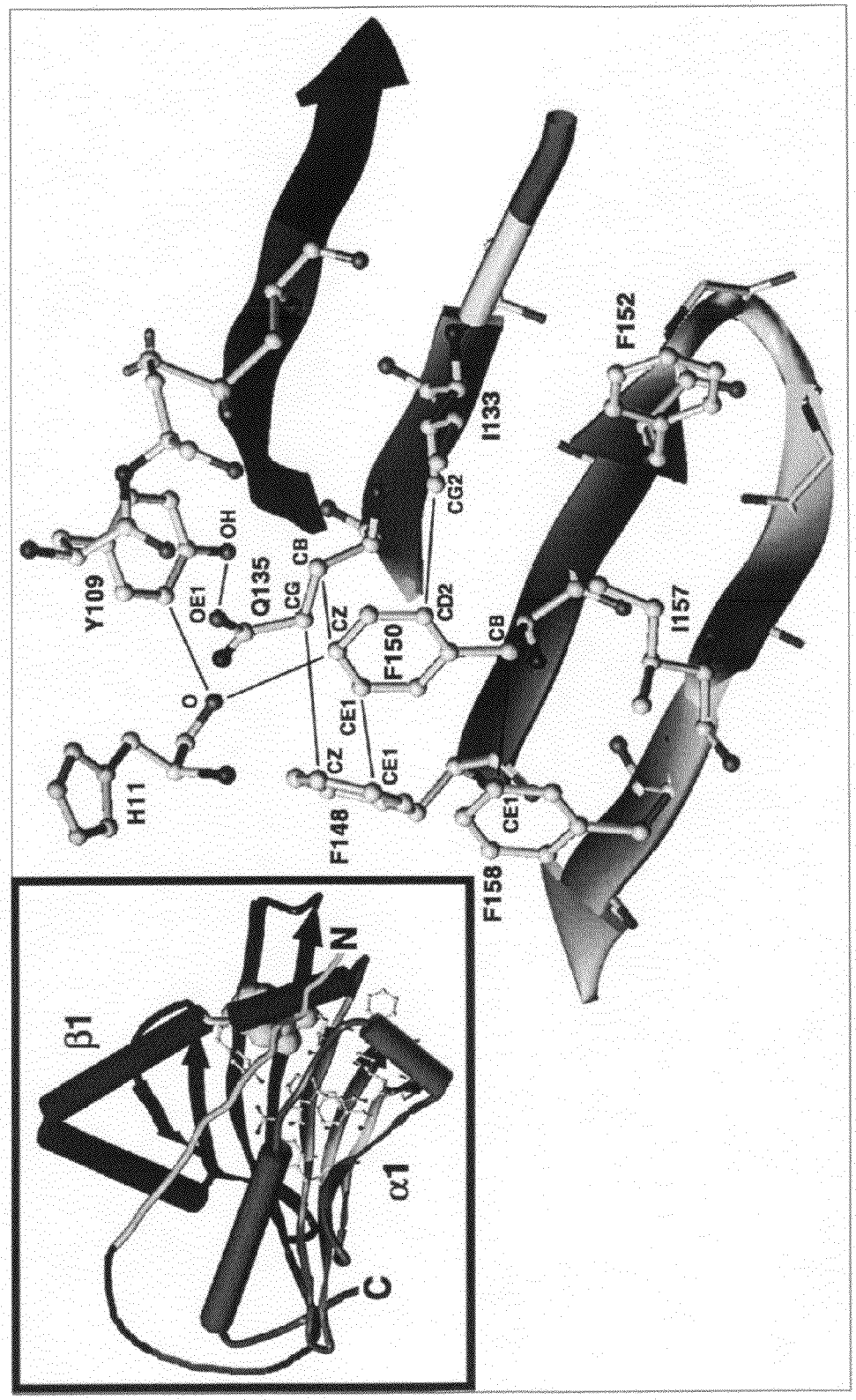
FIG. 14 is a schematic diagram of interactions of atoms within 4 Å of residue F150. Distances were calculated using coordinates from 1BX2. Inset: the location of residue F150 within the RTL303 molecule.

The F150L modified RTL301 molecule showed a 48% decrease in alpha-helical content (Table 1) and a 21% (16° C.) decrease in thermal stability compared to RTL303. RTL300, which had the F150L modification and lacked the covalently-coupled Ag-peptide, showed cooperativity during structure loss in thermal denaturation studies, but was extremely unstable ($T_m$=48° C.) relative to RTL302 and RTL303, and the secondary structure could not be determined from the CD data (FIGS. 16, 17; Table 1). An explanation for the thermal stability data comes from molecular modeling studies using the coordinates from DR2a and DR2b MHC class II crystal structures (PDB accession codes 1 FV1 and 1BX2; Smith et al., 1998; Li et al., 2000). These studies demonstrated that F150 is a central residue within the hydrophobic core of the RTL structure (FIG. 14), part of a conserved network of aromatic side chains that appears to stabilize the secondary structure motif that is completely conserved in human class II molecules and is highly conserved between rat, mouse and human MHC class II.

TABLE 2

Interactions of residues within 4Å of F150[a]

| atom 1 ID | atom 2 ID | distance (Å) |
|---|---|---|
| I133.CG2 (A: I7)[b] | F150.CD2 (A: F24) | 3.75 |
| I133.CG2 | F150.CE2 | 3.75 |
| Q135.CB (A: Q9) | F150.CE1 | 3.65 |
| Q135.CG | F148.CZ (A: F22) | 4.06 |
| Q135.OE1 | Y109.OH (B: Y78) | 2.49 |
| F148.CE1 | F150.CE1 | 4.07 |
| F150.CB | F158.CE1 (A: F32) | 3.64 |
| F150.CZ | H11.O (C: H90) | 3.77 |
| Y109.CE1 | H11.O | 3.12 |

[a]F150 (RTL303 numbering) is F24 of the beta chain of DR2. The distances were calculated using coordinates from 1BX2 (Smith et al., 1998).
[b]The residue are numbered as shown in FIG. 7, with the 1BX2 residue number in parenthesis. For example, F150.CE2 is equivalent to B: F24.CE2; atom CE2 of residue F24 on chain B of the heterodimeric 1BX2 crystal structure. Chain C is the bound antigenic peptide.

TABLE 1

Secondary structure analysis of RTLs and MHC class II β-1/α-1 domains.

| Molecule | description | α-helix | β- | othe | total | Reference |
|---|---|---|---|---|---|---|
| RTL201 | RT1.B β1α1/Gp-MBP72- | 0.28 | 0.39 | 0.33 | 1.0 | Burrows et al., |
| RTL300 | DR2 β1α1(F150L)a | — | — | — | ND[B] | Chang et al., 2001 |
| RTL301 | DR2 β1α1/hu-MBP85-99 | 0.20 | 0.35 | 0.46 | 1.0 | Chang et al., 2001 |
| RTL302 | DR2 β1α1(empty) | 0.26 | 0.31 | 0.43 | 1.0 | Chang et al., 2001 |
| RTL303 | DR2 β1α1/hu-MBP85-99 | 0.38 | 0.33 | 0.29 | 1.0 | Chang et al., 2001 |
| 1BX2 | DR2 (DRA*0101, | 0.32 | 0.37 | 0.31 | 1.0 | Smith et al., 1998 |
| 1AQD | DR1 (DRA*0101, DRB1 | 0.32 | 0.37 | 0.31 | 1.0 | Murthy et al., 1997 |
| 1IAK | murine I-A$^k$ | 0.34 | 0.37 | 0.29 | 1.0 | Fremont et al., |
| 1IEA | murine I-E$^k$ | 0.27 | 0.31 | 0.42 | 1.0 | Fremont et al., | aF150L based on RTL303 numbering (See FIG. 2).
[B]RTL300 CD data could not be fit using the variable selection method.
c β-sheet includes parallel and anti-parallel β-sheet and β-turn structures.

The motif couples three anti-parallel beta-sheet strands to a central unstructured stretch of polypeptide between two alpha-helical segments of the α-1 domain. The structural motif is located within the α-1 domain and "caps" the α-1 domain side at the end of the peptide binding groove where the amino-terminus of the bound Ag-peptide emerges.

Thus, soluble single-chain RTL molecules have been constructed from the antigen-binding β1 and α1 domains of human MHC class II molecule DR2. The RTLs lack the α2 domain, the β2 domain known to bind to CD4, and the transmembrane and intra-cytoplasmic sequences. The reduced size of the RTLs gave us the ability to express and purify the molecules from bacterial inclusion bodies in high yield (15-30 mg/L cell culture). The RTLs refolded upon dialysis into PBS and had excellent solubility in aqueous buffers.

Figure 8:
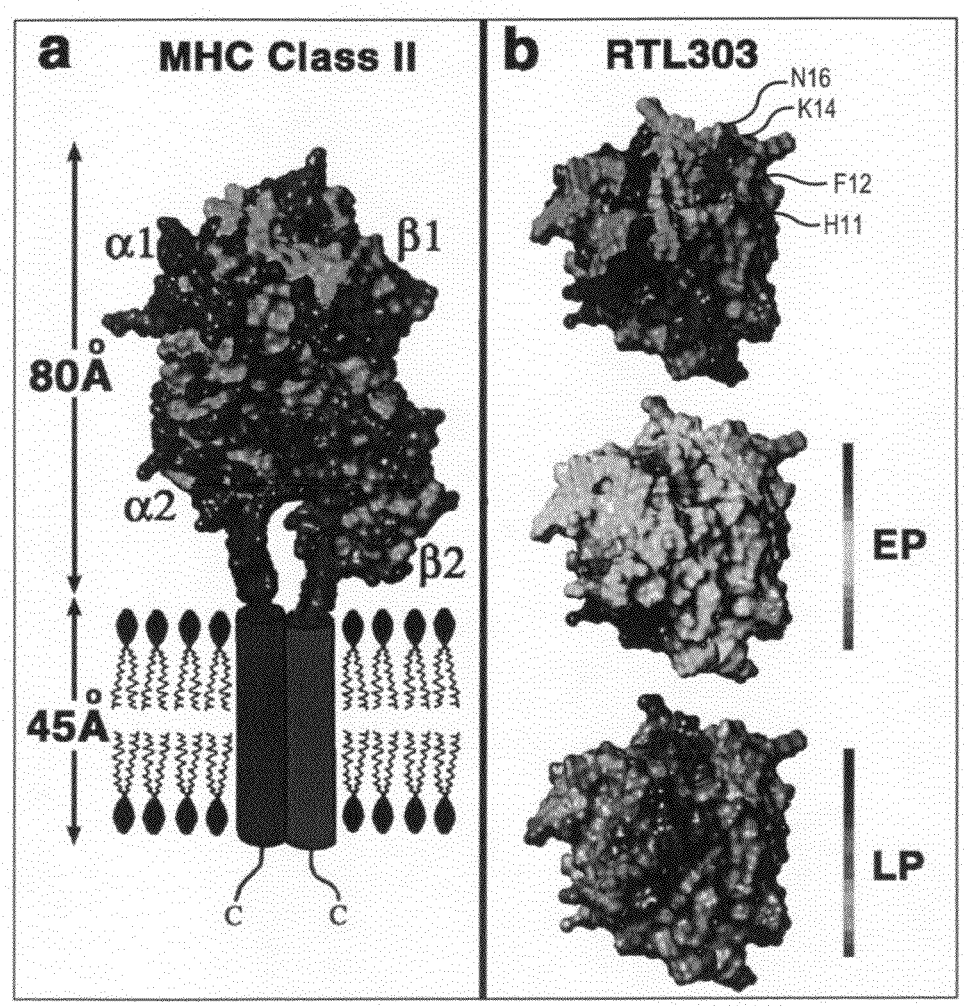
FIG. 8 shows schematic models of human HLA-DR2-derived recombinant T-cell receptor ligands (RTLs).

The data presented herein demonstrate clearly that the human DR2-derived RTL302 and RTL303 retain structural and conformational integrity consistent with crystallographic data regarding the native MHC class II structure. MHC class II molecules form a stable heterodimer that binds and presents antigenic peptides to the appropriate T-cell receptor (FIG. 8). While there is substantial structural and theoretical evidence to support this model (Brown et al., 1993; Murthy et al., 1997; Fremont et al., 1996; Ploegh et al., 1993; Schafer et al., 1995), the precise role that contextual information provided by the MHC class II molecule plays in antigen presentation, T-cell recognition and T-cell activation remains to be elucidated. The approach described herein used rational protein engineering to combine structural information from X-ray crystallographic data with recombinant DNA technology to design and produce single chain TCR ligands based on the natural MHC class II peptide binding/T-cell recognition domain. In the native molecule this domain is derived from portions of the alpha and beta polypeptide chains which fold together to form a tertiary structure, most simply described as a beta-sheet platform upon which two anti-parallel helical segments interact to form an antigen-binding groove. A similar structure is formed by a single exon encoding the α-1 and α-2 domains of MHC class I molecules, with the exception that the peptide-binding groove of MHC class II is open-ended, allowing the engineering of single-exon constructs that incorporate the peptide binding/T-cell recognition domain and an antigenic peptide ligand (Kozono et al., 1994).

From a drug engineering and design perspective, this prototypic molecule represents a major breakthrough. Development of the human RTL molecules described herein separates the peptide binding (1β1 domains from the platform 2β2 Ig-fold domains) allowing studies of their biochemical and biological properties independently, both from each other and from the vast network of information exchange that occurs at the cell surface interface between APC and T-cell during MHC/peptide engagement with the T-cell receptor. Development of human RTL molecules described herein allows careful evaluation of the specific role played by a natural TCR ligand independent from the platform (2β2 Ig-fold domains of MHC class II).

When incubated with peptide specific Th1 cell clones in the absence of APC or costimulatory molecules, RTL303 initiated a subset of quantifiable signal transduction processes through the TCR. These included rapid ζ chain phosphorylation, calcium mobilization, and reduced ERK kinase activity, as well as IL-10 production. Addition of RTL303 alone did not induce proliferation. T-cell clones pretreated with cognate RTLs prior to restimulation with APC and peptide had a diminished capacity to proliferate and secrete IL-2, and secreted less IFN-γ (Importantly, IL-10 production persisted (see below)). These data elucidate for the first time the early signaling events induced by direct engagement of the external TCR interface, in the absence of signals supplied by co-activation molecules.

Modeling studies have highlighted a number of interesting features regarding the interface between the β1α1 and α2β2-Ig-fold domains. The α1 and β1 domains showed an extensive hydrogen-bonding network and a tightly packed and buried hydrophobic core. The RTL molecules composed of the α1 and β1 domains may have the ability to move as a single entity independent from the α2β2-Ig-fold "platform." Flexibility at this interface may be required for freedom of movement within the α1 and β1 domains for binding/exchange of peptide antigen. Alternatively or in combination, this interaction surface may play a potential role in communicating information about the MHC class II/peptide molecules interaction with TCRs back to the APC.

Critical analysis of the primary sequence of amino acid residues within two helical turns (7.2 residues) of the conserved cysteine 110 (RTL303 numbering) as well as analysis of the β-sheet platform around the conserved cysteine 46 (RTL303 numbering) reveal a number of interesting features of the molecule, the most significant being very high diversity along the peptide-binding groove face of the helix and β-sheet platform. Interestingly, the surface exposed face of the helix composed of residues L99, E100, R103, A104, D107, R111, and Y114 (FIG. 1) is conserved in all rat, human and mouse class II and may serve an as yet undefined function.

Cooperative processes are extremely common in biochemical systems. The reversible transformation between an alpha-helix and a random coil conformation is easily quantified by circular dicroism. Once a helix is started, additional turns form rapidly until the helix is complete. Likewise, once it begins to unfold it tends to unfold completely. A normalized plot of absorption of circularly polarized light at 222 nm versus temperature (melting curve) was used to define a critical melting temperature ($T_m$) for each RTL molecule. The melting temperature was defined as the midpoint of the decrease in structure loss calculated from the loss of absorption of polarized light at 222 nm. Because of their size and biochemical stability, RTLs will serve as a platform technology for development of protein drugs with engineered specificity for particular target cells and tissues.

EXAMPLE 9

TCR Signaling

Development of a minimal TCR ligand allows study of TCR signaling in primary T-cells and T-cell clones in the absence of costimulatory interactions that complicate dissection of the information cascade initiated by MHC/peptide binding to the TCR α and β chains. A minimum "T-cell receptor ligand" conceptually consists of the surface of an MHC molecule that interacts with the TCR and the 3 to 5 amino acid residues within a peptide bound in the groove of the MHC molecule that are exposed to solvent, facing outward for interaction with the TCR. The biochemistry and biophysical characterization of Recombinant TCR Ligands (RTLs) derived from MHC class II are described above, such as the use of the α-1 and β-1 domains of HLA-DR2 as a single exon of approximately 200 amino acid residues with various amino-terminal extensions containing antigenic peptides. These HLA-DR2-derived RTLs fold to form the peptide binding/T-cell recognition domain of the native MHC class II molecule.

Inflammatory Th1, CD4+ T-cells are activated in a multi-step process that is initiated by co-ligation of the TCR and CD4 with MHC/peptide complex present on APCs. This primary, antigen-specific signal needs to be presented in the proper context, which is provided by co-stimulation through interactions of additional T-cell surface molecules such as CD28 with their respective conjugate on APCs. Stimulation through the TCR in the absence of co-stimulation, rather than being a neutral event, can induce a range of cellular responses from full activation to anergy or cell death (Quill et al., 1984). As described herein Ag-specific RTLs were used induce a variety of human T-cell signal transduction processes as well as modulate effector functions, including cytokine profiles and proliferative potential.

Synthetic Peptides.

MBP85-99 peptide (ENPVVHFFKNIVTPR, SEQ ID NO:38) and "CABL", BCR-ABL b3a2 peptide (ATGFKQSSKALQRPVAS, SEQ ID NO:39) (ten Bosch et al., 1995) were prepared on an Applied Biosystems 432A (Foster City, Calif.) peptide synthesizer using fmoc solid phase synthesis. The MBP peptide was numbered according to the bovine MBP sequence (Martenson, 1984). Peptides were prepared with carboxy terminal amide groups and cleaved using thianisole/1,2-ethanedithiol/dH$_2$O in trifluoroacetic acid (TFA) for 1.5 hours at room temperature with gentle shaking. Cleaved peptides were precipitated with 6 washes in 100% cold tert-butylmethyl ether, lyophilized, and stored at −70 □C under nitrogen. The purity of peptides was verified by reverse phase HPLC on an analytical Vydac C18 column.

T-Cell Clones.

Peptide-specific T-cell clones were selected from peripheral blood mononuclear cells (PBMC) of a multiple sclerosis (MS) patient homozygous for HLA-DRB1*1501 and an MS patient homozygous for HLA-DRB1*07, as determined by standard serological methods and further confirmed by PCR amplification with sequence-specific primers (PCR-SSP) (Olerup et al., 1992). Frequencies of T-cells specific for human MBP85-99 and CABL were determined by limiting dilution assay (LDA). PBMC were prepared by ficoll gradient centrifugation and cultured with 10 μg/ml of either MBP85-99 or CABL peptide at 50,000 PBMC/well of a 96-well U-bottomed plate plus 150,000 irradiated (2500 rad) PBMC/well as antigen-presenting cells (APCs) in 0.2 ml medium (RPMI 1640 with 1% human pooled AB serum, 2 mM L-glutamine, 1 mM sodium pyruvate, 100 unit/ml penicillin G, and 100 μg/ml streptomycin) for 5 days, followed by adding 5 ng/ml IL-2 (R & D Systems, Minneapolis, Minn.) twice per week. After three weeks, the culture plates were examined for cellular aggregation or "clump formation" by visual microscopy and the cells from the "best" 20-30 clump-forming wells among a total of 200 wells per each peptide Ag were expanded in 5 ng/ml IL-2 for another 1-2 weeks. These cells were evaluated for peptide specificity by the proliferation assay, in which 50,000 T-cells/well (washed 3×) were incubated in triplicate with 150,000 freshly isolated and irradiated APC/well plus either medium alone, 10 mg/ml MBP85-99 or 10 mg/ml CABL pep-tide for three days, with $^3$H-Tdy added for the last 18 hours. Stimulation index (S.I.) was calculated by dividing the mean CPM of peptide-added wells by the mean CPM of the medium alone control wells. T-cell isolates with the highest S.I. for a particular peptide antigen were selected and expanded in medium containing 5 ng/ml IL-2, with survival of 1-6 months, depending on the clone, without further stimulation.

Sub-Cloning and Expansion of T-Cell Number.

Selected peptide-specific T-cell isolates were sub-cloned by limiting dilution at 0.5 T-cells/well plus 100,000 APC/well in 0.2 ml medium containing 10 ng/ml anti-CD3 (Pharmingen, San Diego, Calif.) for three days, followed by addition of 5 ng/ml IL-2 twice per week for 1-3 weeks. All wells with growing T-cells were screened for peptide-specific response by the proliferation assay and the well with the highest S.I. was selected and continuously cultured in medium plus IL-2. The clonality of cells was determined by RT-PCR, with a clone defined as a T-cell population utilizing a single TCR V β□gene. T-cell clones were expanded by stimulation with 10 ng/ml anti-CD3 in the presence of 5×10$^6$ irradiated (4500 rad) EBV-transformed B cell lines and 25×10$^6$ irradiated (2500 rad) autologous APC per 25 cm$^2$ flask in 10% AB pooled serum (Bio-Whittaker, MD) for 5 days, followed by washing and resuspending the cells in medium containing 5 ng/ml IL-2, with fresh IL-2 additions twice/week. Expanded T-cells were evaluated for peptide-specific proliferation and the selected, expanded T-cell clone with the highest proliferation S.I. was used for experimental procedures.

Cytokine Detection by ELISA.

Cell culture supernatants were recovered at 72 hours and frozen at −80 □C until use. Cytokine measurement was performed by ELISA as previously described (Bebo et al., 1999) using cytokine specific capture and detection antibodies for IL-2, IFN-γ, IL-4 and IL-10 (Pharmingen, San Diego, Calif.). Standard curves for each assay were generated using recombinant cytokines (Pharmingen), and the cytokine concentration in the cell supernatants was determined by interpolation.

Flow Cytometry.

Two color immunofluorescent analysis was performed on a FACSCAN flow cytometer instrument (Becton Dickinson, Mountain View, Calif.) using CELLQUEST software. Quadrants were defined using isotype matched control Abs.

Phosphotyrosine Assay

T-cells were harvested from culture by centrifuging at 400×g for 10 min, washed, and resuspended in fresh RPMI. Cells were treated with RTLs at 20 μM final concentration for various amounts of time at 37° C. Treatment was stopped by addition of ice-cold RPMI, and cells collected by centrifugation. The supernatant was decanted and lysis buffer (50 mM Tris pH 7.5, 150 mM NaCl, 1% NP-40, 0.5% deoxycholate, 0.1% SDS, 1 mM AEBSF [4-(2-aminoethyl)benzenesulfonylfluoride, HCl], 0.8 μM aprotinin, 50 μM bestatin, 20 μM leupeptin, 10 μM pepstatin A, 1 mM activated sodium orthovanadate, 50 mM NaF, 0.25 mM bpV [potassium bisperoxo (1,10-phenanthroline)oxovanadate], 50 μM phenylarsine oxide) was added immediately. After mixing at 4° C. for 15 min to dissolve the cells, the samples were centrifuged for 15 min. The cell lysate was collected and mixed with an equal volume of sample loading buffer, boiled for 5 min and then separated by 15% SDS-PAGE. Protein was transferred to PVDF membrane for western blot analysis. Western blot block buffer: 10 mM Tris-HCl (pH 7.5), 100 mM NaCl, 0.1% Tween-20, 1% BSA. Primary antibody: anti-phosphotyrosine, clone 4G10, (Upstate Biotechnology, Lake Placid, N.Y.). Secondary and tertiary antibody from ECF Western blot kit (Amersham, Picataway, N.J.). The dried blot was scanned using a Storm 840 scanner (Molecular Dynamics, Sunnyvale, Calif.) and chemifluorescence quantified using ImageQuant version 5.01 (Molecular Dynamics).

ERK Activation Assay.

T-cells were harvested and treated with RTLs as for □□phosphotyrosine assay. Western blot analysis was performed using anti-phosph-ERK (Promega, Madison Wis.) at 1:5000 dilution or anti-ERK kinase (New England Biolabs, Beverly, Mass.) at 1:1500 dilution and visualized using ECF Western Blotting Kit. Bands of interest were quantified as described for □phosphotyrosine assay.

Ca$^{2+}$ Imaging.

Human T-cells were plated on polylysine-coated 35 mm glass bottom dishes and cultured for 12-24 hr in medium containing IL-2. Fura-2 AM (5 mM) (Molecular Probes) dissolved in the culture medium was loaded on the cells for 30 min. in CO2 incubator. After rinse of fura-2 and additional 15 min. incubation in the culture medium, the cells were used for calcium measurement. Fluorescent images were observed by an upright microscope (Axioskop FS, Zeiss) with a water immersion objective (UmplanFL 60×/0.8, Olympus). Two wavelengths of the excitation UV light (340 nm or 380 nm) switched by a monochromator (Polychrome 2, Till Photonics) were exposed for 73 msec at 6 seconds interval. The intensity of 380 nm UV light was attenuated by a balancing filter (UG11, OMEGA Optical). The excitation UV light was reflected by a dichroic mirror (FT 395 nm, Carl Zeiss) and the fluorescent image was band-passed (BP500-530, Carl Zeiss), amplified by an image intensifier (C7039-02, Hamamatsu Photonics) and exposed to multiple format cooled CCD camera (C4880, Hamamatsu Photonics). The UV light exposure, CCD control, image sampling and acquisition were done with a digital imaging system (ARGUS HiSCA, Hamamatsu Photonics). The background fluorescence was subtracted by the imaging sys-tem. During the recording, cells were kept in a culture medium maintained at 30° C. by a stage heater (DTC-200, Dia Medical). The volume and timing of drug application were regulated by a trigger-driven superfusion system (DAD-12, ALA Scientific instruments).

EXAMPLE 10

The Effect of Human RTLs on Human T-Cell Clones

Figure 15:
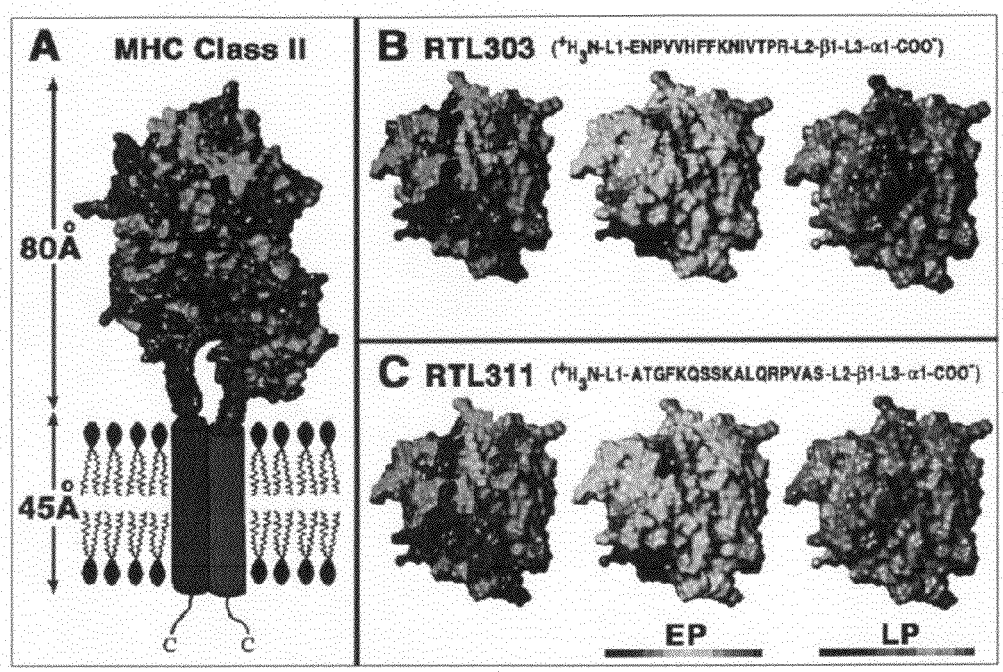
FIGS. 15A, 15B, and 15C illustrate the structure-based design of the human HLA-DR2-derived RTLs. (A) is a schematic scale model of an MHC class II molecule on the surface of an APC. The polypeptide backbone extracellular domain is based on the crystallographic coordinates of HLA-DR1 (PDB accession code 1AQD). The transmembrane domains are shown schematically as 0.5 nm cylinders, roughly the diameter of a poly-glycine alpha-helix. The carboxyl termini of the MHC class II heterodimers are labeled. (B) is a diagram of the HLA-DR2 β1α1-derived RTL303 molecule containing covalently coupled MBP85-99 peptide (SEQ ID NO: 38). (C) is a diagram of the HLA-DR2 β1α1-derived RTL311 molecule containing covalently coupled C-ABL peptide (SEQ ID NO: 39). The view of the RTLs is symmetry-related to the MHC class II molecule in panel (a) by rotation around the long-axis of bound peptide by ~45° (y-axis) and ~45° (Z-axis). Left, the same shading scheme as in panel (A), with primary TCR contact residues labeled. Middle, shaded according to electrostatic potential (EP). The shading ramp for EP ranges from dark (most positive) to light (most negative). Right, shaded according to lipophilic potential (LP). The shading ramp for LP ranges from dark (highest lipophilic area of the molecule) to light (highest hydrophilic area). The program Sybyl (Tripos Associates, St. Louis, Mo.) was used to generate graphic images using an O2 workstation (Silicon Graphics, Mountain View, Calif.) and coordinates deposited in the Brookhaven Protein Data Bank (Brookhaven National Laboratories, Upton, N.Y.). Structure-based homology modeling of RTLs was based on the known crystallographic coordinates of HLA-DR2 complexed with MBP peptide (DRA*0101, DRB1*1501; see, e.g., Smith et al., J. Exp. Med. 188:1511, (1998)). Amino acid residues in the HLA-DR2 MBP peptide complex (PDB accession number 1 BX2) were substituted with the CABL side chains, with the peptide backbone of HLA-DR2 modeled as a rigid body during structural refinement using local energy minimization.

Two different MHC class II DR2-derived RTLs (HLA-DR2b: DRA*0101, DRB1*1501) were used in this study (FIG. 15). RTL303 (β1α1/MBP85-99) and RTL311 (β1α1/CABL) differ only in the antigen genetically encoded at the amino terminal of the single exon RTL. The MBP85-99 peptide represents the immuno-dominant MBP determinant in DR2 patients (Martin et al., 1992) and the C-ABL peptide (ten Bosch et al., 1995) contains the appropriate motif for binding DR2. The human T-cell clones used in this study were selected from a DR2 homozygous patient and a DR7 homozygous MS patient.

Structure-based homology modeling was performed using the refined crystallographic coordinates of human DR2 (Smith et al., 1998) as well as DR1 (Brown et al., 1993; Murthy et al., 1997), murine I-$E_k$ molecules (Fremont et al., 1996), and scorpion toxins (Zhao et al., 1992). Because a number of amino acid residues in human DR2 (PDB accession number 1BX2) were missing/not located in the crystallographic data (Smith et al., 1998), the correct side chains based on the sequence of DR2 were substituted in the sequence and the peptide backbone was modeled as a rigid body during structural refinement using local energy minimization. These relatively small (approx. 200 amino acid residues) RTLs were produced in *Escherichia coli* in large quantities and refolded from inclusion bodies, with a final yield of purified protein between 15-30 mg/L of bacterial culture (Chang et al., 2001). FIG. 15 is a schematic scale model of an MHC class II molecule on the surface of an APC (FIG. 15A). The HLA-DR2 β1α1-derived RTL303 molecule containing covalently coupled MBP-85-99 peptide (FIG. 15B, left) and the HLA-DR2 β1α1-derived RTL311 molecule containing covalently coupled CABL peptide (FIG. 15C, left), are shown in FIG. 15A with the primary TCR contact residues labeled. The P2 His, P3 Phe, and P5 Lys residues derived from the MBP peptide are prominent, solvent exposed residues. These residues are known to be important for TCR recognition of the MBP peptide. The corresponding residues in the C-ABL peptide (P2 Thr, P3 Gly, P5 Lys) are also shown. Immediately striking is the percentage of surface area that is homologous across species. When shaded according to electrostatic potential (EP) (Connolly, 1983) (FIG. 15B, 15C, middle), or according to lipophilic potential (LP) (Heiden et al., 1993) (FIG. 15B, 15C, right), subtleties between the molecules are resolved that likely play a specific role in allowing TCR recognition of antigen in the context of the DR2-derived RTL surface.

The design of the constructs allows for substitution of sequences encoding different antigenic peptides using restriction enzyme digestion and ligation of the constructs. Structural characterization using circular dichroism demonstrated that these molecules retained the anti-parallel beta-sheet platform and antiparallel alpha-helices observed in the native class II heterodimer, and the molecules exhibited a cooperative two-state thermal unfolding transition (Chang et al., 2001). The RTLs with the covalently-linked Ag-peptide showed increased stability to thermal unfolding relative to "empty" RTLs, similar to what was observed for rat RT1.B RTLs.

Figure 16:
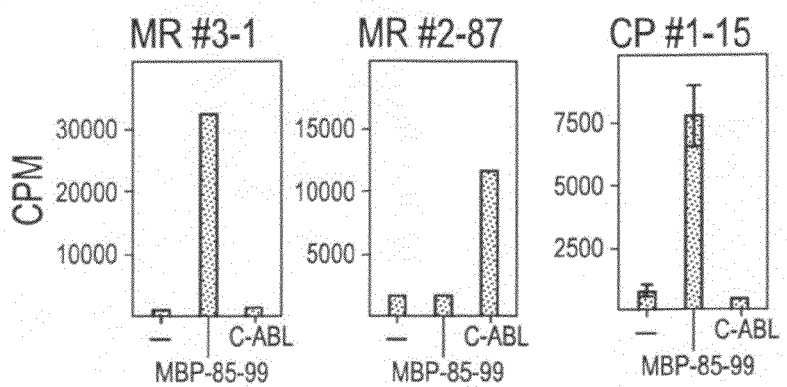
FIG. 16 is a series of bar graphs charting the response of T-cell clones. DR2 restricted T-cell clones MR#3-1, specific for MBP-85-99 peptide, and MR#2-87, specific for CABL-b3a2 peptide, and a DR7 restricted T-cell clone CP#1-15 specific for MBP-85-99 peptide were cultured at 50,000 cells/well with medium alone or irradiated (2500 rad) frozen autologous PBMC (150,000/well) plus peptide-Ag (MBP-85-99 or CABL, 10 μg/ml) in triplicate wells for 72 hr, with $_3$H-thymidine incorporation for the last 18 hr. Each experiment shown is representative of at least two independent experiments. Bars represent CPM±SEM.

DR2 and DR7 homozygous donor-derived Ag-specific T-cell clones expressing a single TCR BV gene were used to evaluate the ability of Ag-specific RTLs to directly modify the behavior of T-cells. Clonality was verified by TCR BV gene expression, and each of the clones proliferated only when stimulated by specific peptide presented by autologous APC. DR2 homozygous T-cell clone MR#3-1 was specific for the MBP85-99 peptide and DR2 homozygous clone MR#2-87 was specific for the CABL peptide. The DR7 homozygous T-cell clone CP#1-15 was specific for the MBP85-99 peptide (FIG. 16).

EXAMPLE 11

RTL Treatment Induced Early Signal Transduction Events

Phosphorylation of the TCR-ζ Chain in the DR2 Homozygous T-Cell Clones

MR#3-1 and MR#2-87 was examined. MR#3-1 is specific for the MBP85-99 peptide carried by RTL303, and MR#2-87 is specific for the CABL peptide carried by RTL311. The antigenic peptides on the amino terminal end of the RTLs are the only difference between the two molecules. The TCR-TCR-ζ chain is constitutively phosphorylated in resting T-cells, and changes in levels of TCR-ζ chain phosphorylation are one of the earliest indicators of information processing through the TCR. In resting clones, TCR-ζ was phosphorylated as a pair of phospho-protein species of 21 and 23 kD, termed p21 and p23, respectively. Treatment of clone MR#3-1 with 20 µM RTL303 showed a distinct change in the p23/p21 ratio that reached a minimum at 10 minutes (FIG. 17). This same distinct change in the p23/p21 ratio was observed for clone MR#2-87 when treated with 20 µM RTL311 (FIG. 17). Only RTLs containing the peptide for which the clones were specific induced this type of phosphorylation, previously observed after T-cell activation by antagonist ligands (27, 28).

Figure 18:
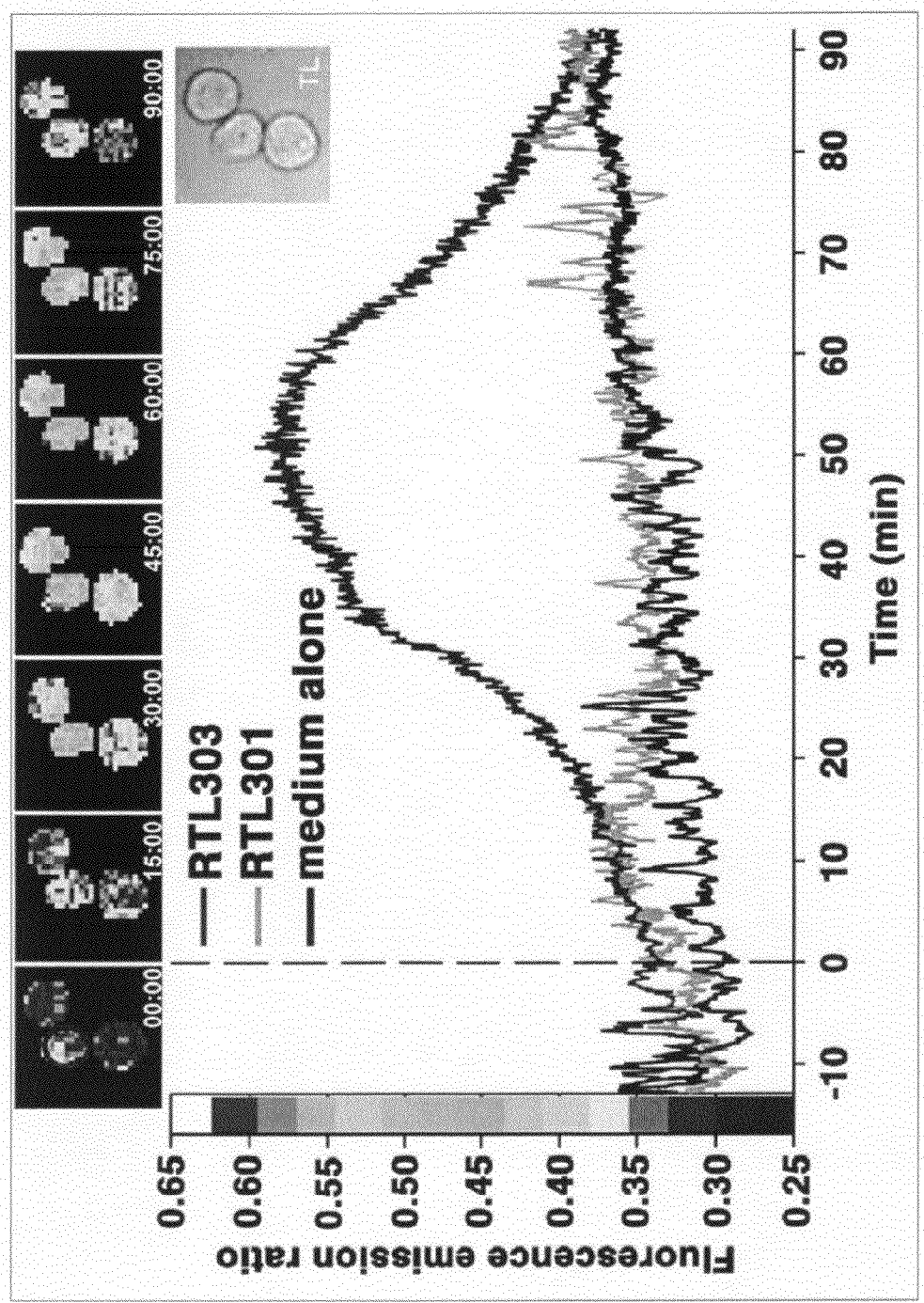
FIG. 18 shows the fluorescence emission ratio of T-cells stimulated with RTLs. RTLs induce a sustained high calcium signal in T-cells. Calcium levels in the DR2 restricted T-cell clone MR#3-1 specific for the MBP-85-99 peptide were monitored by single cell analysis. RTL303 treatment induced a sustained high calcium signal, whereas treatment with RTL301 (identical to RTL303 except a single point mutation, F150L) did not induce an increase in calcium signal over the same time period. The data is representative of two separate experiments with at least 14 individual cells monitored in each experiment.

Calcium levels were monitored in the DR2 homozygous T-cell clone MR#3-1 specific for the MBP85-99 peptide using single cell analysis. While there is a general agreement that calcium mobilization is a specific consequence of T-cell activation, the pattern of response and dosage required for full activation remain controversial (Wülfing et al., 1997). It appears that four general patterns of intra-cellular calcium mobilization occur with only the most robust correlating with full T-cell proliferation. RTL303 treatment induced a sustained high calcium signal, whereas RTL301 (identical to RTL303 except a single point mutation that altered folding properties, F150L) showed no increase in calcium signal over the same time period (FIG. 18).

RTL effects were further evaluated on levels of the extracellular regulated protein kinase ERK, a key component within the Ras signaling pathway known to be involved in the control of T-cell growth and differentiation (Li et al., 1996). The activated form of ERK kinase is itself phosphorylated (Schaeffer et al., 1999), and thus a straightforward measure of ERK activity was to compare the fraction of ERK that is phosphorylated (ERK-P) relative to the total cellular ERK present (T-ERK). Within 15 min. after treatment with RTLs, the level of ERK-P was drastically reduced in an Ag-specific fashion. 20 μM RTL303 reduced ERK-P by 80% in clone #3-1 and 20 μM RTL311 reduced ERK-P by 90% in clone #2-87 (FIG. 19).

The early signal transduction events that were altered by Ag-specific RTL treatment on the cognate T-cell clones led us to investigate the effect of RTL treatment on cell surface markers, proliferation and cytokines. Cell surface expression levels of CD25, CD69 and CD134 (OX40) were analyzed by multicolor flow cytometry at 24 and 48 hr after treatment with RTLs and compared to APC/peptide or Con A stimulated cells. CD69 (Vilanova et al., 1996) was already very high (~80% positive) in these clones. APC/peptide induced Ag-specific increases in both CD25 (Kyle et al., 1989) and CD134 (Weinberg et al., 1996) that peaked between 48 and 72 hours, while RTL treatment had no effect on these cell surface markers. RTL treatment induced only subtle increases in apoptotic changes as quantified using Annexin V staining and these were not Ag-specific. Treatment of T-cell clones with RTLs did not induce proliferation when added in solution, immobilized onto plastic microtiter plates, nor in combination with the addition of anti-CD28.

Upon activation with APC plus Ag, clone MR#3-1 (MBP85-99 specific) and MR#2-87 (CABL specific) showed classic Th1 cytokine profiles that included IL-2 production, high IFN-γ and little or no detectable IL-4 or IL-10. As is shown in FIG. 24A, activation through the CD3-chain with anti-CD3 antibody induced an initial burst of strong proliferation and production of IL-2, IFN-γ, and surprisingly, IL-4, but no IL-10. In contrast, upon treatment with RTL303, clone MR#3-1 continued production of IFN-γ, but in addition dramatically increased its production of IL-10 (FIG. 20A). IL-10 appeared within 24 hours after addition of RTL303 and its production continued for more than 72 hours, to three orders of magnitude above the untreated or RTL311 treated control. In contrast, IL-2 and IL-4 levels did not show RTL induced changes (FIG. 20A). Similarly, after treatment with RTL311, Clone MR#2-87 (CABL specific) also showed a dramatic increase in production of IL-10 within 24 hours that continued for greater than 72 hours above the untreated or RTL303 treated control (FIG. 20B). Again, IL-2 and IL-4 levels did not show detectable RTL induced changes, and IFN-γ production remained relatively constant. The switch to IL-10 production was exquisitely Ag-specific, with the clones responding only to the cognate RTL carrying peptide antigen for which the clones were specific. The DR7 homozygous T-cell clone CP#1-15 specific for MBP-85-99 showed no response to DR2-derived RTLs, indicating that RTL induction of IL-10 was also MHC restricted.

To assess the effects of RTL pre-treatment on subsequent response to antigen, T-cell clones pretreated with anti-CD3 or RTLs were restimulated with APC/peptide, and cell surface markers, proliferation and cytokine production were monitored. RTL pre-treatment had no effect on the cell surface expression levels of CD25, CD69 or CD134 (OX40) induced by restimulation with APC/peptide compared to T-cells stimulated with APC/peptide that had never seen RTLs, and there were no apoptotic changes observed over a 72 hour period using Annexin V staining.

Figure 21:
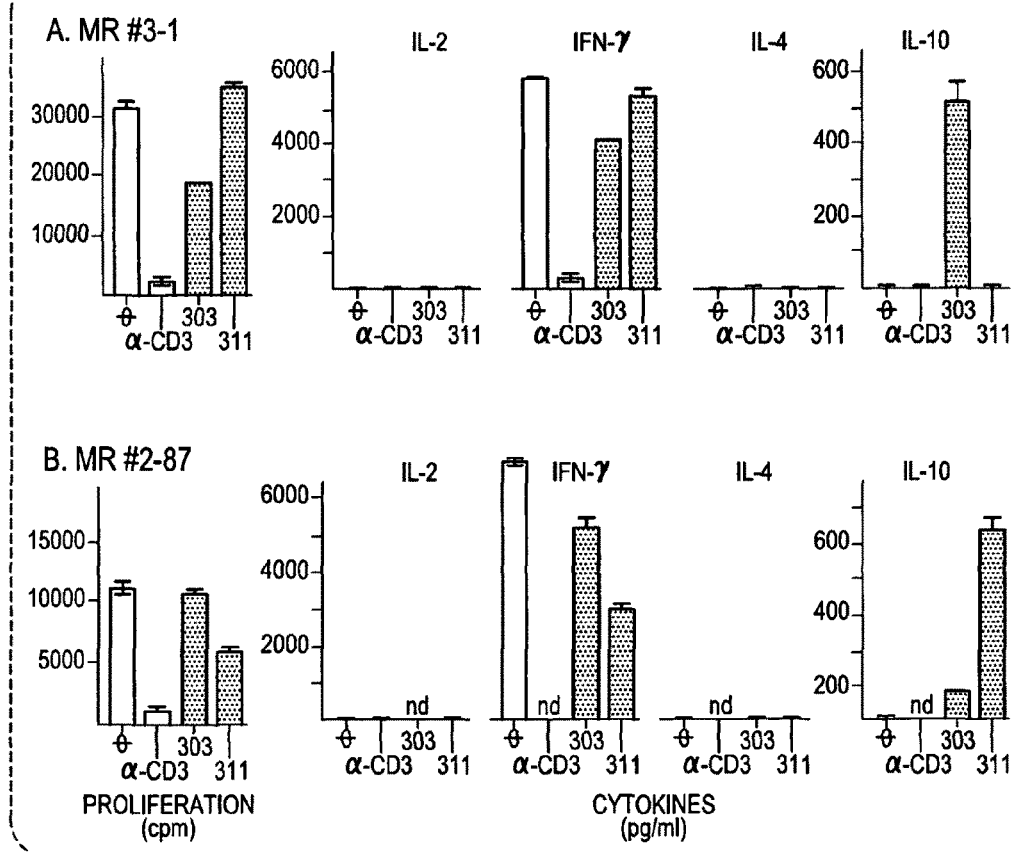
FIG. 21 is a set of graphs indicating that IL-10 cytokine production induced by RTL pre-treatment was maintained after stimulation with APC/peptide. T-cells had a reduced ability to proliferate and produce cytokines after anti-CD3 or RTL treatment, and the RTL effect was antigen and MHC specific. IL-10 was induced only by specific RTLs, and Il-10 production was maintained even after restimulation with APC/antigen. T-cell clones were cultured at 50,000 cells/well with medium, anti-CD3, or 20 µM RTLs in triplicate for 48 hours, and washed once with RPMI. After the wash, irradiated (2500 rad) frozen autologous PBMC (150,000/well) plus peptide-Ag (MBP-85-99 at 10 µg/ml) were added and the cells incubated for 72 hr with $^3$H-thymidine added for the last 18 hr. Each experiment shown is representative of at least two independent experiments. Bars represent mean ☐☐SEM. For cytokine assays, clones were cultured with 10 µg/ml anti-CD3 or 20 µM RTL303 or RTL311 for 48 hours, followed by washing with RPMI and re-stimulation with irradiated autologous PBMC (2500 rad, T:APC=1:4) plus peptide-Ag (10 ☐g/ml) for 72 hours. Cytokines (pg/ml) profiles were monitored by immunoassay (ELISA) of supernatants. Each experiment shown is representative of at least three independent experiments. Bars represent mean ☐☐SEM.

Anti-CD3 pretreated T-cells were strongly inhibited, exhibiting a 71% decrease in proliferation and >95% inhibition of cytokine production, with continued IL-2R (CD25) expression (Table 2; FIG. 21), a pattern consistent with classical anergy (Elder et al., 1994).

TABLE 3

Ag-specific inhibition of T-cell clones by pre-culturing with RTLs.

| | Pre-Cultured with RTL303* | | Pre-Cultured with RTL311 | |
|---|---|---|---|---|
| Untreated | 20 μM | 10 μM | 20 μM | 10 μM |
| Donor 1 Clone #3-1 | | | | |
| +APC** | 439 ± 221 | 549 ± 70 | 406 ± 72 | 491 ± 50 | 531 ± 124 |
| +APC + MBP-85-99 (10 μg/ml) | 31725 ± 592 | 18608 ± 127 | 29945 ± 98 | 35172 ± 41 | 32378 ± 505 |
| Inhibition (%) | — | −42.3 (p < 0.01) | −5.6 | 0 | 0 |
| Clone #2-87 | | | | |
| +APC | 1166 ± 24 | 554 ± 188 | 1229 ± 210 | 1464 ± 281 | 1556 ± 196 |
| +APC + C-ABL-b2a3 (10 μg/ml) | 11269 ± 146 | 11005 ± 204 | 14298 ± 1669 | 5800 ± 174 | 7927 ± 575 |
| Inhibition (%) | — | 0 | 0 | −57.0 (p < 0.001) | −36.9 (p < 0.01) |
| Donor 2 Clone #1-15 | | | | |
| +APC | 258 ±± 48 | 124 ± 7 | ND | 328 ± 56 | ND |
| +APC + MBP-85-99 (10 μg/ml) | 7840 ± 1258 | 7299 ± 1074 | ND | 8095 ± 875 | ND |
| Inhibition (%) | — | −5.1 | | 0 | |

*Soluble RTL303 or RTL311 were co-cultured with T-cell clones at 200,000 T-cells/200 μl medium for 48 hours followed by washing twice with RPMI 1640 prior to the assay.
**2 × 10$^5$ irradiated (2500 rad) autologous PBMC were added at ratio 4:1 (APC:T) for 3 days with $^3$H-Thymidine incorporation for the last 18 hr. The p values were based on comparison to "untreated" control.

Clone MR#3-1 showed a 42% inhibition of proliferation when pretreated with 20 μM RTL303, and clone MR#2-87 showed a 57% inhibition of proliferation when pretreated with 20 μM RTL311 (Table 3; FIG. 21). Inhibition of proliferation was also MHC class II-specific, as clone CP#1-15 (HLA-DR7 homozygous donor; MBP85-99 specific) showed little change in proliferation after pre-treatment with RTL303 or RTL311. Clone MR#3-1 pretreated with RTL303 followed by restimulation with APC/Ag showed a 25% reduction in IL-2, a 23% reduction in IFN-γ and no significant changes in IL-4 production (FIG. 21). Similarly, clone MR#2-87 showed a 33% reduction in IL-2, a 62% reduction in IFN-γ production, and no significant change in IL-4 production. Of critical importance, however, both RTL-pretreated T-cell clones continued to produce IL-10 upon restimulation with APC/peptide (FIG. 21).

The results presented above demonstrate clearly that the rudimentary TCR ligand embodied in the RTLs delivered signals to Th1 cells and support the hypothesis of specific engagement of RTLs with the TCR signaling. Signals delivered by RTLs have very different physiological consequences than those that occur following anti-CD3 antibody treatment.

Figure 20:
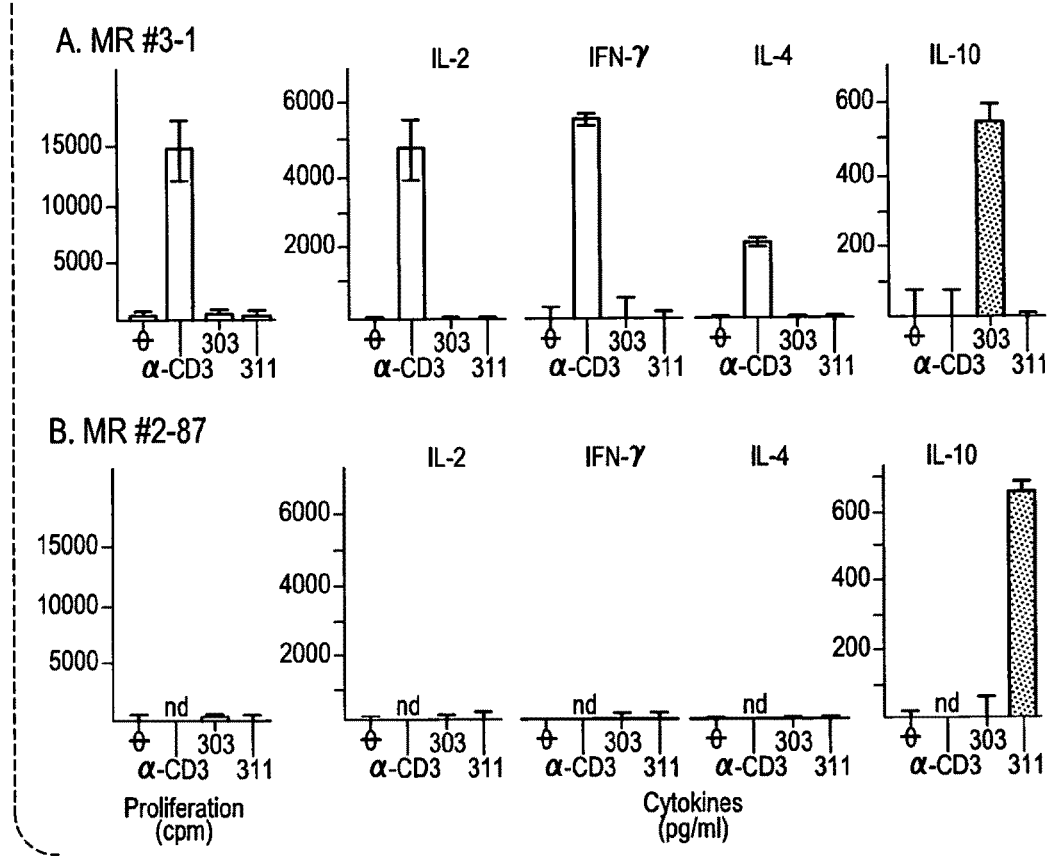
FIG. 20 is a series of graphs showing that direct antigen-specific modulation of IL-10 cytokine production in T-cell clones was induced by RTL treatment. DR2 restricted T-cell clones MR#3-1 and MR#2-87 were cultured in medium alone (-control), anti-CD3 mAb, 20 µM RTL303 or RTL311 for 72 hours. Proliferation was assessed by $^3$H-thymidine uptake. Cytokines (pg/ml) profiles were monitored by immunoassay (ELISA) of supernatants. Each experiment shown was representative of at least three independent experiments. Bars represent mean ☐☐SEM. Clone MR#3-1 showed initial proliferation to anti-CD3, but not to RTLs.

In the system described herein, anti-CD3 induced strong initial proliferation and secretion of IL-2, IFN-γ, and IL-4 (FIG. 20). Anti-CD3 pre-treated T-cells that were restimulated with APC/antigen had markedly reduced levels of proliferation and cytokine secretion, including IL-2, but retained expression of IL-2R, thus recapitulating the classical anergy pathway (FIG. 21). In contrast, direct treatment with RTLs did not induce proliferation, Th1 cytokine responses, or IL-2R expression, but did strongly induce IL-10 secretion (FIG. 20). RTL pretreatment partially reduced proliferation responses and Th1 cytokine secretion, but did not inhibit IL-2R expression upon restimulation of the T-cells with APC/antigen. Importantly, these T-cells continued to secrete IL-10 (FIG. 21). Thus, it is apparent that the focused activation of T-cells through antibody crosslinking of the CD3-chain had vastly different consequences than activation by RTLs presumably through the exposed TCR surface. It is probable that interaction of the TCR with MHC/antigen involves more elements and a more complex set of signals than activation by crosslinking CD3-chains, and the results described herein indicate that signal transduction induced by anti-CD3 antibody may not accurately portray ligand-induced activation through the TCR. Thus, CD3 activation alone likely does not comprise a normal physiological pathway.

The signal transduction cascade downstream from the TCR is very complex. Unlike receptor tyrosine kinases, the cytoplasmic portion of the TCR lacks intrinsic catalytic activity. Instead, the induction of tyrosine phosphorylation following engagement of the TCR requires the expression of non-receptor kinases. Both the Src (Lck and Fyn) family and the Syk/ZAP-70 family of tyrosine kinases are required for normal TCR signal transduction (Elder et al., 1994). The transmembrane CD4 co-receptor interacts with the MHC class II α-2 domain. This domain has been engineered out of the RTLs. The cytoplasmic domain of CD4 interacts strongly with the cytoplasmic tyrosine kinase Lck, which enables the CD4 molecule to participate in signal transduction. Lck contains an SH3 domain which is able to mediate protein-protein interactions (Ren et al., 1993) and which has been proposed to stabilize the formation of Lck homodimers, potentiating TCR signaling following co-ligation of the TCR and co-receptor CD4 (Eck et al., 1994). Previous work indicated that deletion of the Lck SH3 domain interfered with the ability of an oncogenic form of Lck to enhance IL-2 production, supporting a role for Lck in regulating cytokine gene transcription (Van Oers et al., 1996; Karnitz et al., 1992). T-cells lacking functional Lck fail to induce Zap-70 recruitment and activation, which has been implicated in down-stream signaling events involving the MAP kinases ERK1 and ERK2 (Mege et al., 1996).

Figure 17A:
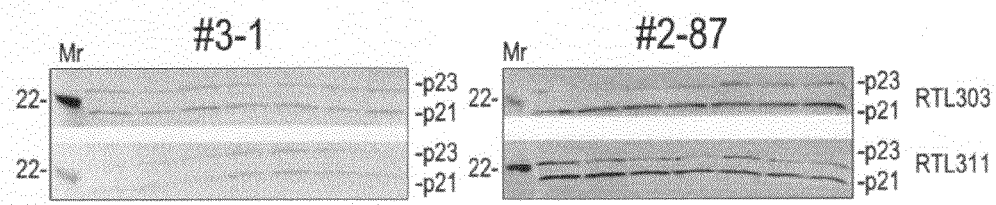
FIG. 17 is a graph illustrating that zeta chain phosphorylation induced by RTL treatment is Ag-specific. DR2 restricted T-cell clones MR#3-1 specific for MBP-85-99 peptide or MR#2-87 specific for CABL-b3a2 peptide, were incubated at 37 □C with medium alone (control), or with 20 μM RTL303 or RTL311. Western blot analysis of phosphorylated □□□zeta) shows a pair of phospho-protein species of 21 and 23 kD, termed p21 and p23, respectively. Quantification of the bands showed a distinct change in the p21/p23 ratio that peaked at 10 minutes. Each experiment shown is representative of at least three independent experiments. Points represent mean □□SEM.
Figure 17B:
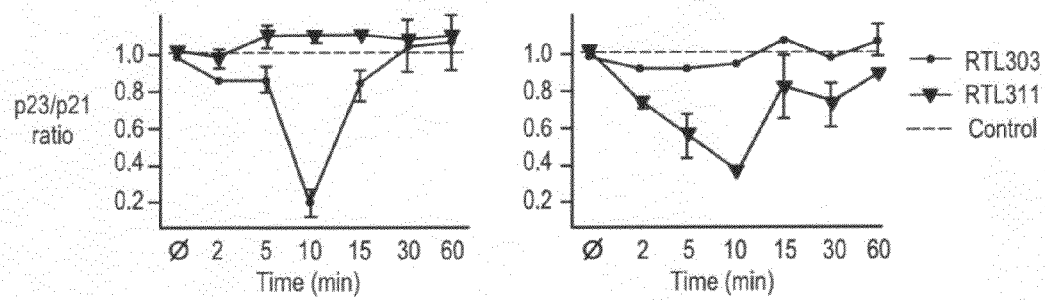

While the complete molecular signal transduction circuitry remains undefined, RTLs induce rapid antagonistic effects on TCR-ζ-chain and ERK kinase activation. The intensity of the p21 and p23 forms of TCR-ζ increased together in a non peptide-Ag specific fashion (FIG. 17A), while the ratio of p23 to p21 varied in a peptide-Ag specific manner (FIG. 17B), due to a biased decrease in the level of the p23 moiety. The antagonistic effect on ERK phosphorylation also varied in a peptide-Ag specific manner (FIG. 17A). RTL treatment also induced marked calcium mobilization (FIG. 18). The fact that all three of these pathways were affected in an antigen specific fashion strongly implies that the RTLs are causing these effects through direct interaction with the TCR.

The results described herein demonstrate the antigen-specific induction by RTLs of IL-10 secretion. This result was unexpected, given the lack of IL-10 production by the Th1 clones when stimulated by APC/antigen or by anti-CD3 antibody. Moreover, the continued secretion of IL-10 upon restimulation of the RTL pre-treated clones with APC/antigen indicates that this pathway was not substantially attenuated during reactivation. This result suggests that TCR interaction with the RTL results in default IL-10 production that persists even upon re-exposure to specific antigen. The elevated level of IL-10 induced in Th1 cells by RTLs has important regulatory implications for autoimmune diseases such as multiple sclerosis because of the known anti-inflammatory effects of this cytokine on Th1 cell and macrophage activation (Negulescu et al., 1996).

EXAMPLE 12

Monomeric RTLs Reduce Relapse Rate and Severity of Experimental Autoimmune Encephalomyelitis Through Cytokine Switching Oligomeric recombinant TCR ligands (RTLs) are useful for treating clinical signs of experimental autoimmune encephalomyelitis (EAE) and inducing long-term T-cell tolerance against encephalitogenic peptides. In the present example, monomeric I-A$^s$/PLP 139-151 peptide constructs (RTL401) are produced and demonstrated to be useful for alleviating autoimmune responses in SJL/J mice that develop relapsing EAE after injection of PLP 139-151 peptide in CFA. RTL401 given i.v. or s.c., but not empty RTL400 or free PLP 139-151 peptide, prevented relapses and significantly reduced clinical severity of EAE induced by PLP 139-151 peptide in SJL/J or (C57BL/6×SJL)F$_1$ mice, but did not inhibit EAE induced by PLP 178-191 or MBP 84-104 peptides in SJL/J mice, or MOG 35-55 peptide in (C57BL/6× SJL/J)F$_1$ mice. RTL treatment of EAE caused stable or enhanced T-cell proliferation and secretion of IL-10 in the periphery, but reduced secretion of inflammatory cytokines and chemokines. In the central nervous system (CNS), there was a modest reduction of inflammatory cells, reduced expression of very late activation Ag-4, lymphocyte function-associated Ag-1, and inflammatory cytokines, chemokines, and chemokine receptors, but enhanced expression of Th2-related factors, IL-10, TGF-β3, and CCR3. These results indicate that monomeric RTL therapy induces a cytokine switch that curbs the encephalitogenic potential of PLP 139-151-specific T-cells without fully preventing their entry into CNS, wherein they reduce the severity of inflammation. This mechanism differs from that observed using oligomeric RTL therapy in other EAE models. These results indicate clinical utility of this novel class of peptide/MHC class II constructs in patients with multiple sclerosis who have focused T-cell responses to known encephalitogenic myelin peptides.

As noted above, RTLs designed for modulating of T-cell activity will typically include only the minimal TCR interface, which involves the α1 and β1 MHC domains covalently linked to peptide without CD4 binding. These constructs signal directly through the TCR as a partial agonist (Wang et al., 2003), prevented and treated MBP-induced monophasic EAE in Lewis rats (Burrows et al., 1998; Burrows et al., 2000), inhibited activation but induced IL-10 secretion in human DR2-restricted T-cell clones specific for MBP 85-99 or cABL peptides (Burrows et al., 2001; Chang et al., 2001), and reversed chronic clinical and histological EAE induced by MOG 35-55 peptide in DR2 transgenic mice (Vandenbark et al., 2003). To further evaluate the therapeutic properties of recombinant TCR ligands (RTLs), an RTL was designed and tested for use in SJL mice that develop a relapsing form of EAE after injection with PLP 139-151 peptide in CFA. This RTL, comprised of an I-A$^s$/PLP 139-151 peptide construct (RTL401), prevented relapses and reversed clinical and histological EAE through a mechanism involving cytokine switching that differs strikingly from our previous studies using rat and human RTLs in other models of EAE.

Mice

SJL/J and (C57BL/6×SJL)F$_1$ mice were obtained from Jackson Immunoresearch Laboratories (Bar Harbor, Me.) at 6-7 wk of age. The mice were housed in the Animal Resource Facility at the Portland Veterans Affairs Medical Center (Portland, Oreg.) in accordance with institutional guidelines.

Antigens

Mouse PLP 139-151 (HSLGKWLGHPDKF (SEQ ID NO:40)), PLP 178-191 (NTWTTCQSIAFPSK (SEQ ID NO:41)), MOG 35-55 (MEVGWYRSPFSRVVHLYRNGK (SEQ ID NO:42)), and MBP 84-104 (VHFFKNIVTPRTPPPSQGKGR (SEQ ID NO:43)) peptides were synthesized using solid phase techniques and purified by HPLC at Beckman Institute, Stanford University (Palo Alto, Calif.).

RTL Construction and Production

General methods for the design, cloning, and expression of RTLs have been described herein above and elsewhere (see, e.g., Burrows et al., 1998; Burrows et al., 1999; Chang et al., 2001). In brief, mRNA was isolated from the splenocytes of SJL mice using an OLIGOTEX Direct mRNA mini-kit (Qiagen, Valencia, Calif.). cDNA of the Ag binding/TCR recognition domain of murine I-A$^s$ MHC class II β1 and α1 chains was derived from mRNA using two pairs of PCR primers. The two chains were sequentially linked by a 5-aa linker (GGQDD (SEQ ID NO:44)) in a two-step PCR with NcoI and XhoI restriction sites added to the amino terminus of the β1 chain and to the carboxyl terminus of the α1 chain, respectively, to create RTL400. The PLP 139-151 peptide with a linker (GGGGSLVPRGSGGGG (SEQ ID NO:45)) was covalently linked to the 5' end of the β1 domain of RTL400 to form RTL401. RTL 402 and RTL 403 were made similarly, with insertion of the sequence encoding PLP 178-191 (SEQ ID NO:41) and MBP-84-104 (SEQ ID NO:43) respectively. The murine I-A$^s$β1α1 inserts were then ligated into pET21d(+) vector and transformed into Nova blue *Escherichia coli* host (Novagen Inc., Madison, Wis.) for positive colony selection and sequence verification. The plasmid constructs were then transformed into *E. coli* strain BL21 (DE3) expression host (Novagen Inc.). The purification of proteins has been described previously (Chang et al., 2001). The final yield of purified protein varied between 15 and 30 mg/L bacterial culture for each protein.

Dynamic Light Scattering (DLS) Analysis

Light scattering experiments were conducted in a DynaPro molecular sizing instrument (Protein Solutions, Charlottesville, Va.). The protein samples, in 20 mM Tris-Cl buffer at pH 8.5, were filtered through 100 nm Anodisc membrane filters (Whatman, Clifton, N.J.) at a concentration of 1.0 mg/ml, and 20 μl of filtered sample were loaded into a quartz cuvette and analyzed with a 488-nm laser beam. Fifty spectra were collected at 4° C. to get an estimation of the diffusion coefficient and relative polydispersity of the protein in aqueous solution. Data were then analyzed with Dynamics software V.5.25.44 (Protein Solutions) and buffer baselines were subtracted. Data were expressed as the means of hydrodynamic radius of the sample using nanometer as a unit. The m.w. of the RTLs was estimated with Dynamics software V.5.25.44 (Protein Solutions).

Circular Dichroism (CD) Analysis

CD analyses were performed as previously described (Chang et al., 2001) using an Aviv Model 215 CD spectrometer (Aviv Associates, Lakewood, N.J.), except that the recombinant proteins were in Tris-Cl buffer at pH 8.5. Spectra were averaged and smoothed using built-in algorithms with buffer baselines subtracted. Secondary structure was estimated using a deconvolution software package (CDNN version 2.1) and the Variable Selection method (Compton et al., 1986).

Induction of EAE and Treatment with RTLs

SJL mice were inoculated s.c. in the flanks with 0.2 ml of an emulsion containing 150 μg of PLP 139-151 peptide and an equal volume of CFA containing 150 μg of heat-killed *Mycobacterium tuberculosis* H37RA (M.Tb.; Difco, Detroit, Mich.) as described previously (Bebo et al., 2001). The (C57BL/6×SJL)F$_1$ mice were immunized s.c in the flanks with 0.2 ml of an emulsion containing 200 μg of MOG 35-55 peptide or 150 μg of PLP 139-151 peptide and an equal amount of CFA containing 200 μg of heat-killed M.Tb. In a separate experiment, SJL mice were immunized s.c in the flanks with 0.2 ml of an emulsion containing 150 μg of PLP 139-151 or 150 μg of PLP 178-191 peptides, or 0.1 ml of an emulsion containing 200 μg of MBP 84-104 peptide and an equal volume of CFA containing 200 μg of heat-killed *M. tuberculosis*. The mice immunized with MBP 84-104 peptide were boosted a week later with the same peptide in CFA. On the day of immunization boost and 2 days after, the mice were injected i.p. with 200 ng of pertussis toxin (Ptx; List Biological Laboratories, Campbell, Calif.). The mice were assessed daily for signs of EAE according to the following scale; 0, normal; 1, limp tail or mild hindlimb weakness; 2, moderate hindlimb weakness or mild ataxia; 3, moderately severe hindlimb weakness; 4, severe hindlimb weakness or mild forelimb weakness or moderate ataxia; 5, paraplegia with no more than moderate forelimb weakness; and 6, paraplegia with severe forelimb weakness or severe ataxia or moribund condition.

At disease onset, mice were treated with either vehicle (20 mM Tris-HCl); 100 μg of RTL400 or RTL401 given i.v. daily for 3 or 4 days, or 8 consecutive days with antihistamine (25 mg/kg); 100 μg of RTL400 and RTL401 given s.c. for 8 days; 10 μg free PLP 139-151 peptide given i.v. or s.c. for 8 consecutive days; or 100 μg of either RTL 401, RTL402, RTL403, or RTL 401+RTL 403 given s.c. for 8 days. Groups of control and treated mice were evaluated statistically for differences in disease incidence, day of onset, mortality, and presence or absence of relapse ($x^2$ test), and for differences in Peak Clinical Score and Cumulative Disease Index (sum of daily scores) (Kruskal-Wallis Test). Mice were sacrificed at different time points following treatment with RTL401 for immunological and histological analyses.

Histopathology

The intact spinal cords were removed from mice at the peak of clinical disease and fixed in 10% formalin. The spinal cords were dissected after fixation and embedded in paraffin before sectioning. The sections were stained with luxol fast blue/periodic acid-Schiff-hematoxylin to assess demyelination and inflammatory lesions, and analyzed by light microscopy. Semiquantitative analysis of inflammation and demyelination was determined by examining at least 10 sections from each mouse.

Proliferation Assay

Draining lymph node (LN) and spleens were harvested from vehicle- and RTL-treated mice at varying time points after immunization as indicated. A single cell suspension was prepared by homogenizing the tissue through a fine mesh screen. Cells were cultured in a 96-well flat-bottom tissue culture plate at $4 \times 10^5$ cells/well in stimulation medium either alone (control) or with test Ags (PLP 139-151, PLP 178-191, and MBP 84-104 peptides) at varying concentrations. Cells were incubated for 3 days at 37° C. in 7% $CO_2$. Cells were then pulsed with 0.5 μCi of [methyl-$^3$H]thymidine (PerkinElmer, Boston, Mass.) for the final 18 h of incubation. The cells were harvested onto glass fiber filters, and tritiated thymidine uptake was measured by a liquid scintillation counter. Means and standard deviations (SD) were calculated from triplicate wells. Net cpm was calculated by subtracting control cpm from Ag-induced cpm.

Cytokine Determination by Cytometric Bead Array (CBA)

LN and spleen cells were cultured at $4 \times 10^6$ cells/well in a 24-well flat-bottom culture plate in stimulation medium with 2 μg/ml PLP 139-151 peptide for 48 h. Supernatants were then harvested and stored at −80° C. until tested for cytokines. The mouse inflammation CBA kit was used to detect IL-12, TNF-α, IFN-γ, MCP-1, IL-10, and IL-6 simultaneously (BD Biosciences, San Diego, Calif.). Briefly, 50 μl of sample was mixed with 50 μl of the mixed capture beads and 50 μl of the mouse PE detection reagent. The tubes were incubated at room temperature for 2 h in the dark, followed by a wash step. The samples were then resuspended in 300 μl of wash buffer before acquisition on the FACSCAN flow cytometer instrument. The data were analyzed using the CBA software (BD Biosciences). Standard curves were generated for each cytokine using the mixed bead standard provided in the kit, and the concentration of cytokine in the supernatant was determined by interpolation from the appropriate standard curve.

FACS Staining for Very Late Activation Ag (VLA-4) and Lymphocyte Function-Assisted Ag (LFA-1) Expression Mononuclear cells from the brain were isolated on a Percoll density gradient as previously described (Bourdette et al., 1991). Cells were then stained with CD3 FITC (BD PharMingen, San Diego, Calif.) and VLA-4-PE or LFA-1-PE (Southern Biotechnology Associates, Birmingham, Ala.) expression by adding 1 μl of Ab per $1 \times 10^6$ cells. Cells were incubated at 4° C. for 20 min, and then washed two times with staining medium (1×PBS, 3% FBS, 0.02% sodium azide) before FACS analysis on a FACSCAN flow cytometer instrument (BD Biosciences) using CELLQUEST software (BD Biosciences). Dual positive T-cells were calculated as a percentage of total mononuclear cells analyzed.

RNA Isolation and RT-PCR

Total RNA was isolated from spinal cords using the RNEASY mini-kit protocol (Qiagen) and then converted to cDNA using oligo(dT), random hexamers, and SUPERSCRIPT RT II enzyme (Invitrogen, Grand Island, N.Y.). Real-time PCR was performed using QUANTITECT SYBR Green PCR master mix (Qiagen) and primers (synthesized by Applied Biosystems, Foster City, Calif.). Reactions were conducted on the ABI PRISM 7000 Sequence Detection System (Applied Biosystems) using the listed primer sequences (5' to 3') to detect the following genes: L32: (F: GGA AAC CCA GAG GCA TTG AC (SEQ ID NO:46); R: TCA GGA TCT GGC CCT TGA AC (SEQ ID NO:47)); IFN-γ: (F: TGC TGA TUG GAG GAG ATG TCT (SEQ ID NO:48); R: TGC TGT CTG GCC TGC TOT TA (SEQ ID NO:49)); TNF-α (F: CAG CCC ATG GGT TGT ACC TT (SEQ ID NO:50); R: GGC AGC CTT GTC CCT TGA (SEQ ID NO:51)); IL-10: (F: GAT GCC CCA GGC AGA GAA (SEQ ID NO:52); R: CAC CCA GGG AAT TCA AAT GC (SEQ ID NO:53)); IL-6: (F: CCA CGG CCT TCC CTA CTT C (SEQ ID NO:54); R: TGG GAG TGG TAT CCT CTG TGA A (SEQ ID NO:55)); TGF-β3: (F: GGG ACA GAT CTT GAG CAA GC (SEQ ID NO:56); R: TGC AGC CTT CCT CCC TCT C (SEQ ID NO:57)); RANTES: (F: CCT CAC CAT CAT CCT CAC TGC A (SEQ ID NO:58); R: TCT TCT CTG GGT TGG CAC ACA C (SEQ ID NO:59)); macrophage-inflammatory protein (MIP)-2: (F: TGG GCT GCT GTC CCT CAA (SEQ ID NO:60); R: CCC GGG TGC TGT TTG TTT T (SEQ ID NO:61)); IP-10: (F: CGA TGA CGG GCC AGT GA (SEQ ID NO:62); CGC AGG GAT GAT TTC AAG CT (SEQ ID NO:63)); CCR1; (F: GGG CCC TAG CCA TCT TAG CT (SEQ ID NO:64); R: TCC CAC TGG GCC TTA AAA AA (SEQ NO:65)); CCR2: (F: GTG TAC ATA GCA ACA AGC CTC AAA (I (SEQ ID NO:66); R: CCC CCA CAT AGG GAT CAT GA (SEQ ID NO:67)); CCR3: (F: GGG CAC CAC CCT GTG AAA (SEQ ID NO:68); R: TGG AGG CAG GAG CCA TGA (SEQ ID NO:69)); CCR5: (F: CAA TTT TCC AGC AAG ACA ATC CT (SEQ ID NO:70); R: TCT CCT GTG GAT CGG GTA TAG AC (SEQ ID NO:71)); CCR6: (F: AAG ATG CCT GGC TTC CTC TGT (SEQ ID NO:72); R: GGT CTG CCT GGA GAT GTA GCT T (SEQ ID NO:73)); CCR7: (F: CCA GGC ACG CAA CTT TGA G (SEQ ID NO:74); R: ACT ACC ACC ACG GCA ATG ATC (SEQ ID NO:75)); CCR8: (F: CCA GCG ATC TTC CCA TTC TTC (SEQ ID NO:76); R: GCC CTG CAC ACT CCC CTT A (SEQ ID NO:77)).

In the studies described above, RTLs were shown to reverse clinical and histological signs of disease in Lewis rats that developed monophasic EAE (Burrows et al., 1998; Burrows et al., 1999), as well as in Tg DR2 (DRB1*1501) mice that developed chronic EAE (Vandenbark et al., 2003). In the instant example, the efficacy of RTL therapy on relapsing EAE induced by PLP 139-151 peptide in SJL/J mice was further demonstrated. Treatment of EAE in SJL mice required mouse MHC class II design modifications and included the α1 and β1 domains of the I-A$^s$ molecule covalently bound to the PLP 139-151 peptide (RTL401) or the RTL without bound peptide (RTL400).

Biochemical Characterization of Mouse RTLs

Figure 22:
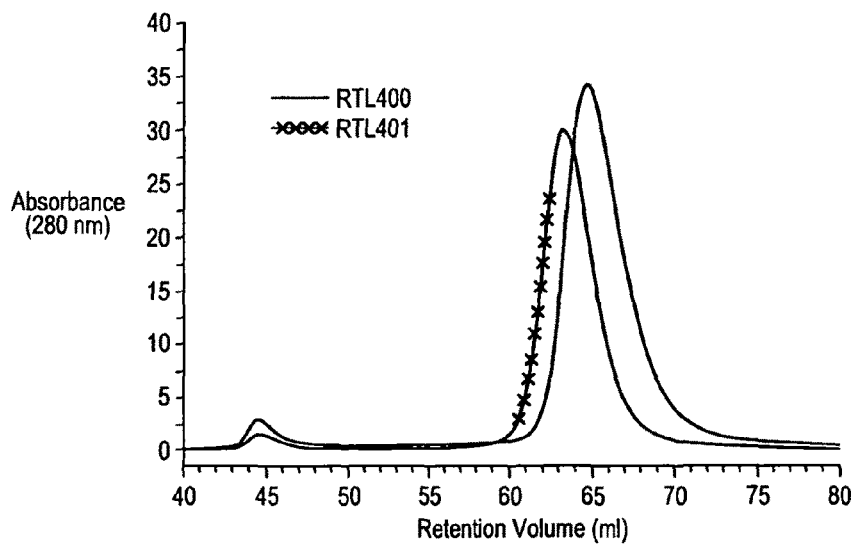
FIG. 22 presents size exclusion chromatography data for modified RTLs. Purified and refolded modified RTL400 and 401 were analyzed by size exclusion chromatography. A SUPERDEX 75 (16/60) size exclusion column was calibrated with a set of known m.w. proteins, and Y=−0.029X+6.351 (r=0.995) was calculated from the slope of the standard curve, and subsequently used to estimate the size of modified RTL400 and 401.

CD analysis shows that the human RTLs have a secondary structure composition similar to the TCR recognition/peptide-binding α1β1 domain of native human MHC class II molecule as determined by x-ray crystallography (Chang et al., 2001; Smit et al., 1998; Li et al., 2000). CD data observed in the current investigation showed that murine RTLs shared a similar anti-parallel β-sheet platform, and α-helix secondary structure common to all murine MHC class II Ag-binding domains (Fremont et al., 1998; He et al., 2002; Scott et al., 1998). The size exclusion chromatography data (FIG. 22) and hydrodynamic analysis using DLS indicated that the purified and refolded RTL400 and RTL401 were monodispersed molecules in Tris-Cl buffer. Fractions of each peak from the size exclusion column were collected and analyzed by CD. Secondary structure analysis using the Variable Selection method (Compton et al., 1986) indicated that murine RTLs maintain a high order of secondary structure similar to native murine I-A$^k$ and I-A$^u$ MHC class II molecules (Fremont et al., 1998; He et al., 2002).

Dose-Dependent Inhibition of PLP Peptide-Induced EAE in SJL Mice

In initial preclinical studies, SJL/J mice with established signs of EAE were treated with varying numbers of daily i.v. injections of 100 μg of RTL401 containing PLP 139-151 peptide. Control mice typically developed a relapsing EAE disease course, with onset of the initial episode of acute disease occurring on day 11-12 after injection of PLP 139-151 peptide/CFA and peak clinical scores developing on day 15, followed by a clinical improvement that lasted until day 20. The first relapse was evident by day 22 in essentially all the mice, reaching a second peak on days 27-28. The mice generally had subsequent remissions and may have had additional relapses or developed chronic EAE, but these variations in clinical course occurred sporadically in individual mice.

Treatment with 100 μg of RTL401 i.v. beginning on day 12 and continuing for 8 consecutive days had the greatest effect on clinical EAE (Table 4), although fewer daily i.v. injections (3 or 4 consecutive days) were only nominally less effective (Table 4). Compared with vehicle-treated controls, all three regimens ameliorated clinical disease within the first 24 h, reduced the peak severity of the first clinical episode, and essentially eliminated relapses (Table 4). RTL401 treatment reduced the daily clinical score to minimally detectable disease that was maintained even after cessation of treatment for nearly 4 wk, and significantly reduced the cumulative disease index (Table 4). Mice receiving eight daily i.v. doses of 100 μg of RTL401 were treated with antihistamines to prevent development of allergic responses to RTLs. Treatment of mice with the same regimen of antihistamine alone had no effect on the course of relapsing EAE (Table 4). In contrast to mice treated with RTL401, mice treated with the eight daily i.v. doses of 100 μg of empty RTL400 construct or a molar equivalent dose of free PLP 139-151 peptide (10 μg peptide/injection) with antihistamine did not experience significant clinical benefit compared with untreated control mice (Table 4).

TABLE 4

Effect of RTL401 and RTL400 treatment on EAE in SJL/J mice immunized with PLP 139-151/CFA

|  | Incidence<br>Onset<br>Peak<br>Mortality<br>Relapse<br>CDI |
|---|---|
| Control | 13/13<br>11.2 ± 0.6<br>4.2 ± 1.4<br>0/13<br>9/13<br>96.7 ± 33.7 |
| PLP 139-151 (10 μg) | 4/4<br>11 ± 0.0<br>4.7 ± 0.5<br>0/4<br>3/4<br>87.1 ± 19.3 |
| Anti-histamine | 4/4<br>11.5 ± 0.6<br>5.2 ± 0.3<br>0/4<br>3/4<br>118 ± 24.9 |
| RTL400 | 6/6<br>11.2 ± 0.4<br>4.8 ± 0.9<br>1/6<br>4/6<br>116.2 ± 43.3 |
| RTL401 (3 days i.v.) | 4/4<br>11.5 ± 0.6<br>3.1 ± 1.1$^{abcd}$<br>0/4<br>0/4<br>45.3 ± 12.6$^{abcd}$ |
| RTL401 (4 days i.v.) | 4/4<br>11.7 ± 0.9<br>3.9 ± 0.9$^d$<br>0/4<br>0/4<br>50.5 ± 22.2$^{abcd}$ |
| RTL401 (8 days i.v.) | 14/14<br>11.2 ± 0.4<br>2.9 ± 1.4$^{abcd}$<br>0/14<br>1/14$^{abcd}$<br>35.4 ± 25.5$^{abcd}$ |

$^a$Significant difference compared to control, p < 0.05.
$^b$Significant difference compared to peptide, p < 0.05.
$^c$Significant difference compared to RTL400, p < 0.05.
$^d$Significant difference compared to anti-histamine, p < 0.05.

As is shown in Table 5, eight daily injections of 100 μg of RTL401 administered by the s.c. route was also effective in treating EAE, nominally reducing the relapse rate, and significantly reducing daily clinical scores and the cumulative disease index in a manner similar to i.v. injections. In contrast, comparable s.c. injections of the empty RTL400 construct or a molar equivalent dose of free PLP 139-151 peptide did not have any effect on the clinical course of EAE in SJL mice. These results demonstrate that both i.v. and s.c. administration of RTL401 reduced relapses of EAE and produced long-lasting clinical benefit even after cessation of RTL treatment on day 20.

TABLE 5

Effect of RTL401 treatment on SJL females immunized with PLP 139-151, PLP 178-191 or MBP 84-104

|  | Incidence<br>Onset<br>Peak<br>Mortality<br>Relapse<br>Mean CDI |
|---|---|
| Control (PLP 139-151) | 13/13<br>11.2 ± 0.6<br>4.2 ± 1.4<br>0/13<br>9/13<br>96.7 ± 33.7 |
| RTL i.v. | 14/14<br>11.2 ± 0.4<br>2.9 ± 1.4$^a$<br>0/14<br>1/14$^a$<br>35.4 ± 25.5$^a$ |

TABLE 5-continued

Effect of RTL401 treatment on SJL females immunized with PLP 139-151, PLP 178-191 or MBP 84-104

| | Incidence<br>Onset<br>Peak<br>Mortality<br>Relapse<br>Mean CDI |
|---|---|
| RTL s.c | 12/12<br>11.2 ± 0.4<br>3.1 ± 1.3<br>0/12<br>4/12<br>45.5 ± 16.8[a] |
| Control(PLP 178-191) | 5/5<br>11.4 ± 0.6<br>3.0 ± 1.5<br>0/5<br>2/5<br>53.3 ± 16.1 |
| RTL i.v. | 6/6<br>11.3 ± 0.5<br>2.1 ± 1.8<br>0/6<br>3/6<br>39.2 ± 15.7 |
| Control(MBP 84-104) | 6/6<br>11.3 ± 0.5<br>3.8 ± 1.7<br>0/6<br>4/6<br>51.3 ± 23.6 |
| RTL i.v. | 6/6<br>11.5 ± 0.6<br>2.2 ± 1.0<br>0/6<br>4/6<br>41.9 ± 14.0 |

[a]Significant difference between control and treatment groups, p < 0.05. Incidence: number of mice that get sick in a group. Onset: Day when first clinical signs of EAE is observed. Peak: Maximum EAE score. Relapse: Number of mice that show a decrease in EAE score by 1 point for 48 h followed by an increase in EAE score for 48 h. Mean CDI: Cumulative disease index; sum of the daily scores for the entire length of the experiment.

RTL Treatment Effect on EAE is Peptide-Specific and Requires Cognate MHC

To evaluate peptide specificity of RTL treatment in vivo, RTL401 was used to treat EAE induced in SJL/J mice with two different encephalitogenic peptides, PLP 178-191 and MBP 84-104, both restricted by I-As. Eight daily i.v. injections of 100 μg of RTL401 did not significantly affect the overall severity or relapse rate of EAE induced by either peptide compared with vehicle-treated control mice (p>0.2), although in each case a nominal reduction in the cumulative disease index was observed. Day 42 LN responses in PLP 178-191 and MBP 84-104 peptide-immunized mice with EAE were specific only for the immunizing peptide, and no responses were observed to PLP 139-151 peptide, indicating a lack of epitope spreading.

Figure 28:
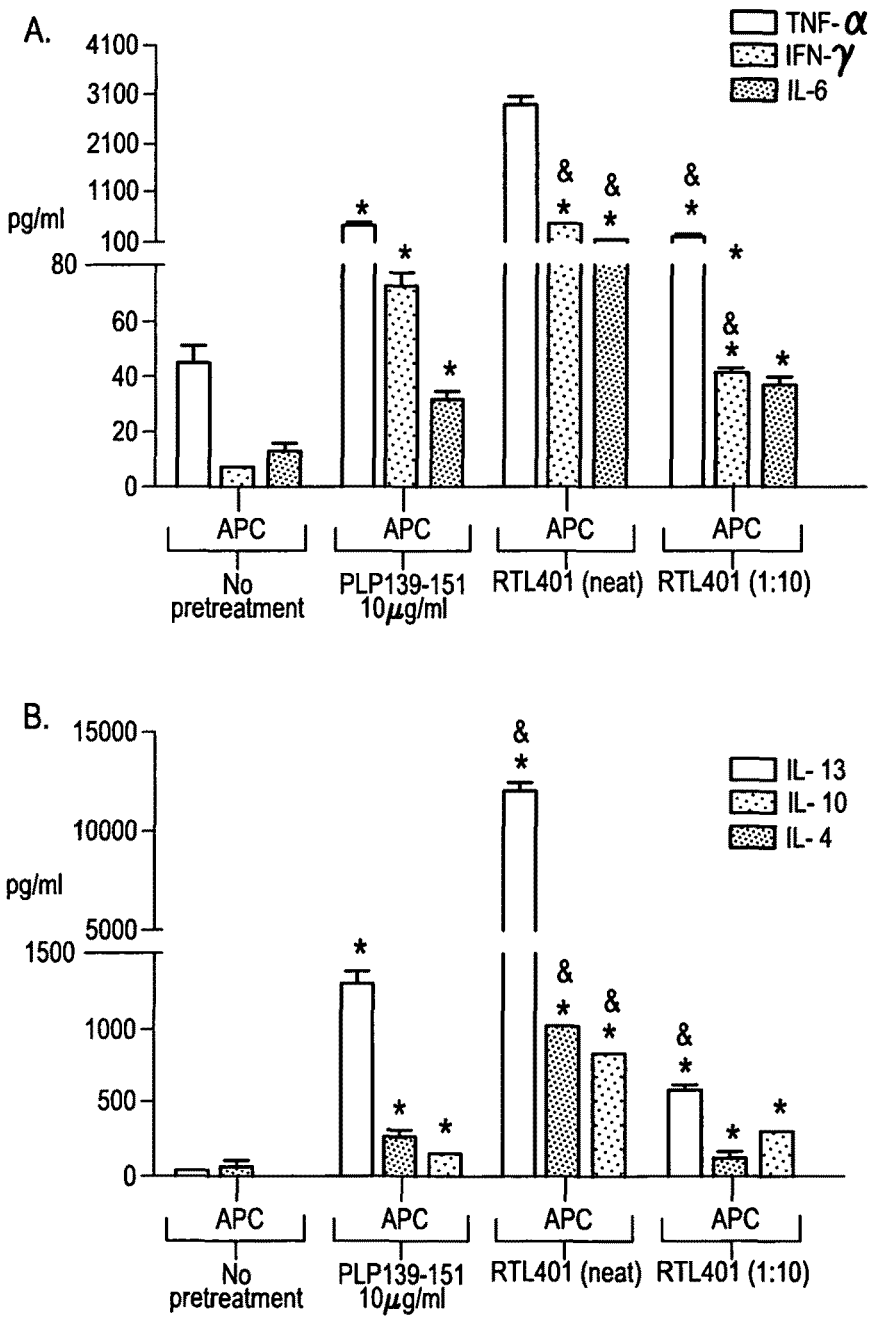
FIGS. 28A and 28B are graphs demonstrating that RTL401 induces increased expression of IL-13 and other cytokines in vitro in T-cells specific for PLP-139-151 peptide incubated for 24 h with 100 µg/ml RTL401 (neat), 10 µg/ml RTL401 (1:10), 10 µg/ml PLP-139-151 peptide, or medium prior to washing and incubation for 48 hours with APC but without added PLP peptide. (*) indicates significant difference (p<0.05) compared to medium pre-treated T-cells. (&) indicates significant difference (p<0.05) compared to PLP-139-151 peptide pre-treated T-cells. The data are pooled from three separate experiments.

To further evaluate the requirement for MHC and peptide specificity of RTL treatment, RTL401 was used to treat EAE induced by either PLP 139-151 peptide or MOG 35-55 peptide in (C57BL/6×SJL) F$_1$ mice. These mice express both I-A$^s$ and I-E$^b$ MHC class II molecules that restrict PLP 139-151 (I-A$^s$) and MOG 35-55 (I-E$^b$) peptides, in both cases producing an encephalitogenic response. As is shown in FIG. 28, treatment at disease onset with eight daily i.v. injections of 100 μg of RTL401 significantly reduced the severity of EAE induced by PLP 139-151 peptide, but had no effect on EAE induced by MOG 35-55 peptide. For comparison purposes, RTL 402 and 403 were also used to treat EAE induced by PLP 139-151 peptide. As can be seen in FIG. 50 and Table 6, while treatment with RTL401 significantly reduced the severity of EAE induced by PLP 139-151 peptide as evaluated by the mean clinical score and the cumulative disease index (CDI), RTL 402 and 403 had no effect.

TABLE 6

Effect of RTL 401, RTL402 and RTL403 treatment on EAE in SJL/J mice immunized with PLP 139-151/CFA

| Group | Incidence | Onset | Peak | Mortality | CDI |
|---|---|---|---|---|---|
| Control | 8/8 | 10.5 ± 0.7 | 3.6 ± 0.8 | 0/8 | 72.5 ± 20.5 |
| RTL401 | 8/8 | 10.5 ± 0.7 | 2.0 ± 0.4 | 0/8 | 24.7 ± 12.9* |
| RTL402 | 8/8 | 10.5 ± 0.7 | 3.1 ± 1.2 | 0/8 | 66.5 ± 37.1 |
| RTL403 | 8/8 | 10.5 ± 0.7 | 3.7 ± 1.5* | 0/8 | 67.3 ± 32.1 |

The specificity of the response to treatment of EAE induced with a single encephalitogenic peptide was further confirmed in the treatment of mice with EAE induced by MBP-84-104/CFA. As shown in Table 7, in which mice were treated at disease onset with 8 s.c. doses of 0.1 mg of vehicle, RTL 401, 402 and 403, respectively, mice treated with RTL403 had significantly reduced CDI scores whereas mice treated with RTL401 or RTL402 had CDI scores similar to those of the controls.

TABLE 7

Effect of RTL401, RTL402, and RTL403 treatment on EAE in SJL/J mice immunized with MBP84-104/CFA

| Group | Incidence | Onset | Peak | Mortality | CDI |
|---|---|---|---|---|---|
| Control | 8/8 | 7 ± 0 | 3.9 ± 0.5 | 1/8 | 97.6 ± 15.7 |
| RTL401 | 8/8 | 7.5 ± 0.7 | 3.9 ± 0.6 | 0/8 | 70.3 ± 43.2 |
| RTL402 | 8/8 | 7.5 ± 0.7 | 3.5 ± 0.3 | 0/8 | 99.1 ± 17.7 |
| RTL403 | 8/8 | 7 ± 0 | 2.1 ± 1.7 | 0/8 | 56.3 ± 39.3* |

These data demonstrate that RTL treatment of EAE is specific for the cognate combination of MHC and neuroantigen peptide.

RTL Treatment Effect on EAE Induced by Multiple Encephalitogenic Peptides

To determine the effect of treatment of EAE induced by multiple encephalitogenic peptides, SJL/J mice were injected s.c. with both MBP-84-104 and PLP-139-151 in CFA and evaluated as described above for disease progression. Mice were then treated with 0.1 mg/day of vehicle, RTL401, RTL 403, or RTL401 and RTL403 for eight days. As can be seen in Table 8, while, as expected, EAE progression was significantly reduced in mice treated with the combination of RTL 401 and RTL 403, EAE progression was also significantly reduced in mice treated with either RTL 401 or RTL 403.

TABLE 8

Effect of treatment with RTL 401, RTL403, or both on EAE in SJL/J mie immunized with MBP84-104 and PLP 139-151/CFA.

| Group | Incidence | Onset | Peak | Mortality | CDI |
|---|---|---|---|---|---|
| Control | 8/8 | 10 ± 0.5 | 4.8 ± 0.5 | 1/8 | 93.5 ± 22.7 |
| RTL401 | 8/8 | 11 ± 1.4 | 2.6 ± 0.8* | 0/8 | 35.3 ± 19.8* |
| RTL403 | 8/8 | 10.6 ± 0.7 | 2.9 ± 0.9* | 0/8 | 47.5 ± 16.3* |
| RTL401 + 403 | 8/8 | 10.6 ± O.5 | 3.5 ± 1.2* | 0/8 | 55.8 ± 19.9* |

These experiments demonstrate that treatment of EAE induced by multiple encephalitogenic peptides can be effectuated with any of the cognate RTLs containing one of the injected encephalitohenic peptides that induced the disease.

The effectiveness of treatment with a single cognate RTL on the reduction of the severity of EAE induced by multiple encephalitogenic peptides was confirmed by inducing EAE with whole spinal cord homogenates. Mouse spinal cords were emulsified in CFA and injected s.c. on days 0 and 7. The mice were then treated s.c. at onset of EAE (day 12) with 0.1 mg/day of vehicle or RTL401 for eight days. As shown in FIG. 53, mice treated with RTL401 had reduced severity of EAE.

Effects of RTL401 Treatment on Peripheral T-Cell Responses Ex Vivo

Figure 23:
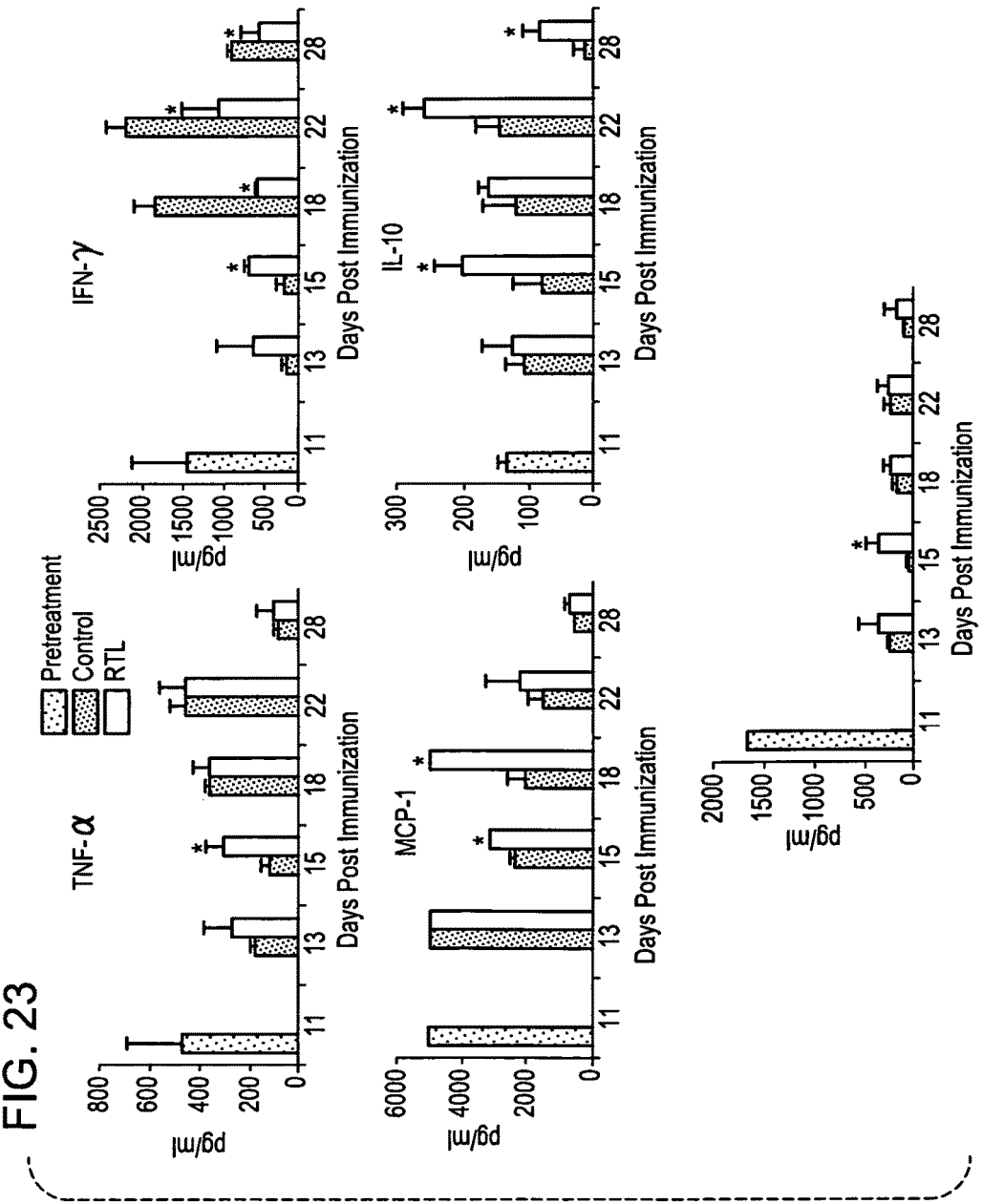
FIG. 23 illustrates T-cell cytokine response patterns. SJL mice were sacrificed at different time points following treatment with RTL401. Spleens were harvested and set up in vitro with 10 µg of PLP 139-151 peptide. Supernatants were harvested after 48 h and assayed for cytokine production by cytometric bead array as described below. Significant differences between control and experimental groups were determined using Student's t test (*, p<0.05). Data are presented as the mean and SD of two mice at each time point per group.

LNs and spleen cells from vehicle control and RTL401 treated (eight daily i.v. injections of 100 μg) SJL/J mice with EAE were analyzed during the course of treatment for proliferation and cytokine responses to the immunizing PLP 139-151 peptide. Immune cell responses were assessed just after disease onset but before treatment (day 11), 24 h after initiation of treatment (day 13), at the peak of the initial clinical episode (day 15), at the first remission (day 18), at the beginning of the first relapse (day 22), at the peak of the first relapse (day 28), and at the end of the first relapse (day 42). In contrast to previously published results in DR2-expressing mice (Vandenbark et al., 2003), there was no significant inhibitory effect of RTL treatment on proliferation responses at any time during the course of EAE. As exemplified in FIG. 29, treatment with RTL401 nominally inhibited proliferation responses to PLP 139-151 peptide in LN cultures, but significantly enhanced proliferation of splenocyte cultures at several time points, including on day 42 as shown in FIG. 29. In contrast, RTL401 treatment had mixed effects on cytokine secretion from PLP 139-151-stimulated splenocytes (FIG. 23). One day after initiation of RTL401 treatment (day 13), there were no significant changes in cytokine responses compared with control mice. Surprisingly, at the peak of the first episode of EAE (day 15), there was enhanced secretion of both inflammatory (TNF-α, IFN-γ, MCP-1, and IL-6) and anti-inflammatory (IL-10) factors in splenocyte cultures from RTL401-treated vs. control mice. However, during remission from the first episode of EAE (day 18), the cytokine picture changed dramatically, with strongly reduced levels of IFN-γ, still enhanced levels of MCP-1, but no significant differences in TNF-α, IL-6, or IL-10 in RTL401-treated mice. At onset of the first relapse (day 22), there was again a significant reduction in secreted IFN-γ in RTL401-treated mice, but no significant differences in the other inflammatory factors (FIG. 23). Of possible importance for systemic regulation, there was a significant increase in secreted IL-10 levels by PLP 139-151-reactive splenocytes from RTL401-treated mice at both the onset and peak of the first relapse (days 22 and 28, respectively). Both IgG1 and IgG2a Abs were detected in serum during the course of EAE, but levels showed only minor fluctuations as a result of RTL401 treatment.

Effects of RTL401 Treatment on CNS During EAE

Figure 24:
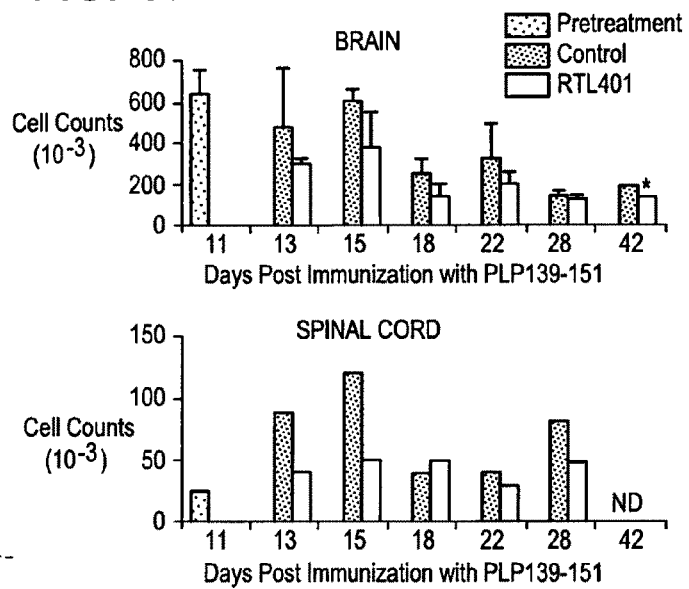
FIG. 24 shows additional CNS effects of RTL treatment. Mononuclear cells were isolated from brains and spinal cords harvested from mice at different time points following RTL401 treatment. Cells were counted by trypan blue exclusion method. Results presented are counts from two to three pooled brains or spinal cords.
Figure 25:
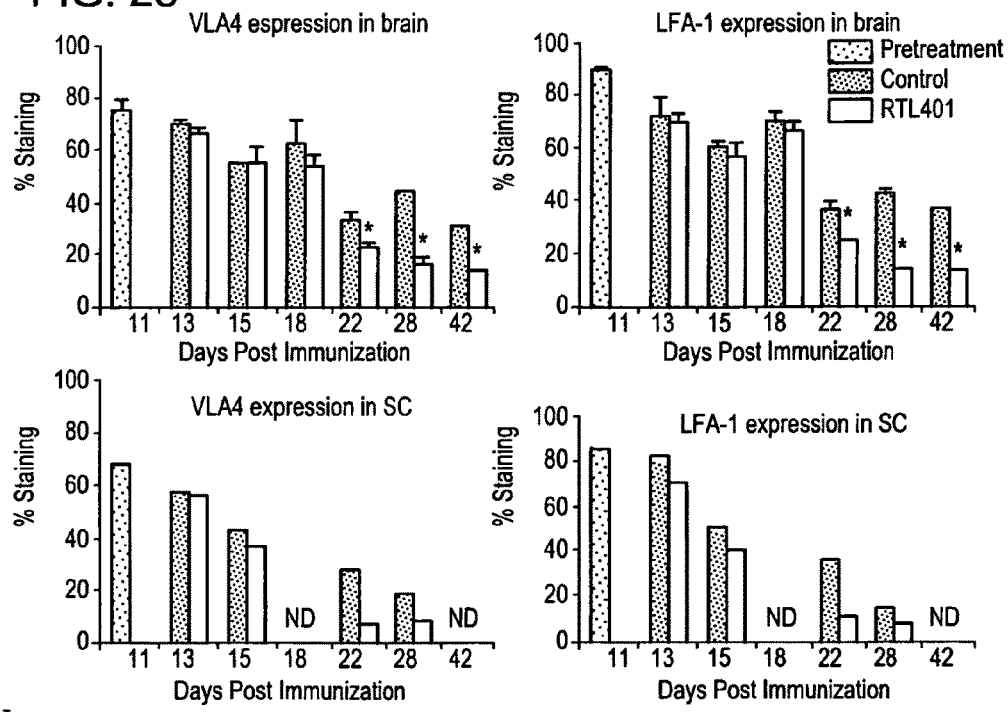
FIG. 25 illustrates that RTL treatment significantly decreases adhesion molecule expression on T-cells in the CNS. MNC's were isolated from brains and spinal cords harvested from two representative mice at different time points following RTL401 treatment. Cells were then stained with anti-mouse CD3 and anti-mouse VLA-4 or anti-mouse LFA-1 to identify the expression of these adhesion molecules on T-cells infiltrating the CNS. Data presented are percentage of total gated cells that were dual positive for CD3 and VLA-4 or LFA-1. Significance between control and experimental groups were determined using Student's t test (*, p<0.05).
Figure 26:
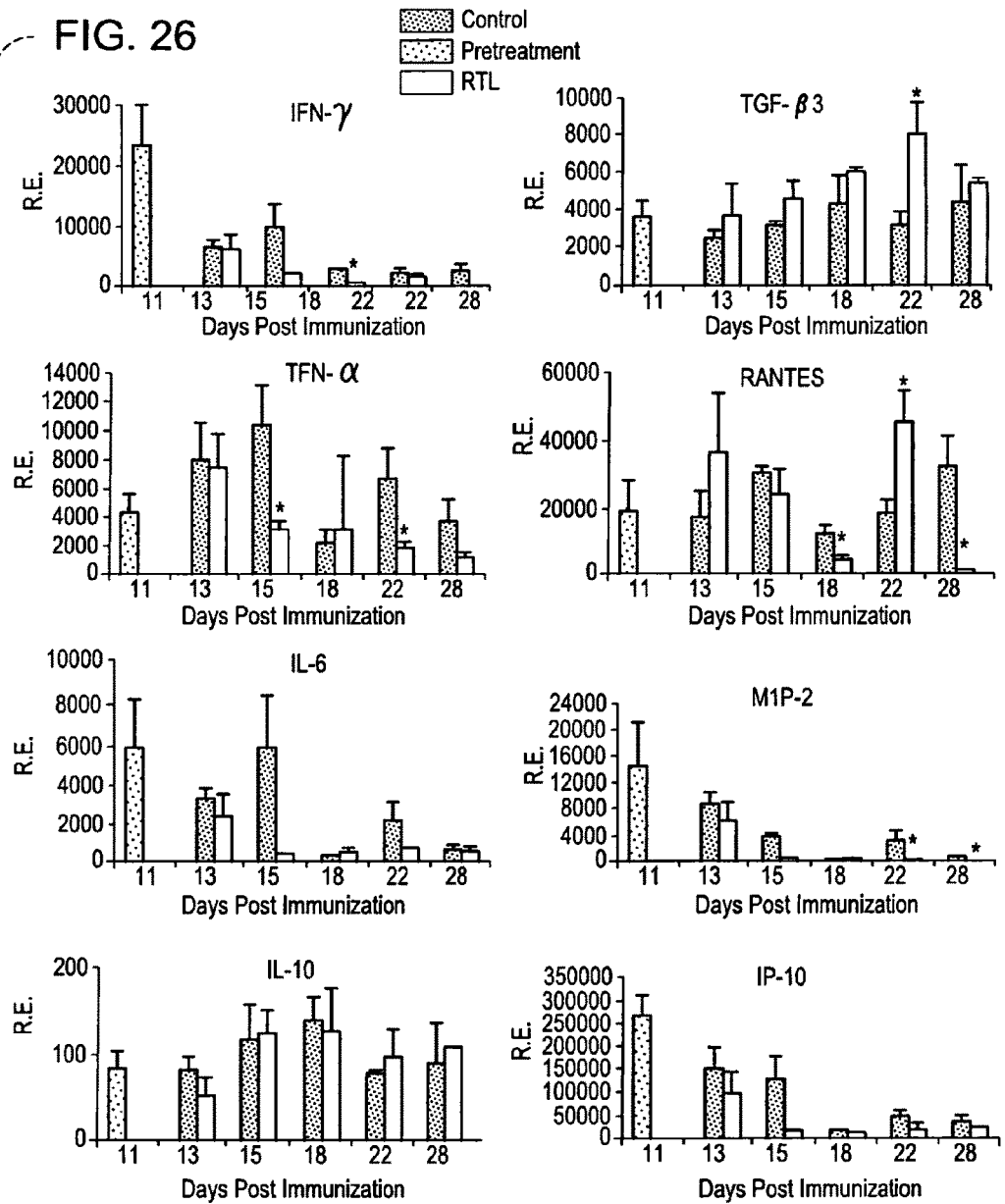
FIG. 26 illustrates the effects of RTL treatment on cytokine and chemokine gene expression as determined by real-time PCR. mRNA was isolated from whole frozen spinal cords harvested from two control and two RTL treated mice at different time points. cDNA was synthesized and real-time PCR was performed using primers specific for IFN-γ, TNF-α, IL-6, IL-10, TGF-β3, RANTES, MIP-2, and IP-10. Expression of each gene was calculated relative to the expression of housekeeping gene, L32. Significance between control and experimental groups was determined using Student's t test (*, p<0.05).
Figure 27:
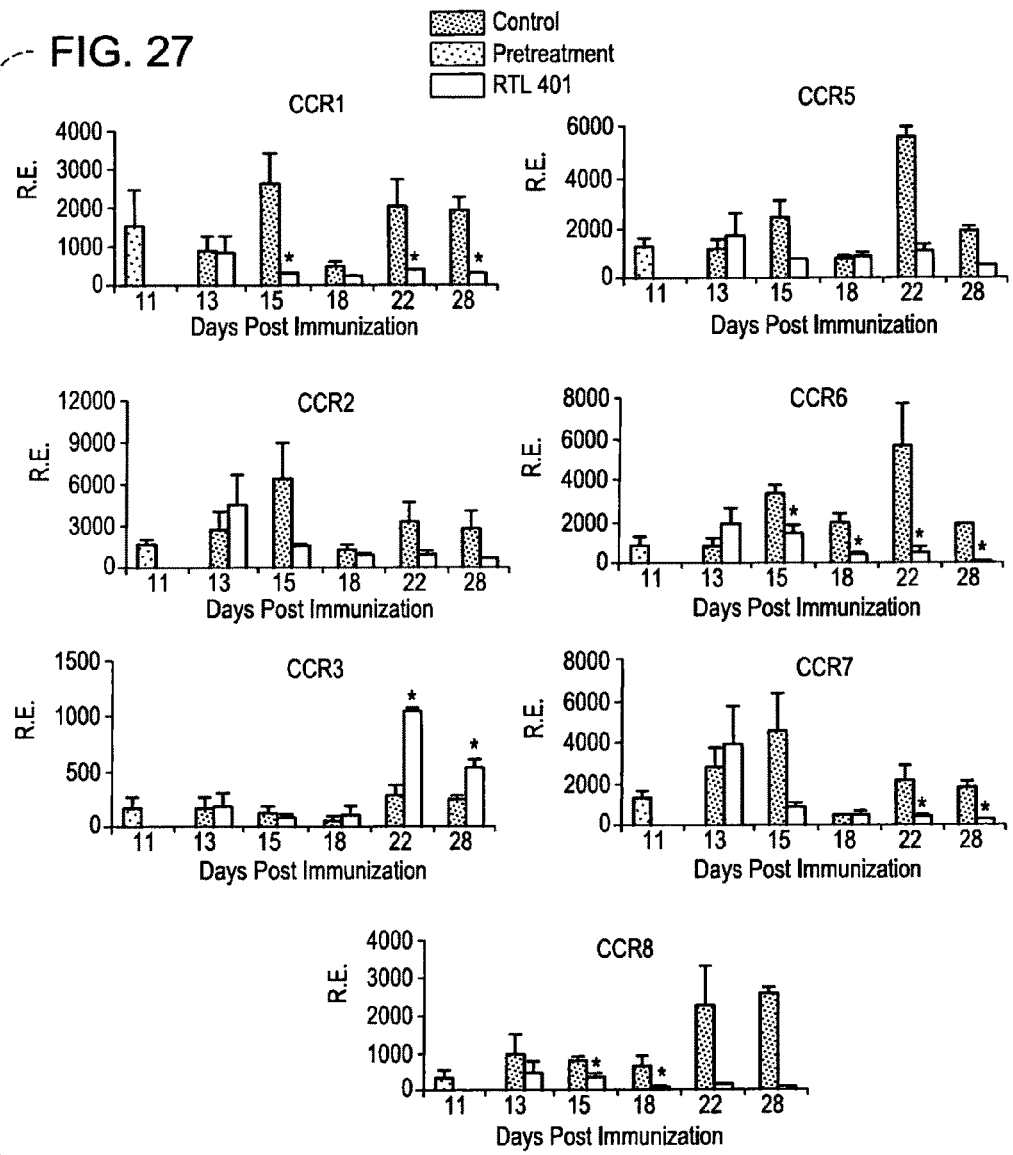
FIG. 27 provides real-time PCR quantification of relative expression of chemokine receptor genes from spinal cords of vehicle- and RTL-treated mice. mRNA was isolated from whole frozen spinal cords harvested from two control and two RTL-treated mice at different time points. cDNA was synthesized and real-time PCR was performed using primers specific for CCR1, CCR2, CCR3, CCR5, CCR6, CCR7, and CCR8. Expression of each gene was calculated relative to the expression of housekeeping gene, L32. Significance between control and experimental groups was determined using Student's t test (*, p<0.05).

To further evaluate the effects of RTL401 therapy on EAE, histological sections were obtained and phenotypic and functional analyses of CNS cells were conducted. Histological sections of spinal cords taken on day 46 showed reduced inflammatory lesions and decreased demyelination in RTL401-treated vs. control mice. More specifically, spinal cords from RTL-treated mouse showed dense mononuclear infiltration with only very slight or no apparent loss of myelin stain in the surrounding myelinated tissue. Spinal cords from control, non-RTL-treated mouse showed multiple regions of dense mononuclear cell infiltration with considerable, diffuse loss of myelin stain in the regions adjacent to the mononuclear infiltrate. This reduction in inflammatory activity found in RTL401-treated mice was reflected by a decrease in the number of inflammatory mononuclear cells obtained from brain and spinal cord tissue over the course of treatment (FIG. 24). The reduction of inflammatory cells was most pronounced at onset and peak of the first clinical episode (days 13 and 15), and at onset of the first relapse (day 22), was marked by an overall decrease of $CD4^+$ T-cells (from 43 to 23%) but an increase in $CD11b^+$ monocytes/macrophages (from 38 to 60%) as determined by FACS analysis. Moreover, the number of T-cells expressing adhesion/homing markers VLA-4 and LFA-1 was consistently reduced in brains and spinal cords from RTL401-treated mice on days 22, 28, and 42 (brain only) after EAE induction (FIG. 25). From day 15 on, RT-PCR analysis of spinal cord tissue from RTL-401-treated mice also showed moderate to strong reduction in expression of mRNA for inflammatory cytokines (IFN-γ, TNF-α, and IL-6) and chemokines (RANTES, MIP-2, and IP-10), but enhanced expression of TGF-β3 (FIG. 33), consistent with other data indicating a protective role for this cytokine (Matejuk et al., 2004). Expression of IL-10 was very low throughout the EAE disease course in spinal cords from RTL-treated mice, with only a slight enhancement in RTL401-treated mice during the first relapse (day 22; FIG. 33). Interestingly, expression of most chemokine receptors (CCR1, CCR2, CCR5, CCR6, CCR7, and CCR8) was moderately to strongly reduced in spinal cord tissue from RTL401-treated mice beginning at the peak of the first episode (day 15; FIG. 27). In contrast, expression of CCR3 (Th2 associated) appeared to be uniquely enhanced in spinal cord tissue collected from RTL401-treated vs. control mice during the first relapse (days 22 and 28, FIG. 27).

Effects of RTL401 on Thoracic Spinal Cord White Matter

In another experiment, RTL401 was used to treat EAE induced by PLP-139-151 in SL/J mice. Onset of EAE was evident on day 11 with the peak reached on day 20. The mice received five consecutive treatments of RTL401 by i.v. starting on day 20 and three consecutive treatments s.c. starting on day 32. Mice were sacrificed on day 60 by $CO_2$ inhalation. Spinal cords were removed by insufflation and fixed in 10% formalin/PBS. Paraffin sections were prepared and stained with hematoxylin and eosin. Neurological lesions were graded on each of 10 cross sections per spinal cord. As can be seen in FIG. 43 and Tables 12 and 13, treatment with RTL 401 significantly decreased the amount of myelin damage in the dorsal, lateral and ventral white matter of the thoracic section of the spinal cord.

TABLE 9

Clinical scores of individual mice.

| Mouse# | Onset | Peak | Control | RTL401 |
|---|---|---|---|---|
| 1 | 1.5 | 4.5 | 4.5 | 2 |
| 2 | 1.5 | 4.5 | 4 | 1.5 |
| 3 | 1.5 | 4.5 | 4 | 1.5 |

TABLE 10

One-way ANOVA analysis of variance followed by Newman-Kuels multiple comparisons tests.

| Comparison | Dorsal | Lateral and Ventral |
|---|---|---|
| Peak vs. Onset | $P < 0.05*$ | $P < 0.001*$ |
| Vehicle vs. Onset | $P < 0.001*$ | $P < 0.001*$ |
| Vehicle vs. Peak | $P < 0.01*$ | $P < 0.01*$ |
| RTL401 vs. Vehicle | $P < 0.001*$ | $P < 0.001*$ |

TABLE 10-continued

One-way ANOVA analysis of variance followed
by Newman-Kuels multiple comparisons tests.

| Comparison | Dorsal | Lateral and Ventral |
|---|---|---|
| RTL401 vs. Peak | P < 0.05* | P < 0.001* |
| RTL401 vs. Onset | P > 0.05 | P > 0.05 |

*Comparison significant statistically.

The foregoing disclosure evinces successful design and demonstration of the efficacy of oligomeric RTLs specific for both human and rat T-cells that reversed clinical EAE and induced long-term T-cell tolerance. In the current example, the design characteristics and therapeutic effects of a monomeric murine RTL401 (I-A$^s$/PLP 139-151 peptide) on a relapsing model of EAE in SJL/J mice are demonstrated. Generally, RTL401 had very similar structural characteristics and therapeutic effects on EAE compared with previously designed molecules, although some important differences were noted in its effects on the activation and inflammatory properties of targeted encephalitogenic T-cells. A similar monomeric form of human DR2 RTL has been produced and tested in HLA-DR2 transgenic mice developing chronic EAE, which is also useful within various embodiments of the current invention (see, e.g., U.S. Provisional Patent Application No. 60/500,660, filed Sep. 5, 2003; and U.S. patent application Ser. No. 10/936,467, filed Sep. 7, 2004; and Huan et al., 2004, each of which is incorporated herein by reference in its entirety).

Secondary structure analysis from CD spectra of murine RTLs indicated that RTL400 and RTL401 maintained a high order of secondary structure similar to native murine I-A$^k$ and I-A$^u$ MHC class II molecules (Fremont et al., 1998; He et al., 2002). The recombinant RTL is a relatively small molecule (~24 kDa) containing a native disulfide bond between cysteine 17 and 79 (RTL401 amino acid numbering, corresponding to murine I-A$^s$ β-chain residues 42 and 104). This disulfide bond was retained upon refolding, demonstrated by comparing mobility during electrophoresis (SDS-PAGE) of the RTL in the presence or absence of the reducing reagent, 2-ME. Both RTL400 and RTL401 showed a higher mobility in the absence of 2-ME, indicative of a more compact structure compared with the reduced RTLs. Together, these data represent a primary confirmation of the conformational integrity of the molecule. Unlike the human HLA-DR2 construct and rat I-A constructs that tended to aggregate during the refolding process, the mouse RTL constructs appeared to be monodispersed molecules, based on light scattering and size exclusion chromatography analyses.

Of potential clinical importance, these monodispersed molecules induced specific and significant inhibition of PLP 139-151 peptide-induced EAE, but not EAE induced by other myelin peptides when administered in vivo. The investigations herein demonstrate potent activity of this minimal TCR ligand to reverse clinical signs of EAE and prevent relapses for at least 26 days after completion of a single 3-, 4-, or 8-day course of daily RTL injections. Disease expression after RTL treatment was minimal, although persistent, unlike the complete abrogation of clinical signs observed in RTL-treated DR2 Tg mice (Vandenbark et al., 2003). One explanation for chronic low-level EAE might be epitope spreading (Lehman et al., 1992; Vanderlught, 2003). It is notable in this context that the RTL-treated mice described herein did not develop T-cell responses to other known subdominant encephalitogenic peptides, including PLP 178-191 or MBP 84-104. Although i.v. injections provided the lowest cumulative EAE scores, s.c. injections were also highly effective. This finding will facilitate future application of RTL therapy to humans, in whom the s.c route of injection is preferable due to ease of injection and reduced risk of hypersensitivity reactions. Such reactions were noted in i.v. RTL-treated SJL/J mice, but could be controlled by injection of antihistamines.

Mechanistically, the murine RTL401 appeared to possess several differences compared with our human DR2/MOG 35-55 construct that inhibited chronic EAE in DR2 transgenic mice (Vandenbark et al., 2003) and our rat RT-1B$^1$/MBP 72-89 construct that inhibited monophasic EAE in Lewis rats (Burrows et al., 2000). Both previous constructs were oligomeric and induced a striking reduction of LN T-cell responses, as assessed by proliferation and secretion of inflammatory cytokines including IFN-γ and TNF-α. In contrast, the murine I-A$^s$/PLP 139-151 construct did not significantly reduce T-cell proliferation responses to PLP 139-151 peptide, but instead, enhanced splenocyte proliferation and secretion of both inflammatory (TNF-α and IFN-γ) and anti-inflammatory (IL-10) cytokines during the first 3 days of treatment (FIG. 23). In general, variations in expression of inflammatory cytokines mirrored periods of EAE relapses and remission in control SJL/J mice, with more expression noted on days 15 (peak of initial episode) and 22 (first relapse) than on day 18 (remission). However, continued treatment with RTL401 resulted in strongly decreased levels of IFN-γ, while at the same time maintaining elevated IL-10 levels (FIG. 23). These data indicate that in SJL mice, RTLs induced a cytokine switch rather than anergy or apoptosis in treated T-cells that still allowed homing to the target organ (CNS). Interestingly, treatment of human T-cell clones in vitro with DR2/MBP 85-99 or DR2/cABL peptide RTLs led to a similar enhancement of IL-10 secretion, raising the possibility of an RTL-induced cytokine switch mechanism in humans as well (Burrows et al., 2001). Other Th2 cytokines such as IL-4 and IL-5 may also be involved.

The mechanistic differences observed in the periphery apparently resulted in differences in CNS as well. Histological sections of spinal cord tissue from RTL-treated SJL mice showed less demyelination, but only a modest reduction of inflammatory lesions. Moreover, both brain and spinal cord tissue from RTL401-treated mice had only a slight reduction in numbers of infiltrating cells, unlike in RTL312-treated DR2 mice protected from EAE that had a more drastic reduction of infiltrating CNS cells (Vandenbark et al., 2003). During the first relapse, the RTL-treated SJL/J mice had a significant reduction in the percent of infiltrating cells expressing VLA-4 and LFA-1, adhesion molecules that are known to be important in EAE to direct homing of leukocytes to the perivascular sites of inflammatory lesions in CNS tissue (Gordon et al., 1995; Theien et al., 2001). Further analysis of mRNA from CNS tissue also demonstrated a striking reduction in expression of inflammatory cytokines (IFN-γ, TNF-α, and IL-6) and chemokines (RANTES, MIP-2, and IP-10), but enhanced expression of anti-inflammatory cytokines (TGF-β3 and IL-10). IL-10 is known to inhibit IFN-1 production and clinical expression of EAE (Cua et al., 1999), and an association with increased expression of TGF-β3 and EAE protection has also been reported (Matejuk et al., 2004). The expression pattern for inflammatory chemokine receptors in CNS appeared to be related to the clinical disease course of EAE, with strongest expression at the peak of the initial episode and/or the beginning of the first relapse.

In addition to these findings, CCR1, CCR2, and CCR7 appeared to be expressed preferentially in control mice during the first episode of EAE, whereas CCR5, CCR6, CCR8 were more strongly expressed during the first relapse. Of importance, treatment with RTL401 reduced expression of all these CCRs during both clinical episodes of EAE (FIG. 27). In studies in C57BL/6 mice with EAE, enhanced expression of CCR1, CCR2, and CCR5 in CNS at the peak of EAE was observed (Matejuk et al., 2001). Moreover, in vitro treatment of encephalitogenic T-cells with IL-12 and IL-18, respectively, enhanced expression of IFN-γ/CCR5 and TNF-α/CCR4/CCR7 and potentiated transfer of EAE (Ito et al., 2003). CCR5 up-regulation by IL-12 has also been reported to enhance LFA-1-mediated adhesiveness (Mukai et al., 2000), and CCR7 binding to its ligand, MIP-3b, promotes proliferation of $CD4^+$ T-cells and progression of autoimmunity (Ploix et al., 2001). Based on their pattern of expression during EAE and their strong down-regulation by RTL401, the current findings also implicate CCR6 (Schutyser, 2003) and CCR8 (Romagnani, 2002) as inflammatory CCRs that may contribute to EAE. In contrast to its inhibitory effects on inflammatory CCRs, RTL401 treatment strongly enhanced expression of CCR3 that has been associated with Th2 responses (Salusto et al., 1998) during the initiation and peak of the first relapse (FIG. 27). This enhancement of CCR3 in EAE-protected mice is reminiscent of the strong up-regulation of CCR3 in BV8S2 transgenic mice successfully treated with TCR BV8S2 determinants (Matejuk et al., 2000). Taken together, these findings indicate that regulation of CCR expression is an important function of the RTL treatment mechanism.

Thus, the systemic effects of RTL therapy that promoted a cytokine switch in response to the encephalitogenic PLP 139-151 peptide apparently produced a non-encephalitogenic T-cell phenotype that retained some ability to infiltrate CNS tissue. However, the infiltrating cells from RTL401-treated mice clearly had reduced inflammatory capability, enhanced secretion of anti-inflammatory factors, and enhanced expression of a protective CCR. Thus, replacement of the disease-initiating encephalitogenic T-cells in CNS by RTL-altered T-cells was associated with partial resolution of inflammatory lesions and reversal of clinical disease. However, the persistent low-level EAE might result from incomplete regulation induced by our postulated T-cell cytokine switch mechanism and the residual compact lesions found in the spinal cord sections. The cytokine switch mechanism considered here differs from an anergy mechanism reported previously in SJL/J mice by others using purified natural four domain I-$A^s$ molecules loaded with PLP 139-151 peptide, or from an apparent deletional mechanism in HLA-DR2 mice treated with an aggregated form of a two-domain RTL (Vandenbark et al., 2003).

In conclusion, the instant example demonstrates for the first time the potent therapeutic effects of a murine minimal TCR ligand in a relapsing model of EAE in SJL mice. A single course of i.v. or s.c. RTL injections prevented relapses and induced long-term clinical benefits that appeared to be mediated by a cytokine switch mechanism involving IL-10, TGF-β3, and CCR3, leading to a moderation of CNS inflammation and demyelination. These results strongly support the clinical application of this novel class of peptide/MHC class II constructs as treatment for T-cell-mediated autoimmune diseases such as multiple sclerosis.

EXAMPLE 13

RTL Treatment Reduces CNS Infiltrating Cells in EAE

GFP+C57BL/6 mice (GFP/B6 mice) were obtained from Jackson Immunoresearch Laboratories (Bar Harbor, Me.) at 6-7 wk of age. The mice were housed in the Animal Resource Facility at the Portland Veterans Affairs Medical Center (Portland, Oreg.) in accordance with institutional guidelines.

RTL Construction and Production

Methods for the design, cloning and expression of RTL 551 were employed as described above in Example 12 for other exemplary RTLs of the invention. cDNA of the Ag binding/TCR recognition domain of murine I-$A^s$ MHC class II β1 and α1 chains was derived from mRNA using two pairs of PCR primers. The two chains were sequentially linked by a 5-aa linker (GGQDD (SEQ ID NO:44)) in a two-step PCR with NcoI and XhoI restriction sites added to the amino terminus of the β1 chain and to the carboxyl terminus of the α1 chain, respectively, to create RTL400. The MOG-35-55 peptide with a linker ((MEVGWYRSPFSRVVHLYRNGK (SEQ ID NO:42)) was covalently linked to the 5' end of the β1 domain of RTL400 to form RTL551. The murine I-$A^s$ β1α1 insert was then ligated into pET21d(+) vector and transformed into Nova blue *E. Coli* host (Novagen, Inc., Madison, Wis.) for positive colony selection and sequence verification. RTL 551 plasmid constructs were then transformed into *E. Coli* strain BL21(DE3) expression host (Novagen, Inc., Madison, Wis.). The purification of proteins was conducted as described previously (Chang et al., 2001). The final yield of purified protein varied between 15 to 30 mg/L of bacterial culture.

Induction of EAE and Treatment with RTLs

The GFP+C57BL/6 mice were immunized s.c. in the flanks with 0.2 ml of an emulsion containing 200 μg of MOG-35-55 peptide and an equal amount of CFA containing 200 μg of heat killed *M. tuberculosis*. After 8-10 days, lymph node and spleen cells were removed from the mice and cells were cultured with MOG-35-55 peptide. After two days, the cultures were harvested, washed, and 50 million cells were injected i.p. into recipient naïve Wild Type C57BL/6 mice to induce EAE. The mice were assessed daily for signs of EAE according to the following scale; 0, normal; 1, limp tail or mild hindlimb weakness; 2, moderate hindlimb weakness or mild ataxia; 3, moderately severe hindlimb weakness; 4, severe hindlimb weakness or mild forelimb weakness or moderate ataxia; 5, paraplegia with no more than moderate forelimb weakness; and 6, paraplegia with severe forelimb weakness or severe ataxia or moribund condition.

At disease onset, mice were treated with vehicle (20 mM Tris-HCl); 100 μg of RTL551 given s.c. for 8 days. Groups of control and treated mice were evaluated statistically for differences in disease incidence, day of onset, mortality, and presence or absence of relapse ($x^2$ test), and for differences in Peak Clinical Score and Cumulative Disease Index (sum of daily scores) (Kruskal-Wallis Test). Mice were sacrificed at the indicated time points following treatment with RTL551 for immunological and histological analyses.

Histopathology

The intact spinal cords were removed from mice at the indicated times after onset of clinical disease and fixed in 10% formalin. The spinal cords were dissected after fixation and embedded in paraffin before sectioning. The sections were stained with luxol fast blue/periodic acid-Schiff-hematoxylin to assess demyelination and inflammatory lesions, and analyzed by light microscopy. Semiquantitative analysis of inflammation and demyelination was determined by examining at least 10 sections from each mouse. In experiments using transferred GFP+ cells to induce EAE, the mice were perfused with saline, and spinal cords were removed and sectioned, and evaluated for the distribution of GFP+ cells using a fluorescence microscope.

Cytokine Determination by Luminex.

LN and spleen cells were cultured at $4 \times 10^6$ cells/well in a 24-well flat-bottom culture plate in stimulation medium with 2 µg/ml MOG-35-55 peptide for 48 h. Supernatants were then harvested and stored at −80° C. until tested for cytokines. The Luminex detection kit was used to quantify IL-1β, IL-2, IL-4, IL-5, IL-6, IL-10, IL-13, IL-17, TNF-α and IFN-γ simultaneously (BioRad). Standard curves were generated for each cytokine, and the concentration of cytokine in the supernatant was determined by interpolation from the appropriate standard curve.

Reduction in Infiltrating EAE Cells in the CNS

Treatment of the GFP/B6mice immunized with MOG-35-55 was begun at disease onset. As can be seen in FIGS. 54, and 55 and 56 respectively, the infiltration of GFP+ cells is visibly reduced in RTL551 treated mice (B and D in FIGS. 54, 55 and 56) the day after treatment began (FIG. 54) three days after treatment initiation (FIG. 55). GFP+ cells are virtually eliminated eight days after treatment initiation (FIG. 56). Correspondingly, the EAE clinical scores for the control and treated mice differed, with the scores for the treated mice improving over the course of treatment. In FIG. 54, the EAE clinical score for the control mouse was 3.4 in comparison to 1.5 for the RTL551 treated mouse. In FIGS. 55 and 56, the EAE clinical score of the control mouse was 5 and the RTL551 treated mouse was 0.5

Inhibition of Secretion of Highly Inflammatory Cytokines

Figure 32:
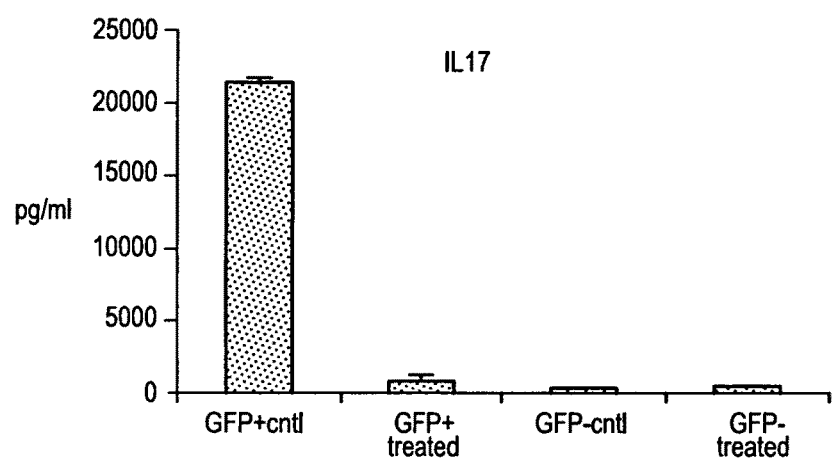
FIG. 32 is a chart showing the attenuation of IL-17 production by encephalitogenic cells after treatment with RTL551.

Additionally, RTL551 treatment of mice with passive EAE dramatically reduced the production of the inflammatory cytokine IL-17 (FIG. 32). GFP+ and GFP− cells from spleens of control and RTL551-treated mice were collected on day 19 (5 days after the end of the treatment period), sorted and evaluated for secretion of a battery of cytokines and for intracellular expression of IL-17. As is shown in FIG. 32, GFP+ cells from control mice that were cultured with MOG-35-55 peptide for 3 days had very high levels of IL-17. However, the IL-17 levels were almost undetectable in GFP+ cells from RTL551-treated mice. No IL-17 was detected in GFP− cells that were retained from the sorting procedure, indicating all of the IL-17 was produced by the transferred MOG-specific T cells that induced EAE in the recipient WT B6 mice. There was a reduction in not only the amount of IL-17 produced, but also in the percentage of MOG-reactive cells expressing IL-17 (3.1% in RTL551 treated mice vs 9.8% in control mice). A similar pattern of reduced expression of TNF-α in GFP+ cells with no expression in GFP− cells was also observed in sorted splenocytes from RTL551-treated mice. Additionally, two other cytokines, IL-2 and IL-6, were strongly expressed in control mice but were nearly undetectable in RTL551-treated mice. These cytokines, however, were also strongly expressed in the host GFP− cell populations in both treated and control groups. Moreover, anti-inflammatory cytokines IL-4, IL-5, IL-10, and IL-13 were more strongly or preferentially expressed in GFP− vs. GFP+ cells from both control and treated mice.

These experiments demonstrate that RTL therapy strongly inhibits secretion of highly inflammatory cytokines, exemplified by IL-17 and TNFα, that are selectively secreted by the transferred GFP+encephalitogenic T cells. Other inflammatory cytokines produced by the GFP+ cells, including IL-2 and IL6, were also inhibited in RTL-treated mice, but secretion for these two cytokines also occurred in GFP-cells and was not affected by the RTL therapy, suggesting specificity of the RTL 551 effects for the encephalitogenic GFP+ mice.

EXAMPLE 14

RTL Treatment of Ischemic Stroke

Autoimmune disorders, such as multiple sclerosis (MS) or other immunological conditions amenable to treatment according to the invention are mediated by one or more antigenic determinants that elicit aberrant (e.g., pathological) T-cell responses. These aberrant T-cell responses can be related to the occurrence and/or severity of other conditions, for example stroke in the case of autoimmune responses directed toward components of the central nervous system (CNS), for example brain or spinal cord tissues, including particularly neurons and surrounding cells/tissues in the CNS that may be affected by autoimmune conditions (e.g., demyelenation, recruitment into the CNS of pathogenic or aberrant signaling T-cells, macrophages and other cells involved in pathogenesis or inflammation mediated by activated T-cells. In this context, RTLs of the invention can be constructed that are effective to reduce or limit secondary or downstream effects of autoimmune responses, for example secondary effects in multiple sclerosis or other immune disorders affecting cells or tissues of the CNS. In exemplary embodiments RTLs are constructed to reduce or limit the onset or severity of ischemic stroke, for example by targeting antigenic determinants involved in aberrant immune responses, including autoimmune responses, that target the CNS (e.g., by stimulating proliferation or recruitment of T-cells or marcrophages into the brain, by inducing inflammatory responses, either through cytokine induction, cellular migration, or cellular destructive activity (e.g., by macrophages, dendritic cells, or NK cells). Useful antigenic determinants to target in these contexts can be complete proteins, or portions or "domains" of proteins that elicit the aberrant T-cell immune response.

In most autoimmune diseases, aberrant T-cell immune responses are elicited by one or more "immunodominant" autoantigens, which are proteins, or parts of proteins, that elicit aberrant T-cell activity causally involved in the autoimmune disease pathogenesis. The aberrant T-cell activity may include any of a variety of activities, including T-cell proliferation, modulation of cytokine expression (e.g., upregulation of inflammatory cytokines), migration/recruitment of T-cells to sites of disease pathology, and signaling or activation of other immune cells, including other T-cells or macrophages. Any of these or related aberrant immune responses may be inhibited or prevented as part of the activity of RTLs to reduce or prevent secondary or downstream CNS symptoms or conditions, such as ischemic stroke in patients presenting with an autoimmune or other immune condition attended by adverse CNS conditions (e.g., inflammation, pathogenic cell recruitment or activity, neuronal demyelenation or death, etc.) Target antigenic determinants within the invention that are covalently linked or non-covalently associated within an RTL complex include any antigenic determinant that plays a role in the targeted immune disorder or related condition (such as ischemic stroke), for example any autoantigen involved in a targeted autoimmune disease adversely affecting the CNS. Typically the antigenic determinant linked or otherwise associated within the RTL complex will be a portion (e.g., a fragment, domain, or discrete "antigenic epitope") of the target antigenic protein, for example a portion of a MBP or PLP known to contain an autoantigenic epitope specifically recognized by T-cells associated with onset or progression of an aberrant CNS immune condition. For all target autoantigenic proteins such as MBP and PLP, various publications describe "epitope mapping" techniques and studies, whereby persons skilled in the art can readily determine which portions, domains, or fragments of a targeted autoantigenic protein mediate T-cell activation involved in the subject CNS disease onset or progression. From these studies there is a wide array of useful antigenic protein segments, including various discrete autoantigenic epitopes, for incorporation into RTL complexes of the invention to treat or prevent primary or secondary disorders or adverse symptoms of the CNS, including ischemic stroke. Using well known epitope mapping techniques, other useful antigenic determinants for incorporation into RLTs can be routinely identified and tested for activity. In the case of ischemic stroke, a wide array of useful RTLs for treating, preventing or limiting the effects of ischemic stroke and other CNS disorders can be produced that are associated or bound to any of a diverse array of known autoantigenic epitopes or other antigenic determinants (e.g., protein fragments containing one or more autoantigenic determinant(s)) that are specifically recognized by T-cells activated by such antigenic determinants to thereby acquire pathogenic pathogenic activity or potential.

In exemplary embodiments of the invention, pathogenesis of MS is targeted for immunological intervention to prevent adverse CNS affects. Pathogenesis of MS can involve autoreactive Th1 cells directed at one or more immunodominant myelin peptides, including MBP-85-99. RTLs such as RTL303 can induce IL-10 production by these T-cells, thus neutralizing their pathogenic potential. Other mechanisms of RTL activity, e.g., other pathways of cytokine induction or switching, chemokine modulation, modulation of cell proliferation and/or recruitment can similarly be targeted for intervention. In one aspect of the invention, local production of IL-10 after Ag-stimulation in the CNS results in inhibition of activation of bystander T-cells that may be of the same or different Ag specificity, as well as macrophages that participate in demyelination. Thus, the important new finding herein evince potent regulatory potential of RTLs that extends beyond RTL-ligated neuroantigen specific T-cell activation. RTL induction of IL-10 in specific T-cell populations that recognize CNS antigens can be used to regulate the immune system while preserving the T-cell repertoire, and thus represents a novel strategy for therapeutic intervention of complex T-cell mediated autoimmune diseases such as MS, and related tools and methods for preventing or reducing related, secondary CNS disorders such as ischemic stroke.

RTL Construction and Production

Methods for the design, cloning and expression of RTL 551 were employed as described above. cDNA of the Ag binding/TCR recognition domain of murine I-A$^s$ MHC class II β1 and α1 chains was derived from mRNA using two pairs of PCR primers. The two chains were sequentially linked by a 5-aa linker (GGQDD (SEQ ID NO:44)) in a two-step PCR with NcoI and XhoI restriction sites added to the amino terminus of the β1 chain and to the carboxyl terminus of the α1 chain, respectively, to create RTL400. The MOG-35-55 peptide with a linker ((MEVGWYRSPFSRVVHLYRNGK (SEQ ID NO:42)) was covalently linked to the 5' end of the β1 domain of RTL400 to form RTL551. The murine I-A$^s$ β1α1 insert was then ligated into pET21d(+) vector and transformed into Nova blue E. Coli host (Novagen, Inc., Madison, Wis.) for positive colony selection and sequence verification. RTL 551 plasmid constructs were then transformed into E. Coli strain BL21(DE3) expression host (Novagen, Inc., Madison, Wis.). The purification of proteins was conducted as described previously (Chang et al., 2001). The final yield of purified protein varied between 15 to 30 mg/L of bacterial culture.

Mice were subjected to middle cerebral artery occlusion (MCAO) by inserting a sterile filament into the blood vessel under anesthesia. Mice were anesthetized with 1% to 1.2% halothane in $O_2$-enriched air by face mask, and rectal and temporalis muscle temperatures were controlled at 37±0.5° C. throughout the experiment with heating lamps and water pads. Unilateral MCA occlusion was performed by inserting a 6-0 nylon monofilament into the internal carotid artery via an external carotid artery stump and then positioning the filament tip for occlusion at a distance of 6 mm beyond the internal carotid/pterygopalatine artery bifurcation. After securing the filament in place, the surgical site was sutured closed and infiltrated with 0.5% buvivacaine as needed for postoperative analgesia. The animal was then awakened and grossly assessed for neurological damage as follows: 0=no deficit, 1=failure to extend forelimb, 2=circling, 3=unilateral weakness, 4=no spontaneous motor activity. Mice with clear neurological deficits were reanesthetized with halothane for suture removal at 60 minutes of occlusion. Control mice are constructed by carrying out identical procedures except that the filament is not inserted into the blood vessel. Post surgery, mice were treated with either RTL551 or vehicle by subcutaneous injection at the onset of reperfusion, then at 24, 48 and 72 hours of reperfusion. At 96 hours of reperfusion, the brain was harvested for analysis of infarction and for immunological testing.

The brain was postfixed in formalin and 30% sucrose in phosphate buffer, cut as serial coronal sections (40 μm) on a freezing microtome, and stained with cresyl violet. A set of 12 evenly spaced sections through the forebrain was mounted for determination of infarction volume by image analysis (Inquiry, Loats Inc, Westminster, Md.). The following areas were measured in each section: cortical infarct, total ipsilateral cortex, total contralateral cortex, striatal infarct, total ipsilateral striatum, and total contralateral striatum. Because larger infarcts were associated with significant edema, areas in each section were corrected for edema as follows. The relative size of the cortical infarct was expressed as a percentage: 100%×[contralateral cortex−(total ipsilateral cortex−cortical infarct)]/ipsilateral cortex. The relative size of each striatal infarct was similarly corrected. Corresponding volumes were then calculated for the total set of slices.

Figure 33A:
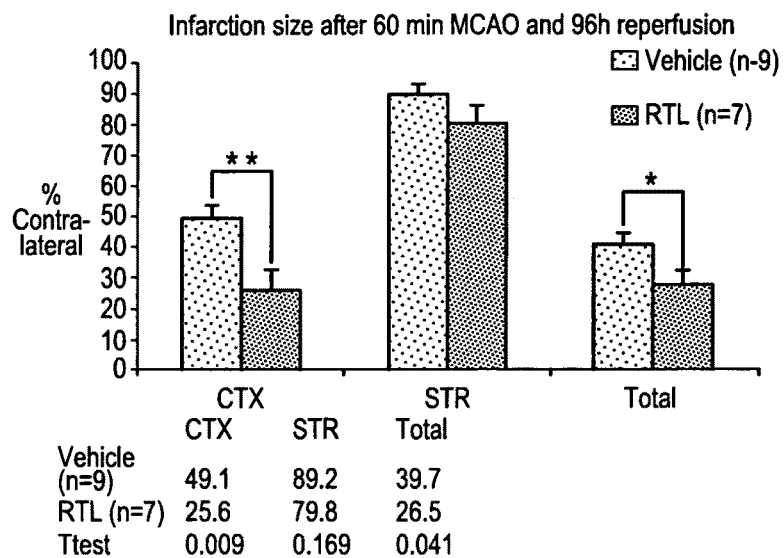
FIGS. 33 (A) and (B) are charts showing (A) infarction size in the cortex and the striatum in 96 hours after reperfusion in mice subjected to 60 minutes MCAO and then treated with vehicle or RTL551 at the onset of reperfusion and 24, 48 and 72 after onset of reperfusion and (B) cell counts from the spleen and thymus in mice 96 hours after reperfusion in mice subjected to 60 minutes MCAO and then treated with vehicle or RTL551 at the onset of reperfusion and 24, 48 and 72 after onset of reperfusion.
Figure 33B:
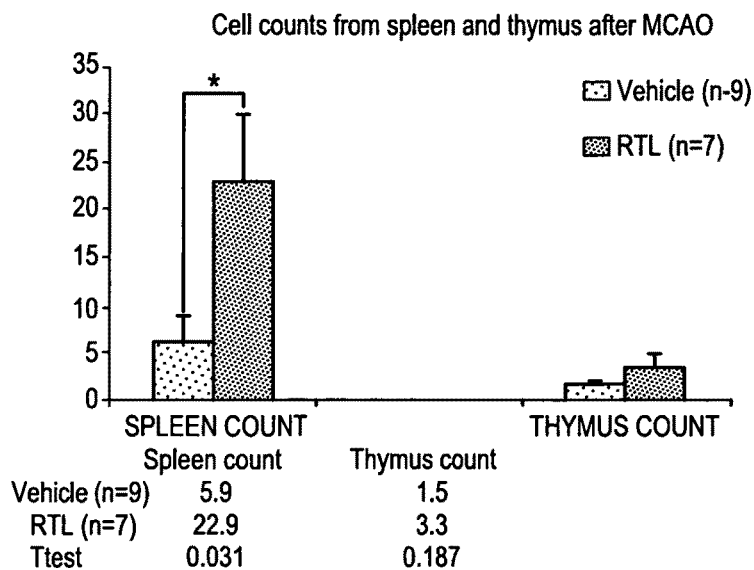

As can be seen in FIG. 33A, the benefit that RTL confers in this stroke model appears to be most visible in the cortex. RTL551 treatment of mice with stroke produced a highly significant reduction in the size of the damaged cortex tissue and in the total stroke volume, but did not have a significant effect on the striatum. Moreover, as shown in FIG. 33B, RT1551 treatment of mice with stroke prevented the characteristic reduction in the size and cellularity of the spleen (but not the thymus) compared to vehicle treated mice with stroke.

Figure 34:
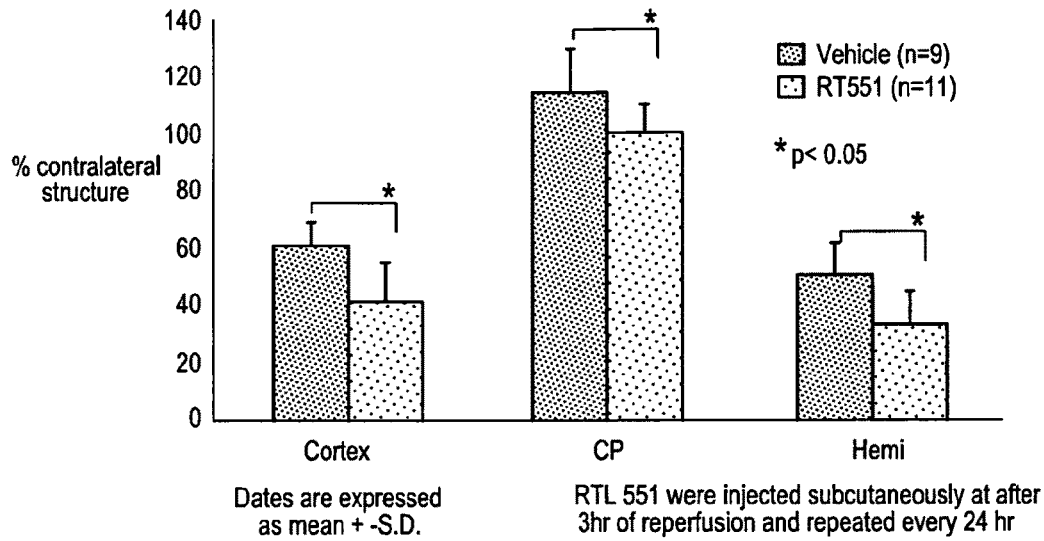
FIG. 34 is a chart showing infarction size in C57blk5 mice at 96 hours after 60 minute MCAO (injected with RTL551 subcutaneously after 3 hours of reperfusion and repeated every 24 hours).
Figure 35:
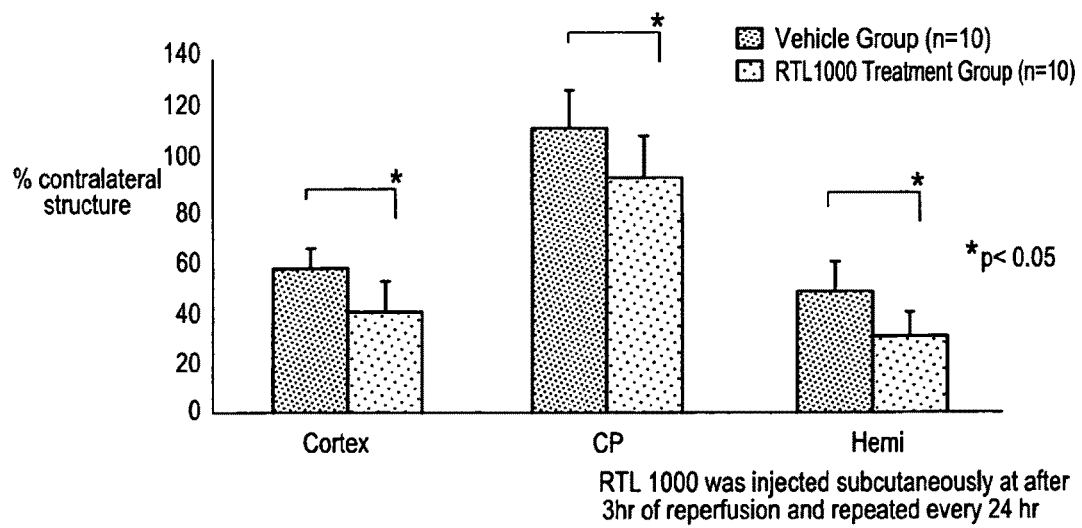
FIG. 35 is a chart showing infarction size in DR2 mice at 96 hours after 60 minute MCAO (injected with RTL1000 subcutaneously after 3 hours of reperfusion and repeated every 24 hours).

The foregoing exemplary studies demonstrate that RTL 550 reduced L reduced infarct size in cortex and total hemisphere by approximately 50% after middle cerebral artery occlusion (MCAO, 60 mins duration). In this exemplary study, RTL was administered subcutaneously at the onset of reperfusion after vascular occlusion, and repeated every 24 hours until the 96 hour end-point of the study. Additional studies were conducted to examine the efficacy of RTL in a more clinically relevant time window, delivering the drug at 3 hours of reperfusion. Experiments were conducted in either male C57BL/6 or HLA-DRB1 mice. As in the foregoing example, MCAO was induced for 60 minutes, followed by 96 hours of reperfusion. RTL injection was subcutaneous at the 3 hr point after reperfusion, and repeated every 24 hr at a dose of 0.1 ml (1 mg/cc). At 96 hr, brain was harvested, stained by TTC for visualization of the infarct, and infarct size was digitally analyzed. Referring to FIGS. 34 and 35, values are shown as means and SEM and infarct is reported as a percentage of the contralateral, uninjured structure. RTL treatment initiated at 3 hr after return of reperfusion significantly reduced infarct size in both C57bl/6 mice (RTL551) and HLA-DRB1 mice using another construct designated RTL 1000.

The foregoing exemplary studies and other observations we have made demonstrate that the methods and compositions provide powerful, effective new immunotherapies to inhibit immune disease processes, particularly autoimmune diseases. The novel RTL constructs provided herein modulate immune effector mechanisms to prevent or ameliorate immune disorders mediated by specific T-cells, in an antigen-specific manner. The invention provides powerful tools and methods to suppress ongoing inflammation and other adverse immune responses affecting the CNS, whereby related conditions such as ischemic stroke can be substantially reduced or prevented. Among the RTL constructs of the invention, RTL551 was effective to reduce adverse immune responses affecting the CNS associated with ischemic stroke, including by reducing cellular proliferation, recruitment and inflammation. Other clinical and histological effects of RTLs for reducing and preventing symptoms of stroke underscore the potency and versatility of RTL constructs for treating T-cell mediated autoimmune diseases and other immunological disorders and conditions. Treatment of CNS immune conditions with RTLs effectively reduce or even abolish clinical and histological signs of T-cell-mediated pathogenecity associated with ischemic stroke, not only when delivered with the first onset of clinical disease but with later attacks of inflammation.

The overall effects of immunosuppression by RTLs included marked reduction in infiltrating cells into the CNS and reduction of histological signs of CNS pathology. The lack of inflammation observed in the CNS is partially due to an altered proinflammatory cytokine and chemokine expression, thereby reducing or preventing cell recruitment and pathogenicity in the CNS. The invention also provides for more specific attributes of targeted autoimmune disorders to be targeted to implement effective treatments for a broad range of immunological diseases and conditions using RTL immunotherapy—specifically targeting pathogenic T cells to alter their activity (e.g., by effecting changes in T-cell cytokine profiles from pro- to anti-inflammatory) based on a "cytokine switch" model of RTL activity.

RTL treatment in the present studies acts in an antigen-specific manner, since RTLs without immunizing peptide or nonspecific peptide have no effect on the suppression of targeted CNS disease symptoms. However, the antigen specificity of RTLs suggests that RTLs of multiple antigen specificities will be more successful in treating or preventing autoimmune conditions such as MS, and other CNS conditions such as stroke, where there may be more than one autoantigen responsible for triggering or expanding the severity of the disease. It is within the level of ordinary skill to identify important proteins involved in autoimmune diseases, and more specifically to identify important antigens or epitopes within immune inductive proteins (e.g., immunodominant autoantigens) that mediate specific T-cell autoimmune responses. Nonetheless, recently published studies on RTL treatment of EAE mice injected with spinal cord homogenate or combinations of 2 different peptides to induce disease have shown showed that treatment with single RTLs can reverse EAE (provided that targeted T cells are present in the periphery (see, e.g., Sinha et al., 2009). In this context, the invention provides effective compositions and methods employing a single RTL to suppression autoimmune responses mediated by multiple antigens, which suppression may involve either or both novel mechanisms of cytokine switching and bystander suppression described herein. More specifically, RTLs can induce a cytokine switch in cognate T cells that inhibits both the antigen specific, target T-cell as well as bystander T-cells, further evincing therapeutic efficacy of RTLs for treating autoimmune diseases and other aberrant immune conditions, and related CNS disorders such as stroke.

RTL engagement with TCRs in the absence of CD4 binding results in rapid TCR phosphorylation, calcium mobilization and reduced extracellular, signal-related kinase activity, as well as in a deviation from a Th1 to a Th0 cell phenotype based on cytokine production. Elevated levels of IL10 induced in Th1 cells by RTLs have important regulatory implications for autoimmunity, because IL-10 is known for its anti-inflammatory effects on Th1 cell and macrophage activation in EAE. Besides the anti-inflammatory effect of IL-10 in EAE, it has been reported that intraocular expression of IL-10 by intravitreal injection of AAV2/2-tetON-vIL-10 protected from S-Ag-induced EAU in Lewis rats with vIL-10 expressed over a long period of time (Smith et al., 2005). In other studies, increased secretion of IL-10 by splenocytes from RTL-treated rats correlated with changes in cytokine expression that apparently suppress recruitment of inflammatory cells to affected areas. In general, RTL therapies in mice and rats inhibited the systemic production of pathogenic cytokines by the targeted specific T cells but also inhibited "downstream", local recruitment and retention of inflammatory cells in the CNS as well as in the eye. In EAE studies using the C57BL/6 model, in which $IA^b$-restricted T cells specific for myelin oligodendrocyte glycoprotein peptide (MOG-34-45) are implicated in disease pathology, RTL551 (carrying covalently tethered MOG35-55 peptide) treatment of mice strongly and selectively reduced the secretion of IL-17 and TNF-α, the latter of which was associated with the downregulation of chemokines and their receptors, and the inhibition of vascular cell adhesion molecule-1 and intercellular adhesion molecule-1 expression on endothelial cells (Sinha et al., 2007) IL-17 was also found to play a role in the pathogenesis of EAU, showing that systemic and local IL-17 response correlated with disease severity in EAU mice (Peng et al., 2007). Targeting IL-17, even late in the disease process, ameliorated pathology, indicating an effector role for this cytokine in the pathogenesis of EAU (Luger et al., 2008). These and other results showed a considerably reduced systemic and local secretion of IL-17 after RTL treatment of acute and recurrent disease. Moreover, CCL2, CCL3 and CCL5 were suppressed in the eyes with EAU. It is widely accepted that synthesis and secretion of inflammatory chemokines play an important part in the pathogenesis of ocular inflammation (Crane et al., 2001, Crane et al., 2006). Both CCL2 and CCL5 are associated with infiltrating inflammatory cells and are potent chemoattractants for T lymphocytes and macrophages, which are related to infiltrating cells observed in the posterior segment of eyes with EAU (Id., Adamus, 1997). Thus, decreased chemokine levels mediated by RTLs indicate that RTLs of the invention can ameliorate or prevent autoimmune response by reducing or preventing downstream activities, e.g., infiltration/recruitment, of T lymphocytes, macrophages and other immune cells involved in autoimmune signaling and/or pathology, including for example immune cells that cause CNS symptoms leading to onset or progression of ischemic stroke.

All publications and patents cited herein are incorporated herein by reference for the purpose of describing and disclosing, for example, the materials and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

REFERENCES

Abbas, A. K., Murphy, K. M. Functional diversity of helper T lymphocytes. *Nature* 383:787 (1996).

Adamus G. et al., Treatment of autoimmune anterior uveitis with recombinant TCR ligands. Inv. Opthal & V is Sci. 47:2555-2561, 2006.

Alderuccio, Frank and Toh, Ban Hock. Spontaneous Autoimmune Gastritis in C3H/He Mice: *A New Mouse Model for Gastric Autoimmunity. AJP* 153 (4): 1311-1317 (1998).

Altman, J. D. et al. Phenotypic analysis of antigen-specific T lymphocytes. *Science* 274, 94-96 (1996).

Arimilli, S., Cardoso, C., Mukku, P., Baichwal, V. & Nag, B. Refolding and reconstitution of functionally active complexes of human leukocyte antigen DR2 and myelin basic protein peptide from recombinant alpha and beta polypeptide chains. Journal of Biological Chemistry 270 (2), 971-977 (1995).

Auffray et al. Isotypic and allotypic variation of human class II histocompatibility antigen alpha-chain genes. Nature 308 (5957), 327-333 (1984).

Ausubel et al. *In Current Protocols in Molecular Biology*, Greene Publishing Associates and Wiley-Intersciences (1987).

Barone F C, Furestein G Z, Inflammatory mediators and stroke: new opportunities for novel therapies. *Cerebral Blood Flow Metab* 19:819-34 (1999).

Bebo, B. F. Jr., Jeanette C. Schuster, Arthur A. Vandenbark, Halina Offner. 1999. Androgens alter the cytokine profile and reduce encephalitogenicity of myelin reactive T-cells. *J. Immunol.* 162:35.

Bebo, B. F., Jr, A. Fyfe-Johnson, K. Adlard, A. G. Beam, A. A. Vandenbark, H. Offner. Low-dose estrogen therapy ameliorates experimental autoimmune encephalomyelitis in two different inbred mouse strains. *J. Immunol.* 166:2080 (2001).

Benoist et al. The murine Ia alpha chains, E alpha and A alpha, show a surprising degree of sequence homology. *Proc. Natl. Acad. Sci. U.S.A.* 80 (2), 534-538 (1983).

Bolstad, Anne Isine Bolstad and Jonsson, Roland. Genetic aspects of Sjögren's syndrome. *Arthritis Res,* 4:353-359 (2002).

Boniface, J. J. & Davis, M. M. T-cell recognition of antigen. A process controlled by transient intermolecular interactions. *Annals New York Acad Sciences.* 766, 62-69 (1995).

Bourdette, D. N. et al. Myelin basic protein specific T-cells in the CNS and lymph nodes of rats with EAE are different. *J. Neurosci. Res.* 30, 308-315 (1991).

Brogdon, J., Eckels, D. D., Davies, C., White, S, and Doyle, C. A site for CD4 binding in the beta-1 domain of the MHC class II protein HLA-DR1. *J. Immunol.* 161:5472 (1988).

Brown, J. H., Jardetzky, T. S., Gorga, J. C., Stern, L. J., Urban, R. G. & Strominger, J. L Three dimensional structure of the human class II histocompatibility antigen HLA-DR1. *Nature* 364, 33-39 (1993).

Browning et al., The HLA-A, B, C genotype of the class I negative cell line Daudi reveals novel HLA-A and -B alleles. Tissue Antigens 45 (3), 177-187 (1995).

Burley, S. K., and Petsko, G. A. *Science* 229, 23-28 (1985).

Burrows, G. G. Bebo, B. F. Jr., Adlard, K. L., Vandenbark, A. A., and Offner, H. *J. Immunol.* 161, 5987-5996 (1998).

Burrows, G. G., Adlard, K. L., Bebo, B. F. Jr., Chang, J. W., Tenditnyy, K., Vandenbark, A. A. and Offner, H. *J. Immunol.* 164, 6366-6371 (2000).

Burrows, G. G., Chang, J. W., Bachinger, H-P., Bourdette, D. N., Wegmann, K. W., Offner, H. and Vandenbark A. A. *Protein Engineering* 12, 771-778 (1999).

Burrows, G. G., Y. K. Chou, C. Wang, J. W. Chang, T. P. Finn, N. E. Culbertson, J. Kim, D. N. Bourdette, D. A. Lewinsohn, D. M. Lewinsohn. Rudimentary TCR signaling triggers default IL-10 secretion by human Th1 cells. *J. Immunol.* 167:4386, (2001).

Burrows, G. G. et al. Multiple Class I Motifs Revealed by Sequencing Naturally Processed Peptides Eluted from Rat T-cell MHC Molecules. Rapid Communication. *J. Neurosci. Res.* 49, 107-116 (1997).

Burrows, G. G. et al. Variation in $H-2K^k$ peptide motif revealed by sequencing naturally processed peptides from T-cell hybridoma class I molecules. *J. Neurosci. Res.* 45, 803-811 (1996).

Cammarota, G. et al. Identification of a CD4 binding site on the $b_2$ domain of HLA-DR molecules. *Nature* 356, 799-801 (1992).

Caspi, R. R. et al. A new model of autoimmune disease: Experimental autoimmune uveorentinitis induced in mice with two different retinal antigens. *J. Immunol.* 140, 1490-1495 (1988).

Chang, J. W. et al., Design, engineering, and production of human recombinant T-cell receptor ligands derived from human leukocyte antigen DR2. *J. Biol. Chem.* 276:24170, (2001).

Chaurhary et al. *Nature* 339: 394-397 (1989).

Chen, G. C. and Yang, J. T. *Anal. Letters* 10, 1195-1207 (1977).

Cobbold, S. P., Nash, J. A., Prospero, T. D. & Waldham, H. Therapy with monoclonal antibodies by elimination of T-cell subsets in vivo. *Nature* 312, 548-551 (1988).

Cobbold, S. P., Nash, J. A., Prospero, T. D. & Waldham, H. Therapy with monoclonal antibodies by elimination of T-cell subsets in vivo. *Nature* 312, 548-551 (1988).

Collins et al. *Nature* 371 (6498): 626-629 (1994).

Compton, L. A., and Johnson, W. C. Jr. *Analytical Biochemistry* 155, 155-67 (1986).

Connolly, M. L. *Science* 221, 709-13 (1983).

Connolly, M. L. *Biopolymers* 25, 1229-47 (1986).

Corr, M. et al. T-cell receptor-MHC class I peptide interactions: affinity, kinetics, and specificity. *Science* 265, 946-949 (1995).

Cua, D. J., H. Groux, D. R. Hinton, S. A. Stohlman, R. L. Coffman. Transgenic interleukin 10 prevents induction of experimental autoimmune encephalomyelitis. *J. Exp. Med.* 189:1005 (1999).

Cush, J. J. & Lipsky, P. E. Phenoytpic analysis of synovial tissue and peripheral blood lymphocytes isolated from patients with rheumatoid arthritis. *Arthritis Rheum.* 31, 1230-1238 (1988).

Das et al. Structure and nucleotide sequence of the heavy chain gene of HLA-DR. *Proc. Natl. Acad. Sci. U.S.A.* 80 (12), 3543-3547 (1983).

Davis, M. M., Boniface, J. J., Reich, Z., Lyons, D., Hampl, J., Arden, B., Chien, Y. Ligand recognition by alpha beta T-cell receptors. *Annu. Rev. Immunol.* 16:523 (1998).

Derman, A. I., Prinz, W. A., Belin, D. & Beckwith, J. Mutations that allow disulfide bond formation in the cytoplasm of *Escherichia coli. Science* 262, 1744-1747 (1993).

Desbarats, J., Freed, J. H., Campbell, P. A., & Newell, M. K. Fas (CD95) expression and death-mediating function are induced by CD4 cross-linking on CD4+ T-cells. *PNAS* 93, 11014-11018 (1996).

deVries, J. E. The role of IL-13 and its receptor in allergy and inflammatory responses. *J Allergy Clin Immunol* 102:165 (1998).

Eck, M. J., Atwell, S. K., Shoelson, S. E., and Harrison, S. C. Structure of the regulatory domains of the Src-family tyrosine kinase Lck. *Nature* 368:764 (1994).

Edwards et al. *Science* 276 (5320): 1868-1871 (1997).

Elder, M. E., Lin, D., Clever, J., Chan, A. C., Hope, T. J., Weiss, A., and Parslow, T. G. Human severe combined immunodeficiency due to a defect in ZAP-70, a T-cell tyrosine kinase. *Science* 264:1596 (1994).

Estess et al. Sequence analysis and structure-function correlations of murine q, k, u, s, and f haplotype I-A beta cDNA clones. Proc. Natl. Acad. Sci. U.S.A. 83 (11), 3594-3598 (1986).

Fearon, D. T., Locksley, R. M. The instructive role of innate immunity in the acquired immune response. *Science* 272: 50 (1996).

Ferrin, T. E., Huang, C. C., Jarvis, L. E. & Langridge, R. The MIDAS display system. *J. Mol. Graphics* 6, 13-27 (1988).

Fleury et al., CELL 66, 1037-1049 (1991).

Fremont, D. H., D. Monnaie, C. A. Nelson, W. A. Hendrickson, E. R. Unanue. Crystal structure of I-A$^k$ in complex with a dominant epitope of lysozyme. *Immunity* 8:305 (1998).

Fremont, et al. Structures of an MHC class II molecule with covalently bound single peptides. *Science* 272, 1001-1004 (1996).

Fujii, Y. et al. Experimental autoimmune adrenalitis: a murine model for Addison's disease. *Autoimmunity* 12 (1):47-52 (1992).

Germain, R. N. Major histocompatibility complex-dependent antigen processing and peptide presentation: providing ligands for the clonal activation of T lymphocytes. *Cell* 76:287 (1994).

Gold, D. P., H. Offner, D. Sun, S. Wiley, A. A. Vandenbark and D. B. Wilson. Analysis of T-cell receptor chains in Lewis rats with experimental autoimmune encephalomyelitis: Conserved complementarity determining region 3. *J. Exp. Med.* 174:1467 (1991).

Golding, H., J. McCluskey, T. I. Munitz, R. N. Germain, D. H. Margulies and A. Singer. T-cell recognition of a chimaeric class II/class I MHC molecule and the role of L3T4. *Nature,* 317:425 (1985).

Gordon, E. J., K. J. Myers, J. P. Dougherty, H. Rosen, Y. Ron. Both anti-CD11 a (LFA-1) and anti-CD11b (MAC-1) therapy delay the onset and diminish the severity of experimental autoimmune encephalomyelitis. *J. Neuroimmunol.* 62:153 (1995).

Govaerts, A. et al. HLA and multiple sclerosis: population and family studies. *Tissue Antigens* 25, 187-199 (1985).

Harlow and Lane (1988). *Antibodies, A Laboratory Manual*, Cold Spring Harbor Laboratory, New York.

Hashim, G. A., Day, E. D., Fredane, L., Intintola, P., and Carvalho, E. Biological activity of region 65 to 102 of the myelin basic protein. *J. Neurosci. Res.* 16, 467-478 (1986).

He, X., C. Radu, J. Sidney, A. Sette, E. S. Ward, K. C. Garcia. Structural snapshot of aberrant antigen presentation linked to autoimmunity: the immunodominant epitope of MBP complexed with I-A$^u$. *Immunity* 17:83 (2002).

Heiden, W., Moeckel, G., and Brickmann, J. *J. Comp.—Aided Mol. Design*. 7, 503-514. (1993)

Hemmer, B., Fleckenstein, B. T., Vergelli, M., Jung, G., McFarland, H., Martin, R. and Wiesmüller, K. H. *J. Exp. Med.* 185, 1651-1660 (1997).

Hershey, G. K. K. 2003. IL-13 receptors and signaling pathways: An evolving web. *J Allergy Clin Immunol* 111:677 (2003).

Housset, D., Habersetzer-Rochat, C., Astier, J. P. & Fontecilla-Camps, J. C. Crystal structure of toxin II from the scorpion *Androctonus Australis* Hector refined at 1.3 angstroms resolution. *J. Mol. Biol.* 238, 88 (1994).

Howell, M. D. et al. Vaccination against experimental allergic encephalomyelitis with T-cell receptor peptides. *Science* 246, 668-670 (1989).

Huan, J., et al., MHC class II derived recombinant T-cell receptor ligands protect DBA/1LacJ mice from collagen-induced arthritis, J. immunol. 180:1249-1257, 2008.

Huan, J., S. Subramanian, R. Jones, C. Rich, J. Link, J. Mooney, D. N. Bourdette, A. A. Vandenbark, G. G. Burrows, and H. Offner. Monomeric recombinant TCR ligand reduces relapse rate and severity of experimental autoimmune encephalomyelitis in SJL/J mice through cytokine switch. *J Immunol* 172:4556 (2004).

Huang, B., Yachou, A., Fleury, S., Hendrickson, W. & Sekaly, R. Analysis of the contact sites on the CD4 molecule with class II MHC molecule. *J. Immunol.* 158, 216-225 (1997).

Hurn P D et al., T and B cell deficient mice with experimental stroke have reduced lesion size and inflammation. J. Cereb. Blood Flow Metab. 27:1798-1805.

Ide T., et al. An experimental animal model of primary biliary cirrhosis induced by lipopolysaccharide and pyruvate dehydrogenase. *Kurume Med. J.* 43 (3):185-8 (1996).

Innis et al. *PCR Protocols, A Guide to Methods and Applications*, Innis et al. (eds.), Academic Press, Inc., San Diego, Calif. (1990).

Ito, A., A. Matejuk, C. Hopke, H. Drought, J. Dwyer, A. Zamora, S. Subramanian, A. A. Vandenbark, H. Offner. Transfer of severe experimental autoimmune encephalomyelitis by IL-12- and IL-18-potentiated T-cells is estrogen sensitive. *J. Immunol.* 170:4802 (2003).

Jameson, B. A., McDonnel, J. M., Marini, J. C. & Korngold, R. A rationally designed CD4 analogue inhibits experimental allergic encephalomyelitis. *Nature* 368, 744-746 (1994).

Janes, P. W., Ley, S. C., Magee, A. I. Aggregation of lipid rafts accompanies signaling via the T-cell antigen receptor. *J. Cell Biol.* 14: 447 (1999).

Janeway & Travers. *Immunobiology: the immune system in health and disease*, Current Biology Ltd./Garland Publishing, Inc. New York (1997).

Janeway, C. A. Jr. and Bottomly, K. *Cell* 76, 275-285 (1994).

Janeway, C. A., Jr. Presidential Address to The American Association of Immunologists. The road less traveled by: the role of innate immunity in the adaptive immune response. *J. Immunol.* 161:539 (1998).

Kanellis, John et al., Modulation of Inflammation by Slit Protein In vivo in Experimental Crescentic Glomerulonephritis *American Journal of Pathology*, 165, (1): 341-352 (2004).

Karnitz, L., Sutor, S. L., Torigoe, T., Reed, J. C., Bell, M. P., McKean, D. J., Leibson, P. J., and Abraham, R. T. Effects of p56lck deficiency on the growth and cytolytic effector function of an interleukin-2-dependent cytotoxic T-cell line. *Mol. Cell. Biol.* 12:4521. (1992)

Kato et al., Molecular analysis of HLA-B39 subtypes. Immunogenetics 37 (3), 212-216 (1993).

Kelly & Trowsdale. Complete nucleotide sequence of a functional HLA-DP beta gene and the region between the DP beta 1 and DP alpha 1 genes: comparison of the 5' ends of HLA class II genes Nucleic Acids Res. 13 (5), 1607-1621 (1985).

Kersh, E. N., Kersh, G. J., Allen, P. M. Partially phosphorylated T-cell receptor zeta molecules can inhibit T-cell activation. *J. Exp. Med.* 190:1627 (1999).

Kim, J S et al., Expression of monocyte chemoattractant protein-1 and macrophage inflammatory protein-1 after focal cerebral ischemia in a rat. *Neuroimmunol* 56: 127-34 (1995).

King, J. and Leimmli, U. K. Bacteriophage T4 tail assembly: structural proteins and their genetic identification. *J. Mol. Biol.* 75, 315-337 (1973).

König, R., Huang, L. Y. & Germain, R. MHC class II interaction with CD4 mediated by a region analogous to the MHC class I binding site for CD8. *Nature* 356, 796-798 (1992).

König, R., Shen, X. & Germain, R. N. Involvement of both major histocompatibility complex class II and β chains in CD4 function indicates a role for ordered oligomerization in T-cell activation. *J. Exp. Med.* 182, 779-787 (1995).

Kozono, H., White, J., Clements, J., Marrack, P. & Kappler, J. Production of soluble MHC class II proteins with covalently bound single peptides. *Nature* 369, 151-154 (1994).

Kress et al., Alternative RNA splicing in expression of the H-2K gene. Nature 306 (5943), 602-604 (1983).

Krishnan, V V., et al. Effect of mysoin B on guinea pig muscles—light microscopic and immunologic aspects. *Indian J. Exp. Biol.* 32 (6):405-8 (1994).

Kyle, V., Coughlan, R. J., Tighe, H., Waldmann, H., and Hazleman, B. L. Beneficial effect of monoclonal antibody to interleukin 2 receptor on activated T-cells in rheumatoid arthritis. *Ann Rheum Dis.* 48:428 (1989).

Larhammar et al. Exon-intron organization and complete nucleotide sequence of a human major histocompatibility antigen DC beta gene. Proc. Natl. Acad. Sci. U.S.A. 80 (23), 7313-7317 (1983).

Lawrence et al. The genomic organisation and nucleotide sequence of the HLA-SB(DP) alpha gene *Nucleic Acids Res.* 13 (20), 7515-7528 (1985).

Lehmann, P. V., T. Forsthuber, A. Miller, E. E. Sercarz. Spreading of T-cell autoimmunity to cryptic determinants of an autoantigen. *Nature* 358:155 (1992).

Li, W., Whaley, C. D., Mondino, A. and Mueller, D. L. Blocked Signal Transduction to the ERK and JNK Protein Kinases in Anergic CD4+ T-cells *Science* 271:1272 (1996).

Li, Y., Li, H., Martin, R., and Mariuzza, R. A. *J. Mol. Biol.* 304, 177-188 (2000).

Link J M, et al., Monomeric DR2/MOG-35-55 recombinant TCR ligand treats relapses of experimental encephalomyelitis in DR2 transgenic mice. Clin Immunol. 123:95-104, 2007.

Liu, T et al., Interleukin-1β mRNA expression in ischemic rat cortex. *Stroke* 24:1746-51 (1993)

Liu, T et al., Tumor necrosis factor α expression in ischemic neurons. *Stroke* 25:1481-8 (1994).

MacDonald, H. R., Casanova, J. L., Maryanski, J. L., Cerottini, J. C. Oligoclonal expansion of major histocompatibility complex class I-restricted cytolytic T lymphocytes during a primary immune response in vivo: direct monitoring by flow cytometry and polymerase chain reaction. *J. Exp. Med.* 177, 1487-1492 (1993).

Madden, D. R., Gorga, J. C., Strominger, J. L. & Wiley, D. C. The structure of HLA-B27 reveals nonamer self-peptides bound in an extended conformation. *Nature* 353, 321-325 (1991).

Martenson, R. E. Myelin basic protein speciation in Experimental Allergic Encephalomyelitis: A useful Model for Multiple Sclerosis. Alan R. Liss, Inc., 150 Fifth Avenue, New York, N.Y. 10011. pp. 511-521 (1984).

Martin R, Utz U, Coligan J E, Richert J R, Flerlage M, Robinson E, Stone R, Biddison W E, McFarlin D E, McFarland H F. Diversity in fine specificity and T-cell receptor usage of the human CD4+ cytotoxic T-cell response specific for the immunodominant myelin basic protein peptide 87-106. *J. Immunol.* 148:1359 (1992).

Matejuk, A., A. A. Vandenbark, G. G. Burrows, B. F. Bebo, Jr, H. Offner. Reduced chemokine and chemokine receptor expression in spinal cords of TCR BV8S2 transgenic mice protected against experimental autoimmune encephalomyelitis with BV8S2 protein. *J. Immunol.* 164:3924 (2000).

Matejuk, A., J. Dwyer, C. Hopke, A. A. Vandenbark, and H. Offner. Differential expression of TGF-β3 is associated with protection against experimental autoimmune encephalomyelitis. *Cytokine* 25:45 (2003).

Matejuk, A., J. Dwyer, C. Hopke, A. A. Vandenbark, H. Officer. Differential expression of TGF-β3 is associated with protection against experimental autoimmune encephalomyelitis. *Cytokine* 25:45 (2004).

Matejuk, A., K. Adlard, A. Zamora, M. Silverman, A. A. Vandenbark, H. Offner. 17b-estradiol inhibits cytokine, chemokine, and chemokine receptor mRNA expression in the central nervous system of female mice with experimental encephalomyelitis. *J. Neurosci. Res.* 65:529 (2001).

Matsubara, S., et al. Experimental allergic myositis in SJL/J mouse. Reappraisal of immune reaction based on changes after single immunization. *J. Neuroimmunol.* 119 (2):223-30 (2001).

Matsui, K. et al. Low affinity interaction of peptide-MHC complexes with T-cell receptors. *Science* 254, 1788-1791 (1991).

Matsui, K., Boniface, J. J., Steffner, P., Reay, P. A., Davis, M. M. Kinetics of T-cell receptor binding to peptide/I-$E^K$ complexes: correlation of the dissociation rate with T-cell responsiveness. *Proc. Natl. Acad. Sci. U.S.A.* 91, 12862-12866 (1994).

McHeyzer, M. G., Davis, M. M. Antigen specific development of primary and memory T-cells in vivo. *Science* 268, 106-111 (1995).

Mege, D., Di Bartolo, V., Germain, B., Tuosto, L., Michel, F., and Acuto, O. Mutation of Tyrosines 492/493 in the Kinase Domain of ZAP-70 Affects Multiple T-cell Receptor Signaling Pathways *J. Biol. Chem.* 271:32644 (1996).

Miltenyi et al. *Cytometry* 11: 231-238 (1990).

Mitragotri et al. Pharmaceutical Research 13 (3): 411-20 (1996).

Moebius, U., Pallai, P., Harrison, S. C. & Reinherz, E. L. Delineation of an extended surface contact area on human CD4 involved in class II MHC binding. *PNAS* 90, 8259-8263 (1993).

Moon, Changjong and Shin, Taekyun, Increased expression of osteopontin in the spinal cords of Lewis rats with experimental autoimmune neuritis. *J. Vet. Sci.* 5 (4), 289-293 (2004)

Moore et al. DNA sequence of a gene encoding a BALF/c mouse Ld transplantation antigen. Science 215 (4533), 679-682 (1982).

Mosmann, T. R., Cherwinski, H., Bond, M. W., Giedlin, M. A., Coffman, R. L. Two types of murine helper T-cell clones. I. Definition according to profiles of lymphokine activities and secreted proteins. *J. Immunol.* 136:2348 (1986).

Mowatt, McI. Prostoglandins and the Induction of Food Sensitivity Enteropathy. *Gut* 46:154-155 (2000).

Mukai, T., M. Iwawake, P. Gao, M. Tomura, Y. Yashiro-Ohtani, S. Ono, M. Murai, K. Matsushima, M. Durimoto, M. Kogo. IL-12 plays a pivotal role in LFA-1-mediated T-cell adhesiveness by up-regulation of CCR5 expression. *J. Leukocyte Biol.* 70:422 (2000).

Murthy, V. L., and Stern, L. J. *Structure* 5, 1385-1396 (1997).

Nag B. et al. Stimulation of T-cells by antigenic peptide complexed with isolated chains of major histocompatibility complex class II molecules. *Proceedings of the National Academy of Sciences of the United States of America* 90 (4), 1604-1608 (1993).

Nag B., Arimilli S., Mukku P. V. & Astafieva, I. Functionally active recombinant alpha and beta chain-peptide complexes of human major histocompatibility class II molecules. *Journal of Biological Chemistry* 271 (17), 10413-10418 (1996).

Nag, B., Deshpande, S. V., Sharma, S. D., & Clark, B. R. Cloned T-cells internalize peptide from bound complexes of peptide and purified class II major histocompatibility complex antigen. *J. Biol. Chem.* 268, 14360-14366 (1993).

Nag, B., Kendrick, T., Arimilli, S., Yu, S. C., & Sriram, S. Soluble MHC II-peptide complexes induce antigen-specific apoptosis in T-cells. *Cell. Immunol.* 170, 25-33 (1996).

Nag, B., Passmore, D., Kendrick, T., Bhayani, H., & Sharma, S. D. N-linked oligosaccharides of murine major histocompatibility complex class II molecule. Role in antigenic peptide binding, T-cell recognition, and clonal nonresponsiveness. *J. Biol. Chem.* 267, 22624-22629 (1992).

Negulescu, P. A., T. B. Krasieva, A. Khan, H. H. Kerschbaum, and M. D. Cahalan. Polarity of T-cell shape, motility, and sensitivity to antigen. *Immunity* 4:421 (1996).

Ng, H. P. et al. Development of a Murine Model of Autoimmune Thyroiditis Induced with Homologous Mouse Thyroid Peroxidase. *Endocrinology* 145 (2):809-816 (2004).

Offner H. et al. Treatment of passive EAE in SJL mice with recombinant TCR ligand induces IL-13 and prevents axonal injury. J. immunol. 175:4103-4111, 2005.

Nicolle, M. W. et al. Specific tolerance to an acetylcholine receptor epitope induced in vitro in myasthenia gravis CD4+ lymphocytes by soluble major histocompatibility complex class II-peptide complexes. *J Clin Invest.* 93, 1361-1369 (1994).

O'Neill L A, Kaltschmidt C. NF-kappa B: a crucial transcription factor for glial and neuronal cell function. *Trends Neurosci* 20:252-8 (1997).

Offner H. et al. Experimental stroke induces massive, rapid activation of the peripheral immune system. J. Cereb Blood Flow Metab. 26:654-665, 2006.

Offner H., et al. Splenic atrophy in experimental stroke is accompanied by increased Treg cells and circulating macrophages. J. Immunol. 176:6523-6531, 2006.

Offner, Halina, et al., Experimental stroke induces massive, rapid activation of the peripheral immune system. *Journal of Cerebral Blood Flow & Metabolism* 26, 654-655 (2006).

Ohman, L. et al. Acellular *Bordetella pertussis* vaccine enhances mucosal interleukin-10 production, induces apoptosis of activated Th1 cells and attenuates colitis in Galphai-2 deficient mice. *Clin. Exp. Immunol.* 141 (1):37-46 (2005).

Oksenberg, J. R. et al. Selection of T-cell receptor V-D-J gene rearrangements with specificity for a MBP peptide in brain lesions of MS. *Nature* 362, 68-70 (1993).

Oldenborg, Per-Arne et al. Lethal autoimmune hemolytic anemia in CD47-deficient nonobese diabetic (NOD) mice. *Blood* 99 (10):3500-3504 (2002).

Olerup, O., and Zetterquist, H. HLA-DR typing by PCR amplification with sequence specific primers (PCR-SSP) in two hours: An alternative to serological DR typing in clinical practice including donor-recipient matching in cadaveric transplantation. *Tissue Antigens* 39:225 (1992).

Ota, K. et al. T-cell recognition of an immunodominant myelin basic protein epitope in multiple sclerosis. *Nature* 346, 183-187 (1990).

Paterson, P. Y. *J. Chron. Dis.* 26, 119-26 (1973).

Paterson, P. Y. Multiple sclerosis: An immunologic reassessment. *J Chron. Dis.* 26, 119-125 (1981).

Pitt, D., P. Werner, and C. S. Raine. Glutamate excitotoxicity in a model of multiple sclerosis. *Nature Med* 6:67 (2000).

Ploegh, H. and Benaroch, P. *Nature* 364, 16-17 (1993).

Ploix, C., D. Lo, M. J. Carson. A ligand for the chemokine receptor CCR7 can influence the homeostatic proliferation of CD4 T-cells and progression of autoimmunity. *J. Immunol.* 167:6724 (2001).

Provencher, S. W. and Glockner, J. *Biochemistry* 20, 33-37 (1981).

Qu, W M, et al. A novel autoimmune pancreatitis model in MRL mice treated with polyinosinic:polycytidylic acid. *Clin. Exp. Immunol.* 129 (1):27-34 (2002).

Quill, H. & Schwartz, R. H. Stimulation of normal inducer T-cell clones with antigen presented by purified Ia molecules in planer lipid membranes: specific induction of a long-lived state of proliferative nonresponsiveness. *J. Immunol.* 138, 3704-3712 (1987).

Redpath, S., Alam, S. M. Lin, C. M., O'Rourke, A. M., and Gascoigne, N. R. Cutting edge: Trimolecular interaction of TCR with MHC class II and bacterial superantigen shows a similar affinity to MHC:peptide ligands. *J. Immunol.* 163:6 (1999).

Reiner, S. L., Wang, Z. E., Hatam, F., Scott, P., Locksley, R. M. TH1 and TH2 cell antigen receptors in experimental leishmaniasis. *Science* 259, 1457-1460 (1993).

Ren, R., Mayer, B. J., Cicchetti, P., and Baltimore, D. Identification of a ten-amino acid proline-rich SH3 binding site. *Science* 259:1157 (1993).

Rhode, P. R. et al. Single-chain MHC class II molecules induce T-cell activation and apoptosis. *J. Immunol.* 157, 4885-4891 (1996).

Riehl, T. et al. TNFR1 mediates the radioprotective effects of Lipopolysaccharides in the mouse intestine. *Am J Physiol Gastrointest Liver Physiol* 286: G166-G173 (2004).

Robertson, Morag et al., Neutralizing Tumor Necrosis Factor-α Activity Suppresses Activation of Infiltrating Macrophages in Experimental Autoimmune Uveoretinitis. *IOVS*, 44 (7):3034-3041 (2003).

Romagnani, P. CCR8 with I-309/CCL1, and CRTH2 with prostaglandin $D_2$ play a critical role in the allergen-induced recruitment of Th2 cells in the target tissues of allergic inflammation. *Mol. Immunol.* 38:881 (2002).

Sallusto, F., D. Lenig, C. R. Mackay, A. Lanzavecchia. Flexible programs of chemokine receptor expression on human polarized T helper 1 and 2 lymphocytes. *J. Exp. Med.* 187:875 (1998).

Sambrook et al. In *Molecular Cloning: A Laboratory Manual*, Cold Spring Harbor, N.Y. (1989).

Samoilova, E. B., J. L. Horton, B. Hilliard, T.-S. T. Liu, and Y. Chen. IL-6-deficient mice are resistant to experimental autoimmune encephalomyelitis: Roles of IL-6 in the activation and differentiation of autoreactive T-cells. *J Immunol* 161:6480 (1998).

Sampei K et al., Stroke in estrogen receptor α-deficient Mice. Stroke 31:738-743, 2000.

Schaeffer, H. J. and Weber, M. J. Mitogen-activated protein kinases: specific messages from ubiquitous messengers. *Mol. Cell. Biol.* 19:2435 (1999).

Schafer, P. H., Pierce, S. K. and Jardetzky T. S. *Seminars in Immunology* 7, 389-98 (1995).

Schepart et al. The nucleotide sequence and comparative analysis of the H-2Dp class I H-2 gene. J. Immunol. 136 (9), 3489-3495 (1986).

Schutyser, E., S. Struyf, J. VanDamme. The CC chemokine CCL20 and its receptor CCR6. *Cytokine Growth Factor Rev.* 14:409 (2003).

Schwartz, R. H. Models of T-cell anergy: is there a common molecular mechanism? *J. Exp. Med.* 184, 1-8 (1996).

Scott, C. A., P. A. Peterson, L. Teyton, I. A. Wilson. Crystal structures of two I-A$^d$-peptide complexes reveal that high affinity can be achieved without large anchor residues. *Immunity* 8:319 (1998).

Seay, A. R. et al. Experimenal viral polymositis: age dependency and immune responses to Ross River virus infection in mice. *Neurology* 31 (6):656-60 (1981).

Service et al. *Science* 277 (5330): 1199-1200 (1997).

Sharma, S. D. et al. Antigen-specific therapy of experimental allergic encephalomyelitis by soluble class II major histocompatibility complex-peptide complexes. *PNAS* 88:11465-11469 (1991).

Sinha S. et al., A promising therapeutic approach for multiple sclerosis: recombinant TCR ligands modulate experimental autoimmune encephalomyelitis by reducing IL-17 production and inhibiting migration of encephalitogenic cells into the central nervous system. J. Neurosci. 27:12531-12539, 2007/

Sloan-Lancaster, J., Shaw, A. S., Rothbard, J. B., Allen, P. M. Partial T-cell signaling: Altered phospho-zeta and lack of Zap70 recruitment in APL-induced T-cell anergy. *Cell* 79:913 (1994).

Smith, K. J., Pyrdol, J., Gauthier, L., Wiley, D. C., and Wucherpfennig, K. W. *J. Exp. Med.* 188, 1511-1520 (1998).

Spack, E. G. et al. Induction of tolerance in experimental autoimmune myasthenia gravis with solubilized MHC class II: acetylcholine receptor complexes. *J. Autoimmun.* 8, 787-807 (1995).

Srinivas et al., Pharmacokinetics and pharmacodynamics of CTLA4Ig (BMS-188667), a novel immunosuppressive agent, in monkeys following multiple doses. *J. Pharm. Sci.* 85 (1):1-4, (1996)).

Steinle et al., Isolation and characterization of a genomic HLA-Cw6 clone. Tissue Antigens 39 (3), 134-137 (1992).

Steinman, L. Autoimmune disease. *Sci. Am.* 269, 106-114 (1993).

Studier, F. W., A. H. Rosenberg, J. J. Dunn, and J. W. Dubendorff. Use of T7 RNA polymerase to direct expression of cloned genes. *Methods Enzymol.* 185:60 (1990).

Swanborg, R. H. Autoimmune effector cells. V. A monoclonal antibody specific for rat helper T lymphocytes inhibits adoptive transfer of auto-immune encephalomyelitis. *J. Immunol.* 130, 1503-1505 (1983).

Syha, J., Henkes, W. & Reske, K. Complete cDNA sequence coding for the MHC class II RTI.B-chain of the Lewis rat. *Nuc. Acids. Res.* 17 (10), 3985 (1989).

Syha-Jedelhauser, J., Wendling, U. & Reske, K. Complete coding nucleotide sequence of cDNA for the Class II RTI.B β-chain of the Lewis rat. *Biochim. Biophys. Acta* 1089, 414-416 (1991).

Sykulev, Y. et al. Kinetics and affinity of reactions between an antigen-specific T-cell receptor and peptide-MHC complexes. *Immunity* 1, 15-22 (1994).

ten Bosch, G. J., Toornyliet, A. C., Friede, T., Melief, C. J., and Leeksma, O. C. Recognition of peptides corresponding to the joining region of p210BCR-ABL protein by human T-cells. *Leukemia* 9:1344 (1995).

Theien, B. E., C. L. Vanderlugt, T. N. Eagar, G. Nickerson-Nutter, R. Nazareno, V. K. Kuchroo, S. D. Miller. Discordant effects of anti-VLA-4 treatment before and after onset of relapsing experimental autoimmune encephalomyelitis. *J. Clin. Invest.* 107:995 (2001).

Thompson, D. and Larson, G. Western blots using stained protein gels. *Biotechniques* 12, 656-658 (1992).

Tonnell et al. Do beta: a new beta chain gene in HLA-D with a distinct regulation of expression. EMBO J. 4 (11), 2839-2847 (1985).

Van Oers, N., Killeen, N., and Weiss, A. Lck regulates the tyrosine phosphorylation of the T-cell receptor subunits and ZAP-70 in murine thymocytes *J. Exp. Med.* 183:1053 (1996).

Vandenbark, A. A., C. Rich, J. Mooney, A. Zamora, C. Wang, J. Huan, L. Fugger, H. Offner, R. Jones, G. G. Burrows. Recombinant TCR ligand induces tolerance to MOG 35-55 peptide and reverses clinical and histological signs of chronic experimental autoimmune encephalomyelitis in HLA-DR2 transgenic mice. *J. Immunol.* 171:127 (2003).

Vandenbark, A. A., Gill, T. & Offner, H. A myelin basic protein specific T lymphocyte line which mediates EAE. *J. Immunol.* 135, 223-228 (1985).

Vandenbark, A. A., Hashim, G. & Offner, H. Immunization with a synthetic T-cell receptor V-region peptide protects against experimental autoimmune encephalomyelitis. *Nature* 341, 541-544 (1989).

Vandenbark, A. A., Vainiene, M., Celnik, B., Hashim, G. A., Buenafe, A. C. & Offner, H. Definition of encephalitogenic and immunodominant epitopes of guinea pig myelin basic protein (Gp-BP) in Lewis rats tolerized neonatally with Gp-BP peptides. *J. Immunol.* 153, 852-861 (1994).

Vanderlugt, C. L., S. D. Miller. Epitope spreading in immune-mediated diseases: implications for immunotherapy. *Nat. Rev. Immunol.* 2:85 (2003).

Veillette, A., Bookman, M. A., Horak, E. M. & Bolen, J. B. The CD4 and CD8 T-cell surface antigens are associated with the internal membrane tyrosine-protein kinase p56$^{lck}$. *Cell* 55, 301-308 (1988).

Vilanova, M., Tavares, D., Ferreira, P., Oliveira, L., Nobrega, A., Appelberg, R., and Arala-Chaves M. Role of monocytes in the up-regulation of the early activation marker CD69 on B and T murine lymphocytes induced by microbial mitogens. *Scand J Immunol.* 43:155 (1996).

Walker, P. R., Ohteki, T., Lopez, J. A., MacDonald, H. R., Maryanski, J. L. Distinct phenotypes of antigen-selected CD8 T-cells emerge at different stages of an in vivo immune response. *J. Immunol.* 155, 3443-3452 (1995).

Walter et al., Genomic organization and sequence of the rat major histocompatibility complex class Ia gene RT1.Au Immunogenetics 41 (5), 332 (1995).

Walter et al., Sequence, expression, and mapping of rat Mhc class Ib gene. Immunogenetics 39 (5), 351-354 (1994).

Wang X K, et al., Expression of interleukin-6, c-fos and zif268 mRNA in rat ischemic cortex. *J Cereb Blood Flow Metab* 15:166-71 (1995).

Wang X K, et al., Concomitant cortical expression of TNFα and IL-1B mRNA following transient focal ischemia *Mol Chem Neuropathol* 23:103-14 (1994).

Wang X K, et al., Increased interleukin-1 receptor and interleukin-1 receptor antagonist gene expression after focal stroke. *Stroke* 28:155-62 (1997).

Wang X K, et al., Monocyte chemoattractant protein-1 (MCP-1) mRNA expression in rat ischemic cortex. *Stroke* 26:661-6 (1995)

Wang X K, et al., Prolonged expression of interferon inducible protein-10 in ischemic cortex after permanent occlusion of the middle cerebral artery in the rat. *J Neruochem* 71:1194-204 (1998)

Wang, C., J. L., Mooney, R. Meza-Romero, Y. K. Chou, J. Huan, A. A. Vandenbark, H. Offner, G. G. Burrows. Recombinant TCR ligand induces early TCR signaling and a unique pattern of downstream activation. *J. Immunol.* 171:1934. (2003)

Wegmann K W, Zhao W., Griffin A C, and Hickey W F. Identification of myocarditogenic peptides derived from cardiac myosin capable of inducing experimental allergic myocarditis in the Lewis rat. The utility of a class II binding motif in selecting self-reactive peptides. *J. Immunol.* 153 (2), 892-900 (1994).

Weinberg, A. D. et al. Target organ specific upregulation of the MRC OX-40 marker and selective production of Th1 lymphokine mRNA by encephalitogenic T helper cells isolated from the spinal cord of rats with experimental autoimmune encephalomyelitis. *J. Immunol.* 152, 4712-5721 (1994).

Weinberg, A. D. et al. TGF-β enhances the in vivo effector function and memory phenotype of Ag-specific T helper cells in EAE. *J. Immunol.* 148, 2109-2117 (1992).

Weinberg, A. D., Bourdette, D. N., Sullivan, T. J., Lemon, M., Wallin, J. J., Maziarz, R., Davey, M., Palida, F., Godfrey, W., Engleman, E., Fulton, R. J., Offner, H., and Vandenbark, A. A. Selective depletion of myelin-reactive T-cells with the anti-OX-40 antibody ameliorates autoimmune encephalomyelitis. *Nature Medicine* 2:183 (1996).

Weiner, H. L. et al. Double-blind pilot trial of oral tolerization with myelin antigens in MS. *Science* 259, 1321-β24 (1993).

White, J., M. Blackman, J. Bill, J. Kappler, P. Marrack, D. P. Gold and W. Born. Two better cell lines for making hybridomas expressing specific T-cell receptors. *J. Immunol.* 143:1822 (1989).

Wülfing, C., Rabinowitz, J. D., Beeson, C., Sjaastad, M. D., McConnell, H. M. and Davis, M. M. Kinetics and Extent of T-cell Activation as Measured with the Calcium Signal. *J. Exp. Med.* 185:1815 (1997).

Yednock, T. A. et al. Prevention of experimental autoimmune encephalomyelitis by antibodies against 4/β1 integrin. *Nature* 356, 63 (1992).

Young, D. A., L. D. Lowe, S. S. Booth, M. J. Whitters, L. Nicholson, V. K. Kuchroo, and M. Collins. IL-4, IL-10, IL-13, and TGF-B from an altered peptide ligand-specific Th2 cell clone down-regulate adoptive transfer of experimental autoimmune encephalomyelitis. *J Immunol* 164: 3563 (2000).

Zhao, B., Carson, M., Ealick, S. E. & Bugg, C. E. Structure of scorpion toxin variant-3 at 1.2 angstroms resolution. J. Mol. Biol. 227, 239-252 (1992).

Zinn-Justin, S., Guenneugues, M., Drakopoulou, Gilquin, B., Vita, C. & Menez, A. Transfer of a beta-hairpin from the functional site of snake curaremimetic toxins to the alpha/beta scaffold of scorpion toxins: Three-dimensional solution structure of the chimeric protein. *Biochemistry* 35 (26): 8535-43 (1996).

Zurawski, G., and J. E. deVries. Interleukin 13, an interleukin 4-like cytokine that acts on monocytes and B cells, but not on T-cells. *Immunol Today* 15:19 (1994).

What is claimed is:

1. A method for treating damage caused by stroke in a mammalian subject comprising:

administering to the mammalian subject who has suffered a stroke an immune-modulatory effective amount of a composition comprising a purified MHC class II polypeptide comprising covalently linked first and second domains, wherein the first domain is a mammalian MHC class II β1 domain and the second domain is a mammalian MHC class II α1 domain, wherein the amino terminus of the second domain is covalently linked to the carboxy terminus of the first domain, and wherein the MHC class II molecule does not include an α2 or a β2 domain; and an antigenic determinant, wherein the antigenic determinant is MOG 35-55, wherein the MHC class II polypeptide modulates one or more immune responses or immune regulatory activities of a T-cell in said subject.

2. The method of claim 1, wherein covalent linkage between the β1 and α1 domains of said MHC class II polypeptide is provided by a peptide linker sequence.

3. The method of claim 1, wherein said antigenic determinant is covalently linked to the amino terminus of the first domain of said MHC class II polypeptide.

4. The method of claim 1, wherein said method is effective to induce a change in location, migration, chemotaxis, and/or infiltration by a T-cell, a macrophage, a B cell, a dendritic cell, or an NK cell in a peripheral blood, spleen, lymph node, or central nervous system (CNS) compartment of said subject.

5. The method of claim 4, wherein said method is effective to mediate a decrease in numbers of inflammatory mononuclear cells in said CNS compartment.

* * * * *